US009415037B2

(12) United States Patent
Menet et al.

(10) Patent No.: US 9,415,037 B2
(45) Date of Patent: Aug. 16, 2016

(54) COMPOUNDS USEFUL FOR THE TREATMENT OF DEGENERATIVE AND INFLAMMATORY DISEASES

(71) Applicants: Christel Jeanne Marie Menet, Mechelen (BE); Luc Juliaan Corina Van Rompaey, Mechelen (BE); Stephen Robert Fletcher, Herts (GB); Javier Blanc, Mechelen (BE); Nolwenn Jouannigot, Annecy le Vieux (FR); Alastair James Hodges, Essex (GB); Koen Kurt Smits, Boechout (BE)

(72) Inventors: Christel Jeanne Marie Menet, Mechelen (BE); Luc Juliaan Corina Van Rompaey, Mechelen (BE); Stephen Robert Fletcher, Herts (GB); Javier Blanc, Mechelen (BE); Nolwenn Jouannigot, Annecy le Vieux (FR); Alastair James Hodges, Essex (GB); Koen Kurt Smits, Boechout (BE)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/507,396

(22) Filed: Oct. 6, 2014

(65) Prior Publication Data
US 2015/0150856 A1 Jun. 4, 2015

Related U.S. Application Data

(62) Division of application No. 13/055,936, filed as application No. PCT/EP2009/059604 on Jul. 24, 2009, now Pat. No. 8,853,240.

(60) Provisional application No. 61/135,920, filed on Jul. 25, 2008, provisional application No. 61/220,685, filed on Jun. 26, 2009.

(51) Int. Cl.
| A61K 31/437 | (2006.01) |
| C07D 471/04 | (2006.01) |
| A61K 31/4545 | (2006.01) |
| A61K 31/4725 | (2006.01) |
| A61K 31/496 | (2006.01) |
| A61K 31/497 | (2006.01) |
| A61K 31/501 | (2006.01) |
| A61K 31/506 | (2006.01) |
| A61K 31/5377 | (2006.01) |
| A61K 31/541 | (2006.01) |
| A61K 31/551 | (2006.01) |

(52) U.S. Cl.
CPC ........... *A61K 31/437* (2013.01); *A61K 31/4545* (2013.01); *A61K 31/4725* (2013.01); *A61K 31/496* (2013.01); *A61K 31/497* (2013.01); *A61K 31/501* (2013.01); *A61K 31/506* (2013.01); *A61K 31/5377* (2013.01); *A61K 31/541* (2013.01); *A61K 31/551* (2013.01); *C07D 471/04* (2013.01)

(58) Field of Classification Search
CPC .................................................... A61K 31/437
See application file for complete search history.

(56) References Cited

U.S. PATENT DOCUMENTS

| 6,500,854 B1 | 12/2002 | Kitamura et al. |
| 2005/0222171 A1 | 10/2005 | Bold et al. |

FOREIGN PATENT DOCUMENTS

| DE | WO 2007009773 A1 * | 1/2007 | ........... C07D 487/04 |
| EP | 1 391 211 | 2/2004 | |
| WO | 03010167 | 2/2003 | |
| WO | WO 03010167 | 2/2003 | |
| WO | 2004072072 | 8/2004 | |
| WO | 2005124342 | 12/2005 | |
| WO | 2006018735 | 2/2006 | |
| WO | 2006038116 | 4/2006 | |
| WO | WO 2007009773 | 1/2007 | |
| WO | WO 2008025821 | 3/2008 | |

(Continued)

OTHER PUBLICATIONS

Healthline Online "http://www.healthline.com/health/inflammatory-bowel-disease", accessed Sep. 9, 2015.*

(Continued)

*Primary Examiner* — David K O'Dell
(74) *Attorney, Agent, or Firm* — Klauber & Jackson LLC

(57) ABSTRACT

[1,2,4]triazolo[1,5-a]pyridine compounds are disclosed that have a formula represented by the following:

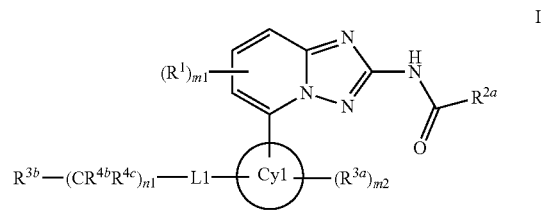

The compounds may be prepared as pharmaceutical compositions, and may be used for the prevention and treatment of a variety of conditions in mammals including humans, including by way of non-limiting example, diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g. diseases involving the anabolic stimulation of chondrocytes), congenital cartilage malformations, diseases associated with hypersecretion of IL6 and transplantation rejection (e.g. organ transplant rejection) and proliferative diseases.

6 Claims, No Drawings

(56) References Cited

FOREIGN PATENT DOCUMENTS

| WO | WO 2008150015 | 11/2008 |
|---|---|---|
| WO | WO 2009010530 | 1/2009 |
| WO | WO 2009017954 | 2/2009 |
| WO | WO 2009/027283 A1 | 3/2009 |
| WO | WO 2009027283 | 3/2009 |
| WO | WO 2009047514 | 4/2009 |
| WO | 2009155565 | 12/2009 |
| WO | 2010010184 | 1/2010 |
| WO | 2010010186 | 1/2010 |
| WO | 2010010187 | 1/2010 |
| WO | 2010010188 | 1/2010 |
| WO | 2010010189 | 1/2010 |
| WO | 2010010191 | 1/2010 |
| WO | 2010141796 | 12/2010 |
| WO | 2010149769 | 12/2010 |
| WO | 2010149771 | 12/2010 |

OTHER PUBLICATIONS

Coksun "Involvement of JAK/STAT signaling in the pathogenesis of inflammatory bowel disease" Pharmacological Research 76 (2013) 1-8.*

Sandborn "Phase2 randomized study of CP-690,550, an oral Janus kinase inhibitor, in active Crohn's disease." Gastroenterology 2011; 140 (Suppl): S124, Abstract 745.*

Laurence, et al., Open Rheumatology Journal, "JAK Kinases in Health and Disease: An Update," 2012; 6(Suppl 2: M4): 232-244.

Changelian, et al., Blood, "The specificity of JAK3 kinase inhibitors," 2008; 111: 2155-2157.

Chen, et al., Immunity, "Janus Kinase Deregulation in Leukemia and Lymphoma," 2012; 36: 529-541.

Drug Discovery and Development, Understanding the R&D process, Pharmaceutical Research and Manufacturers of America, 2007; pp. 1-14.

Dymock, J Develop Drugs, "Recent News in the Fast-Paced Field of JAK Inhibitors," 2013; 2(2): 1-2.

Labadie, et al., Bioorganic & Medicinal Chemistry Letters, Design and evaluation novel 8-0×0-pyridopyrimidine JAK1/2, 2013; 23: 5923-5930.

Milici, et al., Arthritis Reserach & Therapy, Cartilage preservation by inhibition of Janus Kinase 3 in two rodent models of rheumatoid arthritis, 2008; 10: R14.

O'Shea, et al., Immunity, "Cytokine Signaling Modules in Inflammatory Responses," 2008; 28: 477-487.

O'Shea, et al., Immunity, "JAK and STAT Signaling Molecules in Immunoregulation and Immune-Mediated Disease," 2012; 36: 542-550.

Seavey, et al., Biochemical Pharmacology, "The many faces of Janus kinase," 2012; 83: 1136-1145.

Van Vollenhoven, et al., New England Journal of Medicine, Tofacitinib or Adalimumab versus Placebo in Rheumatoid Arthritis, 2012; 367: 508-19.

Yoshida, et al., Biochem & Biophysical Res Commun., "Low dose CP-690,550 (tofacitinib, a pan-JAK inhibitor . . . ," 2012; 418: 234-240.

Bain, J., et al., Biochem. J., "The specificities of protein kinase inhibitors: an update," 2003; 371: 199-204.

Levy, et al., N Engl J Med, "STAT3 signaling and the hyper-IgE syndrome," 2007; 357(16): 1655-8.

McGinnity, et al., Drug Metab Disp, "Evaluation of fresh and cryopreserved hepatocytes as in vitro drug metabolism tools for the prediction of metabolic clearance," 2004; 32(11): 1247-1253.

O'Sulllivan, et al., Mol Immunol, "Cytokine receptor signaling through the Jak-Stat-Socs pathway in disease," 2007; 44(10): 2497-506.

Fabian, Nature Biotech, "A small molecule-kinase interaction map for clinical kinase inhibitors," 2005; 23: 329-336.

Xiang, et al., Blood, "Identification of somatic JAK1 mutations in patients with acute myeloid leukemia," 2008; 111: 4809-4812.

Vainchenker, Pathol Biol, "JAK2, the JAK2 V617F mutant and cytokine receptors," 2008; 55:(2): 88-91.

Choy EH, Panayi GS. (2001). N. Engl J Med. 344: 907-16.

Chubinskaya S and Kuettner KE (2003). Regulation of osteogenic proteins by chondrocytes. The international journal of biochemistry & cell biology 35(9)1323-1340.

Clegg DO et al. (2006) N Engl J Med. 2006 354:795-808. Glucosamine, chondroitin sulfate, and the two in combination for painful knee osteoarthritis.

Firestein GS. (2003). Nature. 423:356-61.

Kachigian LM. (2006) Collagen antibody-induced arthritis, Nature Protocols 2512-2516.

Lee DM, Weinblatt ME (2001). Lancet. 358: 903-11.

Legendre F, Dudhia J, Pujol J-P, Bogdanowicz P. (2003) JAK/STAT but not ERK1/ERK2 pathway mediates interleuking (IL)-6/soluble IL-6R down-regulation of type II collagen, aggrecan core, and link protein transcription in articular chondrocytes. J Biol Chem. 278(5)2903-2912.

Li WQ, Dehnade F, Zafarullah M. (2001) Oncostatin M-induced matrix metalloproteinase and tissue inhibitor of metalloproteinase-3 genes expression in chondrocytes requires jan.

O'Dell Jr. (2004) Therapeutic strategies for rheumatoid arthritis. N Engl J Med. 350(25):2591-602.

Osaki M, Tan L, Choy BK, Yoshida Y, Cheah KSE, Auron PE, Goldring MB. (2003) The TATA-conatining core promoter of the type II collagen gene (COL2A1) is the target of interferon-gamma-mediated inhibition in human chondrocytes: requirement for STAT1alpha, JAK1 and JAK2. Biochem J 369:103-115.

Oste L et al., ECTC Montreal 2007: A high throughput method of measuring bone architectural disturbance in a murine CIA model by micro-CT morphometry.

Otero M, Lago R, Lago F, Gomez Reino JJ, Gualillo O. (2005) Signalling pathway involved in nitric oxide synthase type II activation in chondrocytes: synergistic effect of lept.

Rodig SJ, Meraz MA, White JM, Lampe PA, Riley JK, Arthur CD, King KL, Sheehan KCF, Yin L, Pennica D, Johnson EM, Schreiber RD. (1998) Disruption of the Jak1 gene demonstrates.

Sims NA, Green JR, Glatt M, Schlict S, Martin TJ, Gillespie MT, Romas E. (2004) Targeting osteoclasts with zoledronic acid prevents bone destruction in collagen-induced arthri.

Smolen JS, Steiner G. (2003). Nat Rev Drug Discov. 2: 473-88.

Wernig et al. (2008) Efficacy of TG101348, a selective JAK2 inhibitor, in treatment of a murine model of JAK2V617F-induced polycythemia vera, Cancer Cell 13(4), 311-320.

Geron et al. (2008) Selective inhibition of JAK2-driven erythroid differentiation of polycythemia vera progenitors Cancer Cell 13 (4)5321-30.

Wieland HA, Michaelis M, Kirschbaum BJ, Rudolphi KA. (2005). Nat Rev Drug Discov. 4:331-44. Osteoarthritis—an untreatable disease?.

Wirtz et al. (2007) Mouse Models of Inflammatory Bowel Disease, Advanced Drug Delivery Reviews, 2007, 1073-1083.

Tam, L., McGlynn, L.M., Traynor, P., Mukherjee, R., Bartlett, J.M.S., Edwards, J. (2007) British Journal of Cancer, 97, 378-383.

Constantinescu et al., 2007, Trends in Biochemical Sciences 33(3): 122-131.

Tetsuji Naka, Norihiro Nishimoto and Tadamitsu Kishimoto, Arthritis Res 2002, 4 (suppl 3):S233-S242.

O'Shea, J.J., Pesu, M., Borie, D.C., Changelian, P.S., Nature Reviews, 2004, 555-564.

Nials et al. (2008) Mouse Models of Allergic Asthma: Acute and Chronic Allergen Challenge, Disease Models & Mechanisms, 213-220.

Ip et al. (2006) Interleukin (IL)-4 and IL-13 up-regulate monocyte chemoattractant protein-1 expression in human bronchial epithelial cells: involvement of p38 mitogen-activat.

Pernis et al. (2002) JAK-STAT signaling in asthma J. Clin. Invest. 1279.

Kudlacz et al. (2008) The JAK-3 inhibitor CP-690550 is a potent anti-inflammatory agent in a murine model of pulmonary eosinophilia, Eur J Pharmaco 154-161.

Mullighan CG, Zhang J, Harvey RC, Collins-Underwood, JR, Schulman BA, Phillips LA, Tasian SK, Loh ML, Su X, Liu W, Devidas M, Atlas, SR, Chen I-M, Clifford RJ, Gerhard DS, Carro.

(56) References Cited

OTHER PUBLICATIONS

Argiles JM, Lopez-Soriano FJ. (1998) Catabolic proinflammatory cytokines. Curr Opin Clin Nutr Metab Care. 1:245-51.

Bush KA, Farmer KM, Walker JS, Kirkham BW. (2002) Reduction of joint inflammation and bone erosion in rat adjuvant arthritis by treatment with interleukin-17 receptor IgG1 Fc fusion protein. Arthritis Rheum. 46:802-5.

Jou IM, Shiau AL, Chen SY, Wang CR, Shieh DB, Tsai CS, Wu CL. (2005) Thrombospondin 1 as an effective gene therapeutic strategy in collagen-induced arthritis. Arthritis Rheum.

Nishida K, Komiyama T, Miyazawa S, Shen ZN, Furumatsu T, Doi H, Yoshida A, Yamana J, Yamamura M, Ninomiya Y, Inoue H, Asahara H. (2004) Histone deacetylase inhibitor suppressi.

Rall LC, Roubenoff R.(2004) Rheumatoid cachexia: metabolic abnormalities, mechanisms and interventions. Rheumatology; 10:1219-23.

Salvemini D, Mazzon E, Dugo L, Serraino I, De Sarro A, Caputi AP, Cuzzocrea S. (2001) Amelioration of joint disease in a rat model of collagen-induced arthritis by M40403, a s.

Shelton DL, Zeller J, Ho WH, Pons J, Rosenthal A. (2005) Nerve growth factor mediates hyperalgesia and cachexia in auto-immune arthritis. Pain. 116:8-16.

Walsmith J, Abad L, Kehayias J, Roubenoff R. (2004) Tumor necrosis factor-alpha production is associated with less body cell mass in women with rheumatoid arthritis. J Rheumatol.; 31:23-9.

Lin HS, Hu CY, Chan HY, Liew YY, Huang HP, Lepescheux L, Bastianelli E, Baron R, Rawadi G, Cleément-Lacroix P. (2007) Anti-rheumatic activities of histone deacetylase (HDAC) inhibitors in vivo in collagen-induced arthritis in rodents. Br J Pharmacol. Apr.;150 (7):829-31.

Nettekoven et al., Synthesis, 2003, 11, 1649-1652.

\* cited by examiner

COMPOUNDS USEFUL FOR THE TREATMENT OF DEGENERATIVE AND INFLAMMATORY DISEASES

CROSS REFERENCE TO RELATED APPLICATIONS

The present application is a Division of co-pending non-provisional application Ser. No. 13/055,936 filed Jan. 25, 2011, which is in turn, a National Stage Application claiming the priority of co-pending PCT Application No. PCT/EP2009/059604 filed Jul. 24, 2009, which in turn, claims priority from U.S. Provisional Application Ser. No. 61/135,920 filed Jul. 25, 2008, and Provisional Application Ser. No. 61/220,685 filed Jun. 26, 2009. Applicants claim the benefits of 35 U.S.C. §120 as to the non-provisional U.S. application and the PCT application, and priority under 35 U.S.C. §119 as to the said U.S. provisional applications, and the entire disclosures of all applications are incorporated herein by reference in their entireties.

FIELD OF THE INVENTION

The present invention relates to compounds that are inhibitors of JAK, a family of tyrosine kinases that are involved in the modulation of the degradation of cartilage, joint degeneration and diseases involving such degradation and/or inflammation. The present invention also provides methods for the production of these compounds, pharmaceutical compositions comprising these compounds, methods for the prevention and/or treatment of diseases involving cartilage degradation, bone and/or joint degradation, conditions involving inflammation or immune responses, endotoxin-driven disease states, cancer, and organ transplant rejection; and/or methods for the prevention and/or treatment of diseases involving cartilage degradation, joint degradation and/or inflammation by administering a compound of the invention.

Janus kinases (JAKs) are cytoplasmic tyrosine kinases that transduce cytokine signaling from membrane receptors to STAT transcription factors. Four JAK family members are described, JAK1, JAK2, JAK3 and TYK2. Upon binding of the cytokine to its receptor, JAK family members auto- and/or transphosphorylate each other, followed by phosphorylation of STATs that then migrate to the nucleus to modulate transcription. JAK-STAT intracellular signal transduction serves the interferons, most interleukins, as well as a variety of cytokines and endocrine factors such as EPO, TPO, GH, OSM, LIF, CNTF, GM-CSF, PRL Vainchenker W. et al. (2008).

The combination of genetic models and small molecule JAK inhibitor research revealed the therapeutic potential of several JAKs. JAK3 is validated by mouse and human genetics as an immune-suppression target (O'Shea J. et al. (2004)). JAK3 inhibitors were successfully taken into clinical development, initially for organ transplant rejection but later also in other immuno-inflammatory indications such as rheumathoid arthritis (RA), psoriasis and Crohn's disease (http://clinicaltrials.gov/).

TYK2 is a potential target for immuno-inflammatory diseases, being validated by human genetics and mouse knock-out studies (Levy D. and Loomis C. (2007)).

JAK1 is a novel target in the immuno-inflammatory disease area. JAK1 heterodimerizes with the other JAKs to transduce cytokine-driven pro-inflammatory signaling. Therefore, inhibition of JAK1 and/or other JAKs is expected to be of therapeutic benefit for a range of inflammatory conditions as well as for other diseases driven by JAK-mediated signal transduction.

BACKGROUND OF THE INVENTION

Cartilage is an avascular tissue of which chondrocytes are the main cellular component. The chondrocytes in normal articular cartilage occupy approximately 5% of the tissue volume, while the extra-cellular matrix makes up the remaining 95% of the tissue. The chondrocytes secrete the components of the matrix, mainly proteoglycans and collagens, which in turn supply the chondrocytes with an environment suitable for their survival under mechanical stress. In cartilage, collagen type II, together with the protein collagen type IX, is arranged in solid fibril-like structures which provide cartilage with great mechanical strength. The proteoglycans can absorb water and are responsible for the resilient and shock absorbing properties of the cartilage.

One of the functional roles of cartilage in the joint is to allow bones to articulate on each other smoothly. Loss of articular cartilage, therefore, causes the bones to rub against each other leading to pain and loss of mobility. The degradation of cartilage can have various causes. In inflammatory arthritides, as rheumatoid arthritis for example, cartilage degradation is caused by the secretion of proteases (e.g. collagenases) by inflamed tissues (the inflamed synovium for example). Cartilage degradation can also be the result of an injury of the cartilage, due to an accident or surgery, or exaggerated loading or 'wear and tear'. The ability of cartilage tissue to regenerate after such insults is limited. Chondrocytes in injured cartilage often display reduced cartilage synthesizing (anabolic) activity and/or increased cartilage degrading (catabolic) activity.

The degeneration of cartilage is the hallmark of various diseases, among which rheumatoid arthritis and osteoarthritis are the most prominent. Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Osteoarthritis (also referred to as OA, or wear-and-tear arthritis) is the most common form of arthritis and is characterized by loss of articular cartilage, often associated with hypertrophy of the bone and pain. The disease mainly affects hands and weight-bearing joints such as knees, hips and spines. This process thins the cartilage. When the surface area has disappeared due to the thinning, a grade I osteoarthritis is reached; when the tangential surface area has disappeared, grade II osteoarthritis is reached. There are further levels of degeneration and destruction, which affect the deep and the calcified cartilage layers that border with the subchondral bone. For an extensive review on osteoarthritis, we refer to Wieland et al., 2005.

The clinical manifestations of the development of the osteoarthritis condition are: increased volume of the joint, pain, crepitation and functional disability that lead to pain and reduced mobility of the joints. When disease further develops, pain at rest emerges. If the condition persists without correction and/or therapy, the joint is destroyed leading to disability. Replacement surgery with total prosthesis is then required.

Therapeutic methods for the correction of the articular cartilage lesions that appear during the osteoarthritic disease have been developed, but so far none of them have been able to mediate the regeneration of articular cartilage in situ and in vivo.

Osteoarthritis is difficult to treat. At present, no cure is available and treatment focuses on relieving pain and preventing the affected joint from becoming deformed. Common treatments include the use of non-steroidal anti-inflammatory drugs (NSAIDs). Although dietary supplements such as chondroitin and glucosamine sulphate have been advocated as safe and effective options for the treatment of osteoarthritis, a recent clinical trial revealed that both treatments did not reduce pain associated to osteoarthritis. (Clegg et al., 2006). Taken together, no disease modifying osteoarthritic drugs are available.

In severe cases, joint replacement may be necessary. This is especially true for hips and knees. If a joint is extremely painful and cannot be replaced, it may be fused. This procedure stops the pain, but results in the permanent loss of joint function, making walking and bending difficult.

Another possible treatment is the transplantation of cultured autologous chondrocytes. Here, chondral cellular material is taken from the patient, sent to a laboratory where it is expanded. The material is then implanted in the damaged tissues to cover the tissue's defects.

Another treatment includes the intra-articular instillation of Hylan G-F 20 (e.g. Synvisc®, Hyalgan®, Artz®), a substance that improves temporarily the rheology of the synovial fluid, producing an almost immediate sensation of free movement and a marked reduction of pain.

Other reported methods include application of tendinous, periosteal, fascial, muscular or perichondral grafts; implantation of fibrin or cultured chondrocytes; implantation of synthetic matrices, such as collagen, carbon fiber; administration of electromagnetic fields. All of these have reported minimal and incomplete effects, resulting in a poor quality tissue that can neither support the weighted load nor allow the restoration of an articular function with normal movement.

Stimulation of the anabolic processes, blocking catabolic processes, or a combination of these two, may result in stabilization of the cartilage, and perhaps even reversion of the damage, and therefore prevent further progression of the disease. Various triggers may stimulate anabolic stimulation of chondrocytes. Insulin-like growth factor-I (IGF-I) is the predominant anabolic growth factor in synovial fluid and stimulates the synthesis of both proteoglycans and collagen. It has also been shown that members of the bone morphogenetic protein (BMP) family, notably BMP2, BMP4, BMP6, and BMP7, and members of the human transforming growth factor-β (TGF-β) family can induce chondrocyte anabolic stimulation (Chubinskaya and Kuettner, 2003). A compound has recently been identified that induces anabolic stimulation of chondrocytes (U.S. Pat. No. 6,500,854; EP 1 391 211). However, most of these compounds show severe side effects and, consequently, there is a strong need for compounds that stimulate chondrocyte differentiation without these side effects.

Vandeghinste et al. (WO 2005/124342) discovered JAK1 as a target whose inhibition might have therapeutic relevance for several diseases including OA. JAK1 belongs to the Janus kinase (JAK) family of cytoplasmic tyrosine kinases, involved in cytokine receptor-mediated intracellular signal transduction. The JAK family consists of 4 members: JAK1, JAK2, JAK3 and TYK2. JAKs are recruited to cytokine receptors, upon binding of the cytokine, followed by heterodimerization of the cytokine receptor and a shared receptor subunit (common gamma-c chain, gp130). JAKs are then activated by auto- and/or transphosphorylation by another JAK, resulting in phosphorylation of the receptors and recruitment and phosphorylation of members of the signal transducer and activator of transcription (STATs). Phosphorylated STATs dimerize and translocate to the nucleus where they bind to enhancer regions of cytokine-responsive genes. Knockout of the JAK1 gene in mice demonstrated that JAK1 plays essential and nonredundant roles during development: JAK1−/− mice died within 24 h after birth and lymphocyte development was severely impaired. Moreover, JAK1−/− cells were not, or less, reactive to cytokines that use class II cytokine receptors, cytokine receptors that use the gamma-c subunit for signaling and the family of cytokine receptors that use the gp130 subunit for signaling (Rodig et al., 1998).

Various groups have implicated JAK-STAT signaling in chondrocyte biology. Li et al. (2001) showed that Oncostatin M induces MMP and TIMP3 gene expression in primary chondrocytes by activation of JAK/STAT and MAPK signaling pathways. Osaki et al. (2003) showed that interferon-gamma mediated inhibition of collagen II in chondrocytes involves JAK-STAT signaling. IL1-beta induces cartilage catabolism by reducing the expression of matrix components, and by inducing the expression of collagenases and inducible nitric oxide synthase (NOS2), which mediates the production of nitric oxide (NO). Otero et al., (2005) showed that leptin and IL1-beta synergistically induced NO production or expression of NOS2 mRNA in chondrocytes, and that that was blocked by a JAK inhibitor. Legendre et al. (2003) showed that IL6/IL6 Receptor induced downregulation of cartilage-specific matrix genes collagen II, aggrecan core and link protein in bovine articular chondrocytes, and that this was mediated by JAK/STAT signaling. Therefore, these observations suggest a role for JAK kinase activity in cartilage homeostasis and therapeutic opportunities for JAK kinase inhibitors.

JAK family members have been implicated in additional conditions including myeloproliferative disorders (O'Sullivan et al, 2007, Mol Immunol. 44(10):2497-506), where mutations in JAK2 have been identified. This indicates that inhibitors of JAK in particular JAK2 may also be of use in the treatment of myeloproliferative disorders. Additionally, the JAK family, in particular JAK1, JAK2 and JAK3, has been linked to cancers, in particular leukaemias e.g. acute myeloid leukaemia (O'Sullivan et al, 2007, Mol Immunol. 44(10):2497-506; Xiang et al., 2008, "Identification of somatic JAK1 mutations in patients with acute myeloid leukemia" Blood First Edition Paper, prepublished online Dec. 26, 2007; DOI 10.1182/blood-2007-05-090308) and acute lymphoblastic leukemia (Mullighan et al, 2009) or solid tumours e.g. uterine leiomyosarcoma (Constantinescu et al., 2007, Trends in Biochemical Sciences 33(3): 122-131), prostate cancer (Tam et al., 2007, British Journal of Cancer, 97, 378-383) These results indicate that inhibitors of JAK, in particular of JAK1 and/or JAK2, may also have utility in the treatment of cancers (leukaemias and solid tumours e.g. uterine leiomyosarcoma, prostate cancer).

In addition, Castleman's disease, multiple myeloma, mesangial proliferative glomerulonephritis, psoriasis, and Kaposi's sarcoma are likely due to hypersecretion of the cytokine IL-6, whose biological effects are mediated by intracellular JAK-STAT signaling (Tetsuji Naka, Norihiro Nishimoto and Tadamitsu Kishimoto, Arthritis Res 2002, 4 (suppl 3):S233-S242). This result shows that inhibitor of JAK, may also find utility in the treatment of said diseases.

A link with autoimmune diseases has been established for JAK3 and Tyk2. Mutations in JAK3 but also in the upstream signaling components gamma-c receptor chain and IL7 receptor account in aggregate for ~70% of cases of human severe combined immunodeficiency ('OShea et al., 2004). Note that JAK1 cooperates with JAK3 in transducing signals from the gamma-c receptor chain. Tyk2 polymorphisms are seen in systemic lupus erythematosus (SLE) (O'Sullivan et al, 2007, Mol Immunol. 44(10):2497-506). Hence, targeting the JAK family may provide a therapeutic opportunity in the immuno-inflammation area.

The current therapies are not satisfactory and therefore there remains a need to identify further compounds that may be of use in the treatment of diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). The present invention therefore provides compounds, methods for their manufacture and a pharmaceutical comprising a compound of the invention together with a suitable pharmaceutical carrier. The present invention also provides for the use of a compound of the invention in the preparation of a medicament for the treatment of degenerative joint diseases.

SUMMARY OF THE INVENTION

The present invention is based on the discovery that inhibitors of JAK are useful for the treatment of diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). The present invention also provides methods for the production of these compounds, pharmaceutical compositions comprising these compounds and methods for treating diseases involving cartilage degradation, joint degradation and/or inflammation by administering a compound of the invention.

Accordingly, in a first aspect of the invention, 1,2,4-triazolo[1,5-a]pyridine compounds are disclosed having a Formula (I):

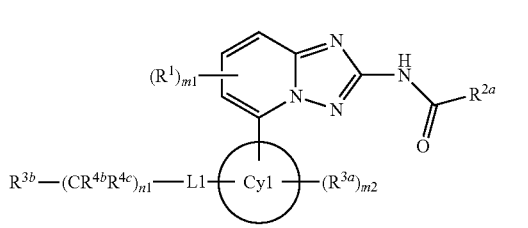

wherein
Cy1 is selected from aryl and heteroaryl;
L1 is selected from a single bond, —O—, —C(O)—, —C[=N($R^{4a}$)]—, —N($R^{4a}$)—, —CON($R^{4a}$)—, —$SO_2$N($R^{4a}$)—, —S(O)$_2$—, —N($R^{4a}$)CO—, —$CH_2$—N($R^{4a}$)— or —N($R^{4a}$)$SO_2$—;
each $R^1$ is independently selected from $C_1$-$C_6$ alkyl, substituted $C_1$-$C_6$ alkyl, acyl, substituted acyl, substituted or unsubstituted acylamino, substituted or unsubstituted $C_1$-$C_6$ alkoxy, substituted or unsubstituted amido, substituted or unsubstituted amino, substituted sulfinyl, substituted sulfonyl, substituted or unsubstituted aminosulfonyl, sulfonic acid, sulfonic acid ester, carboxy, cyano, substituted or unsubstituted $C_3$-$C_7$ cycloalkyl, substituted or unsubstituted 4-7 membered heterocycloalkyl, halo, and hydroxyl;
each $R^{3a}$ is independently selected from $C_1$-$C_6$ alkyl, substituted $C_1$-$C_6$ alkyl, acyl, substituted acyl, substituted or unsubstituted acylamino, substituted or unsubstituted $C_1$-$C_6$ alkoxy, substituted or unsubstituted amido, alkoxycarbonyl, substituted alkoxycarbonyl, arylalkyloxy, substituted arylalkyloxy, substituted or unsubstituted amino, aryl, substituted aryl, arylalkyl, substituted sulfanyl, substituted sulfinyl, substituted sulfonyl, substituted or unsubstituted aminosulfonyl, sulfonic acid, sulfonic acid ester, azido, carboxy, cyano, substituted or unsubstituted $C_3$-$C_7$ cycloalkyl, substituted or unsubstituted 4-7 membered heterocycloalkyl, halo, substituted or unsubstituted heteroaryl, hydroxyl, nitro, and thiol;
$R^{2a}$ is selected from substituted or unsubstituted $C_1$-$C_6$ alkyl and substituted or unsubstituted $C_3$-$C_7$ cycloalkyl;
$R^{3b}$ is independently selected from substituted or unsubstituted aryl, substituted or unsubstituted $C_3$-$C_7$ cycloalkyl, substituted or unsubstituted 4-7 membered heterocycloalkyl, substituted or unsubstituted 5-10 membered heteroaryl; or $R^{3b}$ is independently selected from O—$R^{3c}$, NH—$R^3$, CO—$R^{3c}$, and CON($R^{4a}$)—$R^{3c}$; and $R^{3c}$ is independently selected from substituted $C_1$-$C_6$ alkyl, substituted or unsubstituted aryl, substituted or unsubstituted $C_3$-$C_7$ cycloalkyl, substituted or unsubstituted 4-7 membered heterocycloalkyl, substituted or unsubstituted 5-10 membered heteroaryl;
each $R^{4a}$, $R^{4b}$ and $R^{4c}$ is independently selected from H, $C_1$-$C_6$ alkyl, substituted $C_1$-$C_6$ alkyl, $C_3$-$C_7$ cycloalkyl, or substituted $C_3$-$C_7$ cycloalkyl, substituted or unsubstituted acyl;
m1 is 0, 1, or 2; m2 is 0, 1, 2, or 3; and n1 is 0, 1, 2, 3, or 4;
provided that
i) when L1 is —O—, —N($R^{4a}$)—, —$CH_2$—N($R^{4a}$)—, —CON($R^{4a}$)—, or —$SO_2$N($R^{4a}$)—, and $R^{3b}$ is other than cycloalkyl, aryl or 5-10 membered heteroaryl, then n1 is 1, 2, 3, or 4;

ii) when Cy1 is Ph, L1 is a bond, n1 is 0, and $R^{3b}$ is $-OR^{3c}$, then $R^{3c}$ is other than Me or $CF_3$;

or a pharmaceutically acceptable salts or solvates thereof, or solvates of the pharmaceutically acceptable salts.

In a further aspect, the present invention 1,2,4-triazolo[1,5-a]pyridine compounds according to Formula I are disclosed that are capable of capable of modulating the activity of JAK in vivo.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect of the invention, this invention provides a method of treating a mammal susceptible to or afflicted with a condition from among those listed herein, and particularly, such condition as may be associated with aberrant JAK activity, for example diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection), which method comprises administering an effective amount of one or more of the pharmaceutical compositions or compounds described herein. Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). In a particular embodiment the present invention provides a method for treating conditions selected from inflammation, such as rheumatoid arthritis, juvenile idiopathic arthritis, psoriasis, allergic airways disease (e.g. asthma, rhinitis), inflammatory bowel diseases (e.g. Crohn's disease, colitis), endotoxin-driven disease states (e.g. complications after bypass surgery or chronic endotoxin states contributing to e.g. chronic cardiac failure), and organ transplant rejection; and cartilage, bone and/or joint degradation or degeneration, such as osteoarthritis, which method comprises administering an effective amount of one or more of the pharmaceutical compositions or compounds described herein.

In a further aspect, the present invention provides compounds according to Formula I or a pharmaceutically acceptable salt thereof in the treatment and/or prevention of diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g. diseases involving the anabolic stimulation of chondrocytes), congenital cartilage malformations, diseases associated with hypersecretion of IL6 and transplantation rejection (e.g. organ transplant rejection) or proliferative diseases.

In a further aspect, the present invention provides a method of treating a mammal susceptible to or afflicted with proliferative disorders in particular cancer, (e.g. solid tumours), leukaemias, multiple myeloma or psoriasis.

In a further aspect, the present invention provides a compound of the invention for use in the treatment or prevention of a condition selected from those listed herein, particularly such conditions as may be associated with aberrant JAK activity such as diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). In a specific embodiment, the condition is selected from inflammation, such as rheumatoid arthritis, juvenile idiopathic arthritis, psoriasis, allergic airways disease (e.g. asthma, rhinitis), inflammatory bowel diseases (e.g. Crohn's disease, colitis), endotoxin-driven disease states (e.g. complications after bypass surgery or chronic endotoxin states contributing to e.g. chronic cardiac failure), and organ transplant rejection; and cartilage, bone and/or joint degradation or degeneration, such as osteoarthritis.

In a further aspect, the present invention provides a compound of the invention for use in the treatment or prevention of proliferative disorders, in particular cancer, (e.g. solid tumours), leukaemias, multiple myeloma or psoriasis.

In yet another method of treatment aspect, this invention provides a method for treating a mammal susceptible to or afflicted with a condition that is causally related to abnormal JAK activity as described herein, and comprises administering an effective condition-treating or condition-preventing amount of one or more of the pharmaceutical compositions or compounds herein described.

In a further aspect, the present invention provides a compound of the invention for use in the treatment or prevention of a condition that is causally related to abnormal JAK activity.

In additional aspects, this invention provides methods for synthesizing the compounds of the invention, with representative synthetic protocols and pathways disclosed later on herein.

Accordingly, it is a principal object of this invention to provide a novel series of compounds, which can modify the activity of JAK and thus prevent or treat any maladies that may be causally related thereto.

It is further an object of this invention to provide a series of compounds that can treat or alleviate maladies or symptoms of same, such as cartilage and/or bone degradation and related inflammation, and joint diseases, that may be causally related to the activity of JAK.

A still further object of this invention is to provide pharmaceutical compositions that may be used in the treatment or prevention of a variety of disease states, including the diseases associated with JAK activity such as diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). In a specific embodiment the condition is selected from inflammation, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), and organ transplant rejection; and cartilage, bone and/or joint degradation or degeneration, such as osteoarthritis or cancers (e.g. solid tumours or leukaemias).

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyl' refers to a radical —C(O)R$^{21}$, wherein R$^{21}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —NR$^{22}$C(O)R$^{23}$, where R$^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl and R$^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Exemplary 'acylamino' groups are —NR$^{21'}$C(O)—$C_1$-$C_8$ alkyl, —NR$^{21'}$C(O)—(CH$_2$)$_t$($C_6$-$C_{10}$ aryl), —NR$^{21'}$C(O)—(CH$_2$)$_t$(5-10 membered heteroaryl), —NR$^{21'}$C(O)—(CH$_2$)$_t$($C_3$-$C_{10}$ cycloalkyl), and —NR$^{21'}$C(O)—(CH$_2$)$_t$(4-10 membered heterocycloalkyl), wherein t is an integer from 0 to 4, each R$^{21'}$ independently represents H or $C_1$-$C_8$ alkyl.

'Substituted Acylamino' refers to a radical —NR$^{24}$C(O)R$^{25}$, wherein:

R$^{24}$ is independently

H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and R$^{25}$ is independently H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of R$^{24}$ and R$^{25}$ is other than H.

'Alkoxy' refers to the group —OR$^{26}$ where R$^{26}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, —O-aryl, carboxyl, cyano, $C_3$-$C_{10}$ cycloalkyl, 4-10 membered heterocycloalkyl, halogen, 5-10 membered heteroaryl, hydroxyl, nitro, thioalkoxy, thio-O-aryl, thiol, alkyl-S(O)—, aryl-S(O)—, alkyl-S(O)$_2$— and aryl-S(O)$_2$—. Exemplary 'substituted alkoxy' groups are —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, OCH$_2$CH$_2$NMe$_2$.

'Alkoxycarbonyl' refers to a radical —C(O)—OR$^{27}$ where R$^{27}$ represents an C$_1$-C$_8$ alkyl, C$_3$-C$_{10}$ cycloalkyl, C$_3$-C$_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—C$_1$-C$_8$ alkyl, —C(O)O—(CH$_2$)$_t$(C$_6$-C$_{10}$ aryl), —C(O)O—(CH$_2$)$_t$(5-10 membered heteroaryl), —C(O)O—(CH$_2$)$_t$(C$_3$-C$_{10}$ cycloalkyl), and —C(O)O—(CH$_2$)$_t$(4-10 membered heterocycloalkyl), wherein t is an integer from 1 to 4.

'Substituted Alkoxycarbonyl' refers to a radical —C(O)—OR$^{28}$ where R$^{28}$ represents:
  C$_1$-C$_8$ alkyl, C$_3$-C$_{10}$ cycloalkyl, C$_3$-C$_{10}$ cycloalkylalkyl, or 4-10 membered heterocycloalkylalkyl, each of which is substituted with halo, substituted or unsubstituted amino, or hydroxy; or
  C$_6$-C$_{10}$ aralkyl, or 5-10 membered heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-aryl, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a C$_1$-C$_8$ alkyl group substituted with halo, cyano, nitro, trifluoromethyl, trifluoromethoxy, azido, —NR'"SO$_2$R", —SO$_2$NR"R'", —C(O)R", —C(O)OR", —OC(O)R", —NR'"C(O)R", —C(O)NR"R'", —NR"R'", or —(CR'"R"")$_m$OR'"; wherein each R" is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each of R and R independently represents H or C$_1$-C$_8$ alkyl.

'Amino' refers to the radical —NH$_2$.

'Substituted amino' refers to an amino group substituted with one or more of those groups recited in the definition of 'substituted' herein, and particularly refers to the group —N(R$^{33}$)$_2$ where each R$^{33}$ is independently selected from:
  hydrogen, C$_1$-C$_8$ alkyl, C$_6$-C$_{10}$ aryl, 5-10 membered heteroaryl, 4-10 membered heterocycloalkyl, or C$_3$-C$_{10}$ cycloalkyl; or
  C$_1$-C$_8$ alkyl, substituted with halo or hydroxy; or
  —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl) or —(CH$_2$)$_t$(4-10 membered heterocycloalkyl) wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or
  both R$^{33}$ groups are joined to form an alkylene group.

When both R$^{33}$ groups are hydrogen, —N(R$^{33}$)$_2$ is an amino group. Exemplary 'substituted amino' groups are —NR$^{33'}$—C$_1$-C$_8$ alkyl, —NR$^{33'}$—(CH$_2$)$_t$(C$_6$-C$_{10}$ aryl), —NR$^{33'}$—(CH$_2$)$_t$(5-10 membered heteroaryl), —NR$^{33'}$—(CH$_2$)$_t$(C$_3$-C$_{10}$ cycloalkyl), and —NR$^{33'}$—(CH$_2$)$_t$(4-10 membered heterocycloalkyl), wherein t is an integer from 0 to 4, each R$^{33'}$ independently represents H or C$_1$-C$_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term "substituted amino" includes the groups alkylamino, substituted alkylamino, dialkylamino and substituted dialkylamino as defined below.

'Alkylamino' refers to the group —NHR$^{34}$, wherein R$^{34}$ is C$_1$-C$_8$ alkyl.

'Substituted Alkylamino' refers to the group —NHR$^{35}$, wherein R$^{35}$ is C$_1$-C$_8$ alkyl; and the alkyl group is substituted with halo, substituted or unsubstituted amino, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Dialkylamino' refers to the group —NR$^{42}$R$^{43}$, wherein each of R$^{42}$ and R$^{43}$ are independently selected from C$_1$-C$_8$ alkyl.

'Substituted Dialkylamino' refers to the group —NR$^{44}$R$^{45}$, wherein each of R$^{44}$ and R$^{45}$ are independently selected from C$_1$-C$_8$ alkyl; and the alkyl group is independently substituted with halo, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_{1-4}$ haloalkyl, unsubstituted C$_1$-C$_4$ hydroxyalkyl, or unsubstituted C$_1$-C$_4$ haloalkoxy or hydroxy.

'Aminosulfonyl' or 'Sulfonamide' refers to the radical —S(O$_2$)NH$_2$.

'Substituted aminosulfonyl' or 'substituted sulfonamide' refers to a radical such as —S(O$_2$)N(R$^{48}$)$_2$ wherein each R$^{48}$ is independently selected from:

H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{48}$ is other than H.

Exemplary 'substituted aminosulfonyl' or 'substituted sulfonamide' groups are —S(O$_2$)N(R$^{48'}$)—C$_1$-C$_8$ alkyl, —S(O$_2$)N(R$^{48'}$)—(CH$_2$)$_t$(C$_6$-C$_{10}$ aryl), —S(O$_2$)N(R$^{48'}$)—(CH$_2$)$_t$(5-10 membered heteroaryl), —S(O$_2$)N(R$^{48'}$)—(CH$_2$)$_t$(C$_3$-C$_{10}$ cycloalkyl), and —S(O$_2$)N(R$^{48'}$)—(CH$_2$)$_t$(4-10 membered heterocycloalkyl), wherein t is an integer from 0 to 4; each R$^{48'}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, C$_1$-C$_8$ alkyl, C$_1$-C$_8$ haloalkyl, C$_1$-C$_8$ haloalkoxy, cyano, hydroxy, C$_1$-C$_8$ alkoxy, and amino.

Examples of representative substituted aryls include the following

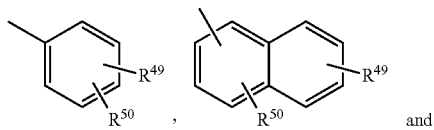

and

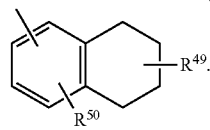

In these formulae one of R$^{49}$ and R$^{50}$ may be hydrogen and at least one of R$^{49}$ and R$^{50}$ is each independently selected from C$_1$-C$_8$ alkyl, 4-10 membered heterocycloalkyl, C$_1$-C$_8$ alkoxy, hetero-O-aryl, alkylamino, NR$^{51}$COR$^{52}$, NR$^{51}$SOR$^{52}$ NR$^{51}$SO$_2$R$^{52}$, COOalkyl, COOaryl, CONR$^{51}$R$^{52}$, CONR$^{51}$OR$^{52}$, NR$^{51}$R$^{52}$, SO$_2$NR$^{51}$R$^{52}$, S-alkyl, SOalkyl, SO$_2$alkyl, Saryl, SOaryl, SO$_2$aryl; or R$^{49}$ and R$^{50}$ may be joined to form a cyclic ring (saturated or unsaturated) from 5 to 8 atoms, optionally containing one or more heteroatoms selected from the group N, O or S. R$^{51}$, and R$^{52}$ are independently hydrogen, C$_1$-C$_8$ alkyl, C$_1$-C$_4$ haloalkyl, C$_3$-C$_{10}$ cycloalkyl, 4-10 membered heterocycloalkyl, C$_6$-C$_{10}$ aryl, substituted aryl, 5-10 membered heteroaryl.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted C$_1$-C$_4$ alkyl, halo, cyano, unsubstituted C$_1$-C$_4$ alkoxy, unsubstituted C$_1$-4 haloalkyl, unsubstituted C$_1$-C$_4$ hydroxyalkyl, or unsubstituted C$_1$-C$_4$ haloalkoxy or hydroxy.

'Azido' refers to the radical —N$_3$.

'Amido' refers to the radical —C(O)NH$_2$.

'Substituted amido' refers to the radical —C(O)N(R$^{53}$)$_2$ wherein each R$^{53}$ is independently H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{53}$ is other than H.

Exemplary 'Substituted Amido' groups are —C(O)NR$^{53'}$—C$_1$-C$_8$ alkyl, —C(O)NR$^{53'}$—(CH$_2$)$_t$(C$_6$-C$_{10}$ aryl), —C(O)N$^{53'}$—(CH$_2$)$_t$(5-10 membered heteroaryl), —C(O)NR$^{53'}$—(CH$_2$)$_t$(C$_3$-C$_{10}$ cycloalkyl), and —C(O)NR$^{53'}$—(CH$_2$)$_t$(4-10 membered heterocycloalkyl), wherein t is an integer from 0 to 4, each R$^{53'}$ independently represents H or C$_1$-C$_8$ alkyl and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, cyclohexyl, cycloheptyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative aryl having hetero atoms containing substitution include the following:

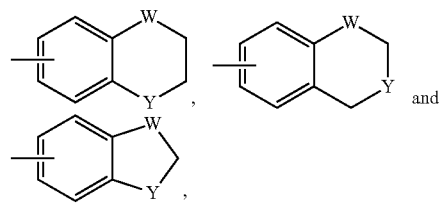

wherein each W is selected from $C(R^{54})_2$, $NR^{54}$, O and S; and each Y is selected from carbonyl, $NR^{54}$, O and S; and $R^{54}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative heteroaryls include the following:

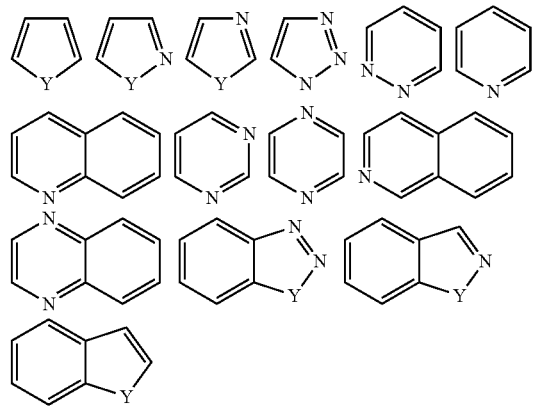

wherein each Y is selected from carbonyl, N, $NR^{55}$, O and S; and $R^{55}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

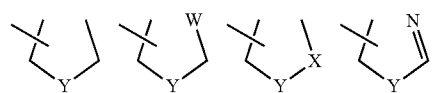

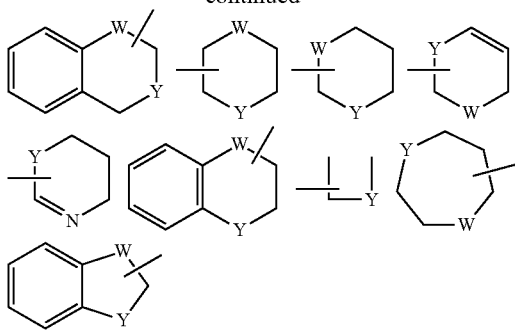

wherein each W is selected from CR$^{56}$, C(R$^{56}$)$_2$, NR$^{56}$, O and S; and each Y is selected from NR$^{56}$, O and S; and R$^{56}$ is independently hydrogen, C$_1$-C$_8$ alkyl, C$_3$-C$_{10}$ cycloalkyl, 4-10 membered heterocycloalkyl, C$_6$-C$_{10}$ aryl, 5-10 membered heteroaryl, These heterocycloalkyl rings may be optionally substituted with one or more groups selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-aryl, azido, carboxyl, cyano, cycloalkyl, halogen, hydroxy, nitro, thiol, —S-allyl, —S-aryl, —S(O)-allyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:
halogen, —R$^{57}$, —O—, =O, —OR$^{57}$, —SR$^{57}$, —S—, =S, —NR$^{57}$R$^{58}$, =NR$^{57}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{57}$, —OS(O)$_2$O$^-$, —OS(O)$_2$R$^{57}$, —P(O)(O$^-$)$_2$, —P(O)(OR$^{57}$)(O$^-$), —OP(O)(OR$^{57}$)(OR$^{58}$), —C(O)R$^{57}$, —C(S)R$^{57}$, —C(O)OR$^{57}$, —C(O)NR$^{57}$R$^{58}$, —C(O)O$^-$, —C(S)OR$^{57}$, —NR$^{59}$C(O)NR$^{57}$R$^{58}$, —NR$^{59}$C(S)NR$^{57}$R$^{58}$, —NR$^{60}$C(NR$^{59}$)NR$^{57}$R$^{58}$ and —C(NR$^{59}$)NR$^{57}$R$^{58}$;

wherein each R$^{57}$, R$^{58}$, R$^{59}$ and R$^{60}$ are independently:
hydrogen, C$_1$-C$_8$ alkyl, C$_6$-C$_{10}$ aryl, arylalkyl, C$_3$-C$_{10}$ cycloalkyl, 4-10 membered heterocycloalkyl, 5-10 membered heteroaryl, heteroarylalkyl; or C$_1$-C$_8$ alkyl substituted with halo or hydroxy; or C$_6$-C$_{10}$ aryl, 5-10 membered heteroaryl, C$_6$-C$_{10}$ cycloalkyl or 4-10 membered heterocycloalkyl substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from: halo, cyano, nitro, trifluoromethyl, trifluoromethoxy, azido, —NR'''SO$_2$R'', —SO$_2$NR"R''', —C(O)R'', —C(O)OR'', —OC(O)R'', —NR'''C(O)R'', —C(O)NR"R''', —NR"R''', —(CR'''R'')$_m$OR''', wherein, each R" is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Each R'" independently represents H or C$_1$-C$_6$alkyl.

'Substituted sulfanyl' refers to the group —SR$^{61}$, wherein R$^{61}$ is selected from:
C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$(C$_3$-C$_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Substituted sulfinyl' refers to the group —S(O)R$^{68}$, wherein R$^{68}$ is selected from:
C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfinyl' groups are —S(O)—(C$_1$-C$_8$ alkyl) and —S(O)—(C$_3$-C$_{10}$ cycloalkyl), —S(O)—(CH$_2$)$_t$(C$_6$-C$_{10}$ aryl), —S(O)—(CH$_2$)$_t$(5-10 membered heteroaryl), —S(O)—(CH$_2$)$_t$(C$_3$-C$_{10}$ cycloalkyl), and —S(O)—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Substituted sulfonyl' refers to the group —S(O)$_2$R$^{75}$, wherein R$^{75}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfonyl' groups are —S(O)$_2$—(C$_1$-C$_8$ alkyl) and —S(O)$_2$—(C$_3$-C$_{10}$ cycloalkyl), —S(O)$_2$—(CH$_2$)$_t$(C$_6$-C$_{10}$ aryl), —S(O)$_2$—(CH$_2$)$_t$(5-10 membered heteroaryl), —S(O)$_2$—(CH$_2$)$_t$(C$_3$-C$_{10}$ cycloalkyl), and —S(O)$_2$—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Sulfo' or 'sulfonic acid' refers to a radical such as —SO$_3$H.

'Substituted sulfo' or 'sulfonic acid ester' refers to the group —S(O)$_2$OR$^{82}$, wherein R$^{82}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'Substituted sulfo' or 'sulfonic acid ester' groups are —S(O)$_2$—O—(C$_1$-C$_8$ alkyl) and —S(O)$_2$—O—(C$_3$-C$_{10}$ cycloalkyl), —S(O)$_2$—O—(CH$_2$)$_t$(C$_6$-C$_{10}$ aryl), —S(O)$_2$—O—(CH$_2$)$_t$(5-10 membered heteroaryl), —S(O)$_2$—O—(CH$_2$)$_t$(C$_3$-C$_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein the term 'condition(s) involving inflammation' refers to the group of conditions including, rheumatoid arthritis, osteoarthritis, juvenile idiopathic arthritis, psoriasis, allergic airway disease (e.g. asthma, rhinitis), inflammatory bowel diseases (e.g. Crohn's disease, colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma) and inflammatory bowel diseases.

As used herein the terms 'condition(s) involving an immune response' or 'autoimmune diseases' are used interchangeably and refer to refers to the group of diseases including obstructive airways disease, including conditions such as COPD, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), multiple sclerosis, type I diabetes mellitus and complications associated therewith, atopic eczema (atopic dermatitis), contact dermatitis and further eczematous dermatitises, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'proliferative disease(s)' refers to conditions such as cancer (e.g. uterine leiomyosarcoma or prostate cancer), myeloproliferative disorders, named in particular Re JAK2 activating mutations (polycythemia vera, essential thrombocythemia, and myeloid metaplasia with myelofibrosis), leukemia (e.g. acute myeloid leukaemia and acute lymphoblastic leukemia), multiple myeloma, psoriasis, restenosis, sclerodermitis or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic rumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

As used herein the term 'leukaemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML) and acute lymphoblastic leukemia (ALL).

As used herein the term 'diseases involving impairment of cartilage turnover' or "diseases involving the anabolic stimulation of chondrocytes" includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'disease(s) associated with hypersecretion of IL6' includes conditions such as Castleman's disease, multiple myeloma, psoriasis, Kaposi's sarcoma and/or mesangial proliferative glomerulonephritis.

'Compound(s) of the invention', and equivalent expressions, are meant to embrace compounds of the Formula(e) as hereinbefore described, which expression includes the prodrugs, the pharmaceutically acceptable salts, and the solvates, e.g., hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is based on the discovery that inhibitors of JAK are useful for the treatment of diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). In particular diseases involving cartilage degradation, bone and/or joint degradation and/or inflammation by administering a compound of the invention. The present compounds may be inhibitors of one or more members of the JAK family; specifically they may inhibit the activity of one or more of JAK1, JAK2, JAK3 and/or TYK2.

Accordingly, in a first aspect of the invention, 1,2,4-triazolo[1,5-a]pyridine compounds are disclosed having a Formula (I):

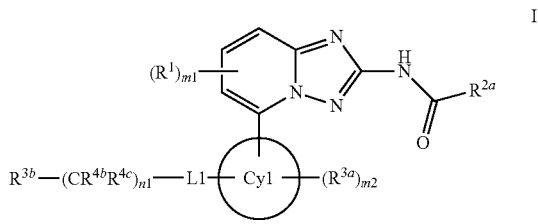

wherein
Cy1 is selected from aryl and heteroaryl;
L1 is selected from a single bond, —O—, —C(O)—, —C[=N($R^{4a}$)]—, —N($R^{4a}$)—, —CON($R^{4a}$)—, —SO$_2$N(R$^{4a}$)—, —S(O)$_2$—, —N(R$^{4a}$)CO—, —CH$_2$—N(R$^{4a}$)— or —N(R$^{4a}$)SO$_2$—;

each R$^1$ is independently selected from C$_1$-C$_6$ alkyl, substituted C$_1$-C$_6$ alkyl, acyl, substituted acyl, substituted or unsubstituted acylamino, substituted or unsubstituted C$_1$-C$_6$ alkoxy, substituted or unsubstituted amido, substituted or unsubstituted amino, substituted sulfinyl, substituted sulfonyl, substituted or unsubstituted aminosulfonyl, sulfonic acid, sulfonic acid ester, carboxy, cyano, substituted or unsubstituted C$_3$-C$_7$ cycloalkyl, substituted or unsubstituted 4-7 membered heterocycloalkyl, halo, and hydroxyl;

each R$^{3a}$ is independently selected from C$_1$-C$_6$ alkyl, substituted C$_1$-C$_6$ alkyl, acyl, substituted acyl, substituted or unsubstituted acylamino, substituted or unsubstituted C$_1$-C$_6$ alkoxy, substituted or unsubstituted amido, alkoxycarbonyl, substituted alkoxycarbonyl, arylalkyloxy, substituted arylalkyloxy, substituted or unsubstituted amino, aryl, substituted aryl, arylalkyl, substituted sulfanyl, substituted sulfinyl, substituted sulfonyl, substituted or unsubstituted aminosulfonyl, sulfonic acid, sulfonic acid ester, azido, carboxy, cyano, substituted or unsubstituted C$_3$-C$_7$ cycloalkyl, substituted or unsubstituted 4-7 membered heterocycloalkyl, halo, substituted or unsubstituted heteroaryl, hydroxyl, nitro, and thiol;

R$^{2a}$ is selected from substituted or unsubstituted C$_1$-C$_6$ alkyl and substituted or unsubstituted C$_3$-C$_7$ cycloalkyl;

R$^{3b}$ is independently selected from substituted or unsubstituted aryl, substituted or unsubstituted C$_3$-C$_7$ cycloalkyl, substituted or unsubstituted 4-7 membered heterocycloalkyl, substituted or unsubstituted 5-10 membered heteroaryl; or R$^{3b}$ is independently selected from O—R$^{3c}$, NH—R$^{3c}$, CO—R$^{3c}$, and CON(R$^{4a}$)—R$^{3c}$; and R$^{3c}$ is independently selected from substituted C$_1$-C$_6$ alkyl, substituted or unsubstituted aryl, substituted or unsubstituted C$_3$-C$_7$ cycloalkyl, substituted or unsubstituted 4-7 membered heterocycloalkyl, substituted or unsubstituted 5-10 membered heteroaryl;

each R$^{4a}$, R$^{4b}$ and R$^{4c}$ is independently selected from H, C$_1$-C$_6$ alkyl, substituted C$_1$-C$_6$ alkyl, C$_3$-C$_7$ cycloalkyl, or substituted C$_3$-C$_7$ cycloalkyl, substituted or unsubstituted acyl;

m1 is 0, 1, or 2; m2 is 0, 1, 2, or 3; and n1 is 0, 1, 2, 3, or 4; provided that
i) when L1 is —O—, —N(R$^{4a}$)—, —CH$_2$—N(R$^{4a}$)—, —CON(R$^{4a}$)—, or —SO$_2$N(R$^{4a}$)—, and R$^{3b}$ is other than cycloalkyl, aryl or 5-10 membered heteroaryl, then n1 is 1, 2, 3, or 4;
ii) when Cy1 is Ph, L1 is a bond, n is 0, and R$^{3b}$ is —OR$^{3c}$, then R$^{3c}$ is other than Me or CF$_3$;
or pharmaceutically acceptable salts or solvates thereof or a solvates of pharmaceutically acceptable salts.

In a further aspect, the present invention provides compounds according to Formula I or a pharmaceutically acceptable salt thereof in the treatment and/or prevention of diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g. diseases involving the anabolic stimulation of chondrocytes), congenital cartilage malformations, diseases associated with hypersecretion of IL6 and transplantation rejection (e.g. organ transplant rejection) or proliferative diseases.

In a further embodiment, the compound is according to Formula (I) above wherein:

Cy1 is selected from aryl and heteroaryl;

L1 is selected from a single bond, —O—, —C(O)—, —C[═N(R$^{4a}$)]—, —N(R$^{4a}$)—, —CON(R$^{4a}$)—, —SO$_2$N(R$^{4a}$)—, —S(O)$_2$—, —N(R$^{4a}$)CO—, —CH$_2$—N(R$^{4a}$)— or —N(R$^{4a}$)SO$_2$—;

each R$^1$ is independently selected from unsubstituted C$_1$-C$_6$ alkyl, unsubstituted acyl, unsubstituted acylamino, unsubstituted C$_1$-C$_6$ alkoxy, unsubstituted amido, unsubstituted amino, unsubstituted aminosulfonyl, sulfonic acid, sulfonic acid ester, carboxy, cyano, unsubstituted C$_3$-C$_7$ cycloalkyl, unsubstituted 4-7 membered heterocycloalkyl, halo, and hydroxyl;

each R$^{3a}$ is independently selected from unsubstituted C$_1$-C$_6$ alkyl, unsubstituted acyl, unsubstituted acylamino, unsubstituted C$_1$-C$_6$ alkoxy, unsubstituted amido, unsubstituted alkoxycarbonyl, unsubstituted arylalkyloxy, unsubstituted amino, unsubstituted aryl, unsubstituted arylalkyl, aminosulfonyl (which aminosulfonyl may be substituted with unsubstituted C$_1$-C$_4$ alkyl), sulfonic acid, sulfonic acid ester, azido, carboxy, cyano, unsubstituted C$_3$-C$_7$ cycloalkyl, unsubstituted 4-7 membered heterocycloalkyl, halo, unsubstituted heteroaryl, hydroxyl, nitro, and thiol;

R$^{2a}$ is selected from unsubstituted C$_1$-C$_6$ alkyl and unsubstituted C$_3$-C$_7$ cycloalkyl;

R$^{3b}$ is independently selected from aryl (which aryl may be substituted with halo, unsubstituted 4-7 membered heterocycloalkyl, unsubstituted C$_1$-C$_4$ alkyl, unsubstituted C$_1$-C$_4$ alkoxy, unsubstituted C$_1$-C$_4$ haloalkyl, unsubstituted C$_1$-C$_4$ haloalkoxy, unsubstituted 5-7-membered heteroaryl, unsubstituted acylamino, unsubstituted amino, cyano, —(CH$_2$)$_{1-4}$—CN), C$_3$-C$_7$ cycloalkyl (which C$_3$-C$_7$ cycloalkyl may be substituted with cyano), 4-7 membered heterocycloalkyl (which 4-7 membered heterocycloalkyl may be substituted with C$_1$-C$_4$ alkyl (which C$_1$-C$_4$ alkyl may be substituted with aryl, heteroaryl, heterocycloalkyl, C$_1$-C$_4$ alkoxy, —O-aryl, —O-heteroaryl, OH), unsubstituted C$_1$-C$_4$ haloalkyl, aryl (which aryl may be substituted with halo, unsubstituted C$_1$-C$_4$ alkoxy), OH, halo, cyano, acyl (which acyl may be substituted with unsubstituted aryl, unsubstituted heterocycloalkyl, unsubstituted C$_1$-C$_4$ alkyl), heteroaryl (which heteroaryl may be substituted with halo), C$_1$-C$_4$ dialkylamino, unsubstituted 4-7 membered heterocycloalkyl, unsubstituted —O-heteroaryl, amido (which heteroaryl may be substituted with unsubstituted C$_1$-C$_4$ alkyl), unsubstituted C$_1$-C$_4$ alkoxy), 5-10 membered heteroaryl (which heteroaryl may be substituted with C$_1$-C$_4$ alkyl (which C$_1$-C$_4$ alkyl may be substituted with unsubstituted aryl), unsubstituted C$_1$-C$_4$ haloalkyl, unsubstituted amido, halo, 4-7-membered heterocycloalkyl (which heterocycloalkyl may be substituted with unsubstituted C$_1$-C$_4$ alkyl), unsubstituted C$_1$-C$_4$ alkoxy, CN, unsubstituted C$_3$-C$_7$ cycloalkyl, OH, aryl (which aryl may be substituted with unsubstituted C$_1$-C$_4$ haloalkyl) unsubstituted 5-7-membered heteroaryl, carboxy (which carboxy may be substituted with unsubstituted C$_1$-C$_4$ alkyl)), or R$^{3b}$ is independently selected from O—R$^{3c}$, NH—R$^{3c}$, CO—R$^{3c}$, and CON(R$^{4a}$)—R$^{3c}$; and R$^{3c}$ is independently selected from C$_1$-C$_6$ alkyl (which C$_1$-C$_4$ alkyl is substituted with aryl (which aryl may be substituted with halo, CN, unsubstituted C$_1$-C$_4$ alkyl, unsubstituted 5-7-membered heterocycloalkyl, unsubstituted 5-10 membered heteroaryl), 5-10 membered heteroaryl (which heteroaryl may be substituted with unsubstituted $C_1$-$C_4$ alkyl)),
aryl (which aryl may be substituted with halo, CN, unsubstituted $C_1$-$C_4$ alkoxy, unsubstituted amido, unsubstituted $C_1$-$C_4$ alkyl, unsubstituted $C_1$-$C_4$, haloalkyl, —$(CH_2)_{1-4}$—CN), $C_3$-$C_7$ cycloalkyl (which $C_3$-$C_7$ cycloalkyl may be substituted with), unsubstituted 4-7 membered heterocycloalkyl, 5-10 membered heteroaryl (which heteroaryl may be substituted with halo, cyano, unsubstituted $C_1$-$C_4$ alkyl, unsubstituted $C_1$-$C_4$ alkoxy, unsubstituted 4-7 membered heterocycloalkyl);
each $R^{4a}$, $R^{4b}$ and $R^{4c}$ is independently selected from H, $C_1$-$C_6$ alkyl (which $C_1$-$C_4$ alkyl may be substituted with unsubstituted $C_1$-$C_4$ alkoxy, unsubstituted dialkylamino, unsubstituted 4-7 membered heterocycloalkyl), unsubstituted $C_3$-$C_7$ cycloalkyl, acyl (which acyl may be substituted with unsubstituted $C_1$-$C_6$ alkyl);
m1 is 0, 1, or 2; m2 is 0, 1, 2, or 3; and n1 is 0, 1, 2, 3, or 4;
provided that
when L1 is —O—, —N($R^{4a}$)—, —CON($R^{4a}$)—, or —$SO_2$N($R^{4a}$)—, and $R^{3b}$ is other than cycloalkyl, aryl or 5-10 membered heteroaryl, then n1 is 1, 2, 3, or 4;
or pharmaceutically acceptable salts or solvates thereof, or solvates of the pharmaceutically acceptable salts.

In a preferred embodiment, the compound is according to Formula I above wherein:
Cy1 is selected from aryl and heteroaryl;
L1 is selected from a single bond, —O—, —C(O)—, —C[=N($R^{4a}$)]—, —N($R^{4a}$)—, —CON($R^{4a}$)—, —$SO_2$N($R^{4a}$)—, —S(O)$_2$—, —N($R^{4a}$)CO—, —$CH_2$—N($R^{4a}$)— or —N($R^{4a}$)$SO_2$—;
each $R^1$ is independently selected from unsubstituted $C_1$-$C_6$ alkyl, unsubstituted acyl, unsubstituted acylamino, unsubstituted $C_1$-$C_6$ alkoxy, unsubstituted amido, unsubstituted amino, unsubstituted aminosulfonyl, sulfonic acid, sulfonic acid ester, carboxy, cyano, unsubstituted $C_3$-$C_7$ cycloalkyl, unsubstituted 4-7 membered heterocycloalkyl, halo, and hydroxyl;
each $R^{3a}$ is independently selected from unsubstituted $C_1$-$C_6$ alkyl, unsubstituted acyl, unsubstituted acylamino, unsubstituted $C_1$-$C_6$ alkoxy, unsubstituted amido, unsubstituted alkoxycarbonyl, unsubstituted arylalkyloxy, unsubstituted amino, unsubstituted aryl, unsubstituted arylalkyl, aminosulfonyl (which aminosulfonyl may be substituted with unsubstituted $C_1$-$C_4$ alkyl), sulfonic acid, sulfonic acid ester, azido, carboxy, cyano, unsubstituted $C_3$-$C_7$ cycloalkyl, unsubstituted 4-7 membered heterocycloalkyl, halo, unsubstituted heteroaryl, hydroxyl, nitro, and thiol;
$R^{2a}$ is selected from unsubstituted $C_1$-$C_6$ alkyl and unsubstituted $C_3$-$C_7$ cycloalkyl;
$R^{3b}$ is independently selected from aryl (which aryl may be substituted with halo, unsubstituted 4-7 membered heterocycloalkyl, unsubstituted $C_1$-$C_4$ alkyl, unsubstituted $C_1$-$C_4$ alkoxy, unsubstituted $C_1$-$C_4$ haloalkyl, unsubstituted $C_1$-$C_4$ haloalkoxy, unsubstituted 5-7-membered heteroaryl, unsubstituted acylamino, unsubstituted amino, cyano, —$(CH_2)_{1-4}$—CN), $C_3$-$C_7$ cycloalkyl (which $C_3$-$C_7$ cycloalkyl may be substituted with cyano), 4-7 membered heterocycloalkyl (which 4-7 membered heterocycloalkyl may be substituted with $C_1$-$C_4$ alkyl (which $C_1$-$C_4$ alkyl may be substituted with aryl, heteroaryl, heterocycloalkyl, $C_1$-$C_4$ alkoxy, —O-aryl, —O-heteroaryl, OH), unsubstituted $C_1$-$C_4$ haloalkyl, aryl (which aryl may be substituted with halo, unsubstituted $C_1$-$C_4$ alkoxy), OH, halo, cyano, acyl (which acyl may be substituted with unsubstituted aryl, unsubstituted heterocycloalkyl, unsubstituted $C_1$-$C_4$ alkyl), heteroaryl (which heteroaryl may be substituted with halo), $C_1$-$C_4$ dialkylamino, unsubstituted 4-7 membered heterocycloalkyl, unsubstituted —O-heteroaryl, amido (which heteroaryl may be substituted with unsubstituted $C_1$-$C_4$ alkyl), unsubstituted $C_1$-$C_4$ alkoxy), 5-10 membered heteroaryl (which heteroaryl may be substituted with $C_1$-$C_4$ alkyl (which $C_1$-$C_4$ alkyl may be substituted with unsubstituted aryl), unsubstituted $C_1$-$C_4$ haloalkyl, unsubstituted amido, halo, 4-7-membered heterocycloalkyl (which heterocycloalkyl may be substituted with unsubstituted $C_1$-$C_4$ alkyl), unsubstituted $C_1$-$C_4$ alkoxy, CN, unsubstituted $C_3$-$C_7$ cycloalkyl, OH, aryl (which aryl may be substituted with unsubstituted $C_1$-$C_4$ haloalkyl) unsubstituted 5-7-membered heteroaryl, carboxy (which carboxy may be substituted with unsubstituted $C_1$-$C_4$ alkyl)),
or $R^{3b}$ is independently selected from O—$R^{3c}$, NH—$R^{3c}$, CO—$R^{3c}$, and CON($R^{4a}$)—$R^{3c}$; and $R^{3c}$ is independently selected from $C_1$-$C_6$ alkyl (which $C_1$-$C_4$ alkyl may be substituted with aryl (which aryl may be substituted with halo, CN, unsubstituted $C_1$-$C_4$ alkyl, unsubstituted 5-7-membered heterocycloalkyl, unsubstituted 5-10 membered heteroaryl), 5-10 membered heteroaryl (which heteroaryl may be substituted with unsubstituted $C_1$-$C_4$ alkyl)), aryl (which aryl may be substituted with halo, CN, unsubstituted $C_1$-$C_4$ alkoxy, unsubstituted amido, unsubstituted $C_1$-$C_4$ alkyl, unsubstituted $C_1$-$C_4$, haloalkyl, —$(CH_2)_{1-4}$—CN), $C_3$-$C_7$ cycloalkyl (which $C_3$-$C_7$ cycloalkyl may be substituted with), unsubstituted 4-7 membered heterocycloalkyl, 5-10 membered heteroaryl (which heteroaryl may be substituted with halo, cyano, unsubstituted $C_1$-$C_4$ alkyl, unsubstituted $C_1$-$C_4$ alkoxy, unsubstituted 4-7 membered heterocycloalkyl);
each $R^{4a}$, $R^{4b}$ and $R^{4c}$ is independently selected from H, $C_1$-$C_6$ alkyl (which $C_1$-$C_4$ alkyl may be substituted with unsubstituted $C_1$-$C_4$ alkoxy, unsubstituted dialkylamino, unsubstituted 4-7 membered heterocycloalkyl), unsubstituted $C_3$-$C_7$ cycloalkyl, acyl (which acyl may be substituted with unsubstituted $C_1$-$C_6$ alkyl);
m1 is 0, 1, or 2; m2 is 0, 1, 2, or 3; and n1 is 0, 1, 2, 3, or 4;
provided that
when L1 is —O—, —N($R^{4a}$)—, —$CH_2$—N($R^{4a}$)—, —CON($R^{4a}$)—, or —$SO_2$N($R^{4a}$)—, and $R^{3b}$ is other than cycloalkyl, aryl or 5-10 membered heteroaryl, then n1 is 1, 2, 3, or 4;
or pharmaceutically acceptable salts or solvates thereof, or solvates of the pharmaceutically acceptable salts.

In one embodiment, with respect to compounds of Formula I, m1 is 0.

In one embodiment, with respect to compounds of Formula I, m1 is 1 or 2; each $R^1$ is independently selected from $C_1$-$C_6$ alkyl, substituted $C_1$-$C_6$ alkyl, and halo.

In a particular embodiment, with respect to compounds of Formula I, m1 is 1 or 2 and each $R^1$ is independently selected from Me, $CF_3$, Cl and F.

In one embodiment, with respect to compounds of Formula I, $R^{2a}$ is substituted or unsubstituted $C_1$-$C_6$ alkyl.

In another embodiment, with respect to compounds of Formula I, $R^{2a}$ is substituted or unsubstituted $C_3$-$C_7$ cycloalkyl.

In a particular embodiment, with respect to compounds of Formula I, $R^{2a}$ is cyclopropyl, cyclobutyl, or cyclopentyl.

In a further embodiment, with respect to compounds of Formula I, $R^{4b}$ and $R^{4c}$ are independently selected from H and Me.

In a more particular embodiment, with respect to compounds of Formula I, the compound is according to Formula II:

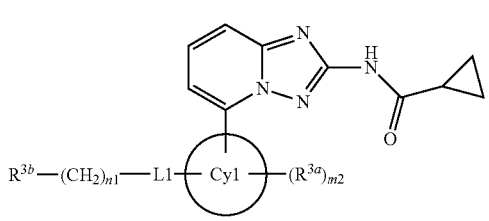

wherein Cy1, L1, $R^{3a}$, $R^{3b}$, m2, and n1 are as described for Formula I.

In one embodiment, with respect to compounds of Formula II, Cy1 is Ph; and m2 is 0.

In one embodiment, with respect to compounds of Formula II, Cy1 is Ph; m2 is 1, 2 or 3; and each $R^{3a}$ is independently $C_1$-$C_6$ alkyl, $C_1$-$C_6$ haloalkyl, $C_1$-$C_6$ alkoxy, or halo.

In a particular embodiment, with respect to compounds of Formula II, Cy1 is Ph; m2 is 1, 2 or 3; and each $R^{3a}$ is independently Cl, F, Me, Et, OMe, $CF_3$, $CONH_2$, $CONMe_2$, CONHMe, CN, NHCOMe, COOH, OH or COOEt.

In another embodiment, with respect to compounds of Formula II, Cy1 is substituted or unsubstituted pyridyl, substituted or unsubstituted pyrrolyl, substituted or unsubstituted pyrazolyl, substituted or unsubstituted imidazolyl, substituted or unsubstituted triazolyl, substituted or unsubstituted oxazolyl, substituted or unsubstituted thiazolyl, substituted or unsubstituted indolyl, substituted or unsubstituted indazolyl, substituted or unsubstituted benzimidazolyl, substituted or unsubstituted benzofuranyl, substituted or unsubstituted benzodioxanyl, substituted or unsubstituted benzoxazolyl, substituted or unsubstituted quinolinyl, or substituted or unsubstituted isoquinolinyl; and m2 is 0.

In a more particular embodiment, the compound is according to Formula III:

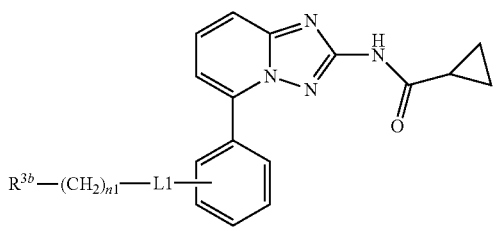

wherein L1, $R^{3b}$, and n1 are as described for Formula I.

In one embodiment, with respect to compounds of Formula III, $R^{3b}$ is substituted or unsubstituted aryl, substituted or unsubstituted 5-10 membered heteroaryl, substituted or unsubstituted $C_3$-$C_7$ cycloalkyl, or substituted or unsubstituted 4-7 membered heterocycloalkyl.

In a particular embodiment, with respect to compounds of Formula III, L1 is selected from a single bond, —O—, —N($R^{4a}$)—, —C(O)—, C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is substituted or unsubstituted aryl, substituted or unsubstituted 5-10 membered heteroaryl, substituted or unsubstituted $C_3$-$C_7$ cycloalkyl, substituted or unsubstituted 4-7 membered heterocycloalkyl.

In another particular embodiment, with respect to compounds of Formula III, L1 is selected from—a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is substituted or unsubstituted $C_3$-$C_7$ cycloalkyl.

In a more particular embodiment, with respect to compounds of Formula III, L1 is selected from—a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —SO$_2$N($R^{4a}$)—, —N($R^{4a}$)SO$_2$— and —N($R^{4a}$)CO—; n1 is 0, 1, 2, 3, or 4; and $R^{3b}$ is substituted or unsubstituted cyclopropyl, substituted or unsubstituted cyclobutyl, substituted or unsubstituted cyclohexyl, or substituted or unsubstituted cyclopentyl.

In one embodiment, with respect to compounds of Formula III, L1 is selected from: a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is substituted or unsubstituted aryl or substituted or unsubstituted 5-10 membered heteroaryl.

In a particular embodiment, with respect to compounds of Formula III, L1 is selected from—a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is substituted or unsubstituted phenyl, substituted or unsubstituted pyridyl, substituted or unsubstituted pyrrolyl, substituted or unsubstituted pyrazolyl, substituted or unsubstituted imidazolyl, substituted or unsubstituted triazolyl, substituted or unsubstituted tetrazolyl, substituted or unsubstituted oxazolyl, substituted or unsubstituted oxadiazolyl, substituted or unsubstituted thiazolyl, substituted or unsubstituted thiophenyl, substituted or unsubstituted indolyl, substituted or unsubstituted indazolyl, substituted or unsubstituted benzimidazolyl, substituted or unsubstituted benzofuranyl, substituted or unsubstituted benzodioxanyl, substituted or unsubstituted benzoxazolyl, substituted or unsubstituted quinolinyl, or substituted or unsubstituted isoquinolinyl.

In one embodiment, with respect to compounds of Formula III, L1 is selected from: a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is substituted or unsubstituted 4-7-membered heterocycloalkyl, provided that when the heterocycle is attached via a heteroatom, and L1 is —O—, —N($R^{4a}$)—, —SO$_2$N($R^{4a}$)—, and —CON($R^{4a}$)—, n1 is not 0 or 1.

In a particular embodiment, with respect to compounds of Formula III, L1 is selected from: a single bond, —O—, —N($R^{4a}$)—, —C(O)—, —C[=N($R^{4a}$)]—, —CON($R^{4a}$)—, —SO$_2$N($R^{4a}$)—, —S(O)$_2$—, —N($R^{4a}$)SO$_2$— and —N($R^{4a}$)CO—; n1 is 0, 1, 2, 3, or 4; and $R^{3b}$ is piperidinyl, morpholinyl, piperazinyl, homopiperazinyl or pyrrolidinyl, each of which may be unsubstituted or substituted with $C_1$-$C_6$ alkyl, acyl, phenyl, or OH, provided that when the heterocycle is attached via an heteroatom, and L1 is —O—, —N($R^{4a}$)—, —SO$_2$N($R^{4a}$)—, and —CON($R^{4a}$)—, n1 is not 0 or 1.

In one particular embodiment, with respect to compounds of Formula III, L1 is a single bond.

In another particular embodiment, with respect to compounds of Formula III, L1 is selected from —O—, and —N($R^{4a}$)—.

In another particular embodiment, with respect to compounds of Formula III, L1 is selected from —C(O)—, and —S(O)$_2$—.

In another particular embodiment, with respect to compounds of Formula III, L1 is selected from —CON(R$^{4a}$)—, and —SO$_2$N(R$^{4a}$)—.

In another particular embodiment, with respect to compounds of Formula III, L1 is selected from —N(R$^{4a}$)SO$_2$— and —N(R$^{4a}$)CO—.

In one particular embodiment, with respect to compounds of Formula III, L1 is —C[=N(R$^{4a}$)]—, In a further aspect of the invention R$^{4a}$ is H, substituted or unsubstituted C$_1$-C$_4$ alkyl, substituted or unsubstituted C$_1$-C$_4$ alkoxy.

In one embodiment, with respect to compounds of Formula I, R$^{4a}$ is H

In one embodiment, with respect to compounds of Formula I, R$^{4a}$ is —(CH$_2$)$_{n2}$—R$^{6a}$; wherein n$_2$ is 0, 1, 2 and R$^{6a}$ is H, CN, NMe$_2$, or tetrahydrofuranyl.

In another embodiment, with respect to compounds of Formula I, R$^{4a}$ is —CH(CH$_3$)—(CH$_2$)$_{n2}$—R$^{6a}$; wherein n2 is 0 or 1 and R$^{6a}$ is H, or OMe.

In another embodiment, with respect to compounds of Formula I, R$^{3b}$ is OPh, and O-(4-F-Ph).

In another embodiment, with respect to compounds of Formula I, R$^{3b}$ is CO—R$^{3c}$; and R$^{3c}$ is:

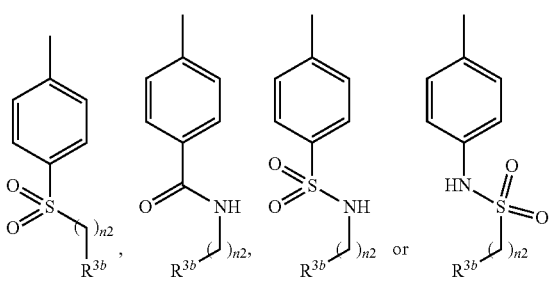

In one embodiment, the compound is according to formula III, and -Ph-L1-(CH$_2$)$_{n1}$—R$^{3b}$ is:

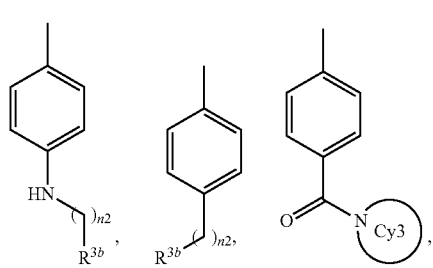

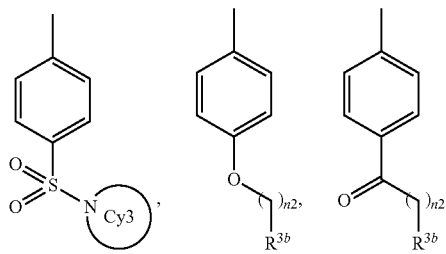

-continued

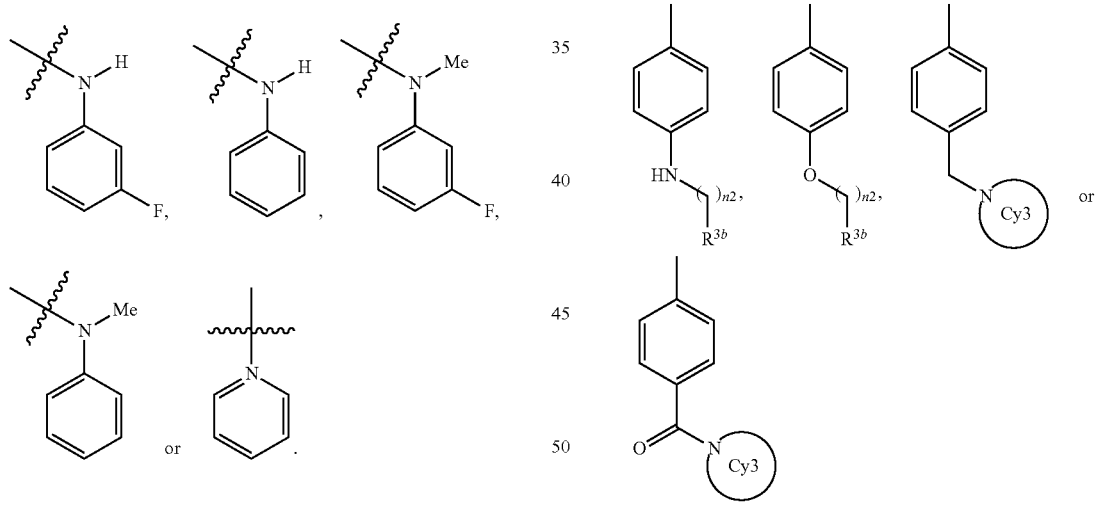

wherein n2 is n1; and R$^{3b}$, and n1 are as described for Formula 1; and Cy3 is a substituted or unsubstituted nitrogen containing 4-7-membered heterocycloalkyl group.

In another embodiment, the compound is according to Formula III, and -Ph-L1-(CH$_2$)$_{n1}$—R$^{3b}$ is:

wherein n2 is n1; and R$^{3b}$, and n1 are as described for Formula 1; and Cy3 is a substituted or unsubstituted nitrogen containing 4-7-membered heterocycloalkyl group.

In one embodiment, the -Ph-L1-(CH$_2$)$_{n1}$—R$^{3b}$ is as described in the preceding paragraphs, and R$^{3b}$ is unsubstituted aryl.

In another embodiment, the -Ph-L1-(CH$_2$)$_{n1}$—R$^{3b}$ is as described in the preceding paragraphs, and R$^{3b}$ is substituted aryl.

In another embodiment, the -Ph-L1-(CH$_2$)$_{n1}$—R$^{3b}$ is as described in the preceding paragraphs, and R$^{3b}$ is

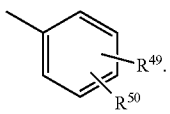

and one of $R^{49}$ and $R^{50}$ may be hydrogen and at least one of $R^{49}$ and $R^{50}$ is each independently selected from $C_1$-$C_8$ alkyl, 4-10 membered heterocycloalkyl, $C_1$-$C_8$ alkoxy, hetero-O-aryl, alkylamino, $NR^{51}COR^{52}$, $NR^{51}SOR^{52}NR^{51}SO_2R^{52}$, COOalkyl, COOaryl, $CONR^{51}R^{52}$, $CONR^{51}OR^{52}$, $NR^{51}R^{52}SO_2NR^{51}R^{52}$, S-alkyl, SOalkyl, $SO_2$alkyl, Saryl, SOaryl, $SO_2$aryl; or $R^{49}$ and $R^{50}$ may be joined to form a cyclic ring (saturated or unsaturated) from 5 to 8 atoms, optionally containing one or more heteroatoms selected from the group N, O or S. $R^{51}$, and $R^{52}$ are independently hydrogen, $C_1$-$C_8$ alkyl, $C_1$-$C_4$ haloalkyl, $C_3$-$C_{10}$ cycloalkyl, 4-10 membered heterocycloalkyl, $C_6$-$C_{10}$ aryl, substituted aryl, 5-10 membered heteroaryl.

In another embodiment, the -Ph-L1-$(CH_2)_{n1}$—$R^{3b}$ is as described in the preceding paragraphs, and $R^{3b}$ is aryl, substituted with one or more of groups selected from halo, $C_1$-$C_8$ alkyl, $C_1$-$C_8$ haloalkyl, $C_1$-$C_8$ haloalkoxy, cyano, hydroxy, $C_1$-$C_8$ alkoxy, and amino.

In another embodiment, the -Ph-L1-$(CH_2)_{n1}$—$R^{3b}$ is as described in the preceding paragraphs, and $R^{3b}$ is phenyl, substituted with one or more of groups selected from halo, $C_1$-$C_8$ alkyl, $C_1$-$C_8$ haloalkyl, $C_1$-$C_8$ haloalkoxy, cyano, hydroxy, $C_1$-$C_8$ alkoxy, and amino.

In one embodiment, the -Ph-L1-$(CH_2)_{n1}$—$R^{3b}$ and $R^3b$ are as described in the preceding paragraph, and the substitution is other than 3-OMe.

In another embodiment, the compound is other than N-[5-[4-[(3-methoxyphenyl)-methoxy]phenyl][1,2,4]triazolo[1,5-a]pyridin-2-yl]-cyclopropanecarboxamide.

In one particular embodiment, the -Ph-L1-$(CH_2)_{n1}$—$R^{3b}$ group is as described in the preceding paragraphs, and $R^{3b}$ is substituted or unsubstituted heteroaryl.

In another embodiment, the -Ph-L1-$(CH_2)_{n1}$—$R^{3b}$ is as described in the preceding paragraphs, and $R^{3b}$ is unsubstituted thiophenyl, pyrrolyl, benzothiophenyl, benzofuranyl, indolyl, pyridyl, quinolinyl, imidazolyl, oxazolyl and pyrazinyl In another embodiment, the -Ph-L1-$(CH_2)_{n1}$—$R^{3b}$ group is as described in the preceding paragraphs, and $R^{3b}$ is thiophenyl, pyrrolyl, benzothiophenyl, benzofuranyl, indolyl, pyridyl, quinolinyl, imidazolyl, oxazoleyl and pyrazineyl, substituted with one or more groups selected from halo, cyano, nitro, trifluoromethyl, trifluoromethoxy, azido, —NR'"$SO_2$R", —$SO_2$NR"R"', —C(O)R", —C(O)OR", —OC(O)R", —NR'"C(O)R", —C(O)NR"R"', —NR"R"', —(CR'"R"')$_m$OR"', wherein, each R" is independently selected from H, $C_1$-$C_8$ alkyl, —$(CH_2)_t(C_6$-$C_{10}$ aryl), —$(CH_2)_t$(5-10 membered heteroaryl), —$(CH_2)_t(C_3$-$C_{10}$ cycloalkyl), and —$(CH_2)_t$(4-10 membered heterocycloalkyl), wherein t is an integer from 0 to 4.

In another embodiment, the -Ph-L1-$(CH_2)_{n1}$—$R^{3b}$ group is as described in the preceding paragraphs, and $R^{3b}$ is unsubstituted pyridyl.

In another embodiment, the -Ph-L-$(CH_2)_{n1}$—$R^{3b}$ group is as described in the preceding paragraphs, and $R^{3b}$ is pyridyl, substituted with one or more groups selected from halo, cyano, nitro, trifluoromethyl, trifluoromethoxy, azido, —NR'"$SO_2$R", —$SO_2$NR"R"', —C(O)R", —C(O)OR", —OC(O)R", —NR'"C(O)R", —C(O)NR"R"', —NR"R"', —(CR'"R"')$_m$OR"', wherein, each R" is independently selected from H, $C_1$-$C_8$ alkyl, —$(CH_2)_t(C_6$-$C_{10}$ aryl), —$(CH_2)_t$(5-10 membered heteroaryl), —$(CH_2)_t(C_3$-$C_{10}$ cycloalkyl), and —$(CH_2)_t$(4-10 membered heterocycloalkyl), wherein t is an integer from 0 to 4.

In another embodiment, the -Ph-L1-$(CH_2)_{n1}$—$R^{3b}$ is as described in the preceding paragraphs, and $R^{3b}$ is pyridyl, substituted with halo, cyano, methyl, or trifluoromethyl.

In another embodiment, the -Ph-L1-$(CH_2)_{n1}$—$R^{3b}$ is as described in the preceding paragraphs, and n1 or n2 is 1.

In another embodiment, the -Ph-L1-$(CH_2)_{n1}$—$R^{3b}$ is as described in the preceding paragraphs, and n1 or n2 is 2.

In a particular embodiment, the compound is according to Formula III and $R^{3b}$ is selected from:

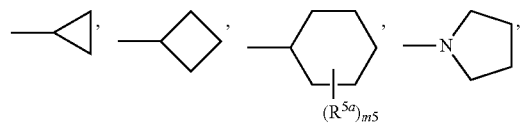

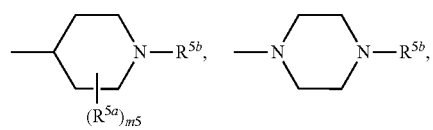

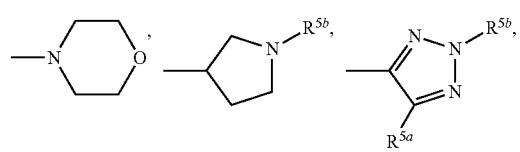

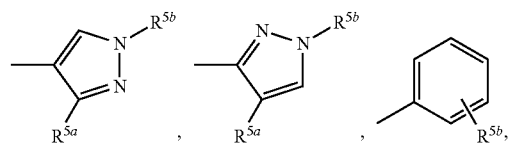

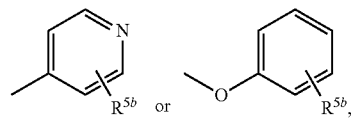

wherein each $R^{5a}$ is independently $C_1$-$C_4$ alkyl, halo, $CF_3$ or Phenyl; $R^{5b}$ is H, aryl, 5-10 membered heteroaryl, heteroaryl, $C_3$-$C_6$ cycloalkyl, or 4-7 membered heterocycloalkyl; and m5 is 0, 1 or 2.

In another particular embodiment, the compound is according to Formula III and $R^{3b}$ is selected from:

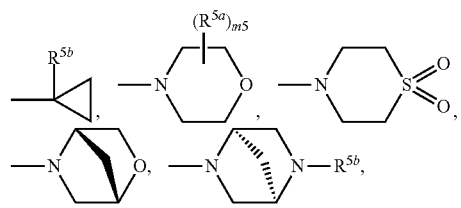

-continued

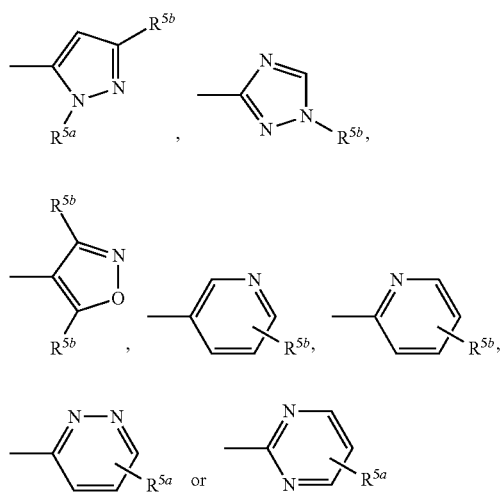

wherein each R^{5a} is independently $C_1$-$C_4$ alkyl, halo, oxo, $CF_3$ or Phenyl; $R^{5b}$ is H, $C_1$-$C_4$ alkyl, aryl, 5-10 membered heteroaryl, heteroaryl, $C_3$-$C_6$ cycloalkyl, or 4-7 membered heterocycloalkyl; and m5 is 0, 1 or 2.

In another particular embodiment, the compound is according to Formula III and Cy3 is selected from:

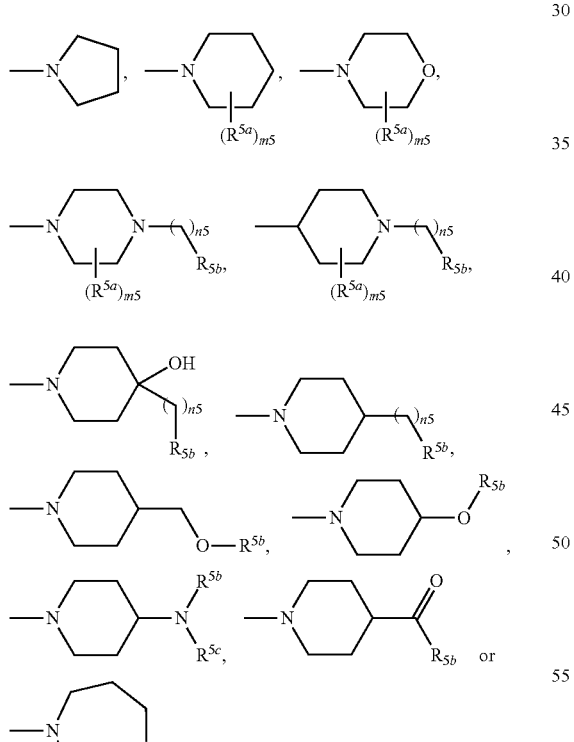

wherein each $R^{5a}$ is independently $C_1$-$C_4$ alkyl, halo, $CF_3$ or Phenyl; $R^{5b}$ is H, aryl, 5-10 membered heteroaryl, $C_3$-$C_6$ cycloalkyl, or 4-7 membered heterocycloalkyl; $R^{5c}$ is H, or $C_1$-$C_4$ alkyl; m5 is 0, 1, or 2; n5 is 0, 1, or 2.

In a more particular embodiment, the compound is according to any one of Formulae IVa, IVb, IVc, IVd, IVe, or IVf:

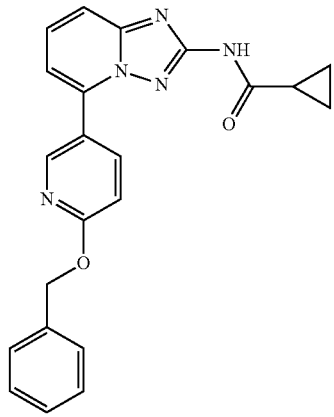
IVa

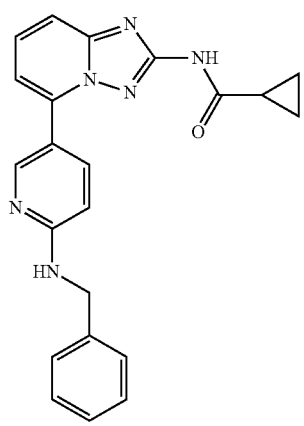
IVb

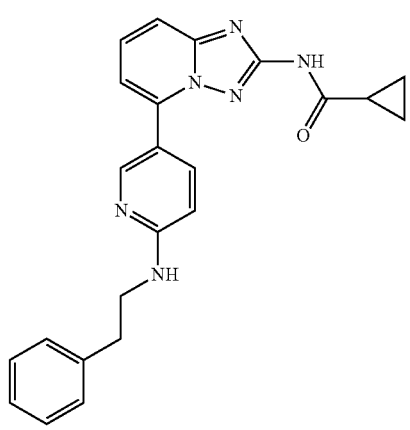
IVc

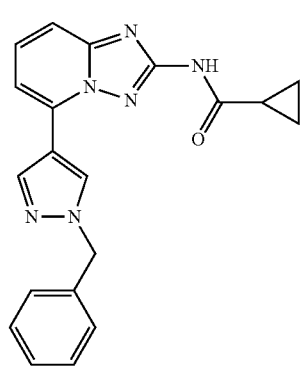
IVd

IVe
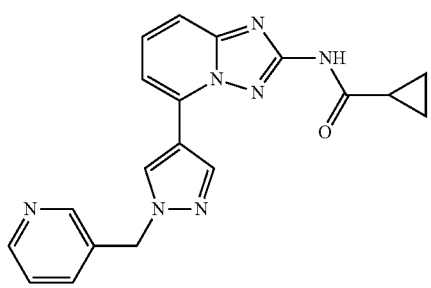
IVf
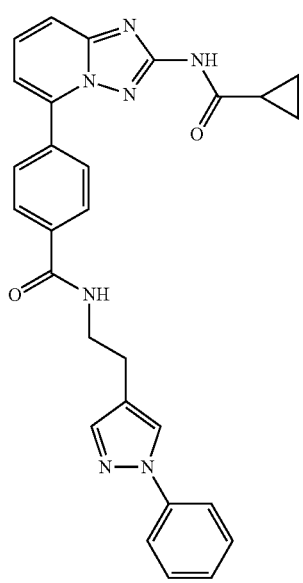
In a more particular embodiment, the compound is according to any one of Formulae Va, Vb, Vc, or Vd:
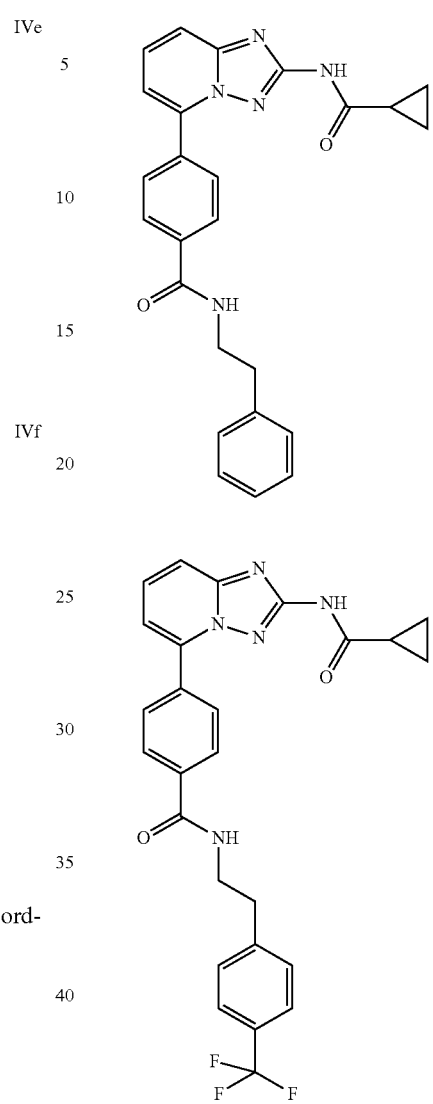
In a more particular embodiment, the compound is according to any one of Formulae VIa, VIb, VIc, or VId:
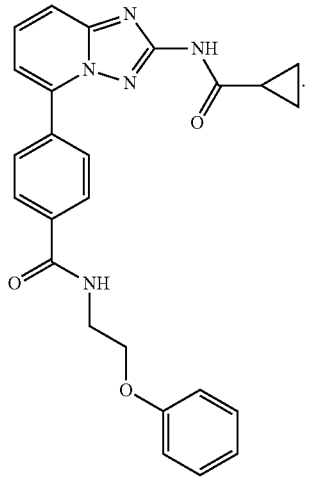

In a more particular embodiment, the compound is according to any one of Formulae VIIa, VIIb, VIIc, VIId, VIIe, or VIIf:

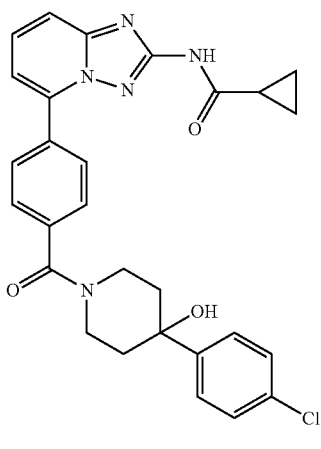
VIIc
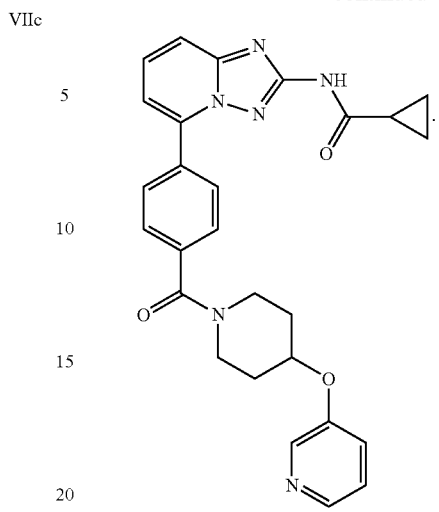
VIIf
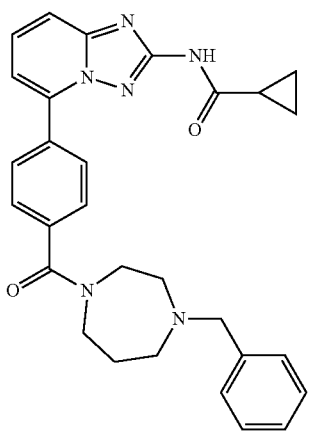
VIId
In another more particular embodiment, the compound is according to any one of Formulae VIIIa, VIIIb, VIIIc, VIIId, VIIIe, VIIIf, VIIIg, VIIIh, VIIIi, VIIIj, VIIIk or VIIIl:
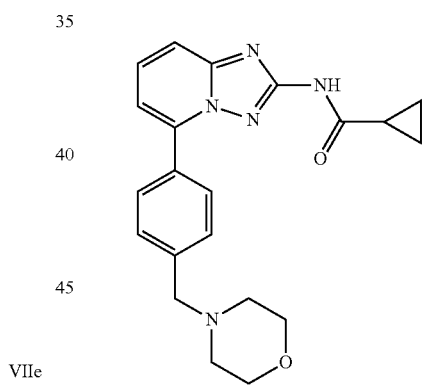
VIIIa
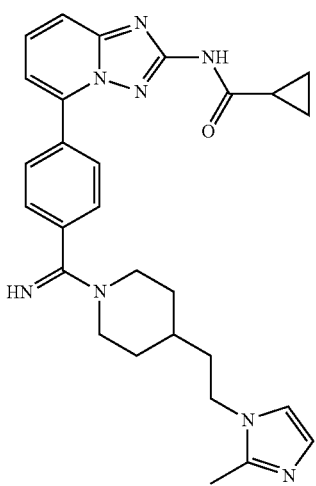
VIIe
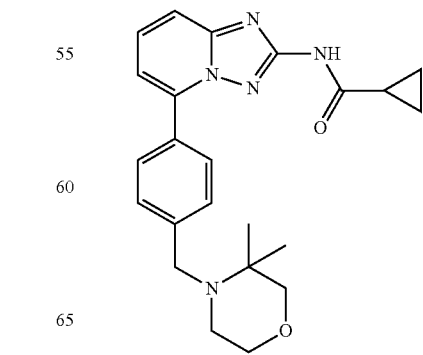
VIIIb

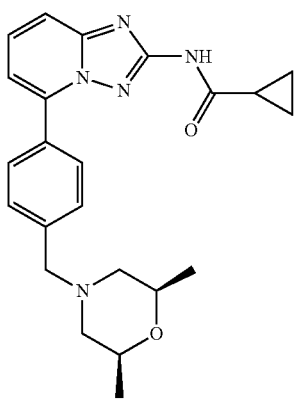
VIIIc
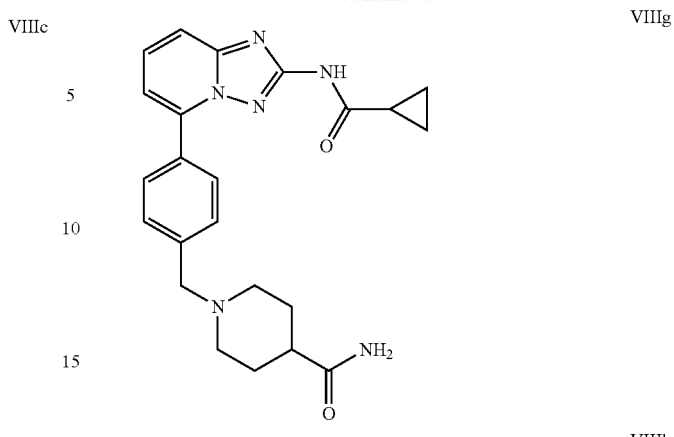
VIIIg
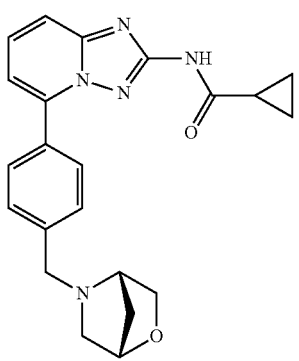
VIIId
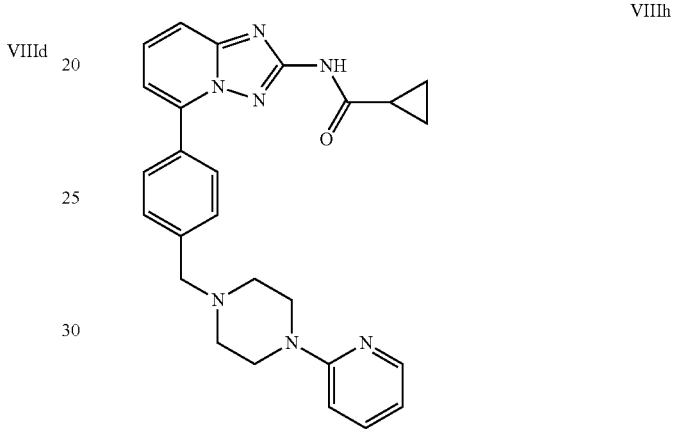
VIIIh
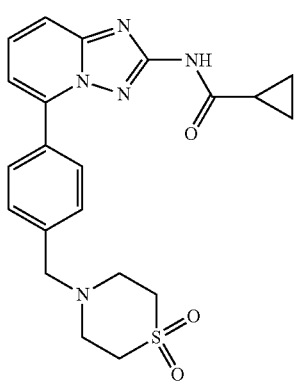
VIIIe
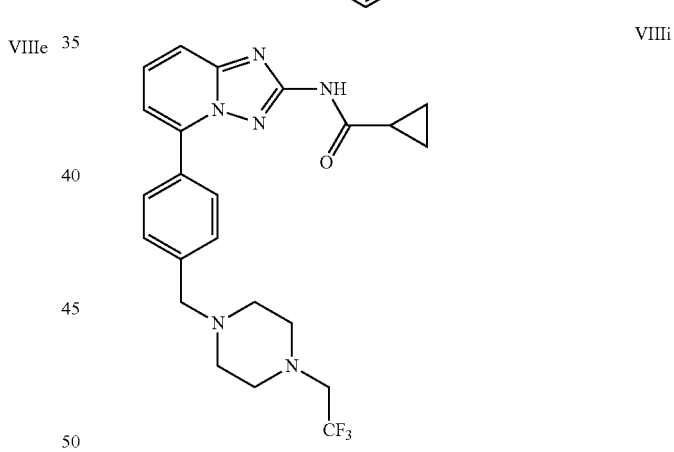
VIIIi
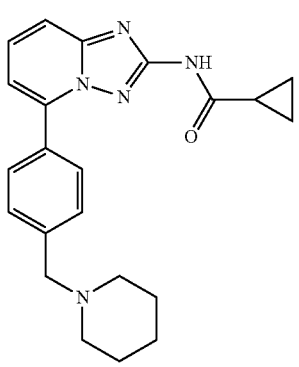
VIIIf
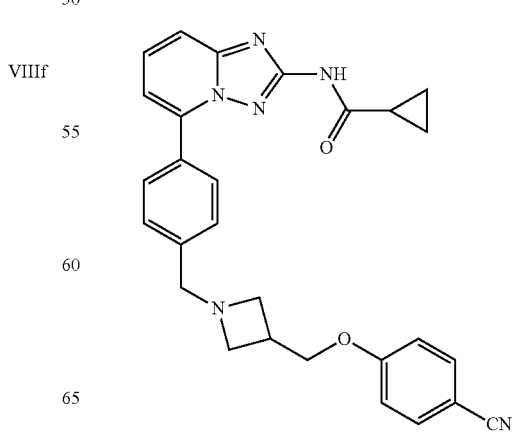
VIIIj VIIIk 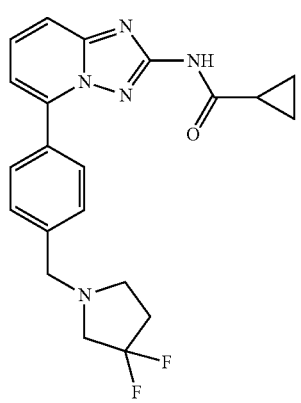
VIIIl 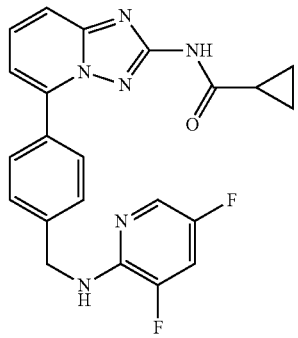
In another more particular embodiment, the compound is according to any one of Formulae IXa, IXb, IXc, IXd, IXe, IXf, IXg, IXh, IXi, IXj, IXk or IXl:
IXa
IXb
IXc 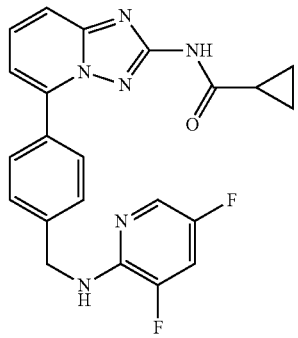
IXd 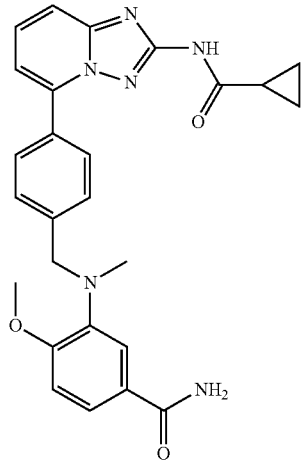
IXe 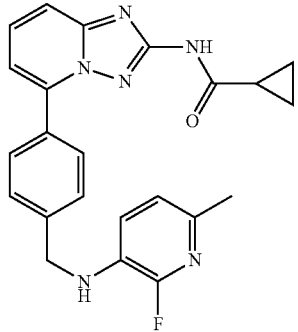
IXf 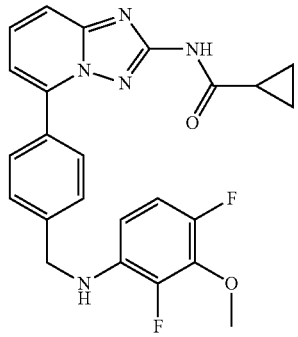

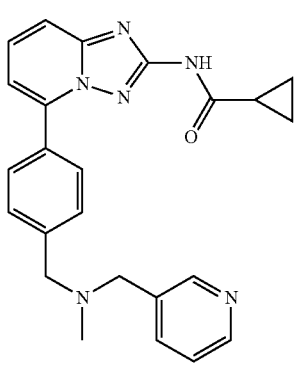
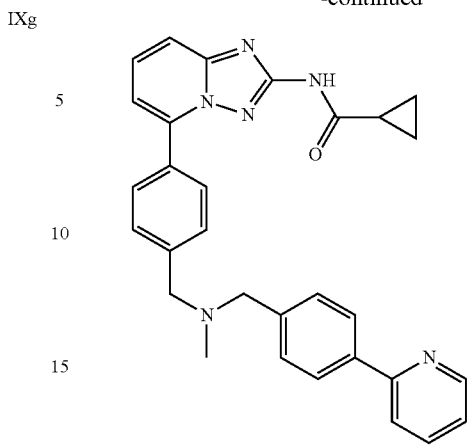
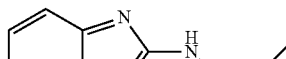
In certain aspects, the present invention provides compounds according to Formula X, or XI:
wherein R$^{3b}$ is substituted or unsubstituted 4-7 membered heterocycloalkyl; provided that when the compound is according to Formula X, the heterocycloalkyl ring is other than unsubstituted morpholin-1-yl.

In one embodiment, the compound is according to Formula X. In another embodiment, the compound is according to Formula XI.

In one particular embodiment, with respect to compounds according to Formula X, $R^{3b}$ is unsubstituted azetidinyl, pyrrolidinyl, piperidinyl, piperazinyl, azepinyl, pyrrolidonyl, pyranyl, dihydrothiophenyl, dihydropyranyl, dihydrofuranyl, dihydrothiazolyl, tetrahydrofuranyl, tetrahydrothiophenyl, dioxanyl, tetrahydropyranyl, imidazolinyl, imidazolidinonyl, oxazolinyl, thiazolinyl, 2-pyrazolineyl, pyrazolidinyl, thiomorpholinyl-S-oxide, and thiomorpholinyl-S,S-dioxide piperidonyl, or piperazonyl.

In one particular embodiment, with respect to compounds of Formula X, $R^{3b}$ is unsubstituted azetidin-1-yl, pyrrolidin-1-yl, piperidin-1-yl, thiomorpholin-1-yl-S,S-dioxide, piperazin-1-yl, or azepin-1-yl.

In one particular embodiment, with respect to compounds of Formula X, $R^{3b}$ is unsubstituted azetidin-1-yl.

In one particular embodiment, with respect to compounds of Formula X, $R^{3b}$ is unsubstituted pyrrolidin-1-yl.

In one particular embodiment, with respect to compounds of Formula X, $R^{3b}$ is unsubstituted piperidin-1-yl or piperazin-1-yl.

In one particular embodiment, with respect to compounds of Formula X, $R^{3b}$ is unsubstituted thiomorpholin-1-yl-S,S-dioxide.

In one particular embodiment, with respect to compounds of Formula X, $R^{3b}$ is unsubstituted azepin-1-yl.

In one particular embodiment, with respect to compounds of Formula X, $R^{3b}$ is azetidin-1-yl, pyrrolidin-1-yl, piperidin-1-yl, morpholin-1-yl, piperazin-1-yl, or azepin-1-yl; substituted with one or more group selected from $C_1$-$C_4$ alkyl, $C_1$-$C_4$ haloalkyl, cyano, amino, dialkylamino, dialkylaminomethyl, hydroxy, halo, acyl, acylamino, $C_1$-$C_4$ hydroxyalkyl, $C_1$-$C_4$ alkoxy, carboxamido, and $C_1$-$C_4$ dialkyl carboxamido.

In one particular embodiment, with respect to compounds of Formula X, $R^{3b}$ is azetidin-1-yl, pyrrolidin-1-yl, piperidin-1-yl, morpholin-1-yl, piperazin-1-yl, or azepin-1-yl; substituted with Me, $CF_3$, F, Cl, difluoro, dimethyl, hydroxy, cyano, dimethylamino, dimethylaminomethyl, hydroxymethyl, carboxamido, N,N-dimethylcarboxamido, methoxy, ethoxy, or 2,2,2-trifluoroethyl.

In one particular embodiment, with respect to compounds of Formula XI, $R^{3b}$ is unsubstituted azetidinyl, pyrrolidinyl, piperidinyl, piperazinyl, azepinyl, pyrrolidonyl, pyranyl, dihydrothiophenyl, dihydropyranyl, dihydrofuranyl, dihydrothiazolyl, tetrahydrofuranyl, tetrahydrothiophenyl, dioxanyl, tetrahydropyranyl, imidazolinyl, imidazolidinonyl, oxazolinyl, thiazolinyl, 2-pyrazolineyl, pyrazolidinyl, morpholinyl, thiomorpholinyl-S-oxide, and thiomorpholinyl-S,S-dioxide piperidonyl, or piperazonyl.

In one particular embodiment, with respect to compounds of Formula XI, $R^{3b}$ is unsubstituted azetidin-1-yl, pyrrolidin-1-yl, piperidin-1-yl, morpholinyl, thiomorpholin-1-yl-S,S-dioxide, piperazin-1-yl, or azepin-1-yl.

In one particular embodiment, with respect to compounds of Formula XI, $R^{3b}$ is unsubstituted azetidin-1-yl.

In one particular embodiment, with respect to compounds of Formula XI, $R^{3b}$ is unsubstituted pyrrolidin-1-yl.

In one particular embodiment, with respect to compounds of Formula XI, $R^{3b}$ is unsubstituted piperidin-1-yl or piperazin-1-yl.

In one particular embodiment, with respect to compounds of Formula XI, $R^{3b}$ is unsubstituted thiomorpholin-1-yl-S,S-dioxide.

In one particular embodiment, with respect to compounds of Formula XI, $R^{3b}$ is unsubstituted morpholin-1-yl.

In one particular embodiment, with respect to compounds of Formula XI, $R^{3b}$ is unsubstituted azepin-1-yl.

In one particular embodiment, with respect to compounds of Formula XI, $R^{3b}$ is azetidin-1-yl, pyrrolidin-1-yl, piperidin-1-yl, morpholin-1-yl, piperazin-1-yl, or azepin-1-yl; substituted with one or more group selected from $C_1$-$C_4$ alkyl, $C_1$-$C_4$ haloalkyl, cyano, amino, dialkylamino, dialkylaminomethyl, hydroxy, halo, acyl, acylamino, $C_1$-$C_4$ hydroxyalkyl, $C_1$-$C_4$ alkoxy, carboxamido, and $C_1$-$C_4$ dialkyl carboxamido.

In one particular embodiment, with respect to compounds of Formula XI, $R^{3b}$ is azetidin-1-yl, pyrrolidin-1-yl, piperidin-1-yl, morpholin-1-yl, piperazin-1-yl, or azepin-1-yl; substituted with Me, $CF_3$, F, Cl, difluoro, dimethyl, hydroxy, cyano, dimethylamino, dimethylaminomethyl, hydroxymethyl, carboxamido, N,N-dimethylcarboxamido, methoxy, ethoxy, or 2,2,2-trifluoroethyl.

In one embodiment, with respect to Formula 1, the compound is selected from the compounds exemplified in Table 1.

In one embodiment the compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of the compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

In certain aspects, the present invention additionally provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of the invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as pharmaceuticals, the compounds of the invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of the invention can be administered by a variety of routes including oral, rectal, transdermal, subcutaneous, intra-articular, intravenous, intramuscular, and intranasal. Depending on the intended route of delivery, the compounds of this invention are preferably formulated as either injectable or oral compositions or as salves, as lotions or as patches all for transdermal administration The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2

Capsules

A compound of the invention may be admixed as a dry powder with a starch diluent in an approximate 1:1 weight ratio. The mixture is filled into 250 mg capsules (125 mg of active amide compound per capsule).

Formulation 3

Liquid

A compound of the invention (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added with stirring. Sufficient water is then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5

Injection

A compound of the invention may be dissolved or suspended in a buffered sterile saline injectable aqueous medium to a concentration of approximately 5 mg/mL.

Formulation 6

Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present compounds are used as therapeutic agents for the treatment of conditions in mammals that are causally related or attributable to aberrant activity of JAK. In particular, conditions related to aberrant activity of one or more of JAK1, JAK2, JAK3 and/or TYK2. Accordingly, the compound of the invention and pharmaceutical compositions of this invention find use as therapeutics for preventing and/or treating diseases involving cartilage degradation, bone and/or joint degradation, for example osteoarthritis; and/or conditions involving inflammation or immune responses, such as Crohn's disease, rheumatoid arthritis, psoriasis, allergic airways disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), diseases involving impairment of cartilage turnover (e.g. diseases involving the anabolic stimulation of chondrocytes), congenital cartilage malformations, diseases associated with hypersecretion of IL6 and transplantation rejection (e.g. organ transplant rejection). Inhibitors of JAK can also find application in the treatment of proliferative diseases. In particular the inhibitors of JAK find application in the treatment of cancers, especially leukaemias and solid tumours (e.g. uterine leiomyosarcoma, prostate cancer). In particular the conditions are selected from inflammatory conditions, conditions related to cartilage and/or joint degradation in mammals including humans. In another embodiment, the compounds and pharmaceutical compositions of this invention find use as therapeutics for preventing and/or treating proliferative disorders in mammals, including humans. In a specific embodiment the compound of the invention and pharmaceutical compositions thereof find use as therapeutics for preventing and/or treating cancer in mammals including humans.

In additional method of treatment aspects, this invention provides methods of treating a mammal susceptible to or afflicted with condition involving an immune response or an autoimmune disease. The methods comprise administering an effective condition-treating or condition-preventing amount of one or more of the pharmaceutical compositions or a compound of the invention herein described. In a specific embodiment, the autoimmune disease is selected from COPD, asthma, systemic lupus erythematosis, type I diabetes mellitus and inflammatory bowel disease.

In another aspect the present invention provides a compound of the invention for use in the treatment, prevention or prophylaxis of a condition involving an autoimmune response or an autoimmune disease. In a specific embodiment, the autoimmune disease is selected from COPD, asthma, systemic lupus erythematosis, type I diabetes mellitus and inflammatory bowel disease.

In a method of treatment aspect, this invention provides a method of treatment, prevention or prophylaxis in a mammal susceptible to or afflicted with diseases involving impairment of cartilage turnover (e.g. a condition associated with, or diseases involving the anabolic stimulation of chondrocytes), for example, osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis, which method comprises administering a therapeutically effective amount of a compound of the invention, or one or more of the pharmaceutical compositions or compounds herein described.

In another aspect the present invention provides a compound of the invention for use in the treatment, prevention or prophylaxis of diseases involving impairment of cartilage turnover (e.g. a condition associated with, or diseases involving the anabolic stimulation of chondrocytes), for example, osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

The present invention also provides a method of treatment of congenital cartilage malformations, including hereditary chondrolysis, chondrodysplasias and pseudochondrodysplasias, in particular, but without limitation, microtia, anotia, metaphyseal chondrodysplasia, and related disorders, which method comprises administering an effective amount of one or more of the compounds of the invention or the pharmaceutical compositions herein described.

In another aspect the present invention provides a compound of the invention for use in the treatment, prevention or prophylaxis of congenital cartilage malformations, including hereditary chondrolysis, chondrodysplasias and pseudochondrodysplasias, in particular, but without limitation, microtia, anotia, metaphyseal chondrodysplasia, and related disorders.

In another aspect, this invention provides a method of treating a mammal susceptible to or afflicted with a condition involving inflammation, which method comprises administering an effective amount of one or more of the compounds of the invention or the pharmaceutical compositions herein described. In additional method of treatment aspects, this invention provides methods of treating a mammal susceptible to or afflicted with diseases and disorders which are mediated by or result in inflammation such as, for example rheumatoid arthritis and osteoarthritis, allergic airway disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), and related diseases involving cartilage, such as that of the joints, which methods comprise administering an effective amount of one or more of the compounds of the invention or the pharmaceutical compositions herein described. In a specific embodiment, the condition involving inflammation is selected from rheumatoid arthritis, osteoarthritis, allergic airway disease (e.g. asthma) and inflammatory bowel diseases. The methods comprise administering an effective condition-treating or condition-preventing amount of one or more of the pharmaceutical compositions or compounds herein described.

In another aspect, this invention provides a compound of the invention for use in the treatment, prevention or prophylaxis of a condition involving inflammation. In another aspect the present invention provides a compound of the invention for use in the treatment, prevention or prophylaxis of diseases and disorders which are mediated by or result in inflammation such as, for example rheumatoid arthritis and osteoarthritis, allergic airway disease (e.g. asthma, rhinitis), juvenile idiopathic arthritis, colitis, inflammatory bowel diseases, endotoxin-driven disease states (e.g. complications after bypass surgery or chronic endotoxin states contributing to e.g. chronic cardiac failure), and related diseases involving cartilage, such as that of the joints. In a specific embodiment, the condition involving inflammation is selected from rheumatoid arthritis, osteoarthritis, allergic airway disease (e.g. asthma) and inflammatory bowel diseases.

In further method of treatment aspects, this invention provides methods of treating a mammal susceptible to or afflicted with a proliferative disease, in particular cancer (e.g. solid tumors such as uterine leiomyosarcoma or prostate cancer), leukemia (e.g. AML or ALL), multiple myeloma and/or psoriasis, which methods comprise administering an effective amount of one or more of the compounds of the invention or the pharmaceutical compositions herein described. In further method of treatment aspects, this invention provides methods of treating a mammal susceptible to or afflicted with cancer (e.g. solid tumors such as uterine leiomyosarcoma or prostate cancer) and/or leukemias, which methods comprise administering an effective amount of one or more of the compounds of the invention or the pharmaceutical compositions herein described.

In another aspect the present invention provides a compound of the invention for use in the treatment, prevention or prophylaxis of a proliferative disease, in particular cancer (e.g. solid tumors such as uterine leiomyosarcoma or prostate cancer), leukemia (e.g. AML or ALL), multiple myeloma and/or psoriasis. In another aspect the present invention provides a compound of the invention for use in the treatment, prevention or prophylaxis of cancer (e.g solid tumors such as uterine leiomyosarcoma or prostate cancer) and/or leukemias.

In further method of treatment aspects, this invention provides methods of treating a mammal susceptible to or afflicted with diseases associated with hypersecretion of IL6, in particular Castleman's disease or mesangial proliferative glomerulonephritis, which methods comprise administering an effective amount of one or more of the compounds of the invention or the pharmaceutical compositions herein described.

In another aspect the present invention provides a compound of the invention for use in the treatment, prevention or prophylaxis of diseases associated with hypersecretion of IL6, in particular Castleman's disease or mesangial proliferative glomerulonephritis.

In further method of treatment aspects, this invention provides methods of treating a mammal susceptible to or afflicted with transplantation rejection, which methods comprise administering an effective amount of one or more of the compounds of the invention or the pharmaceutical compositions herein described. In a specific embodiment, the invention provides methods of treating organ transplant rejection.

In another aspect the present invention provides a compound of the invention for use in the treatment, prevention or prophylaxis of transplantation rejection. In a specific embodiment, the invention provides methods of treating organ transplant rejection.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

A particular regimen of the present method comprises the administration to a subject in suffering from a disease involving inflammation, of an effective amount of a compound of the invention for a period of time sufficient to reduce the level of inflammation in the patient, and preferably terminate, the processes responsible for said inflammation. A particular embodiment of the method comprises administering of an effective amount of a compound of the invention to a subject patient suffering from or susceptible to the development of rheumatoid arthritis, for a period of time sufficient to reduce or prevent, respectively, inflammation in the joints of said patient, and preferably terminate, the processes responsible for said inflammation.

A further particular regimen of the present method comprises the administration to a subject in suffering from a disease condition characterized by cartilage or joint degradation (e.g. osteoarthritis) of an effective amount of a compound of the invention for a period of time sufficient to reduce, and preferably terminate, the self-perpetuating processes responsible for said degradation. A particular embodiment of the method comprises administering of an effective amount of a compound of the invention to a subject patient suffering from or susceptible to the development of osteoarthritis, for a period of time sufficient to reduce or prevent, respectively, cartilage degradation in the joints of said patient, and preferably terminate, the self-perpetuating processes responsible for said degradation. In a particular embodiment said compounds exhibit cartilage anabolic and/or anti-catabolic properties.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as degenerative conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with particular doses each providing from about 0.1 to about 10 mg/kg and especially about 1 to about 5 mg/kg.

Transdermal doses are generally selected to provide similar or lower blood levels than are achieved using injection doses.

When used to prevent the onset of an inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of the invention can be administered as the sole active agent or they can be administered in combination with other agents, including other compounds that demonstrate the same or a similar therapeutic activity, and that are determined to be safe and efficacious for such combined administration. In a specific embodiment, co-administration of two (or more) agents allows for significantly lower doses of each to be used, thereby reducing the side effects seen.

In one embodiment, a compound of the invention is co-administered with another therapeutic agent for the treatment and/or prevention of a disease involving inflammation; particular agents include, but are not limited to, immunoregulatory agents e.g. azathioprine, corticosteroids (e.g. prednisolone or dexamethasone), cyclophosphamide, cyclosporin A, tacrolimus, Mycophenolate Mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prevention of arthritis (e.g. rheumatoid arthritis); particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, and cyclosporin), and biological DMARDS (for example but without limitation Infliximab, Etanercept, Adalimumab, Rituximab, and Abatacept).

In one embodiment, a compound of the invention is co-administered with another therapeutic agent for the treatment and/or prevention of proliferative disorders; particular agents include but are not limited to: methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® or hsp90 inhibitors (e.g. 17-AAG). Additionally, a compound of the invention may be administered in combination with other therapies including, but not limited to, radiotherapy or surgery. In a specific embodiment the proliferative disorder is selected from cancer, myeloproliferative disease or leukaemia.

In one embodiment, a compound of the invention is co-administered with another therapeutic agent for the treatment and/or prevention of autoimmune diseases, particular agents include but are not limited to: glucocorticoids, cytostatic agents (e.g. purine analogs), alkylating agents, (e.g nitrogen mustards (cyclophosphamide), nitrosoureas, platinum compounds, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g., anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab (Remicade), etanercept (Enbrel), or adalimumab (Humira)), mycophenolate, Fingolimod, Myriocin.

In one embodiment, a compound of the invention is co-administered with another therapeutic agent for the treatment and/or prevention of transplantation rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prevention of asthma and/or rhinitis and/or COPD, particular agents include but are not limited to: beta$_2$-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled) Long-acting β$_2$-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine), vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, nonspecific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine, intravenous magnesium sulfate.

In one embodiment, a compound of the invention is co-administered with another therapeutic agent for the treatment and/or prevention of IBD, particular agents include but are not limited to: glucocorticoids (e.g. prednisone, budesonide) synthetis disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prevention of SLE, particular agents include but are not limited to: Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid;

immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prevention of psoriasis, particular agents include but are not limited to: topical treatments such as bath solutions, moisturizers, medicated creams and ointments containing coal tar, dithranol (anthralin), corticosteroids like desoximetasone (Topicort), fluocinonide, vitamin $D_3$ analogues (for example, calcipotriol), Argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive, Enbrel, Humira, Remicade, Raptiva and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic-agents to the patient as part of the same treatment regime, as will be apparent to the skilled person. Whilst the two or more agents may be administered simultaneously in a single formulation this is not essential. The agents may be administered in different formulations and at different times.

GENERAL SYNTHETIC PROCEDURES

General

The compounds of the invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative bicycloheteroaryls that have been listed hereinabove. The compounds of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker DPX 400 NMR spectrometer (400 MHz). Chemical shifts (δ) for $^1$H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), multiplet (m) and broad (br). Coupling constants (J) are given in Hz. Electrospray MS spectra were obtained on a Micromass platform LC/MS spectrometer. Column Used for all LCMS analysis: Waters Acquity UPLC BEH C18 1.7 μm, 2.1 mm ID×50 mm L (Part No. 186002350)). Preparative HPLC: Waters XBridge Prep C18 5 μm ODB 19 mm ID×100 mm L (Part No. 186002978). All the methods are using $MeCN/H_2O$ gradients. $H_2O$ contains either 0.1% TFA or 0.1% $NH_3$.

List of abbreviations used in the experimental section:

| | |
|---|---|
| DCM | Dichloromethane |
| DiPEA | N,N-diisopropylethylamine |
| MeCN | Acetonitrile |
| BOC | tert-Butyloxy-carbonyl |
| MF | N,N-dimethylformamide |
| Cat. | Catalytic amount |
| TFA | Trifluoroacetic acid |
| THF | Tetrahydrofuran |
| NMR | Nuclear Magnetic Ressonance |
| DMSO | Dimethylsulfoxide |
| LC-MS | Liquid Chromatography- Mass Spectrometry |
| Ppm | part-per-million |
| Pd/C | Palladium on Charcoal 10% |
| PMB | Para-methoxy-benzyl |
| PyBOP | benzotriazol-1-yl-oxy-tris-pyrrolidino-phosphonium hexafluoroborate |
| EtOAc | ethyl acetate |
| APCI | atmospheric pressure chemical ionization |
| Rt | retention time |
| s | singlet |
| br s | broad singlet |
| m | multiplet |
| min | minute |
| mL | milliliter |
| μL | microliter |
| g | gram |
| mg | milligram |
| $PdCl_2$dppf | [1,1'-Bis(diphenylphosphino)ferrocene]dichloropalladium(II) |
| TEA | Triethylamine |
| MMP | Matrix Metallo Proteinase |
| NHAC | Normal Human Articular Chondrocytes |
| shRNA | short hairpin RNA |
| RNA | Ribonucleic acid |
| Ad-Si RNA | Adenoviral encoded siRNA |
| PBST | Phosphate buffered saline with Tween 3.2 mM $Na_2HPO_4$, 0.5 mM $KH_2PO_4$, 1.3 mM KCl, 135 mM NaCl, 0.05% Tween 20, pH 7.4 |
| APMA | 4-aminophenylmercuric acetate |
| DMEM | Dulbecco's Modified Eagle Medium |
| FBS | Fetal bovine serum |
| hCAR | human cellular adenovirus receptor |
| 3- MOI | multiplicity of infection of 3 |
| dNTP | deoxyribonucleoside triphosphate |
| QPCR | quantitative polymerase chain reaction |
| cDNA | copy deoxyribonucleic acid |
| GAPDH | Glyceraldehyde phosphate dehydrogenase |

Synthetic Preparation of Compounds of the Invention

A compound of the invention can be produced according to the following scheme.

Preparation of the Core Intermediate

Scheme 1

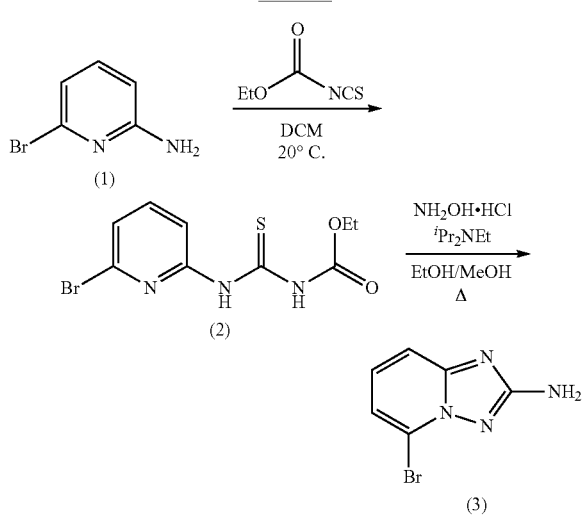

wherein Ar is Cy1—L1—$(CR^{4b}R^{4c})_{n1}$—$R^{3b}$; and Cy1, L1, n1, $R^{2a}$, $R^{3b}$, $R^{4b}$, and $R^{4c}$ are as described herein.

1.1.1 1-(6-Bromo-pyridin-2-yl)-3-carboethoxy-thiourea (2)

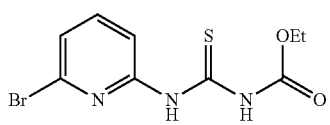

To a solution of 2-amino-6-bromopyridine (1) (253.8 g, 1.467 mol) in DCM (2.5 L) cooled to 5° C. was added ethoxycarbonyl isothiocyanate (173.0 mL, 1.467 mol) dropwise over 15 min. The reaction mixture was then allowed to warm to room temp. (20° C.) and stirred for 16 h. Evaporation in vacuo gave a solid which was collected by filtration, thoroughly washed with petrol (3×600 mL) and air-dried to afford (2). The thiourea was used as such for the next step without any purification. $^1$H (400 MHz, CDCl$_3$) δ 12.03 (1H, br s, NH), 8.81 (1H, d, J 7.8 Hz, H-3), 8.15 (1H, br s, NH), 7.60 (1H, t, J 8.0 Hz, H-4), 7.32 (1H, dd, J 7.7 and 0.6 Hz, H-5), 4.31 (2H, q, J 7.1 Hz, CH$_2$), 1.35 (3H, t, J 7.1 Hz, CH$_3$).

1.1.2 5-Bromo-[1,2,4]triazolo[1,5-a]pyridin-2-ylamine (3)

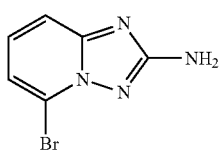

To a suspension of hydroxylamine hydrochloride (101.8 g, 1.465 mol) in EtOH/MeOH (1:1, 900 mL) was added N,N-diisopropylethylamine (145.3 mL, 0.879 mol) and the mixture was stirred at room temp. (20° C.) for 1 h. 1-(6-Bromo-pyridin-2-yl)-3-carboethoxy-thiourea (2) (89.0 g, 0.293 mol) was then added and the mixture slowly heated to reflux (Note: bleach scrubber is required to quench H$_2$S evolved). After 3 h at reflux, the mixture was allowed to cool and filtered to collect the precipitated solid. Further product were collected by evaporation in vacuo of the filtrate, addition of H$_2$O (250 mL) and filtration. The combined solids were washed successively with H$_2$O (250 mL), EtOH/MeOH (1:1, 250 mL) and Et$_2$O (250 mL) then dried in vacuo to afford the triazolopyridine derivative (3) as a solid. The compound was used as such for the next step without any purification. $^1$H (400 MHz, DMSO-d$_6$) δ 7.43-7.34 (2H, m, 2× aromatic-H), 7.24 (1H, dd, J 6.8 and 1.8 Hz, aromatic-H), 6.30 (2H, br, NH$_2$); m/z 213/215 (1:1, M+H$_+$, 100%).

1.1.3 Procedure for mono-acylation to afford intermediate Cyclopropanecarboxylic acid (5-bromo-[1,2,4]triazolo[1,5-a]pyridin-2-yl)-amide

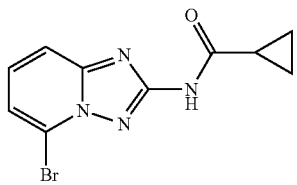 [SMILES: O=C(Nc1nc2cccc(Br)n2n1)C1CC1]

To a solution of the 2-amino-triazolopyridine (3) (7.10 g, 33.3 mmol) in dry CH$_3$CN (150 mL) at 5° C. was added Et$_3$N (11.6 mL, 83.3 mmol) followed by cyclopropanecarbonyl chloride (83.3 mmol). The reaction mixture was then allowed to warm to ambient temperature and stirred until all starting material (3) was consumed. If required, further Et$_3$N (4.64 mL, 33.3 mmol) and the acid chloride (33.3 mmol) were added to ensure complete reaction. Following solvent evaporation in vacuo the resultant residue was treated with 7 N methanolic ammonia solution (50 mL) and stirred at ambient temp. for 1 h to hydrolyse any bis-acylated product. Product isolation was made by removal of volatiles in vacuo followed by trituration with Et$_2$O (50 mL). The solids were collected by filtration, washed with H$_2$O (2×50 mL), acetone (50 mL) and Et$_2$O (50 mL), then dried in vacuo to give the required acyl intermediate (4).

Method A

1.1.4 Preparation of Compounds of the Invention Via Suzuki Coupling (5)

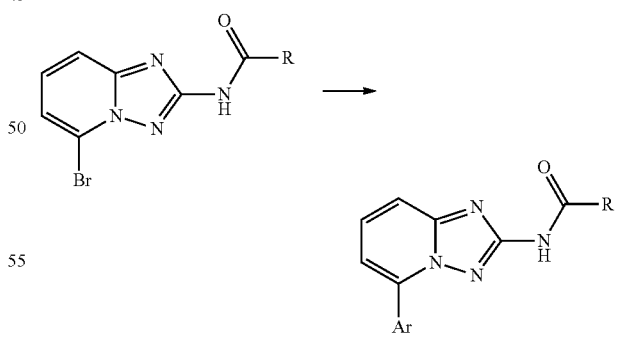

1.1.5

An appropriate boronic acid (2 eq.) is added to a solution of bromo intermediate in 1,4-dioxane/water (5:1). K$_2$CO$_3$ (2 eq.) and PdCl$_2$dppf (5%) are added to the solution. The resulting mixture is then heated in a microwave at 140° C. for 30 min (This reaction can also be carried out by traditional heating in an oil bath at 90° C. for 16 h under N$_2$). Water is added and the solution is extracted with ethyl acetate. The organic layers are dried over MgSO$_4$ and evaporated in vacuo. The final compound is obtained after purification by flash chromatography.

Method B

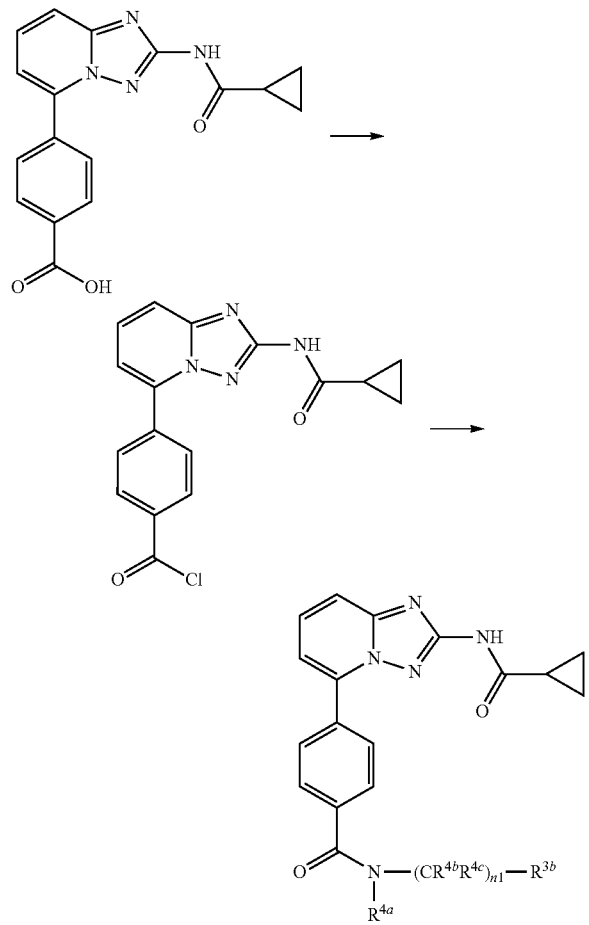

wherein R$^{4a}$, R$^{4b}$, R$^{4c}$, R$^{3b}$ and n1 are as described herein.

B1.4 4-[2-(Cyclopropanecarbonyl-amino)-[1,2,4]triazolo[1,5-a]pyridin-5-yl]-benzoyl chloride 2 Drops of DMF were added to a solution of 4-[2-(cyclopropanecarbonyl-amino)-[1,2,4]triazolo[1,5-a]pyridin-5-yl]-benzoic acid (1 eq) obtained by Method A in DCM under N$_2$ atmosphere. Then oxalyl chloride (2 eq) was added dropwise to this resulting solution (gas release). The mixture was stirred at room temperature for 2 hours. After completion of the reaction by LCMS, the solvent was removed. The crude acid chloride was used without further purification in next step.

B2. Amide Formation

General Method

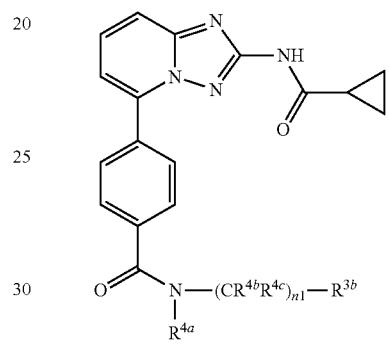

An appropriate amine (1.1 eq; R$^{2b}$, R$^{2c}$ and m1 are as described herein) and Et$_3$N (5 eq) are dissolved in DCM under N$_2$ atmosphere and cooled at 0° C. The acid chloride (B1, 1 eq) dissolved in DCM is added dropwise to this solution. The reaction is stirred at room temperature for 3 h. After this time, reaction is complete. The compound is extracted with EtOAc and water, washed with brine and dried over MgSO$_4$. Organic layers are filtered and evaporated. The final compound is isolated by preparative HPLC. Preparative HPLC: Waters XBridge Prep C18 5 μm ODB 19 mm ID×100 mm L (Part No. 186002978). All the methods are using MeCN/H$_2$O gradients. H$_2$O contains either 0.1% TFA or 0.1% NH$_3$.

Method C

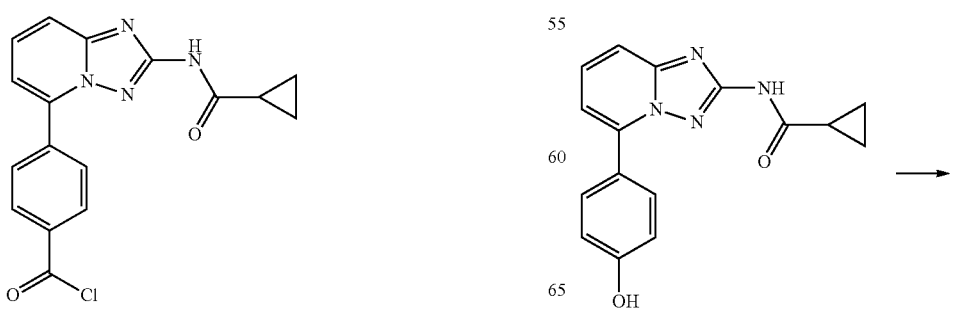

-continued

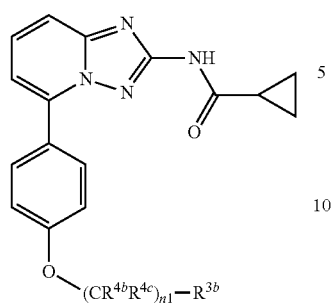

wherein $R^{4a}$, $R^{4b}$, $R^{4c}$, $R^{3b}$ and n1 are as described herein.

Reaction of Alkylation

General Method

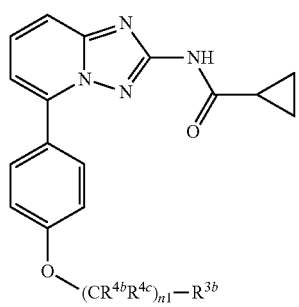

Cyclopropanecarboxylic acid [5-(4-hydroxy-phenyl)-[1,2,4]triazolo[1,5-a]pyridin-2-yl]-amide (1.1 eq) obtained by Method A and $K_2CO_3$ (5 eq) (or $AgCO_3$) are dissolved in DMF under $N_2$ and the appropriate alkylating agent (1.1 eq) is added dropwise. The resulting suspension is heated at 50° C. for 16 h. After this time, the reaction is complete. The compound is extracted with EtOAc and water, washed with brine and dried over $MgSO_4$. Organic layers are filtered and evaporated. The final compound is isolated by preparative HPLC. Preparative HPLC: Waters XBridge Prep C18 5 μm ODB 19 mm ID×100 mm L (Part No. 186002978). All the methods are using MeCN/$H_2O$ gradients. $H_2O$ contains either 0.1% TFA or 0.1% $NH_3$.

Method D

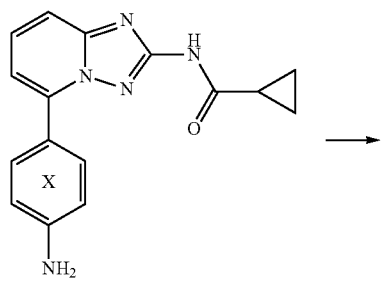

-continued

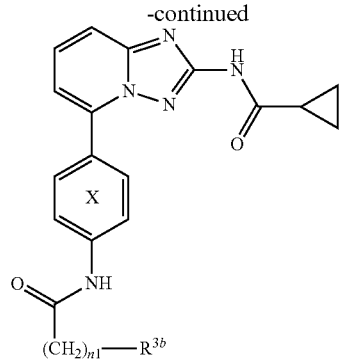

or

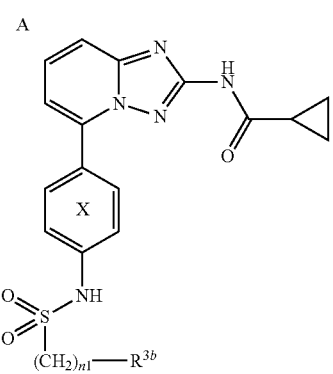

Coupling Reaction

General Method

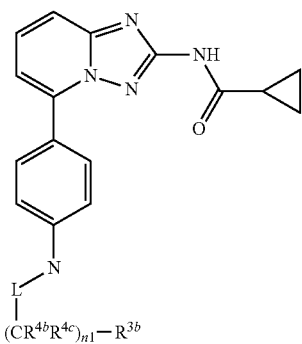

wherein $R^{4a}$, $R^{4b}$, $R^{4c}$, $R^{3b}$ and n1 are as described herein and L is —C(=O)— or —SO$_2$—.

The aniline derivative (1 eq.) obtained by Method A and Et$_3$N (5 eq) are dissolved in DCM under $N_2$ and cooled at 0° C. The appropriate acid chloride (for A) or sulfonyl chloride (for B) (1.5 eq.) dissolved in DCM is added dropwise to this solution. The reaction is stirred at room temperature for 16 h. After this time, the reaction is complete. The compound is extracted with EtOAc and water, washed with brine and dried over MgSO$_4$. Organic layers are filtered and evaporated. The final compound is isolated by preparative HPLC. Preparative HPLC: Waters XBridge Prep C18 5 μm ODB 19 mm ID×100 mm L (Part No. 186002978). All the methods are using MeCN/$H_2O$ gradients. $H_2O$ contains either 0.1% TFA or 0.1% $NH_3$.

Method E

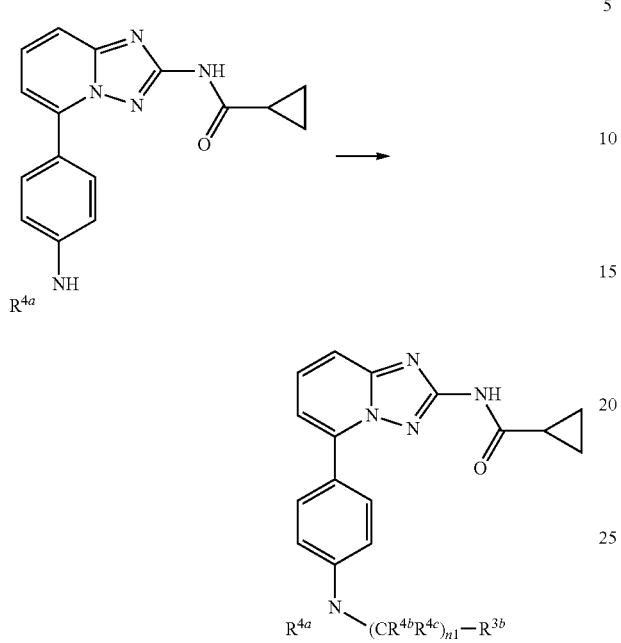

wherein $R^{4a}$, $R^{4b}$, $R^{4c}$, $R^{3b}$ and n1 are as described herein.

Reductive Amination

General Method

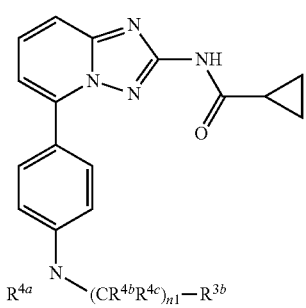

The appropriate aldehyde (2 eq.), the aniline derivative (1 eq.) obtained by Method A and Ti(OPr)$_4$ are mixed and stirred at room temperature for 3 hrs. The mixture is diluted in ethanol and Na(CN)BH$_3$ (1 eq.) was added. The resulting solution is stirred at room temperature for 16 hrs. The mixture is diluted in water and filtered. The filtrate is washed with ethanol. The combined solvent phases are evaporated under vacuum. The final compound is isolated by preparative HPLC.

Preparative HPLC: Waters XBridge Prep C18 5 μm ODB 19 mm ID×100 mm L (Part No. 186002978). All the methods are using MeCN/H$_2$O gradients. H$_2$O contains either 0.1% TFA or 0.1% NH$_3$.

Method F

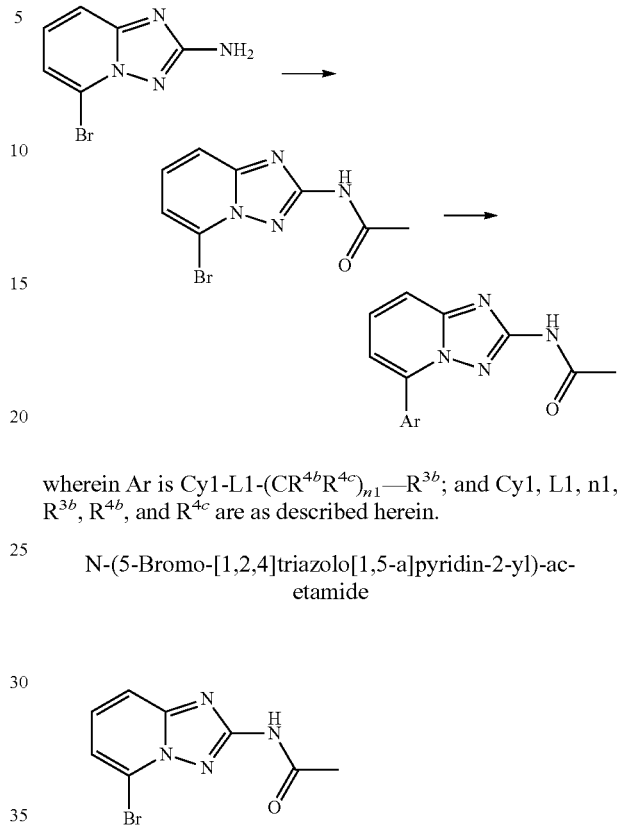

wherein Ar is Cy1-L1-(CR$^{4b}$R$^{4c}$)$_{n1}$—R$^{3b}$; and Cy1, L1, n1, R$^{3b}$, R$^{4b}$, and R$^{4c}$ are as described herein.

N-(5-Bromo-[1,2,4]triazolo[1,5-a]pyridin-2-yl)-acetamide

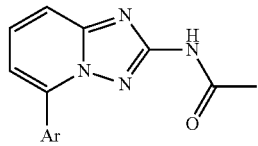

To a solution of the 5-bromo-2-amino-triazolopyridine (1 eq.) in dry CH$_3$CN at 5° C. is added Et$_3$N (2.5 eq.) followed by acetyl chloride (2.5 eq.). The reaction mixture is then allowed to warm to ambient temperature and stirred until all starting material is consumed. If required, further Et$_3$N (1 eq.) and acid chloride (1 eq.) are added to ensure complete reaction. Following solvent evaporation in vacuo the resultant residue is treated with 7 N methanolic ammonia solution and stirred at ambient temp. (for 16 h) to hydrolyse any bisacylated product. Product isolation is made by removal of volatiles in vacuo followed by addition of water and extraction with ethyl acetate. The organic phase is then dried over MgSO$_4$, evaporated in vacuo. The compound may be used without further purification.

Suzuki Reaction

General Method

The boronic acid (2 eq.) is added to a solution of N-(5-Bromo-[1,2,4]triazolo[1,5-a]pyridin-2-yl)-acetamide in 1,4-Dioxane/water (5:1). K$_2$CO$_3$ (2 eq.) and Pd(dppf)Cl$_2$ (5%) (dppf=1,1'-Bis(diphenylphosphino)ferrocene) are added to the solution. The resulting mixture is then heated in a microwave oven (CEM discover) in a scaled tube at 140° C. for 30 min. Water is added and the solution is extracted with ethyl acetate. The organic layers are dried over MgSO$_4$ and evaporated in vacuo. The final compound is obtained after purification by preparative HPLC. Analytical: Waters Acquity UPLC BEH C18 1.7 μm, 2.1 mm ID×50 mm L (Part No. 186002350).

Preparative HPLC: Waters XBridge Prep C18 5 m ODB 19 mm ID×100 mm L (Part No. 186002978). All the methods are using MeCN/H$_2$O gradients. H$_2$O contains either 0.1% TFA or 0.1% NH$_3$.

Method G

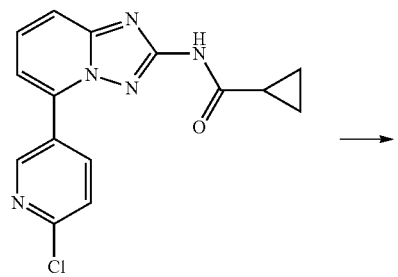

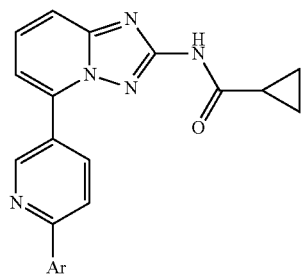

-continued

Suzuki Reaction

General Method

The appropriate boronic acid (2 eq.) is added to a solution of cyclopropanecarboxylic acid [5-(6-chloro-pyridin-3-yl)-[1,2,4]triazolo[1,5-a]pyridin-2-yl]-amide obtained by Method A (1 eq.) in 1,4-dioxane/water (5:1). K$_2$CO$_3$ (2 eq.) and Pd(dppf)Cl$_2$ (5%) (dppf=1,1'-Bis(diphenylphosphino)ferrocene) are added to the solution. The resulting mixture is then heated in a microwave oven (CEM discover) in a sealed tube at 140° C. for 30 min. Water is added and the solution is extracted with ethyl acetate. The organic layers are dried over MgSO$_4$ and evaporated in vacuo. The final compound is obtained after purification by preparative HPLC. Analytical: Waters Acquity UPLC BEH C18 1.7 μm, 2.1 mm ID×50 mm L (Part No. 186002350)

Preparative HPLC: Waters XBridge Prep C18 5 μm ODB 19 mm ID×100 mm L (Part No. 186002978). All the methods are using MeCN/H$_2$O gradients. H$_2$O contains either 0.1% TFA or 0.1% NH$_3$.

Method H

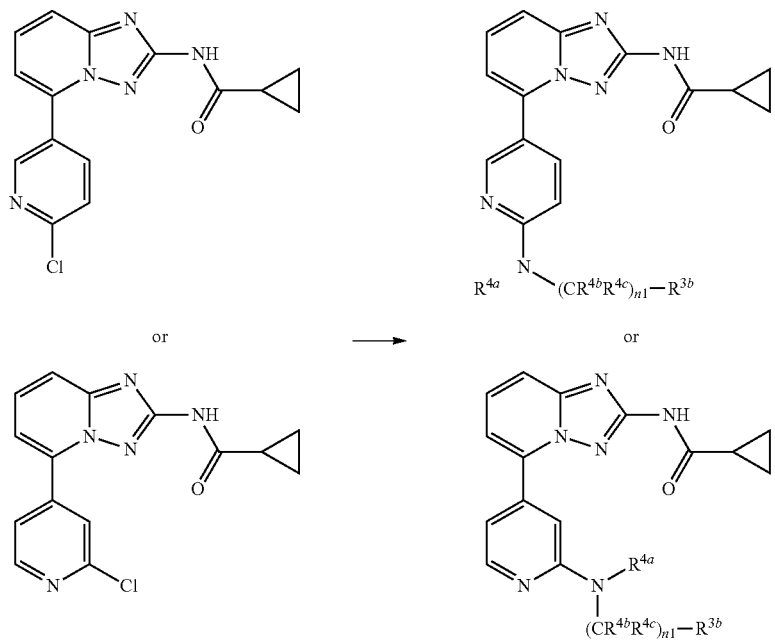

wherein $R^{4a}$, $R^{4b}$, $R^{4c}$, $R^{3b}$ and n1 are as described herein.

Aromatic Nucleophilic Substitution

General Method

The chloropyridine derivative obtained by Method A (1 eq), an appropriate amine (1.5 eq.) are mixed in tert-butanol in a sealed tube. The reaction is heated at 90° C. for 24 hours. Once all the SM disappeared by LCMS, water is added to the reaction mixture and the organics is extracted with ethyl acetate. The organic layer is dried over MgSO$_4$ and evaporater under vacuum. The final compound is isolated by preparative HPLC. Analytical: Waters Acquity UPLC BEH C18 1.7 μm, 2.1 mm ID×50 mm L (Part No. 186002350)

Preparative HPLC: Waters XBridge Prep C18 5 μm ODB 19 mm ID×100 mm L (Part No. 186002978). All the methods are using MeCN/H₂O gradients. H₂O contains either 0.1% TFA or 0.1% NH₃.

Method I

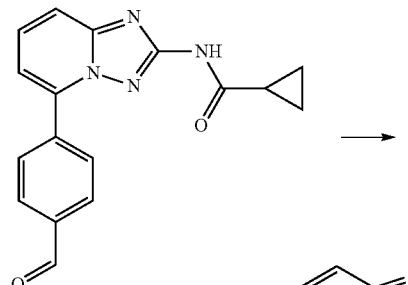

Reductive Alkylation

General Method

An appropriate amine (2 eq.), cyclopropanecarboxylic acid (for example cyclopropanecarboxylic acid [5-(4-formyl-phenyl)-[1,2,4]triazolo[1,5-a]pyridine-2-yl]-amide) prepared by method A (1 eq.) and Ti(OPr)₄ are mixed and stirred at room temperature for 3 hrs. The mixture is diluted in ethanol and Na(CN)BH₃ (1 eq.) is added. The resulting solution is stirred at room temperature for 16 hrs. The mixture is diluted in water and filtered. The solid is washed with ethanol. The combined solvent phases are evaporated under vacuum. The final compound is isolated by preparative HPLC.

Method J

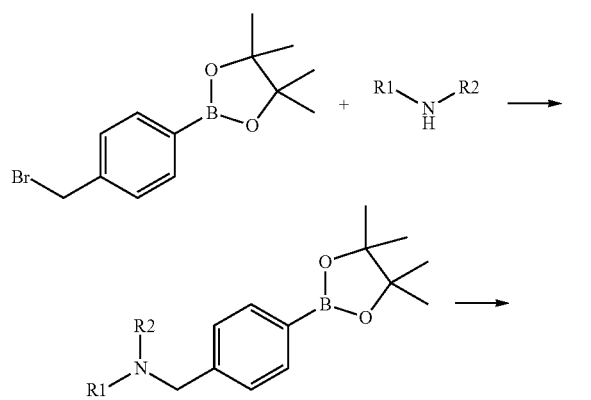

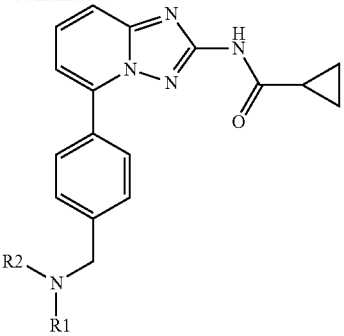

Reaction of Alkylation

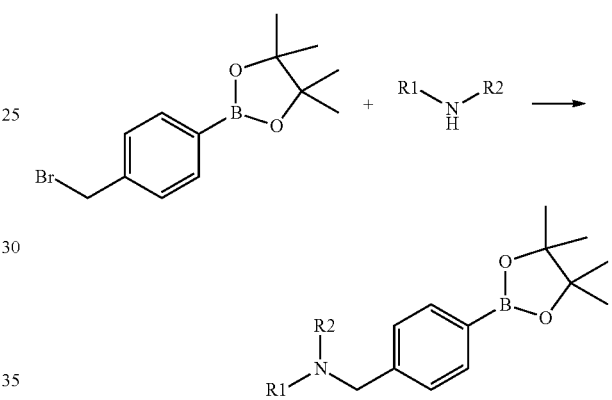

2-(4-Bromomethyl-phenyl)-4,4,5,5-tetramethyl-[1,3,2]dioxaborolane (1 eq) and Et₃N (2 eq) (or AgCO₃) are dissolved in DCM/MeOH (4:1 v:v) under N₂ and an amine (2 eq) is added dropwise. The resulting solution is stirred at room temperature for 16 h. After this time, the reaction is complete. The solvent is evaporated. The compound is extracted with EtOAc and water, washed with brine and dried over MgSO₄. Organic layers are filtered and evaporated. The final compound is isolated by flash chromatography.

Suzuki Coupling

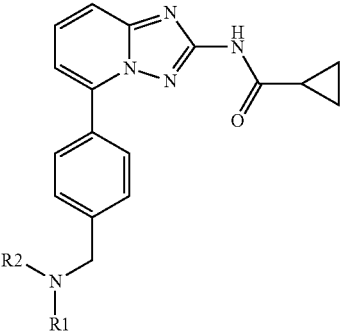

The title compound is then synthesized using method A.

Method K

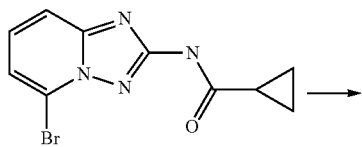

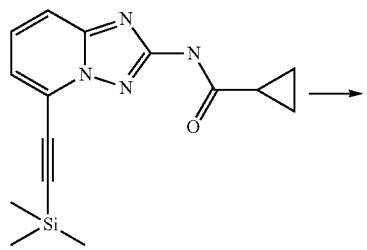

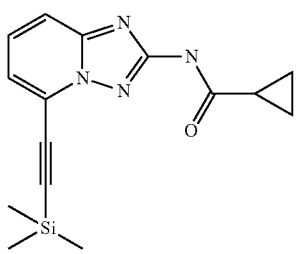 [SMILES: C[Si](C)(C)C#Cc1cccc2nc(NC(=O)C3CC3)nn12]

K.1 Cyclopropanecarboxylic acid (5-trimethylsilanylethynyl-[1,2,4]triazolo[1,5-a]pyridin-2-yl)-amide To a degassed solution of cyclopropanecarboxylic acid (5-bromo-[1,2,4]triazolo[1,5-a]pyridin-2-yl)-amide (0.36 mmol) in THF (3.5 mL) are added CuI (0.036 mmol), Pd(PPh)$_2$Cl$_2$ (0.036 mmol), (iPr)$_2$NH (0.137 mL), and timethylsilylacetylene (0.43 mmol). The reaction is heated at reflux overnight (70° C.), and then the solvent is removed under vacuum. The crude is redissolved with ethyl acetate and washed with water. The organic layer is dried over MgSO$_4$, filtered and the solvent is removed under vacuum to afford the title compound (95 mg, 89% yield). No further purification is carried out.

K.2 Cyclopropanecarboxylic acid (5-ethynyl-[1,2,4]triazolo[1,5-a]pyridin-2-yl)-amide

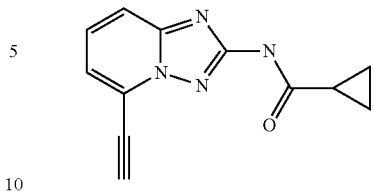

TBAF (0.4 mmol) 1M solution in THF is added to a solution of cyclopropanecarboxylic acid (5-trimethylsilanylethynyl-[1,2,4]triazolo[1,5-a]pyridin-2-yl)-amide (0.32 mmol) in acetonitrile (4 mL) at room temperature. The reaction mixture is stirred at room temperature until all the starting material disappears by LCMS. The solvent of the reaction is removed under vacuum, and the mixture is redissolved in ethyl acetate. The organic phase is washed with water. The organic layer is dried over MgSO$_4$, filtered and the solvent is removed under vacuum to afford the pure product (70 mg, 97% yield). No further purification is carried out on the product.

K.3 Cycloaddition

General Method

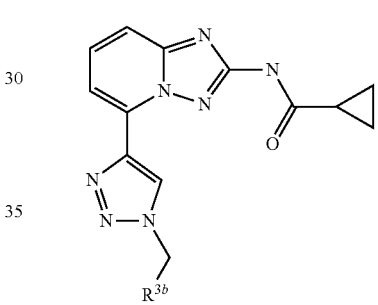

The corresponding azide derivative (0.44 mmol) is added to a solution of cyclopropanecarboxylic acid (5-ethynyl-[1,2,4]triazolo[1,5-a]pyridin-2-yl)-amide (0.44 mmol), CuSO$_4$.5H$_2$O (0.022 mmol) and sodium ascorbate (0.044 mmol) in CHCl$_3$/EtOH/H$_2$O (9:1:1) at room temperature. The reaction mixture is heated at 50° C. until completion of the reaction (monitored by LCMS). The crude mixture is diluted with ethyl acetate and washed with water. The organic phase was dried over MgSO$_4$, filtered and the solvent is evaporated under vacuum. The final compound is purified by preparative HPLC to give the expected compound.

Method L

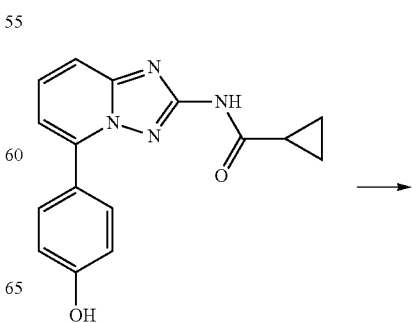

-continued

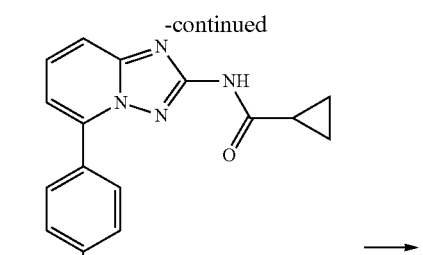

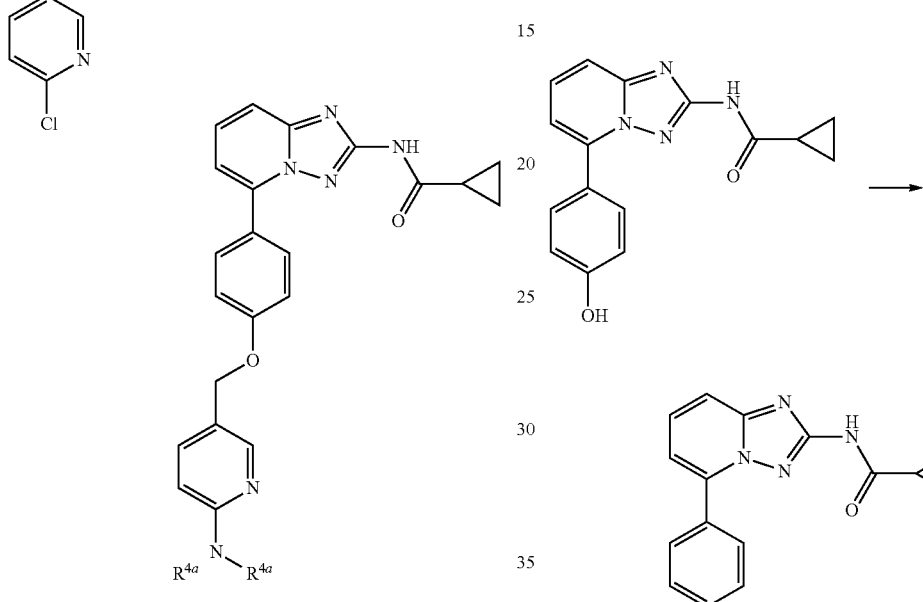

L.1 Nucleophilic Aromatic Substitution

General Method

Cyclopropanecarboxylic acid {5-[4-(6-chloro-pyridin-3-ylmethoxy)-phenyl]-[1,2,4]triazolo[1,5-a]pyridin-2-yl}-amide prepared by method C (1 eq), an appropriate amine, (1.5 eq.) are mixed in DMSO in a sealed tube. The reaction is heated at 100° C. for 24 hours. Once all the SM disappeared by LCMS, water is added to the reaction mixture and the organics is extracted with ethyl acetate. The organic layer is dried over $MgSO_4$ and evaporater under vacuum. The final compound is isolated by preparative HPLC. Analytical: Waters Acquity UPLC BEH C18 1.7 μm, 2.1 mm ID×50 mm L (Part No. 186002350)

Preparative HPLC: Waters XBridge Prep C18 5 μm ODB 19 mm ID×100 mm L (Part No. 186002978). All the methods are using $MeCN/H_2O$ gradients. $H_2O$ contains either 0.1% TFA or 0.1% $NH_3$.

Method M

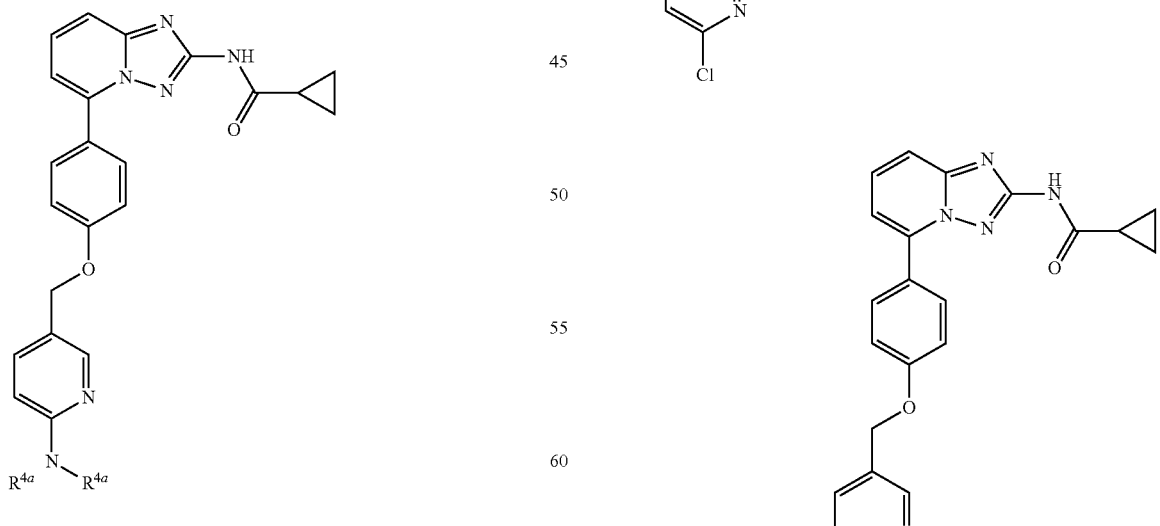

M.1 Suzuki Reaction

General Method

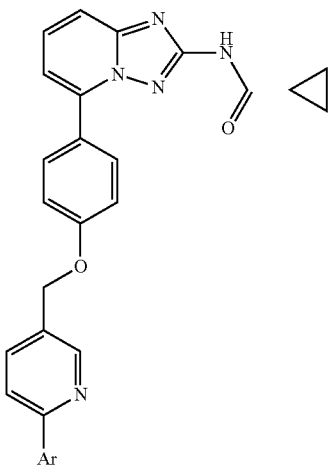

The boronic acid (2 eq.) is added to a solution of cyclopropanecarboxylic acid {5-[4-(6-chloro-pyridin-3-ylmethoxy)-phenyl]-[1,2,4]triazolo[1,5-a]pyridin-2-yl}-amide (prepared by method B) in 1,4-dioxan/water (5:1). $K_2CO_3$ (2 eq.) and $PdCl_2dppf$ (5%) are added to the solution. The resulting mixture is then heated in a microwave at 140° C. for 30 min (This reaction can also be carried out by traditional heating in an oil bath at 90° C. for 16 h under $N_2$). Water is added and the solution is extracted with ethyl acetate. The organic layers are dried over $MgSO_4$ and evaporated in vacuo. The final compound is obtained after purification by preparative HPLC

Method O

General Procedure for the Preparation of Sulfones

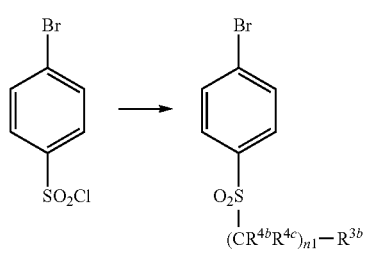

wherein $R^{4b}$, $R^{4c}$ and $R^{3b}$ are as described herein.

A solution of 4-bromobenzenesulfonyl chloride 1 (1.0 g, 3.96 mmol, 1.0 equiv.), sodium sulfite (0.6 g, 4.35 mmol, 1.1 equiv.) and sodium hydrogen carbonate (1.7 g, 79.8 mmol, 5.0 equiv.) in water (10 mL) is heated to 100° C. for 4 hours. The reaction mixture becomes clear and the appropriate halide (4.76 mmol, 1.2 equiv.) is added at 100° C. The mixture is stirred at this temperature for 16 hours. The reaction mixture is cooled to room temperature. Then, additional water is added (50 mL) and the resulting aqueous layer is extracted with dichloromethane (3×50 mL). The combined organic layers are dried over sodium sulfate, filtered and concentrated under reduced pressure. The resulting crude product is purified by chromatography over silica gel to afford the expected sulfone.

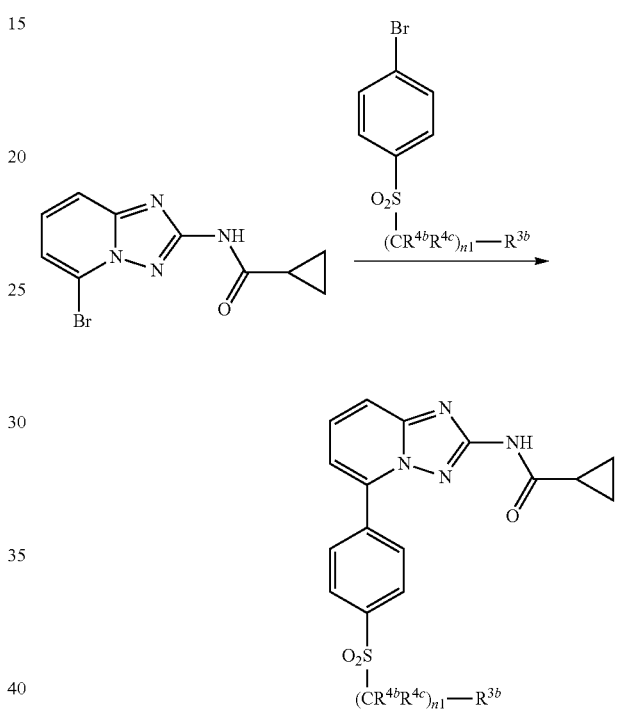

wherein $R^{4b}$, $R^{4c}$ and $R^{3b}$ and n1 are as described herein.

In a microwave vessel, a solution of the sulfone obtained according to the procedure described above (0.84 mmol, 1.5 equiv.), di(pinacolato)diborane (283.0 mg, 1.11 mmol, 2.0 equiv.) potassium acetate (109.0 mg; 1.11 mmol, 2.0 equiv.) in dioxane (2.0 mL) is flushed with argon (3 times). [1,1'-Bis(diphenylphosphino)ferrocene]dichloropalladiumn (II) (20.0 mg, 0.03 mmol, 0.05 equiv.) is then added and the reaction mixture is flushed again with argon (3 times) and heated up to 90° C. for 20 hours until the reaction is complete on TLC.

Then, cyclopropanecarboxylic acid (5-bromo-[1,2,4]triazolo[1,5-a]pyridin-2-yl)-amide (200.0 mg, 0.56 mmol, 1.0 equiv.), sodium hydrogen carbonate (233.0 mg, 2.78 mmol, 5.0 equiv.), [1,1'-Bis(diphenylphosphino)ferrocene]dichloropalladium(II) (20.0 mg, 0.03 mmol, 0.05 equiv.) and dioxane/water 2:1 (1.5 mL) are added to the mixture. The reaction mixture is then submitted several times (1-5 times) to microwave irradiations (P: 150 W, T=120° C., t=15 min.) until complete consumption of the starting material 133. Sodium sulfate is added to the reaction mixture (2.0 g) before diluting the latter with dichloromethane (3.0 mL). Purification by chromatography on silica gel (dichloromethane/methanol, 99:1→90:10) followed by trituration of the collected compound in methanol affords the expected product with a satisfactory HPLC purity.

Method P

Reaction of Alkylation

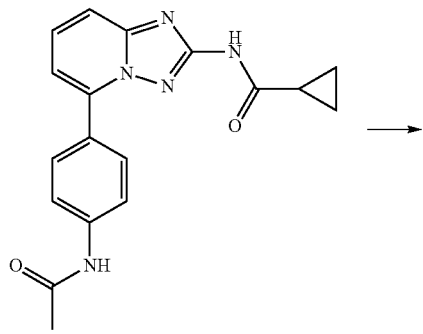

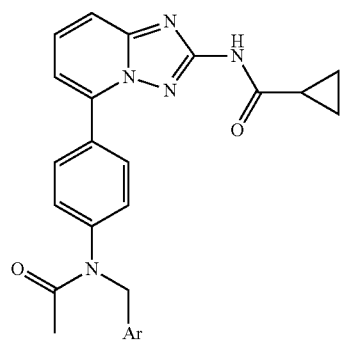

The appropriate alkylating agent (1.5 eq.) is added to a solution of the acetamide derivative (1 eq.) obtained by method A and NaH (2 eq.) in DMF at 0° C. The mixture is stirred for 16 hrs at room temperature. The solution is then diluted in water at 0° C. and the solution is extracted with EtOAc. The organic phases are dried over MgSO$_4$, filtered and the solvent is removed under vacuum. The final compound is isolated by preparative HPLC.

Method Q

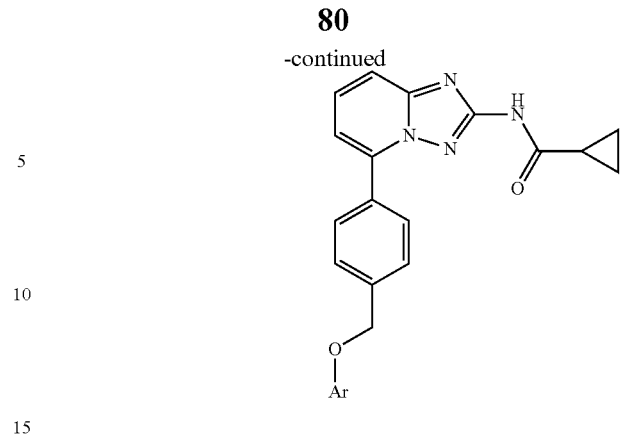

2-(4-Bromomethyl-phenyl)-4,4,5,5-tetramethyl-[1,3,2]dioxaborolane (1 eq.) and K$_2$CO$_3$ (2 eq) (or AgCO$_3$) are dissolved in DMF under N$_2$ and the appropriate phenol (2 eq) is added dropwise. The resulting suspension is heated at 50° C. for 16 h. After this time, the reaction is complete. The compound is extracted with EtOAc and water, washed with brine and dried over MgSO$_4$. Organic layers are filtered and evaporated to afford the desire compound without further purification.

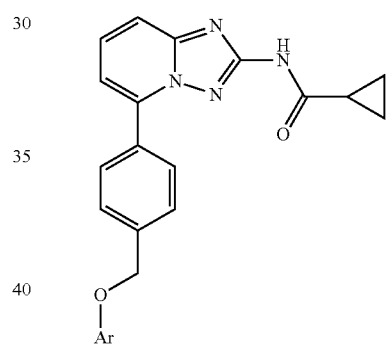

The title compound is obtained by method A using the intermediate boronate ester described above.

Method U

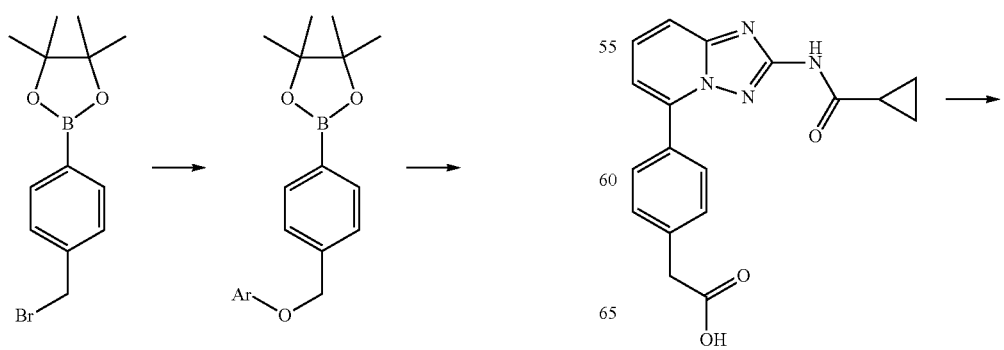

-continued

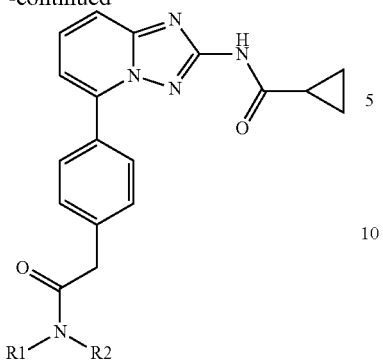

EDCI (1.5 eq.), HOBt (1.5 eq.) and Et₃N (2 eq.) are added to a solution of {4-[2-(cyclopropanccarbonyl-amino)-[1,2,4]triazolo[1,5-a]pyridin-5-yl]-phenyl}-acetic acid in DCM at room temperature. The resulting mixture is stirred for 2 h at room temperature. An appropriate amine is added to the solution and the reaction is stirred for 16 hrs. Water is added to the reaction mixture, and the later is extracted with EtOAc. The organic phases are dried over MgSO₄, filtered and evaporated under vacuum. Purification by flash chromatography affords the expected product.

Synthesis of Representative Compounds of the Invention

Compound 1

This compound was prepared via Method A using 1-methyl-4-[4-(4,4,5,5-tetramethyl-[1,3,2]dioxaborolan-2-yl)-phenyl]-piperazine.

Compound 2

This compound was prepared via Method A using 3-(4-morpholinomethyl)-phenylboronic acid pinacol ester hydrochloride.

Compound 3

This compound was prepared via Method A using 2-(piperidin-1-yl)pyridine-5-boronic acid pinacol ester.

Compound 4

This compound was prepared via Method A using 2-(pyrrolidin-1-yl)pyrimidine-5-boronic acid pinacol ester.

Compound 5

This compound was prepared via Method A using 2-(4-methylpiperazin-1-yl)pyridine-4-boronic acid pinacol ester.

Compound 6

This compound was prepared via Method A using 2-(4-morpholino)pyridine-5-boronic acid pinacol ester.

Compound 7

This compound was prepared via Method A using biphenyl-4-boronic acid.

Compound 8

This compound was prepared via Method A using 2-(4-morpholino)pyrimidine-5-boronic acid pinacol ester.

Compound 9

This compound was prepared via Method A using 2-(piperidin-1-yl)pyrimidine-5-boronic acid pinacol ester.

Compound 10

This compound was prepared via Method A using 4-benzoylphenylboronic acid.

Compound 11

This compound was prepared via Method A using [4-(cyclopropylaminocarbonyl)phenyl]boronic acid.

Compound 12

This compound was prepared via Method A using 4-benzyloxyphenylboronic acid.

Compound 13

This compound was prepared via Method A using 4-(N-cyclopropylsulfonamide)phenylboronic acid pinacol ester.

Compound 14

This compound was prepared via Method A using 3-benzyloxyphenylboronic acid.

Compound 15

This compound was prepared via Method A using 4-benzyloxy-3-fluorophenylboronic acid.

Compound 16

This compound was prepared via Method A using 2-benzyloxyphenylboronic acid.

Compound 17

This compound was prepared via Method A using piperidin-1-yl-[4-(4,4,5,5-tetramethyl-[1,3,2]dioxaborolan-2-yl)-phenyl]-methanone.

Compound 18

This compound was prepared via Method A using 4-[4-(4,4,5,5-tetramethyl-[1,3,2]dioxaborolan-2-yl)-benzyl]-morpholine.

Compound 19

This compound was prepared via Method A using pyrrolidin-1-yl-[4-(4,4,5,5-tetramethyl-[1,3,2]dioxaborolan-2-yl)-phenyl]-methanone.

Compound 20

This compound was prepared via Method A using 4-(2-thienyl)phenylboronic acid.

Compound 21

This compound was prepared via Method D using benzoyl chloride.

Compound 22

This compound was prepared via Method D using 4-trifluoromethyl-benzoyl chloride.

Compound 23

This compound was prepared via Method D using phenylacetyl chloride.

Compound 24

This compound was prepared via Method B using morpholine.

Compound 25

This compound was prepared via Method B using 4-amino-pyridine.

Compound 26

This compound was prepared via Method B using aminocyclohexane.

Compound 27

This compound was prepared via Method B using 4-tert-butyl-piperidine.

Compound 28

This compound was prepared via Method B using [1,4] diazepane.

Compound 29

This compound was prepared via Method B using 3-fluoro-benzylamine.

Compound 30

This compound was prepared via Method B using N-methylaniline.

Compound 31

This compound was prepared via Method B using (4-methoxy-benzyl)-methyl-amine.

Compound 32

This compound was prepared via Method B using 1-methyl-piperidin-4-ylamine.

Compound 33

This compound was prepared via Method D using 4-fluoro-sulfonylchloride.

Compound 34

This compound was prepared via Method D using 2-fluorobenzoylchloride.

Compound 35

This compound was prepared via Method D using pyrazine-2-carbonyl chloride.

Compound 36

This compound was prepared via Method C using 3-bromomethyl-pyridine hydrobromide.

Compound 37

This compound was prepared via Method C using 2-bromomethyl-pyridine hydrobromide.

Compound 38

This compound was prepared via Method C using 3-(trifluoromethoxy)benzyl bromide.

Compound 39

This compound was prepared via Method C using (bromomethyl)cyclobutane.

Compound 40

This compound was prepared via Method C using iodocyclopentane.

Compound 41

This compound was prepared via Method C using (bromomethyl)cyclohexane.

Compound 42

This compound was prepared via Method B using C-pyridin-3-yl-methylamine.

Compound 43

This compound was prepared via Method B using aniline.

Compound 44

This compound was prepared via Method D using benzoyl chloride.

Compound 45

This compound was prepared via Method D using cyclohexanecarbonyl chloride.

Compound 46

This compound was prepared via Method A using 4-phenoxyphenylboronic acid.

Compound 47

This compound was prepared via Method G using phenyl boronic acid.

Compound 48

This compound was prepared via Method C using 3-(chloromethyl)-1-methyl-1H-pyrazole.

Compound 49

This compound was prepared via Method C using 4-(chloromethyl)-3,5-dimethylisoxazole.

Compound 50

This compound was prepared via Method C using 5-(chloromethyl)-1,3-dimethyl-1H-pyrazole.

Compound 51

This compound was prepared via Method C using 4-(2-bromoethyl)-3,5-dimethyl-1H-pyrazole.

Compound 52

This compound was prepared via Method C using 3-(bromomethyl)-5-methylisoxazole.

Compound 53

This compound was prepared via Method D using 3-methoxy-benzoyl chloride.

Compound 54

This compound was prepared via Method D using 2-fluoro-phenyl sulfonyl chloride.

Compound 55

This compound was prepared via Method D using Pyridine-2-carboxylic acid (acid chloride formed by reaction of oxalyl chloride).

Compound 56

This compound was prepared via Method B using benzylamine.

Compound 57: Cyclopropanecarboxylic acid [5-(6-benzyloxy-pyridin-3-yl)-[1,2,4]triazolo[1,5-a]pyridin-2-yl]-amide

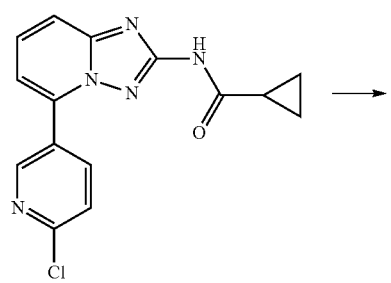

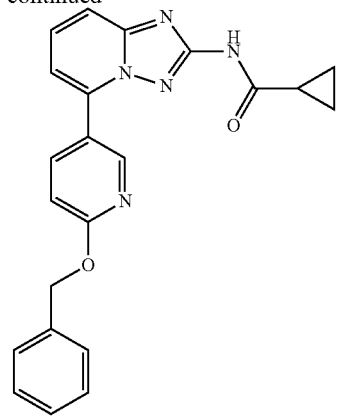

At 0° C. and under $N_2$ atmosphere, benzyl alcohol (2 eq) in a solution of THF was treated with NaH 60% in mineral oil (4 eq) for 30 min. Then cyclopropanecarboxylic acid [5-(6-chloro-pyridin-3-yl)-[1,2,4]triazolo[1,5-a]pyridin-2-yl]-amide prepared by method A was added to the solution and the mixture was stirred at 70° C. for 3 hours. The reaction was completed. The reaction mixture was quenched with water and the compound was extracted with EtOAc. The compound was washed with brine, dried on $MgSO_4$, filtrated and concentrated. Compound was purified on Prep HPLC.

Compound 58

This compound was prepared via Method B using 1,2,3,4-tetrahydro-isoquinoline.

Compound 59

This compound was prepared via Method D using cyclopropanesulfonyl chloride.

Compound 60

This compound was prepared via Method B using 2-phenoxy-ethylamine.

Compound 61

This compound was prepared via Method H using pyrazine.

Compound 62

This compound was prepared via Method C using 3-(chloromethyl)-1,5-dimethyl-1H-pyrazole.

Compound 63

This compound was prepared via Method C using 4-(chloromethyl)-2,5-dimethyl-1,3-oxazole.

Compound 64

This compound was prepared via Method D using pyridine-3-sulfonyl chloride.

Compound 65

This compound was prepared via Method D using 1,3-dimethyl-1H-pyrazole-4-sulfonyl chloride.

Compound 66

3-Pyridineboronic acid (1.1 eq.) was added to a solution of cyclopropanecarboxylic acid [5-(4-bromo-phenyl)-[1,2,4]triazolo[1,5-a]pyridin-2-yl]-amide, prepared by Method A in 1,4-dioxane/water (5:1). K₂CO₃ (2 eq.) and Pd(dppf)Cl₂ (0.03 eq.) (dppf=1,1'-Bis(diphenylphosphino)ferrocene) were added to the solution. The resulting mixture was then heated in a sealed tube at 90° C. for 16 hrs. Water was added and the solution was extracted with ethyl acetate. The organic layers were dried over MgSO₄ and evaporated in vacuo. The final compound was obtained after purification by preparative HPLC. Analytical: Waters Acquity UPLC BEH C18 1.7 μm, 2.1 mm ID×50 mm L (Part No. 186002350).

Compound 67

1H-Pyrazole-4-boronic acid (1.1 eq.) was added to a solution of cyclopropanecarboxylic acid [5-(4-bromo-phenyl)-[1,2,4]triazolo[1,5-a]pyridin-2-yl]-amide, prepared by method A in 1,4-dioxane/water (5:1). K₂CO₃ (2 eq.) and Pd(dppf)Cl₂ (0.03 eq.) (dppf=1,1'-Bis(diphenylphosphino)ferrocene) were added to the solution. The resulting mixture was then heated in a sealed tube at 90° C. for 16 hrs. Water was added and the solution was extracted with ethyl acetate. The organic layers were dried over MgSO₄ and evaporated in vacuo. The final compound was obtained after purification by preparative HPLC. Analytical: Waters Acquity UPLC BEH C18 1.7 m, 2.1 mm ID×50 mm L (Part No. 186002350).

Compound 68

3-Pyridineboronic acid (1.1 eq.) was added to a solution of cyclopropanecarboxylic acid [5-(6-chloro-pyridin-3-yl)-[1,2,4]triazolo[1,5-a]pyridin-2-yl]-amide, prepared by method A in 1,4-dioxane/water (5:1). K₂CO₃ (2 eq.) and Pd(dppf)Cl₂ (0.03 eq.) (dppf=1,1'-Bis(diphenylphosphino)ferrocene) were added to the solution. The resulting mixture was then heated in a sealed tube at 90° C. for 16 hrs. Water was added and the solution was extracted with ethyl acetate. The organic layers were dried over MgSO₄ and evaporated in vacuo. The final compound was obtained after purification by preparative HPLC. Analytical: Waters Acquity UPLC BEH C18 1.7 μm, 2.1 mm ID×50 mm L (Part No. 186002350).

Compound 69

This compound was prepared via Method D using 2-methyl-5-propyl-2H-pyrazole-3-carboxylic acid which was reacted first in presence of oxalyl chloride to obtain the acid chloride.

Compound 70

This compound was prepared via Method D using cyclobutanecarbonyl chloride.

Compound 71

This compound was prepared via Method B using N-methyl pyrazine.

Compound 72

This compound was prepared via Method E using benzaldehyde.

Compound 73

This compound was prepared via Method B using 4-ethoxymethyl-piperidine.

Compound 74

This compound was prepared via Method B using phenyl-piperidin-4-yl-methanone.

Compound 75

This compound was prepared via Method B using 1-benzyl-[1,4]diazepane.

Compound 76

This compound was prepared via Method D using 2-phenyl-ethanesulfonyl chloride.

Compound 77

This compound was prepared via Method D using Phenyl-methanesulfonyl chloride.

Compound 78

This compound was prepared via Method C using 3-(chloromethyl)-6-(trifluoromethyl)pyridine.

Compound 79

This compound was prepared via Method D using phenyl-sulfonyl chloride.

Compound 80

This compound was prepared via Method B using 2-pyrrolidin-1-yl-ethylamine.

Compound 81

This compound was prepared via Method B using 3-morpholin-4-yl-propylamine.

Compound 82

This compound was prepared via Method H using 4-phenethyl-piperidine.

Compound 83

This compound was prepared via Method H using 4-(4-chloro-phenyl)-piperidine.

Compound 84

This compound was prepared via Method H using 3-phenylpiperidine.

Compound 85

This compound was prepared via Method D using 4-propyl-benzenesulfonyl chloride.

Compound 86

This compound was prepared via Method B using 4-(4-chloro-phenyl)-piperidine.

Compound 87

This compound was prepared via Method B using phenethylamine.

Compound 88

This compound was prepared via Method D using 2-(3-fluoro-phenyl)-ethanesulfonyl chloride.

Compound 89

This compound was prepared via Method B using piperidine.

Compound 90

This compound was prepared via Method B using butyl-(3-morpholin-4-yl-propyl)-amine.

Compound 91

This compound was prepared via Method C using 4-(chloromethyl)-2-[4-(trifluoromethyl)phenyl]-thiazole.

Compound 92

This compound was prepared via Method C using 4-acetamidobenzyl chloride.

Compound 93

This compound was prepared via Method H using 2-(tetrahydro-pyran-4-yl)-ethylamine.

Compound 94

This compound was prepared via Method B using 4-(2-piperidin-4-yl-ethyl)-morpholine.

Compound 95

This compound was prepared via Method H using 4-(2-piperidin-4-yl-ethyl)-morpholine.

Compound 96

This compound was prepared via Method B using methyl-phenethyl-amine.

Compound 97

This compound was prepared via Method B using 2-(4-trifluoromethyl-phenyl)-ethylamine.

Compound 98

This compound was prepared via Method C using 1-(2-bromo-ethyl)-1H-pyrazole.

Compound 99

This compound was prepared via Method C using 3-(chloromethyl)-1,2,4-oxadiazole.

Compound 100

This compound was prepared via Method B using 2-phenoxyethylamine.

Compound 101

This compound was prepared via Method B using 4-piperidin-4-yl-morpholine.

Compound 102

This compound was prepared via Method B using 1,1-dimethyl-2-morpholin-4-yl-ethylamine.

Compound 103

This compound was prepared via Method B using benzyl-methyl-piperidin-4-yl-amine.

Compound 104

This compound was prepared via Method H using benzylamine.

Compound 105

This compound was prepared via Method B using [2-(3,4-dimethoxy-phenyl)-ethyl]-methyl-amine.

Compound 106

This compound was prepared via Method B using 2-(1-phenyl-1H-pyrazol-4-yl)-ethylamine.

Compound 107

This compound was prepared via Method A using 1-benzyl-1H-pyrazole-4-boronic acid.

Compound 108

This compound was prepared via Method D using 3-phenoxy-propionyl chloride.

Compound 109

This compound was prepared via Method D using 3-phenyl-propionyl chloride.

Compound 110

This compound was prepared via Method B using 3-(piperidin-4-yloxy)-pyridine.

Compound 111

This compound was prepared via Method B using phenethylamine.

Compound 112

This compound was prepared via Method H using 4-phenethyl-piperidine.

Compound 113

This compound was prepared via Method B using 1-(3-chloro-phenyl)-piperazine.

Compound 114

This compound was prepared via Method B using 3-phenyl-propylamine.

Compound 115

This compound was prepared via Method C using 1-(2-bromoethoxy)-4-fluorobenzene.

Compound 116

This compound was prepared via Method C using N-(chloroacetyl)-3-fluoroaniline.

Compound 117

This compound was prepared via Method C using 1-(4-benzyl-piperidin-1-yl)-2-chloro-ethanone.

Compound 118

This compound was prepared via Method C using 2-chloro-N-methyl-N-phenyl-acetamide.

Compound 119

This compound was prepared via Method B using (S)-1-benzyl-pyrrolidin-3-ylamine.

Compound 120

This compound was prepared via Method B using (R)-1-benzyl-pyrrolidin-3-ylamine.

Compound 121: Cyclopropanecarboxylic acid [5-(1-benzyl-1H-indol-5-yl)-[1,2,4]triazolo[1,5-a]pyridin-2-yl]-amide

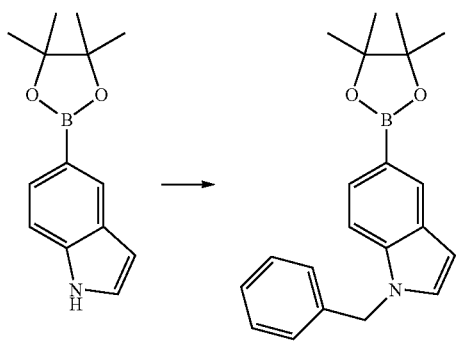 [SMILES: CC1(C)OB(c2ccc3[nH]ccc3c2)OC1(C)C ; CC1(C)OB(c2ccc3c(ccn3Cc3ccccc3)c2)OC1(C)C]

121.1 1-Benzyl-5-(4,4,5,5-tetramethyl-[1,3,2]dioxaborolan-2-yl)-1H-indole

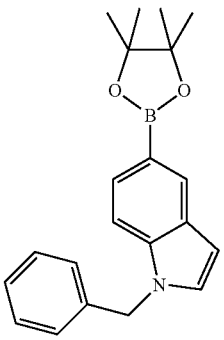 [SMILES: CC1(C)OB(c2ccc3c(ccn3Cc3ccccc3)c2)OC1(C)C]

To a solution of 5-(4,4,5,5-tetramethyl-[1,3,2]dioxaborolan-2-yl)-1H-indole (2.27 mmol; 1.0 equiv.) in acetone (10.0 mL) at room temperature were added under argon benzyl bromide (3.18 mmol; 1.4 aquiv.) and cesium carbonate (3.18 mmol; 1.4 equiv.). The reaction mixture was heated for 4 hours at reflux. The mixture was then cooled to room temperature, quenched by addition of a saturated aqueous solution of sodium hydrogen carbonate (100 mL) and extracted with dichloromethane (2×100 mL). The organic layer was dried over sodium sulfate, filtered and concentrated to dryness. The resulting residue was purified by flash chromatography over silica gel (dichloromethane/ethyl acetate) to afford the expected boronate as a white solid used in the next step without further purification.

121.2 Cyclopropanecarboxylic acid [5-(1-benzyl-1H-indol-5-yl)-[1,2,4]triazolo[1,5-a]pyridin-2-yl]-amide

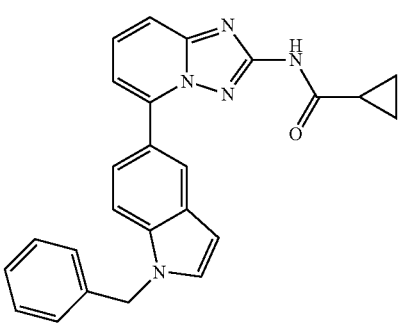 [SMILES: O=C(Nc1nc2cccc(-c3ccc4c(ccn4Cc4ccccc4)c3)n2n1)C1CC1]

The title compound was then synthesised by Method A using 1-benzyl-5-(4,4,5,5-tetramethyl-[1,3,2]dioxaborolan-2-yl)-1H-indol.

Compound 122

This compound was prepared via Method D using 2-phenoxy-ethanesulfonyl chloride.

Compound 123

This compound was prepared via Method H using phenethylamine.

Compound 124

This compound was prepared via Method B using 2-pyridin-3-yl-ethylamine.

Compound 125

This compound was prepared via Method C using the mesylate derivative of (4-pyrazol-1-yl-phenyl)-methanol.

Compound 126

This compound was prepared via Method C using the mesylate derivative of [4-(4-methyl-piperazin-1-ylmethyl)-phenyl]-methanol.

Compound 127

This compound was prepared via Method C using 3-(2-chloro-ethyl)-pyridine.

Compound 128

This compound was prepared via Method B using 2-piperidin-4-yl-1H-benzoimidazole.

Compound 129

This compound was prepared via Method A using 4-[4-(4,4,5,5-tetramethyl-1,3,2-dioxaborolan-2-yl)phenyl]morpholine.

Compound 130

This compound was prepared via Method I using N-methyl-pyrazine.

Compound 131

This compound was prepared via Method B using 4-(2-methoxy-phenyl)-piperidine.

Compound 132

This compound was prepared via Method B using 4-(4-chloro-phenyl)-piperidin-4-ol.

Compound 133

This compound was prepared via Method B using 4-o-tolyloxymethyl-piperidine.

Compound 134

This compound was prepared via Method B using 3,5-dimethyl piperidine.

Compound 135

This compound was prepared via Method B using N-(4-piperidin-1-ylbenzyl)propan-2-amine.

Compound 136

This compound was prepared via Method B using propyl-(tetrahydro-furan-2-ylmethyl)-amine.

Compound 137

This compound was prepared via Method B using 4-fluoropiperidine.

Compound 138

This compound was prepared via Method B using 2-piperidin-4-yl-1H-indole.

Compound 139

This compound was prepared via Method I using piperidine.

Compound 140

This compound was prepared via Method I using piperidine-4-carboxylic acid amide.

Compound 141

This compound was prepared via Method I using 1-piperazin-1-yl-ethanone.

Compound 142

This compound was prepared via Method I using 1-pyridin-2-yl-piperazine.

Compound 143

This compound was prepared via Method I using 2-piperazin-1-yl-pyrimidine.

Compound 144

This compound was prepared via Method B using 2-methylpiperidine.

Compound 145

This compound was prepared via Method B using 3-methylpiperidine.

Compound 146

This compound was prepared via Method B using 4-methyl piperidine.

Compound 147

This compound was prepared via Method B using 4-phenethyl-piperidine.

Compound 148

This compound was prepared via Method B using 4-trifloromethylpiperidine.

Compound 149

This compound was prepared via Method B using 6-fluoro-3-piperidin-4-yl-benzo[d]isoxazole.

Compound 150

This compound was prepared via Method B using N'-benzyl-N,N-dimethylethylenediamine.

Compound 151

This compound was prepared via Method B using (4-fluoro-benzyl)-(2-methoxy-1-methyl-ethyl)-amine hydrochloride.

Compound 152

This compound was prepared via Method B using 1-piperidin-4-yl-1H-benzotriazole.

Compound 153

This compound was prepared via Method B using (4-fluoro-benzyl)-(tetrahydro-furan-2-ylmethyl)-amine.

Compound 154

This compound was prepared via Method B using 4-[2-(2-methyl-imidazol-1-yl)-ethyl]-piperidine.

Compound 155

This compound was prepared via Method I using methyl-phenethyl-amine.

Compound 156

This compound was prepared via Method B using 4-benzyl-piperidin-4-ol.

Compound 157

This compound was prepared via Method E using benzyl bromide.

Compound 158: N-(5-(4-((1H-tetrazol-5-yl)methyl1H-tetrazol-5-yl)methoxy)phenyl)-[1,2,4]triazolo[1,5-a]pyridin-2-yl)cyclopropanecarboxamide

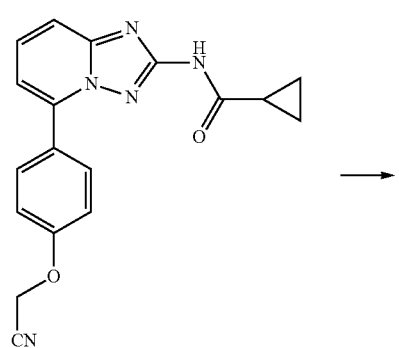

→

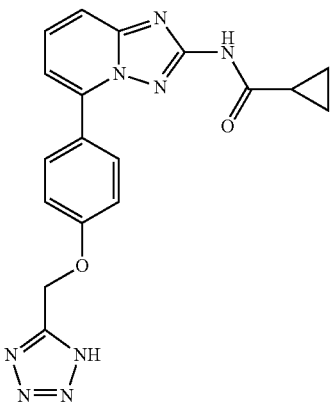

A solution of cyclopropanecarboxylic acid [5-(4-cyanomethoxy-phenyl)-[1,2,4]triazolo[1,5-a]pyridin-2-yl]-amide (1 equiv), sodium azide (2 equiv), and ammonium chloride (2 equiv) was stirred at 0° C. under nitrogen for 30 minutes. Afterwards the mixture was subjected to 100° C. for 16 hours. The crude of the reaction was diluted with ethyl acetate and washed with water. The organic phase was dried over MgSO$_4$, filtered, and dried under vacuum. The crude was diluted with DMSO and submitted for preparative HPLC purification: UPLC system (XBridge™ Prep C18, 5 μm, 19×100 mm column); 8 min LC; flow: 20 mL/min; gradient: from 30% to 70% acetonitrile in water 0.1% TFA; to afford the final pure product (10% yield).

Compound 159

This compound was prepared via Method I using methyl-(4-pyridin-2-yl-benzyl)-amine.

Compound 160

This compound was prepared via Method I using (1,5-dimethyl-1H-pyrazol-3-ylmethyl)-methyl-amine.

Compound 161

This compound was prepared via Method I using methyl-(4-pyrimidin-5-yl-benzyl)-amine.

Compound 162

This compound was prepared via Method I using methyl-pyridin-3-ylmethyl-amine.

Compound 163

This compound was prepared via Method F using 2-(4-benzyloxy-phenyl)-4,4,5,5-tetramethyl-[1,3,2]dioxaborolane.

Compound 164

This compound was prepared via Method B using 3-trifluoromethyl piperidine.

Compound 165

This compound was prepared via Method L using morpholine.

Compound 166

This compound was prepared via Method M using 4-(4,4,5,5-tetramethyl-[1,3,2]dioxaborolan-2-yl)-1H-pyrazole.

Compound 167

This compound was prepared via Method L using N-methyl morpholine.

Compound 168

This compound was prepared via Method B using 4,4-difluoro-piperidine.

Compound 169

This compound was prepared via Method B using 3-phenyl-piperidine.

Compound 170

This compound was prepared via Method E using C-pyridin-3-yl-methylamine.

Compound 171

This compound was prepared via Method E using C-pyridin-2-yl-methylamine.

Compound 172

This compound was prepared via Method E using 2-pyridin-3-yl-ethylamine.

Compound 173

This compound was prepared via Method E using C-(1,5-dimethyl-1H-pyrazol-3-yl)-methylamine.

Compound 174

This compound was prepared via Method L using pirrolidine.

Compound 175

This compound was prepared via Method B using 3,3-dimethyl-piperidine.

Compound 176: N-(5-(4-((6-cyanopyridin-3-yl)methoxy)phenyl)-[1,2,4]triazolo[1,5-a]pyridin-2-yl)cyclopropanecarboxamide

176.1: Synthesis of 5-[4-(4,4,5,5-Tetramethyl-[1,3,2]dioxaborolan-2-yl)-phenoxymethyl]-pyridine-2-carbonitrile

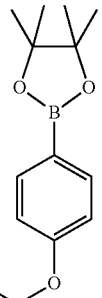

To 4-hydroxyphenylboronic acid pinacol ester (25 g; 0.11 mol; 1.0 equiv.) in acetone (250 mL) at room temperature were added under argon 5-chlomomethyl-pyridine-2-carbonitrile (19 g; 0.12 mol; 1.1 equiv.) and cesium carbonate (73.9 g, 0.22 mol; 2 equiv.). The reaction mixture was heated for 4 hours at reflux. The mixture was then cooled to room temperature, the acetone was evaporated. Water (200 mL) was added and the product was extracted with EtOAc (3×200 mL). The organic layer was dried over magnesium sulfate, filtered and concentrated to dryness. The resulting residue was purified by chromatography over silica gel (petrol:EtOAc 10:1) to afford the expected boronate as a white solid.

176.2: Synthesis of Cyclopropanecarboxylic acid {5-[4-(6-cyano-pyridin-3-ylmethoxy)-phenyl]-[1,2,4]triazolo[1,5-a]pyridin-2-yl}-amide

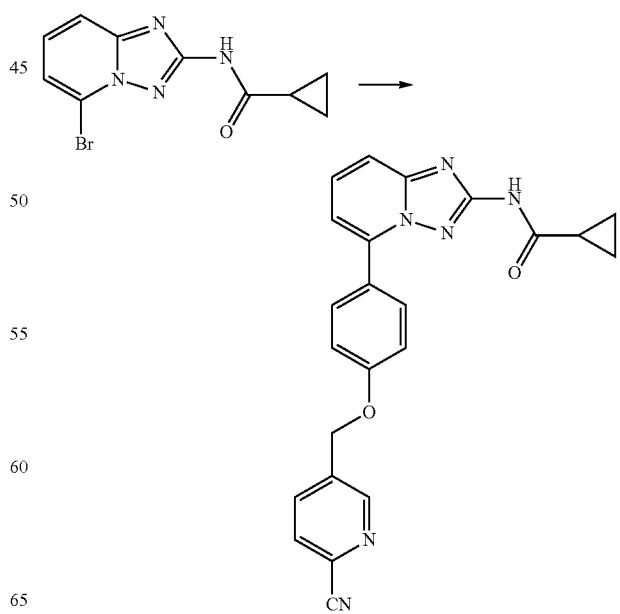

5-[4-(4,4,5,5-Tetramethyl-[1,3,2]dioxaborolan-2-yl)-phenoxymethyl]-pyridine-2-carbonitrile (10 g, 0.03 mol, 1.1 equiv.) was added to a solution of cyclopropanecarboxylic acid (5-bromo-[1,2,4]triazolo[1,5-a]pyridin-2-yl)-amide (7.6 g, 0.027 mol) in 1,4-dioxane/water (4:1; 70 mL). K$_2$CO$_3$ (7.45, 0.054 mol, 2 eq.) and PdCl$_2$dppf (5%) were added to the solution. The resulting mixture was then heated in an oil bath at 90° C. for 4 to 16 h under N$_2$ until completion (monitored by LCMS). 1,4-Dioxane was removed under vacuum, and water/EtOAc were added and the solid was filtered. The obtained solid was dissolved in methanol/DCM, dried over MgSO$_4$ and the final compound was obtained after purification by flash chromatography, eluted with neat EtOAc

Compound 177

This compound was prepared via Method D using 1-cyano-cyclopropanecarbonyl chloride.

Compound 178

This compound was prepared via Method M using 1-methyl-4-(4,4,5,5-tetramethyl-[1,3,2]dioxaborolan-2-yl)-1H-pyrazole.

Compound 179: Cyclopropanecarboxylic acid {5-[1-(3-phenyl-propionyl)-1H-indol-5-yl]-[1,2,4]triazolo[1,5-a]pyridin-2-yl}-amide

179.1 3-Phenyl-1-[5-(4,4,5,5-tetramethyl-[1,3,2]dioxaborolan-2-yl)-indol-1-yl]-propan-1-one

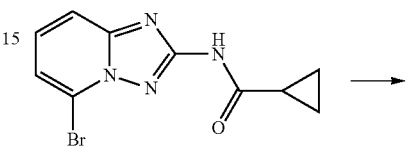

To a solution of 5-(4,4,5,5-tetramethyl-[1,3,2]dioxaborolan-2-yl)-1H-indole (2.27 mmol; 1.0 equiv.) in DMF (10.0 mL) at room temperature were added under argon 3-phenyl-propionyl chloride (3.18 mmol; 1.4 aquiv.) and sodium hydride (3.18 mmol; 1.4 equiv.). The reaction mixture was heated at 60° C. for 16 hrs. The mixture was allowed to cool to room temperature and was quenched by addition of water (100 mL) and extracted with dichloromethane (2×100 mL). The organic layer was dried over sodium sulfate, filtered and concentrated to dryness. The resulting residue was purified by flash chromatography over silica gel (dichloromethane/ethyl acetate) to afford the expected boronate as a white solid used in the next step without further purification.

179.2 Cyclopropanecarboxylic acid {5-[1-(3-phenyl-propionyl)-1H-indol-5-yl]-[1,2,4]triazolo[1,5-a]pyridin-2-yl}-amide

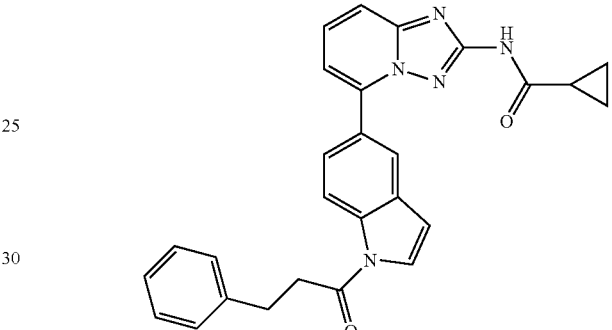

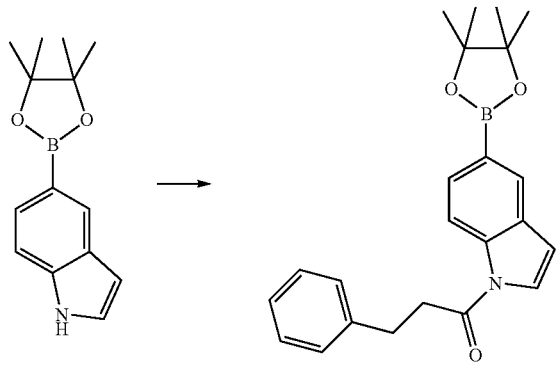 [SMILES: CC1(C)OB(c2ccc3[nH]ccc3c2)OC1(C)C ; CC1(C)OB(c2ccc3c(ccn3C(=O)CCc3ccccc3)c2)OC1(C)C]

The title compound was prepared by Method A using 3-phenyl-1-[5-(4,4,5,5-tetramethyl-[1,3,2]dioxaborolan-2-yl)-indol-1-yl]-propan-1-one.

Compound 180

This compound was prepared via Method D using Benzenesulfonyl chloride.

Compound 181

181.1 Preparation of Phenethylamino-Acetonitrile

Chloro-acetonitrile (1.5) eq was added to a solution of phenethylamine (1 eq) and K$_2$CO$_3$ (2 eq) in CH$_3$CN. The mixture was stirred at 60° C. for 4 hrs. After completion of the reaction, the mixture was filtered and the filtrate was concentrated under reduced pressure. Purification by flash chromatography gave the expected compound.

181.2 Compound 181 was Prepared Using Method B Using Phenethylamino-Acetonitrile

Compound 182

This compound was prepared via Method E using 3-bromomethyl-pyridine.

Compound 183: Cyclopropanecarboxylic acid (5-{4-[6-(2H-tetrazol-5-yl)-pyridin-3-ylmethoxy]-phenyl}-[1,2,4]triazolo[1,5-a]pyridin-2-yl)-amide Compound 185: Cyclopropanecarboxylic acid [5-(1-pyridin-3-ylmethyl-1H-pyrazol-4-yl)-[1,2,4]triazolo[1,5-a]pyridin-2-yl]-amide 185.1 3-[4-(4,4,5,5-Tetramethyl-[1,3,2]dioxaborolan-2-yl)-pyrazol-1-ylmethyl]-pyridine

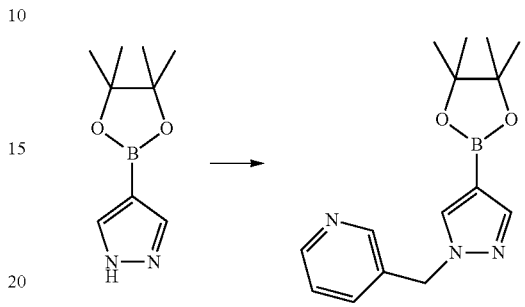

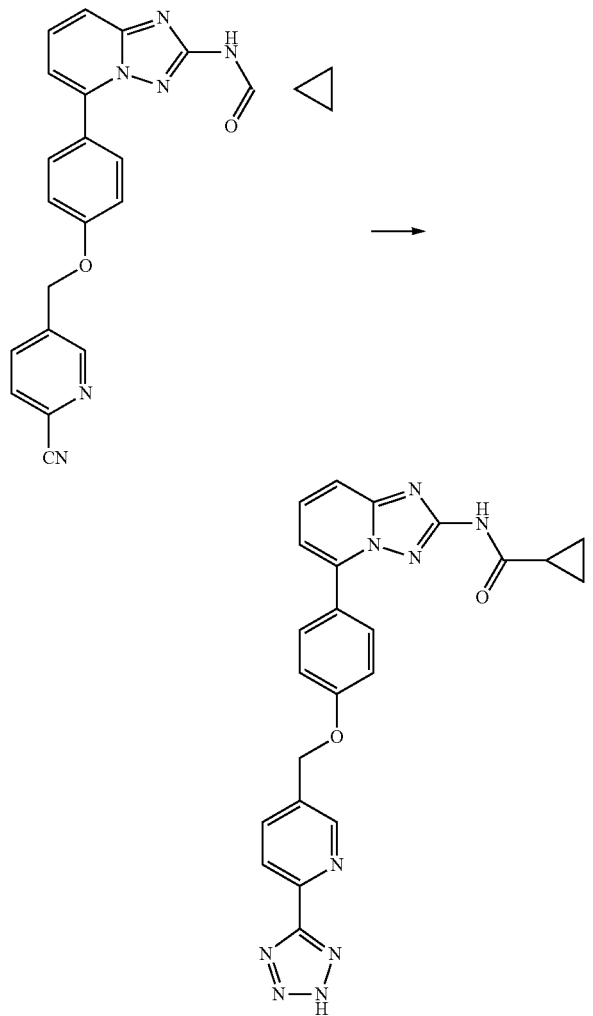

To a solution of 4-(4,4,5,5-tetramethyl-[1,3,2]dioxaborolan-2-yl)-1H-pyrazole (2.27 mmol; 1.0 equiv.) in acetone (10.0 mL) at room temperature were added under argon 3-Chloromethyl-pyridine hydrochloride (3.18 mmol; 1.4 aquiv.) and cesium carbonate (2.8 equiv.). The reaction mixture was heated for 4 hours at reflux. The mixture was then cooled to room temperature, quenched by addition of a saturated aqueous solution of sodium hydrogen carbonate (100 mL) and extracted with dichloromethane (2×100 mL). The organic layer was dried over sodium sulfate, filtered and concentrated to dryness. The resulting residue was purified by flash chromatography over silica gel (dichloromethane/ethyl acetate) to afford the expected boronate as a white solid used in the next step without further purification.

185.2 Cyclopropanecarboxylic acid [5-(1-pyridin-3-ylmethyl-1H-pyrazol-4-yl)-[1,2,4]triazolo[1,5-a]pyridin-2-yl]-amide

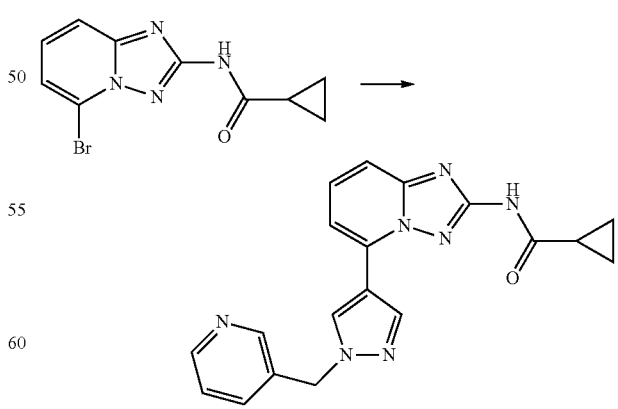

A solution of cyclopropanecarboxylic acid {5-[4-(6-cyano-pyridin-3-ylmethoxy)-phenyl]-[1,2,4]triazolo[1,5-a]pyridin-2-yl}-amide (143 mg, 0.35 mmol, 1 equiv), sodium azide (46 mg, 0.7 mmol, 2 equiv), ammonium chloride (38 mg, 0.7 mmol, 2 equiv) was stirred at 0° C. under nitrogen for 30 minutes. Afterwards the mixture was subjected for 100° C. for 16 hours. The crude of the reaction was diluted with ethyl acetate and washed with water. The organic phase was dried over MgSO$_4$, filtered, and dried under vacuum. The crude was diluted with DMSO and submitted for preparative HPLC purification: UPLC system (XBridge™ Prep C18, 5 μm, 19×100 mm column); 8 min LC; flow: 20 mL/min; gradient: from 30% to 70% acetonitrile in water 0.1% TFA; to afford the final pure product (9 mg, 6% yield).

Compound 184

This compound was prepared via Method D using phenylmethanesulfonyl chloride.

The title compound was prepared by Method A using 3-[4-(4,4,5,5-tetramethyl-[1,3,2]dioxaborolan-2-yl)-pyrazol-1-ylmethyl]-pyridine.

Compound 186: Cyclopropanecarboxylic acid {5-[1-(3-phenyl-propionyl)-1H-pyrazol-4-yl]-[1,2,4]triazolo[1,5-a]pyridin-2-yl}-amide 186.1 3-Phenyl-1-[4-(4,4,5,5-tetramethyl-[1,3,2]dioxaborolan-2-yl)-pyrazol-1-yl]-propan-1-one

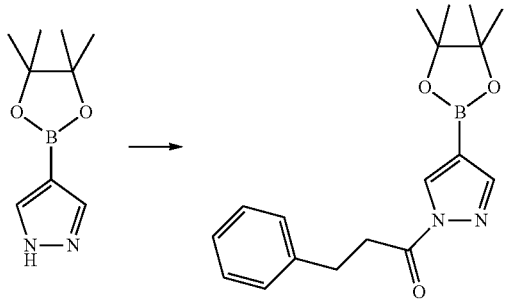

To a solution of 4-(4,4,5,5-tetramethyl-[1,3,2]dioxaborolan-2-yl)-1H-pyrazole (2.27 mmol; 1.0 equiv.) in DMF (10.0 mL) at room temperature were added under argon 3-phenyl-propionyl chloride (3.18 mmol; 1.4 aquiv.) and sodium hydride (3.18 mmol; 1.4 equiv.). The reaction mixture was heated at 60° C. The mixture was allowed to cool to room temperature and quenched by addition of a saturated aqueous solution of water (100 mL) and extracted with dichloromethane (2×100 mL). The organic layer was dried over sodium sulfate, filtered and concentrated to dryness. The resulting residue was purified by flash chromatography over silica gel (dichloromethane/ethyl acetate) to afford the expected boronate as a white solid used in the next step without further purification.

186.2 Cyclopropanecarboxylic acid {5-[1-(3-phenyl-propionyl)-1H-pyrazol-4-yl]-[1,2,4]triazolo[1,5-a]pyridin-2-yl}-amide

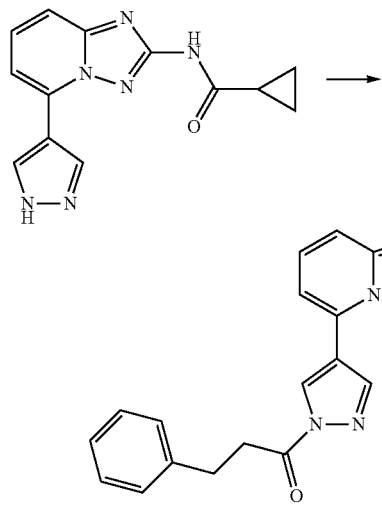

The title compound was prepared by Method A using 3-phenyl-1-[4-(4,4,5,5-tetramethyl-[1,3,2]dioxaborolan-2-yl)-pyrazol-1-yl]-propan-1-one.

Compound 187

This compound was prepared via Method K using azidomethyl-benzene.

Compound 188

This compound was prepared via Method K using 5-azidomethyl-2-trifluoromethyl-pyridine.

Compound 189

This compound was prepared via Method C using the metsylate derivative of 1-pyridin-2-yl-ethanol.

Compound 190

This compound was prepared via Method C using the mesylate derivative of 6-hydroxymethyl-nicotinic acid methyl ester.

Compound 191

This compound was prepared via Method D using cyclopropanesulfonyl chloride.

Compound 192: 5-{4-[2-(Cyclopropanecarbonyl-amino)-[1,2,4]triazolo[1,5-a]pyridin-5-yl]-phenoxymethyl}-pyridine-2-carboxylic acid amide

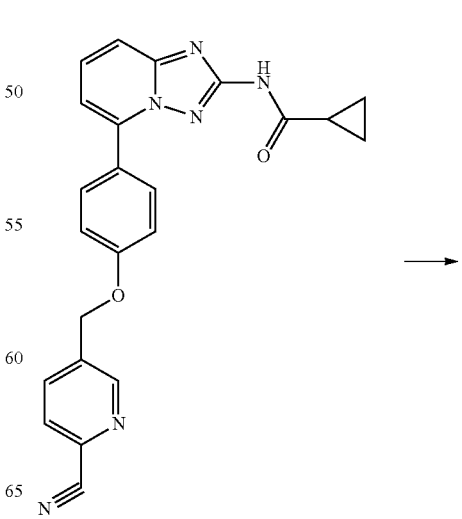

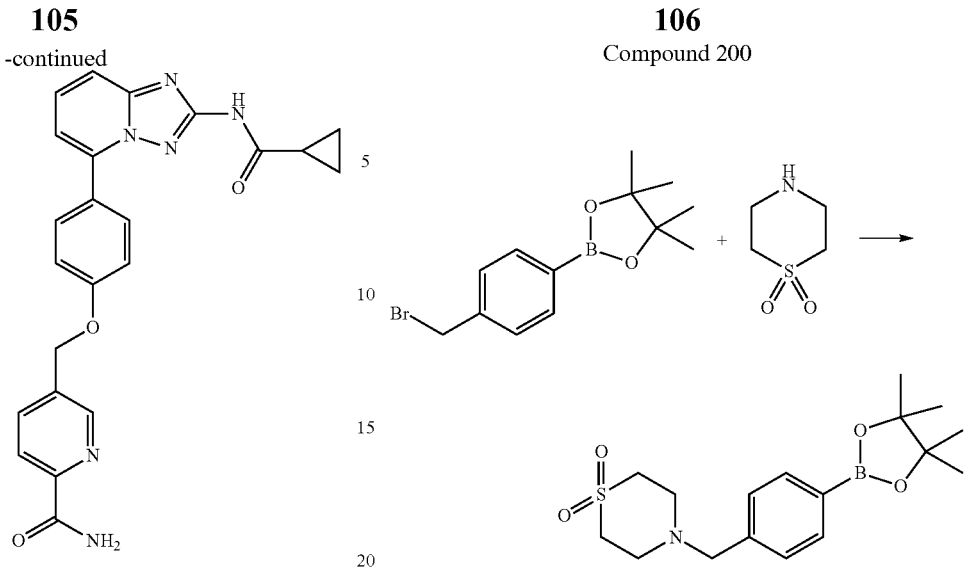

Compound 200

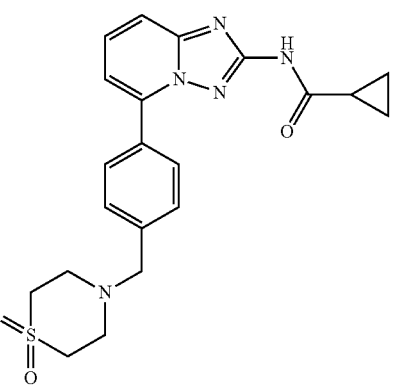

To a solution of cyclopropanecarboxylic acid {5-[4-(6-cyano-pyridin-3-ylmethoxy)-phenyl]-[1,2,4]triazolo[1,5-a]pyridin-2-yl}-amide (30 mg, 0.073 mmol, 1 equiv) and $K_2CO_3$ (10 mg, 0.073 mmol, 1 equiv) in DMSO (0.2 mL) at 10° C., 30% $H_2O_2$ (17 μL, 0.146 mmol, 2 equiv) was added dropwise. After stirring at room temperature the mixture for 4 h, the mixture was diluted with DMSO and filtered. The filtrate was submitted for preparative HPLC purification: UPLC system (XBridge™ Prep C18, 5 μm, 19×100 mm column); 8 min LC; flow: 20 mL/min; gradient: from 30% to 70% acetonitrile in water 0.1% TFA; isolating the final product (25 mg, 81% yield).

Compound 193

This compound was prepared via Method K using 2-azidomethyl-pyridine.

Compound 194

This compound was prepared via Method O using 2-bromomethyl-pyridine.

Compound 195

This compound was prepared via Method O using 3-bromomethyl-pyridine.

Compound 196

This compound was prepared via Method C using 3-chloromethyl-pyridine 1-oxide.

Compound 197

This compound was prepared via Method C using 5-chloromethyl-2-methyl-pyridine.

Compound 198

This compound was prepared via Method C using 2-chloro-5-chloromethyl-pyridine.

Compound 199

This compound was prepared via Method C using 3-chloromethyl-1-methyl-1H-[1,2,4]triazole.

2-(4-Bromomethyl-phenyl)-4,4,5,5-tetramethyl-[1,3,2]dioxaborolane (1 eq) and DIPEA (2 eq) are dissolved in DCM/MeOH (5:1 v:v) under $N_2$ and thiomorpholine 1,1-dioxide (2 eq) was added portionwise. The resulting solution was stirred at room temperature for 16 h. After this time, the reaction was complete. The solvent was evaporated. The compound was extracted with EtOAc and water, washed with brine and dried over $MgSO_4$. Organic layers were filtered and evaporated. The final compound was isolated without further purification.

Suzuki Coupling

4-[4-(4,4,5,5-Tetramethyl-[1,3,2]dioxaborolan-2-yl)-benzyl]-thiomorpholine-1,1-dioxide (1.1 eq.) was added to a solution of cyclopropanecarboxylic acid (5-bromo-[1,2,4]triazolo[1,5-a]pyridin-2-yl)-amide in 1,4-dioxane/water (4:1). $K_2CO_3$ (2 eq.) and $PdCl_2dppf$ (0.03 eq.) were added to the solution. The resulting mixture was then heated in an oil bath at 90° C. for 16 h under $N_2$. Water was added and the solution was extracted with ethyl acetate. The organic layers were dried over $MgSO_4$ and evaporated in vacuo. The final compound was obtained after purification by flash chromatography.

Alternative Route to Compound 200

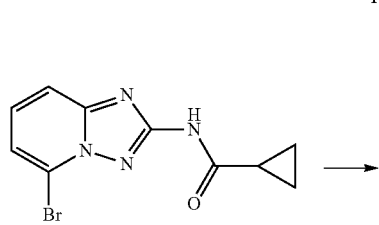

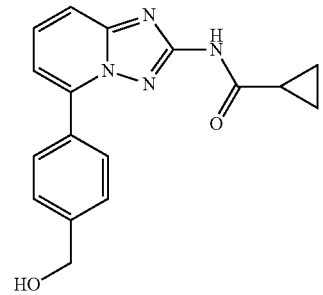

4-(Hydroxymethyl)phenylboronic acid (1.1 eq.) was added to a solution of cyclopropanecarboxylic acid (5-bromo-[1,2,4]triazolo[1,5-a]pyridin-2-yl)-amide in 1,4-dioxane/water (4:1). $K_2CO_3$ (2 eq.) and $PdCl_2dppf$ (0.03 eq.) were added to the solution. The resulting mixture was then heated in an oil bath at 90° C. for 16 h under $N_2$. Water was added and the solution was extracted with ethyl acetate. The organic layers were dried over $MgSO_4$ and evaporated in vacuo. The resulting mixture was used without further purification.

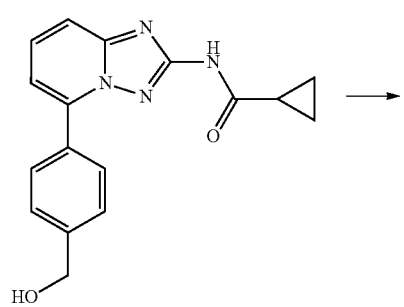

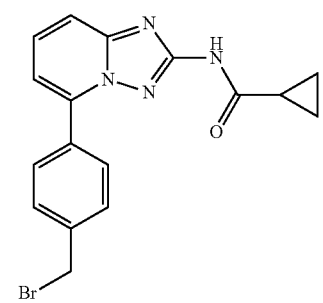

To a solution of cyclopropanecarboxylic acid [5-(4-hydroxymethyl-phenyl)-[1,2,4]triazolo[1,5-a]pyridin-2-yl]-amide (1.0 eq) in chloroform was slowly added the phosphorus tribromide (1.0 equiv.). The reaction mixture was stirred at room temperature for 20 hours, quenched with ice and water (20 mL) and extracted with dichloromethane. The organic layer was dried over $MgSO_4$, filtered and concentrated to dryness. The resulting white residue was triturated in dichloromethane/diethyl ether 2:1 (20 mL) to afford the expected product as a white solid.

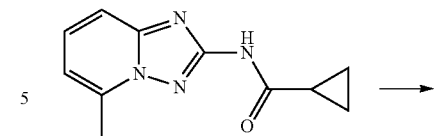

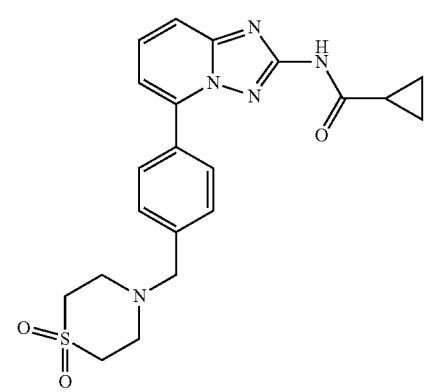

Cyclopropanecarboxylic acid [5-(4-bromomethyl-phenyl)-[1,2,4]triazolo[1,5-a]pyridin-2-yl]-amide (1 eq) and DIPEA (2 eq) were dissolved in DCM/MeOH (5:1 v:v) under $N_2$ and thiomorpholine 1,1-dioxide (1.1 eq) was added dropwise. The resulting solution was stirred at room temperature for 16 h. After this time, the reaction was complete. The solvent was evaporated. The compound was dissolved in DCM, washed with water and dried over $MgSO_4$. Organic layers were filtered and evaporated. The final compound was isolated by column chromatography using EtOAc to afford the desired product.

Compound 201

This compound was prepared via Method C using 4-(2-chloro-ethyl)-3,5-dimethyl-isoxazole.

Compound 202

This compound was prepared via Method P using 3-bromomethyl-pyridine.

Compound 203

This compound was prepared via Method B using 6-methoxy-pyridin-3-ylamine.

Compound 204

This compound was prepared via Method B using 6-morpholin-4-yl-pyridin-3-ylamine.

Compound 205

This compound was prepared via Method B using 6-(4-methyl-piperazin-1-yl)-pyridin-3-ylamine.

Compound 206

This compound was prepared via Method B using pyridin-3-ylamine.

Compound 207

This compound was prepared via Method B using thiomorpholine 1,1-dioxide.

Compound 208

This compound was prepared via Method P using 3-bromomethyl-pyridine.

Compound 209

This compound was prepared via Method B using 4-hydroxy piperidine.

Compound 210

This compound was prepared via Method B using piperidine-4-carbonitrile.

Compound 211: Cyclopropanecarboxylic acid {5-[4-(2-pyridin-2-yl-ethyl)-phenyl]-[1,2,4]triazolo[1,5-a]pyridin-2-yl}-amide

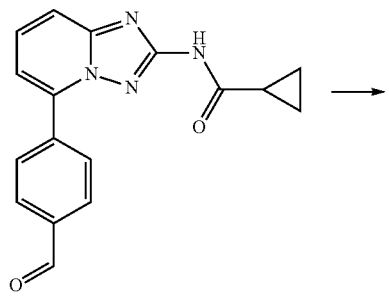

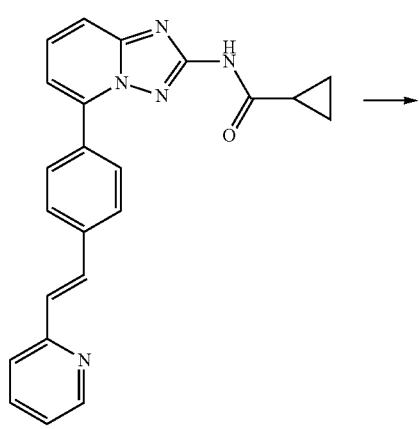

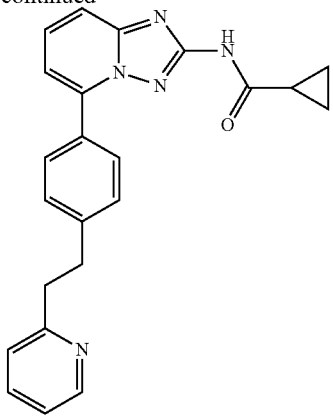

Potassium tert-butoxide (1.3 eq.) was added to an ice-cooled solution of 2-[(triphenyl-λ5-phosphanyl)-methyl]-pyridine (1.1 eq.) in THF (10 mL/mmol). The resulting mixture was stirred for 30 min at 0° C., then at room temperature for another 30 min. A solution of cyclopropanecarboxylic acid [8-(4-formyl-phenyl)-[1,2,4]triazolo[1,5-a]pyridin-2-yl]-amide (1 eq.) in THF (10 mL/mmol) was added dropwise to the reaction mixture. The stirring was maintained for 8 hrs. The reaction was then quenched with water and extracted with ethyl actate. The organic phase was dried aver $MgSO_4$, filtered and removed under vacuum. The solid was washed with methanol to afford the title compound in 69% yield.

Cyclopropanecarboxylic acid {5-[4-((E)-2-pyridin-3-yl-vinyl)-phenyl]-[1,2,4]triazolo[1,5-a]pyridin-2-yl}-amide (320 mg, 0.84 mol) was dissolved in 10 mL MeOH. Pd/C (50 mg) was added and the reaction is put under $H_2$ at normal pressure. The reaction was stirred for 2 hrs. The reaction mixture was filtered through Celite®. The organic solvent was removed under pressure. $NaHCO_3$ saturated solution was added to resulting mixture. The compound was extracted with EtOAc. The organic phase was dried over $MgSO_4$, filtered and removed under vacuum to afford the title compound in 100% yield.

Compound 212

This compound was prepared via Method J using 4-chloro-2-fluoro-phenylamine.

Compound 213

This compound was prepared via Method J using 3,3-dimethyl-morpholine.

Compound 214

This compound was prepared via Method J using cis-2,6-dimethyl-morpholine.

Compound 215

This compound was prepared via Method B using cis-2,6-dimethyl-morpholine.

Compound 216

This compound was prepared via Method B using 3,3-dimethyl-morpholine.

Compound 217

This compound was prepared via Method B using (1S,4S)-2-oxa-5-aza-bicyclo[2.2.1]heptanes.

Compound 218

This compound was prepared via Method B using 5-cyclopropyl-2-methyl-2H-pyrazol-3-ylamine.

Compound 219

This compound was prepared via Method B using morpholin-4-yl-piperidin-4-yl-methanone.

Compound 220

This compound was prepared via Method B using 1-piperazin-1-yl-ethanone.

Compound 221

This compound was prepared via Method B using pyridazin-3-ylamine.

Compound 222

This compound was prepared via Method J using pyridazin-3-ylamine.

Compound 223

This compound was prepared via Method J using pyridin-3-ylamine.

Compound 224

This compound was prepared via Method J using (4-amino-phenyl)-acetonitrile.

Compound 225

This compound was prepared via Method J using (2-amino-phenyl)-acetonitrile.

Compound 226

This compound was prepared via Method J using (4-amino-phenyl)-acetonitrile.

Compound 227

This compound was prepared via Method J using 4-amino-benzamide.

Compound 228

This compound was prepared via Method J using 3-amino-benzamide.

Compound 229

This compound was prepared via Method J using pyrimidin-2-ylamine.

Compound 230

This compound was prepared via Method J using (1S,4S)-2-oxa-5-aza-bicyclo[2.2.1]heptane.

Compound 231

This compound was prepared via Method J using 2-phenyl-morpholine.

Compound 232

This compound was prepared via Method J using piperidine-4-carbonitrile.

Compound 233

This compound was prepared via Method J using 4-fluoropiperidine.

Compound 234

This compound was prepared via Method J using 4,4-difluoropiperidine.

Compound 235

This compound was prepared via Method J using 6-(4-methyl-piperazin-1-yl)-pyridin-3-ylamine.

Compound 236

This compound was prepared via Method J using 6-methoxy-pyridin-3-ylamine.

Compound 237

This compound was prepared via Method J using 6-morpholin-4-yl-pyridin-3-ylamine.

Compound 238

This compound was prepared via Method Q using phenol.

Compound 239: Cyclopropanecarboxylic acid {5-[4-(6-cyano-pyridin-3-yl)-phenyl]-[1,2,4]triazolo[1,5-a]pyridin-2-yl}-amide

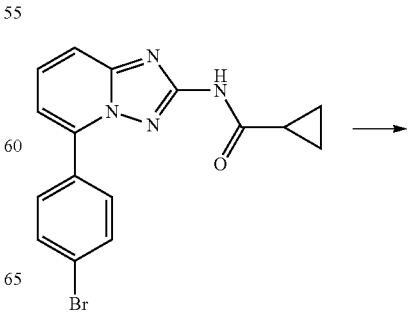

4-(4,4,5,5-tetramethyl-[1,3,2]dioxaborolan-2-yl)-benzonitrile (1.1 eq.) was added to a solution of cyclopropanecarboxylic acid [5-(4-bromo-phenyl)-[1,2,4]triazolo[1,5-a]pyridin-2-yl]-amide, prepared by method A in 1,4-Dioxane/water (5:1). $K_2CO_3$ (2 eq.) and $Pd(dppf)Cl_2$ (0.03 eq.) (dppf=1,1'-Bis(diphenylphosphino)ferrocene) were added to the solution. The resulting mixture was then heated in a sealed tube at 90° C. for 16 hrs. Water was added and the solution was extracted with ethyl acetate. The organic layers were dried over $MgSO_4$ and evaporated in vacuo. The final compound was obtained after purification by preparative HPLC. Analytical: Waters Acquity UPLC BEH C18 1.7 μm, 2.1 mm ID×50 mm L (Part No. 186002350).

Compound 240

This compound was prepared via Method J using 4-trifluoromethyl piperidine.

Compound 241

This compound was prepared via Method J using 1-(2,2,2-trifluoro-ethyl)-piperazine.

Compound 242

This compound was prepared via Method J using 4-hydroxy-piperidine.

Compound 243

This compound was prepared via Method J using 2-piperidin-4-yl-propan-2-ol.

Compound 244

This compound was prepared via Method J using pyridin-2-ylamine.

Compound 245

This compound was prepared via Method J using 2,4-difluoro-3-methoxy-phenylamine.

Compound 246

This compound was prepared via Method J using 2,6-difluoro-phenylamine

Compound 247

This compound was prepared via Method J using diethyl-piperidin-4-yl-amine.

Compound 248

This compound was prepared via Method J using 2-fluoro-5-trifluoromethyl-phenylamine.

Compound 249

This compound was prepared via Method J using 3-amino-4-methyl-benzamide.

Compound 250

This compound was prepared via Method J using piperidin-4-yl-methanol.

Compound 251

This compound was prepared via Method Q using 3-hydroxy-benzamide.

Compound 252

This compound was prepared via Method J using diethyl-pyrrolidin-3-yl-amine.

Compound 253

This compound was prepared via Method J using (1R,4R)-2-ethyl-2,5-diaza-bicyclo[2.2.1]heptane.

Compound 254: Cyclopropanecarboxylic acid {5-[4-(3-oxo-morpholin-4-ylmethyl)-phenyl]-[1,2,4]triazolo[1,5-a]pyridin-2-yl}-amide

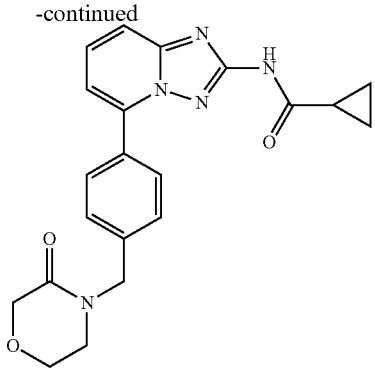

254.1 4-[4-(4,4,5,5-Tetramethyl-[1,3,2]dioxaborolan-2-yl)-benzyl]-morpholin-3-one

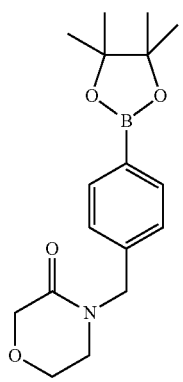 [SMILES: CC1(C)OB(c2ccc(CN3CCOCC3=O)cc2)OC1(C)C]

NaH (81 mg, 3 eq.) was added to a solution of morpholin-3-one in DCM. 2-(4-bromomethyl-phenyl)-4,4,5,5-tetramethyl-[1,3,2]dioxaborolane was added to the resulting solution and the reaction was stirred at room temperature for 16 hrs. DCM was evaporated, followed by addition of water. The solution was extracted with EtOAc. The organic layers were dried over $MgSO_4$ and evaporated in vacuo to afford the title product used in the next step without further purification.

254.2 Cyclopropanecarboxylic acid {5-[4-(3-oxo-morpholin-4-ylmethyl)-phenyl]-[1,2,4]triazolo[1,5-a]pyridin-2-yl}-amide

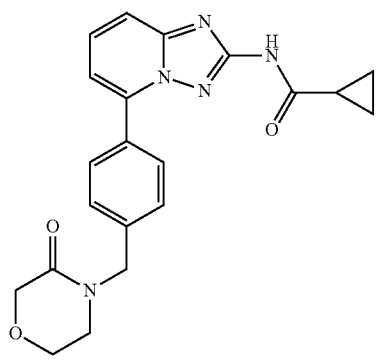 [SMILES: O=C(Nc1nc2cccc(-c3ccc(CN4CCOCC4=O)cc3)n2n1)C1CC1]

The title compound was then synthesized by Method A.

Compound 255

This compound was prepared via Method J using 3-amino-4-methoxy-benzamide.

Compound 256

This compound was prepared via Method J using 2-fluoro-6-methyl-pyridin-3-ylamine.

Compound 257

This compound was prepared via Method J using 3,5-difluoro-pyridin-2-ylamine.

Compound 258

This compound was prepared via Method J using 4-amino-3-fluoro-benzonitrile.

Compound 259

This compound was prepared via Method J using 2-fluoro-4-methyl-phenylamine.

Compound 260

This compound was prepared via Method J using pyrrolidine.

Compound 261

This compound was prepared via Method J using aniline.

Compound 262

This compound was prepared via Method J using N-methyl-N-pyrrolidin-3-yl-acetamide.

Compound 263

This compound was prepared via Method J using dimethyl-pyrrolidin-3-yl-amine.

Compound 264

This compound was prepared via Method J using 3,3-difluoro-pyrrolidine.

Compound 265

This compound was prepared via Method J using 4-(azetidin-3-ylmethoxy)-benzonitrile.

Compound 266

This compound was prepared via Method U using piperidine.

Compound 267

This compound was prepared via Method U using thiomorpholine 1,1-dioxide.

Compound 268

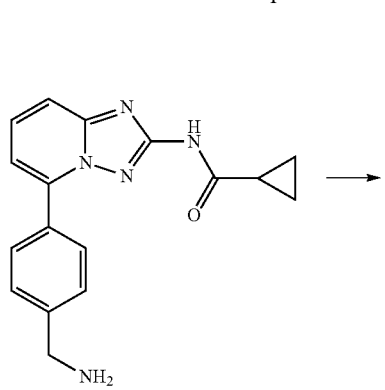

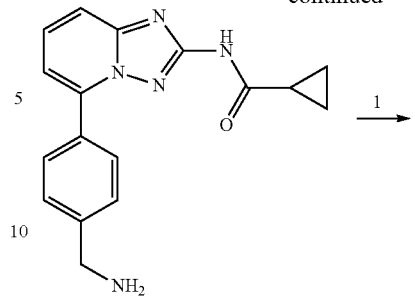

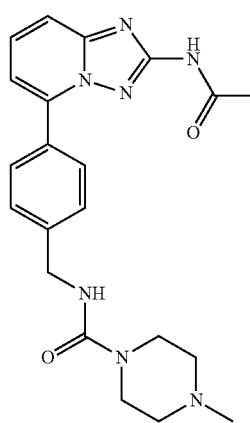

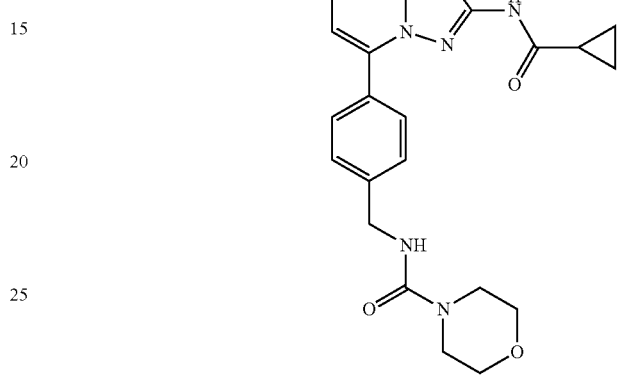

Cyclopropanecarboxylic acid [5-(4-aminomethyl-phenyl)-[1,2,4]triazolo[1,5-a]pyridin-2-yl]-amide (1 eq), CDI (1.1 eq) and Et₃N (2.5 eq) in DCM were mixed together at 50° C. for 1 h. The solvent was evaporated and the resulting mixture was dissolved in DMF. N-methyl-pyrazine was added to the obtained mixture. The solution was stirred at 50° C. for 18 h. After completion of the reaction water was added and the organic phase was extracted with EtOAc. The organic layers were dried over MgSO₄ and evaporated in vacuo to afford the title product purified by flash chromatography.

Morpholine (1 eq), CDI (1.1 eq) and Et₃N (2.5 eq) in THF were mixed together at reflux for 18 h. The solvent was evaporated and the resulting mixture was dissolved in acetonitrile. Methyl Iodide was added to the resulting solution. The reaction was allowed to stir at room temperature for 18 h. The solvent was evaporated and the resulting mixture was dissolved in DMF. Cyclopropanecarboxylic acid [5-(4-aminomethyl-phenyl)-[1,2,4]triazolo[1,5-a]pyridin-2-yl]-amide (1 eq) and Et₃N (2.5 eq) were added to the solution which was then allowed to stirred at room temperature for 18 hrs. Water was added and the solution was extracted with EtOAc. The organic layers were dried over MgSO₄ and evaporated in vacuo to afford the title product purified by flash chromatography.

Compound 269

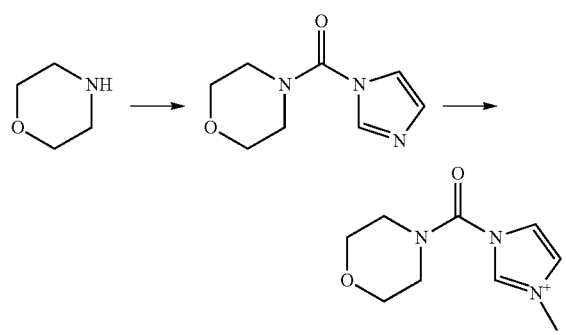

Compound 268

This compound was prepared via Method V using cyclobutanecarbonyl chloride.

Compound 269

This compound was prepared via Method B using dimethyl-piperidin-3-yl-amine.

Compound 270

This compound was prepared via Method B using piperidin-3-ol.

Compound 271

This compound was prepared via Method B using 3,3-difluoro-pyrrolidine.

Compound 272

This compound was prepared via Method V using cyclopropanecarbonyl chloride.

Compound 273

This compound was prepared via Method B using (1,1-dioxo-tetrahydrothiophen-3-yl)-methyl-amine.

Compound 274

This compound was prepared via Method B using piperidine-4-carboxylic acid amide.

Compound 275

This compound was prepared via Method B using piperidine-2-carboxylic acid amide.

Compound 276

This compound was prepared via Method B using piperidin-3-yl-methanol.

Compound 277

This compound was prepared via Method B using piperazin-2-one.

Compound 278

This compound was prepared via Method J using 4-(azetidin-3-yloxy)-benzonitrile.

Compound 279

This compound was prepared via Method J using azetidin-3-yl-carbamic acid tert-butyl ester.

Compound 280

This compound was prepared via Method J using 4-trifluoromethyl-piperidine.

Compound 281

This compound was prepared via Method J using 4-methoxy-piperidine.

Compound 282

This compound was prepared via Method J using 4-ethoxy-piperidine.

Compound 283

This compound was prepared via Method J using N-azetidin-3-yl-N-methyl-acetamide.

Compound 284

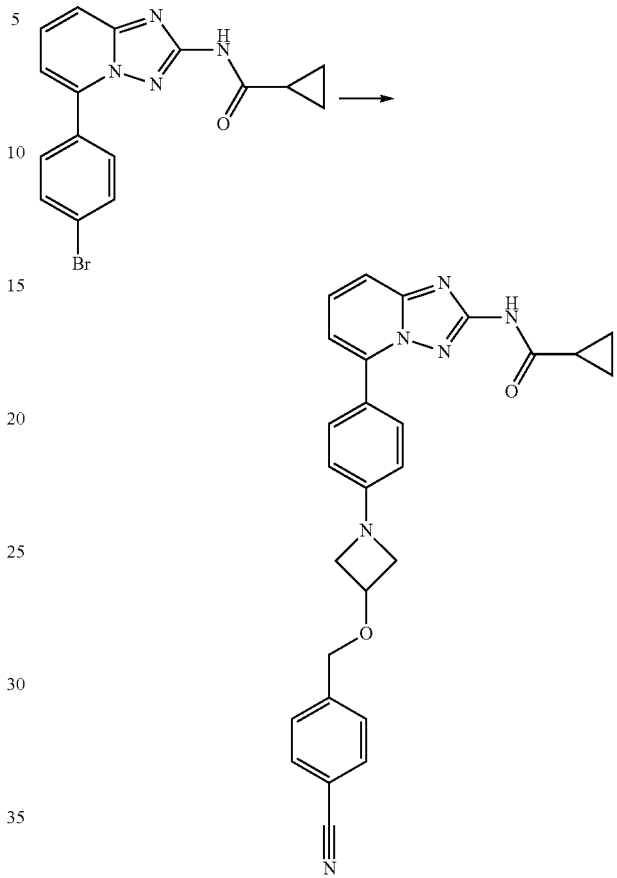

The crude cyclopropanecarboxylic acid [5-(4-bromo-phenyl)-[1,2,4]triazolo[1,5-a]pyridin-2-yl]-amide (1.0 equiv.) prepared by Method A was mixed together with 4-(azetidin-3-yloxymethyl)-benzonitrile (1.2 equiv.) and potassium tert-butoxide (2.0 equiv.), in dry 1,4-dioxane (1 mL). The mixture was stirred at 80° C. under nitrogen. Afterwards, Pd(OAc)$_2$ (0.1 equiv.) and BINAP (0.1 equiv.) in dry 1,4-dioxane (1 mL), were added with a syringe to the reaction mixture. The reaction was stirred overnight. LCMS showed the presence of the desired product. The mixture was filtered and submitted for preparative HPLC purification, to afford the pure product.

Compound 285

This compound was prepared via Method B using diethyl-pyrrolidin-3-yl-amine.

Compound 286

This compound was prepared via Method B using 4-phenyl-piperidin-4-ol.

Compound 287

This compound was prepared via Method B using N-azetidin-3-yl-acetamide.

Compound 288

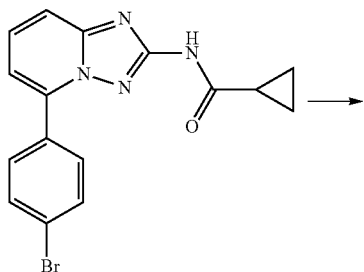 →

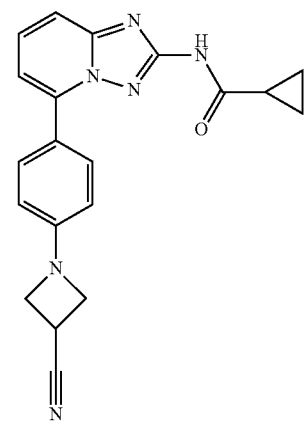

The crude cyclopropanecarboxylic acid [5-(4-bromo-phenyl)-[1,2,4]triazolo[1,5-a]pyridin-2-yl]-amide (1.0 equiv.) prepared by method A was mixed together with azetidine-3-carbonitrile (1.2 equiv.) and potassium tert-butoxide (2.0 equiv.), in dry 1,4-dioxane (1 mL). The mixture was stirred at 80° C. under nitrogen. Afterwards, Pd(OAc)$_2$ (0.1 equiv.) and BINAP (0.1 equiv.) in dry 1,4-dioxane (1 mL), were added with a syringe to the reaction mixture. The reaction was stirred overnight. LCMS showed the presence of the desired product. The mixture was filtered and submitted for preparative HPLC purification, to afford the pure product.

Compound 289

This compound was prepared via Method B using dimethyl-pyrrolidin-3-yl-amine.

Compound 290

This compound was prepared via Method B using piperidin-1-yl-piperidin-3-yl-methanone.

Compound 291

This compound was prepared via Method J using azetidin-3-yl-dimethyl-amine.

Compound 292

This compound was prepared via Method B using 3-(piperidin-4-ylmethoxy)-pyridine.

Compound 293

This compound was prepared via Method B using 4-methoxy-piperidine.

Compound 294

This compound was prepared via Method B using 4-ethoxy-piperidine

Compound 295

This compound was prepared via Method B using Piperidine-3-carboxylic acid diethylamide.

Compound 296

This compound was prepared via Method B using N-piperidin-3-yl-acetamide.

Compound 297

This compound was prepared via Method P using 5-chloromethyl-pyridine-2-carbonitrile.

Compound 298

This compound was prepared via Method J using azetidin-3-ylmethyl-dimethyl-amine.

Compound 299

This compound was prepared via Method J using azetidine-3-carboxylic acid dimethylamide.

Compound 300

This compound was prepared via Method J using 4-piperidin-4-yl-morpholine.

Compound 301

This compound was prepared via Method Q using (4-hydroxy-phenyl)-acetonitrile.

Compound 302

This compound was prepared via Method J using isoxazol-3-ylamine.

Compound 303

This compound was prepared via Method J using azetidine-3-carbonitrile.

Compound 304

This compound was prepared via Method J using 1,1-dioxo-tetrahydrothiophen-3-ylamine.

Compound 305

This compound was prepared via Method J using (S)-pyrrolidin-3-ol.

Compound 306

This compound was prepared via Method J using 2-aminobenzamide.

Compound 307

This compound was prepared via Method using (R)-pyrrolidin-3-ol.

123

Compound 308

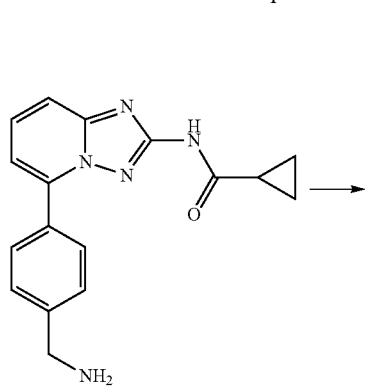

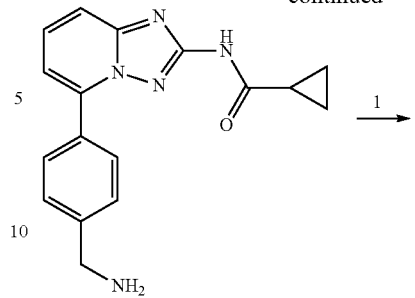

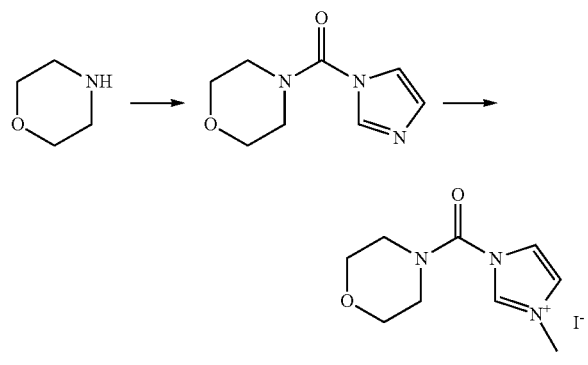

Cyclopropanecarboxylic acid [5-(4-aminomethyl-phenyl)-[1,2,4]triazolo[1,5-a]pyridin-2-yl]-amide (1 eq), CDI (1.1 eq) and Et₃N (2.5 eq) in DCM were mixed together at 50° C. for 1 h. The solvent was evaporated and the resulting mixture was dissolved in DMF. N-methyl-pyrazine was added to the obtained mixture. The solution was stirred at 50° C. for 18 h. After completion of the reaction water was added and the organic phase was extracted with EtOAc. The organic layers were dried over MgSO₄ and evaporated in vacuo to afford the title product purified by flash chromatography.

Compound 309

124

-continued

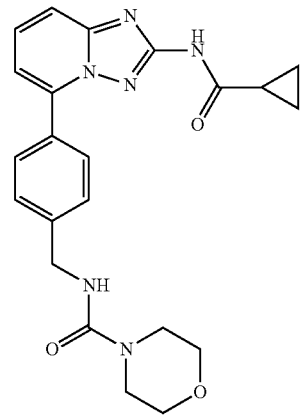

Morpholine (1 eq), CDI (1.1 eq) and Et₃N (2.5 eq) in THF were mixed together at reflux for 18 h. The solvent was evaporated and the resulting mixture was dissolved in acetonitrile. Methyl iodide was added to the resulting solution. The reaction was allowed to stir at room temperature for 18 h. The solvent was evaporated and the resulting mixture was dissolved in DMF. Cyclopropanecarboxylic acid [5-(4-aminomethyl-phenyl)-[1,2,4]triazolo[1,5-a]pyridin-2-yl]-amide (1 eq) and Et₃N (2.5 eq) were added to the solution which was then allowed to stirred at room temperature for 18 hrs. Water was added and the solution was extracted with EtOAc. The organic layers were dried over MgSO₄ and evaporated in vacuo to afford the title product purified by flash chromatography.

Compound 310

This compound was prepared via Method J using piperidin-4-yl-carbamic acid tert-butyl ester.

Compound 311

This compound was prepared via Method J using piperazin-2-one.

Compound 312

This compound was prepared via Method J using cyclopropylamine.

Compound 313

This compound was prepared via Method J using 3-hydroxy-piperidine.

Compound 314

This compound was prepared via Method J using 3,3-dimethylazetidine.

Compound 315

This compound was prepared via Method J using 3,4-difluoro-azetidine

Compound 316

This compound was prepared via Method U using pyridin-3-ylamine.

Compound 317

This compound was prepared via Method U using 3,3-difluoro-azetidine.

Compound 318

This compound was prepared via Method U using azetidine.

Compound 319

This compound was prepared via Method U using 4-trifluoromethyl-piperidine.

Compound 320

This compound was prepared via Method U using 4,5-dimethyl piperidine.

Compound 321

This compound was prepared via Method U using 3-methoxy-azetidine.

Compound 322

This compound was prepared via Method U using N-azetidin-3-yl-acetamide.

Compound 323

This compound was prepared via Method U using N-piperidin-4-yl-acetamide.

Compound 324

This compound was prepared via Method U using azetidine-3-carboxylic acid dimethylamide.

Compound 325

This compound was prepared via Method B using 4-(azetidin-3-yloxymethyl)-benzonitrile.

Compound 326

This compound was prepared via Method B using 4-azetidin-3-yl-morpholine.

Compound 327

This compound was prepared via Method B using azetidin-3-yl-dimethyl-amine

Compound 328

This compound was prepared via Method B using azetidine-3-carbonitrile.

Compound 329

This compound was prepared via Method B using azetidin-3-ylmethyl-dimethyl-amine.

Compound 330

This compound was prepared via Method B using 3,3-dimethyl-azetidine.

Compound 331

This compound was prepared via Method B using 1H-[1,2,4]triazol-3-ylamine

The exemplary compounds that have been or can be prepared according to the synthetic methods described herein are listed in Table I below. The NMR spectral data of some representative compounds of the invention is given in Table II.

TABLE I

| Cpd # | Structures | Name | MW | MS Mes'd |
|---|---|---|---|---|
| 1 | 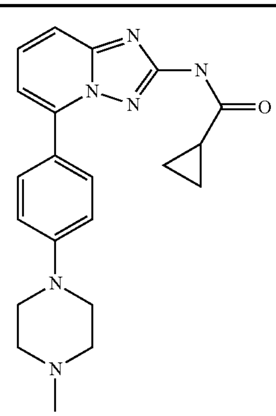 | N-(5-(4-(4-methylpiperazin-1-yl)phenyl)-[1,2,4]triazolo[1,5-a]pyridin-2-yl)cyclopropanecarboxamide | 376 | N/A |

TABLE I-continued

| Cpd # | Structures | Name | MW | MS Mes'd |
|---|---|---|---|---|
| 2 | 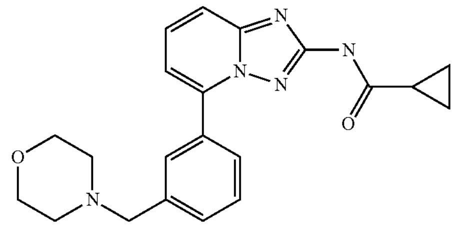 [SMILES: O=C(Nc1nc2cccc(-c3cccc(CN4CCOCC4)c3)n2n1)C1CC1] | N-(5-(3-(morpholinomethyl)phenyl)-[1,2,4]triazolo[1,5-a]pyridin-2-yl)cyclopropanecarboxamide | 377.45 | 378.20 |
| 3 | 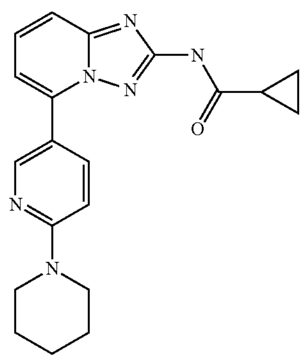 [SMILES: O=C(Nc1nc2cccc(-c3ccc(N4CCCCC4)nc3)n2n1)C1CC1] | N-(5-(6-(piperidin-1-yl)pyridin-3-yl)-[1,2,4]triazolo[1,5-a]pyridin-2-yl)cyclopropanecarboxamide | 362.44 | 363.10 |
| 4 | 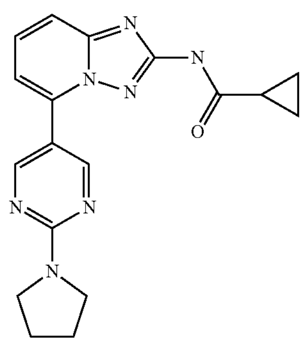 [SMILES: O=C(Nc1nc2cccc(-c3cnc(N4CCCC4)nc3)n2n1)C1CC1] | N-(5-(2-(pyrrolidin-1-yl)pyrimidin-5-yl)-[1,2,4]triazolo[1,5-a]pyridin-2-yl)cyclopropanecarboxamide | 349.40 | 350.10 |
| 5 | 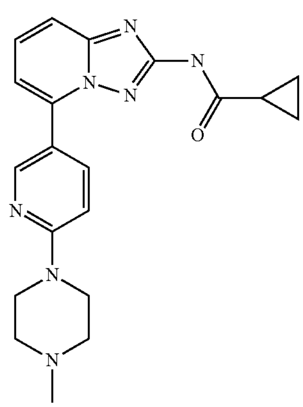 [SMILES: CN1CCN(c2ccc(-c3cccc4nc(NC(=O)C5CC5)nn34)cn2)CC1] | N-(5-(6-(4-methylpiperazin-1-yl)pyridin-3-yl)-[1,2,4]triazolo[1,5-a]pyridin-2-yl)cyclopropanecarboxamide | 377.45 | 378.20 |

TABLE I-continued
| Cpd # | Structures | Name | MW | MS Mes'd |
|---|---|---|---|---|
| 6 | 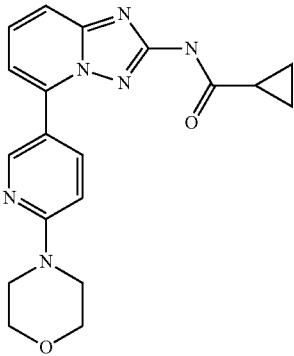 | N-(5-(6-morpholinopyridin-3-yl)-[1,2,4]triazolo[1,5-a]pyridin-2-yl)cyclopropanecarboxamide | 364.41 | 365.10 |
| 7 | 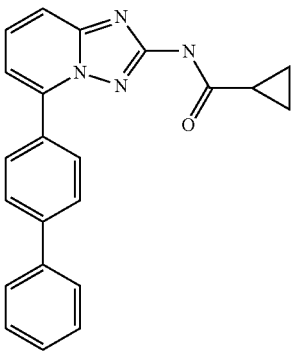 [SMILES: O=C(Nc1nc2cccc(-c3ccc(-c4ccccc4)cc3)n2n1)C1CC1] | N-(5-(biphenyl-4-yl)-[1,2,4]triazolo[1,5-a]pyridin-2-yl)cyclopropanecarboxamide | 354.41 | 355.10 |
| 8 | 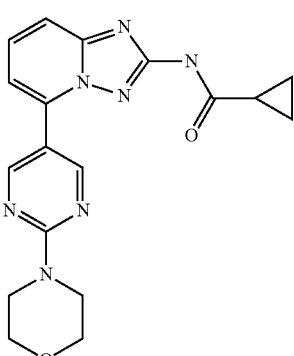 | N-(5-(2-morpholinopyrimidin-5-yl)-[1,2,4]triazolo[1,5-a]pyridin-2-yl)cyclopropanecarboxamide | 365.40 | 366.10 |
| 9 | 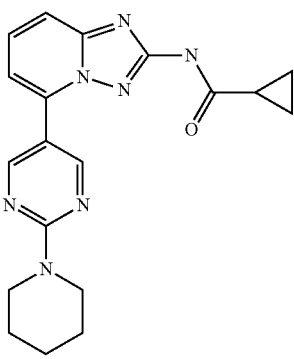 [SMILES: O=C(Nc1nc2cccc(-c3cnc(N4CCCCC4)nc3)n2n1)C1CC1] | N-(5-(2-(piperidin-1-yl)pyrimidin-5-yl)-[1,2,4]triazolo[1,5-a]pyridin-2-yl)cyclopropanecarboxamide | 363.43 | 364.10 |

TABLE I-continued

| Cpd # | Structures | Name | MW | MS Mes'd |
|---|---|---|---|---|
| 10 | 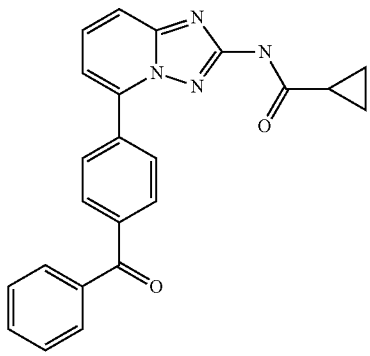 [SMILES: O=C(c1ccccc1)c1ccc(-c2cccc3nc(NC(=O)C4CC4)nn23)cc1] | N-(5-(4-benzoylphenyl)-[1,2,4]triazolo[1,5-a]pyridin-2-yl)cyclopropanecarboxamide | 382.43 | 383.10 |
| 11 | 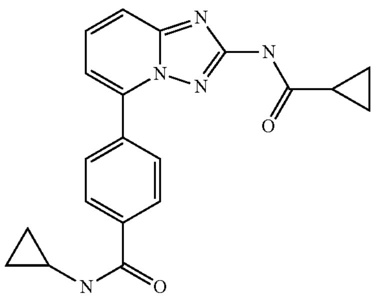 [SMILES: O=C(NC1CC1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-cyclopropylbenzamide | 361.41 | 362.10 |
| 12 | 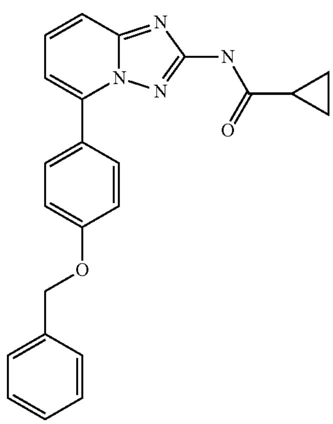 [SMILES: O=C(Nc1nc2cccc(-c3ccc(OCc4ccccc4)cc3)n2n1)C1CC1] | N-(5-(4-(benzyloxy)phenyl)-[1,2,4]triazolo[1,5-a]pyridin-2-yl)cyclopropanecarboxamide | 384.44 | 385.10 |
| 13 | 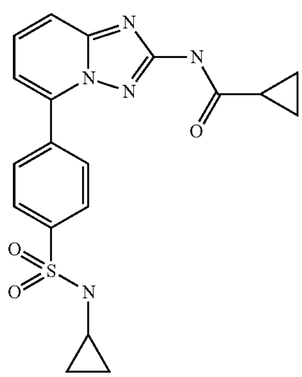 [SMILES: O=C(Nc1nc2cccc(-c3ccc(S(=O)(=O)NC4CC4)cc3)n2n1)C1CC1] | N-(5-(4-(N-cyclopropylsulfamoyl)phenyl)-[1,2,4]triazolo[1,5-a]pyridin-2-yl)cyclopropanecarboxamide | 397.46 | 398.10 |

TABLE I-continued
| Cpd # | Structures | Name | MW | MS Mes'd |
|---|---|---|---|---|
| 14 | 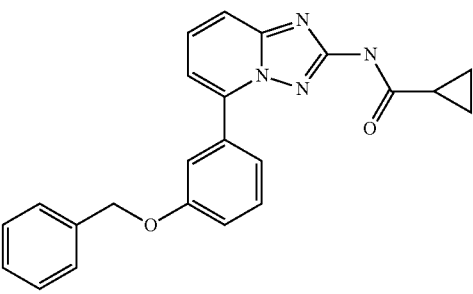 [SMILES: O=C(Nc1nc2cccc(-c3cccc(OCc4ccccc4)c3)n2n1)C1CC1] | N-(5-(3-(benzyloxy)phenyl)-[1,2,4]triazolo[1,5-a]pyridin-2-yl)cyclopropanecarboxamide | 384.44 | 385.20 |
| 15 | 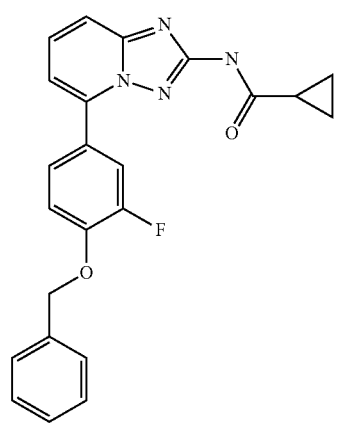 [SMILES: O=C(Nc1nc2cccc(-c3ccc(OCc4ccccc4)c(F)c3)n2n1)C1CC1] | N-(5-(4-(benzyloxy)-3-fluorophenyl)-[1,2,4]triazolo[1,5-a]pyridin-2-yl)cyclopropanecarboxamide | 402.43 | 403.10 |
| 16 | 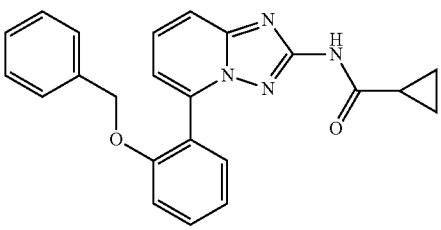 [SMILES: O=C(Nc1nc2cccc(-c3ccccc3OCc3ccccc3)n2n1)C1CC1] | N-(5-(2-(benzyloxy)phenyl)-[1,2,4]triazolo[1,5-a]pyridin-2-yl)cyclopropanecarboxamide | 384.44 | 385.20 |
| 17 | 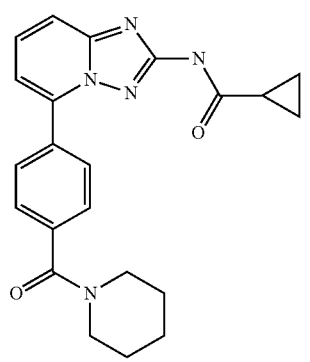 [SMILES: O=C(Nc1nc2cccc(-c3ccc(C(=O)N4CCCCC4)cc3)n2n1)C1CC1] | N-(5-(4-(piperidine-1-carbonyl)phenyl)-[1,2,4]triazolo[1,5-a]pyridin-2-yl)cyclopropanecarboxamide | 389.46 | 390.10 |

TABLE I-continued
| Cpd # | Structures | Name | MW | MS Mes'd |
|---|---|---|---|---|
| 18 | 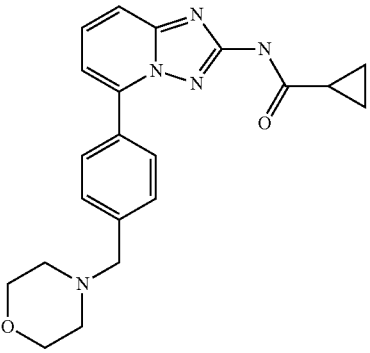 [SMILES: O=C(Nc1nc2cccc(-c3ccc(CN4CCOCC4)cc3)n2n1)C1CC1] | N-(5-(4-(morpholinomethyl)phenyl)-[1,2,4]triazolo[1,5-a]pyridin-2-yl)cyclopropanecarboxamide | 377.45 | 378.20 |
| 19 | 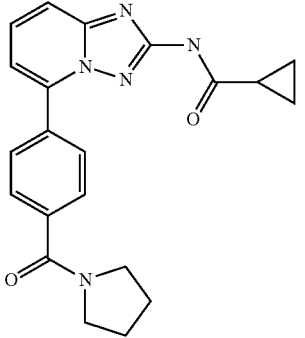 [SMILES: O=C(Nc1nc2cccc(-c3ccc(C(=O)N4CCCC4)cc3)n2n1)C1CC1] | N-(5-(4-(pyrrolidine-1-carbonyl)phenyl)-[1,2,4]triazolo[1,5-a]pyridin-2-yl)cyclopropanecarboxamide | 375.43 | 376.20 |
| 20 | 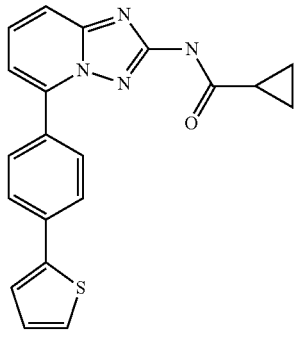 [SMILES: O=C(Nc1nc2cccc(-c3ccc(-c4cccs4)cc3)n2n1)C1CC1] | N-(5-(4-(thiophen-2-yl)phenyl)-[1,2,4]triazolo[1,5-a]pyridin-2-yl)cyclopropanecarboxamide | 360.44 | 361.00 |
| 21 | 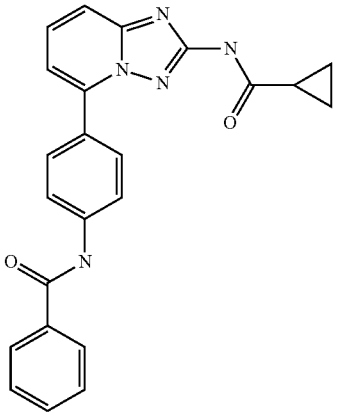 [SMILES: O=C(Nc1ccc(-c2cccc3nc(NC(=O)C4CC4)nn23)cc1)c1ccccc1] | N-(4-(2-(cyclopropanecarboxamido)-[1,2,4]triazolo[1,5-a]pyridin-5-yl)phenyl)benzamide | 397.44 | 398.00 |

TABLE I-continued

| Cpd # | Structures | Name | MW | MS Mes'd |
|---|---|---|---|---|
| 22 | 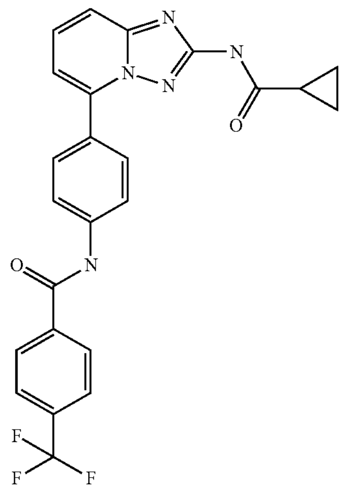 [SMILES: O=C(Nc1ccc(-c2cccc3nc(NC(=O)C4CC4)nn23)cc1)c1ccc(C(F)(F)F)cc1] | N-(4-(2-(cyclopropanecarboxamido)-[1,2,4]triazolo[1,5-a]pyridin-5-yl)phenyl)-4-(trifluoromethyl)benzamide | 465.44 | 465.90 |
| 23 | 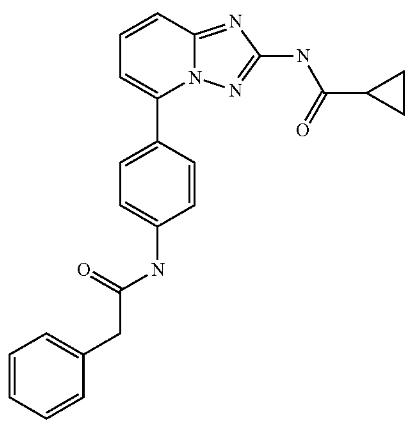 [SMILES: O=C(Cc1ccccc1)Nc1ccc(-c2cccc3nc(NC(=O)C4CC4)nn23)cc1] | N-(5-(4-(2-phenylacetamido)phenyl)-[1,2,4]triazolo[1,5-a]pyridin-2-yl)cyclopropanecarboxamide | 411.47 | 412.00 |
| 24 | 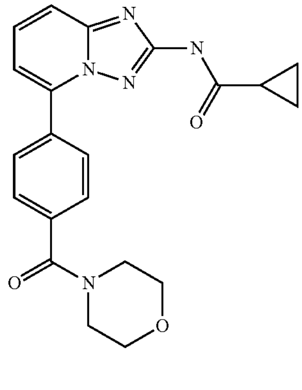 [SMILES: O=C(Nc1nc2cccc(-c3ccc(C(=O)N4CCOCC4)cc3)n2n1)C1CC1] | N-(5-(4-(morpholine-4-carbonyl)phenyl)-[1,2,4]triazolo[1,5-a]pyridin-2-yl)cyclopropanecarboxamide | 391.43 | 392.00 |

TABLE I-continued

| Cpd # | Structures | Name | MW | MS Mes'd |
|---|---|---|---|---|
| 25 | 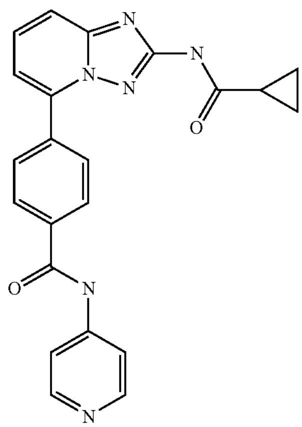 [SMILES: O=C(Nc1ccncc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(pyridin-4-yl)benzamide | 398.43 | 399.00 |
| 26 | 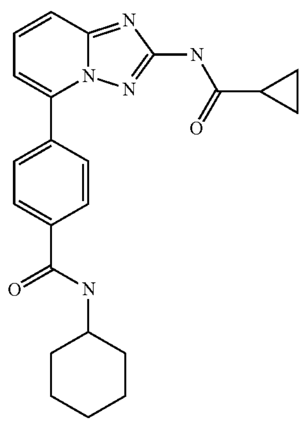 [SMILES: O=C(NC1CCCCC1)c1ccc(-c2cccc3nc(NC(=O)C4CC4)nn23)cc1] | N-cyclohexyl-4-(2-(cyclopropanecarboxamido)-[1,2,4]triazolo[1,5-a]pyridin-5-yl)benzamide | 403.49 | 404.00 |
| 27 | 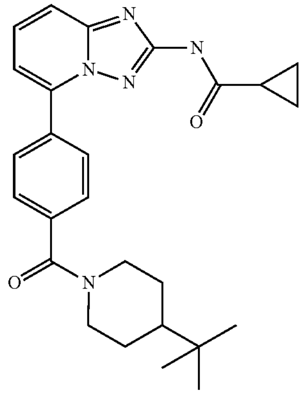 [SMILES: CC(C)(C)C1CCN(C(=O)c2ccc(-c3cccc4nc(NC(=O)C5CC5)nn34)cc2)CC1] | N-(5-(4-(4-tert-butylpiperidine-1-carbonyl)phenyl)-[1,2,4]triazolo[1,5-a]pyridin-2-yl)cyclopropanecarboxamide | 445.57 | 446.00 |

TABLE I-continued
| Cpd # | Structures | Name | MW | MS Mes'd |
|---|---|---|---|---|
| 28 | 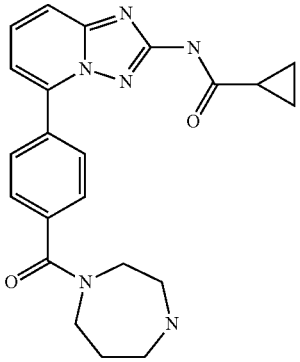 [SMILES: O=C(Nc1nc2cccc(-c3ccc(C(=O)N4CCCNCC4)cc3)n2n1)C1CC1] | N-(5-(4-(1,4-diazepane-1-carbonyl)phenyl)-[1,2,4]triazolo[1,5-a]pyridin-2-yl)cyclopropanecarboxamide | 404.48 | 405.00 |
| 29 | 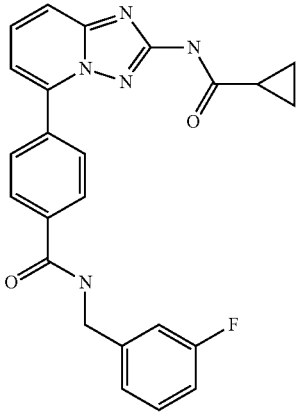 [SMILES: O=C(NCc1cccc(F)c1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(3-fluorobenzyl)benzamide | 429.46 | 430.00 |
| 30 | 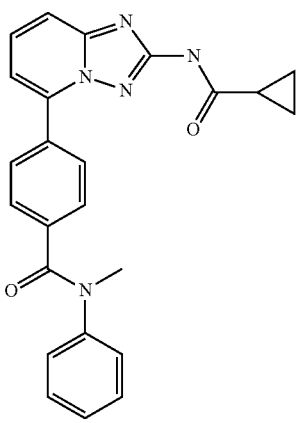 [SMILES: CN(C(=O)c1ccc(-c2cccc3nc(NC(=O)C4CC4)nn23)cc1)c1ccccc1] | 4-(2-(cyclopropanecarboxamido)-[1,2,4]triazolo[1,5-a]pyridin-5-yl)-N-methyl-N-phenylbenzamide | 411.47 | 412.00 |

TABLE I-continued

| Cpd # | Structures | Name | MW | MS Mes'd |
|---|---|---|---|---|
| 31 | 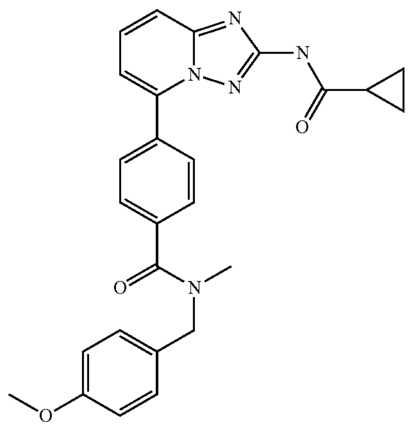 [SMILES: COc1ccc(CN(C)C(=O)c2ccc(-c3cccc4nc(NC(=O)C5CC5)nn34)cc2)cc1] | 4-(2-(cyclopropanecarboxamido)-[1,2,4]triazolo[1,5-a]pyridin-5-yl)-N-(4-methoxybenzyl)-N-methylbenzamide | 455.52 | 456.00 |
| 32 | 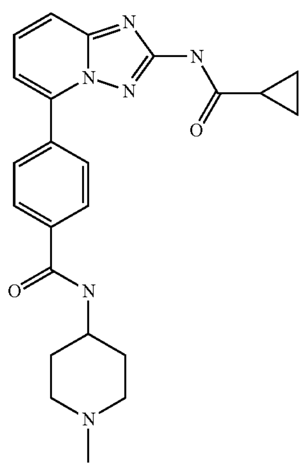 [SMILES: CN1CCC(NC(=O)c2ccc(-c3cccc4nc(NC(=O)C5CC5)nn34)cc2)CC1] | 4-(2-(cyclopropanecarboxamido)-[1,2,4]triazolo[1,5-a]pyridin-5-yl)-N-(1-methylpiperidin-4-yl)benzamide | 418.50 | 419.0 |
| 33 | 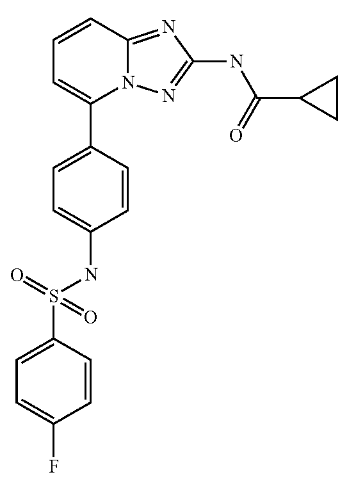 [SMILES: O=C(Nc1nc2cccc(-c3ccc(NS(=O)(=O)c4ccc(F)cc4)cc3)n2n1)C1CC1] | N-(5-(4-(4-fluorophenylsulfonamido)phenyl)-[1,2,4]triazolo[1,5-a]pyridin-2-yl)cyclopropanecarboxamide | 451.48 | 451.90 |

TABLE I-continued

| Cpd # | Structures | Name | MW | MS Mes'd |
|---|---|---|---|---|
| 34 | 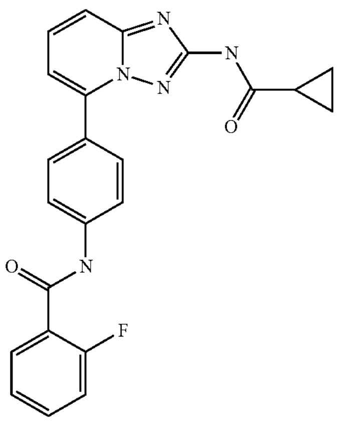 [SMILES: O=C(Nc1ccc(-c2cccc3nc(NC(=O)C4CC4)nn23)cc1)c1ccccc1F] | N-(4-(2-(cyclopropanecarboxamido)-[1,2,4]triazolo[1,5-a]pyridin-5-yl)phenyl)-2-fluorobenzamide | 415.43 | 416.00 |
| 35 | 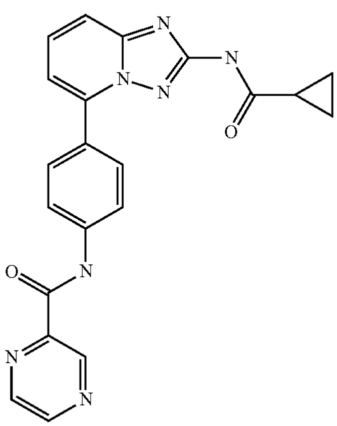 [SMILES: O=C(Nc1ccc(-c2cccc3nc(NC(=O)C4CC4)nn23)cc1)c1cnccn1] | N-(4-(2-(cyclopropanecarboxamido)-[1,2,4]triazolo[1,5-a]pyridin-5-yl)phenyl)pyrazine-2-carboxamide | 399.42 | 400.00 |
| 36 | 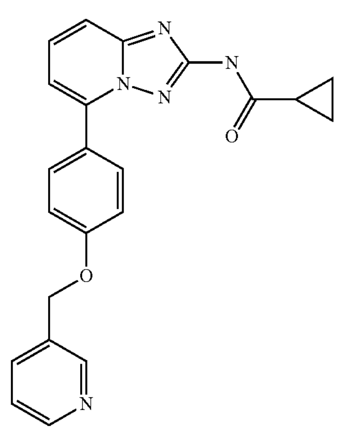 [SMILES: O=C(Nc1nc2cccc(-c3ccc(OCc4cccnc4)cc3)n2n1)C1CC1] | N-(5-(4-(pyridin-3-ylmethoxy)phenyl)-[1,2,4]triazolo[1,5-a]pyridin-2-yl)cyclopropanecarboxamide | 385.43 | 408.0 (M⁺ + Na) |

TABLE I-continued

| Cpd # | Structures | Name | MW | MS Mes'd |
|---|---|---|---|---|
| 37 | 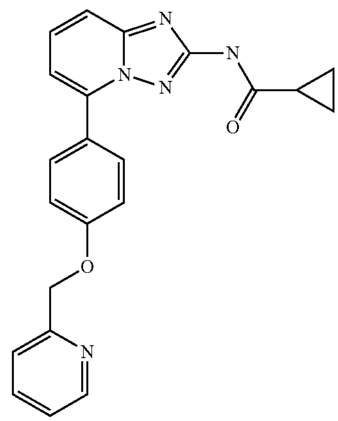 | N-(5-(4-(pyridin-2-ylmethoxy)phenyl)-[1,2,4]triazolo[1,5-a]pyridin-2-yl)cyclopropanecarboxamide | 385.43 | 408.0 (M$^+$ + Na) |
| 38 | 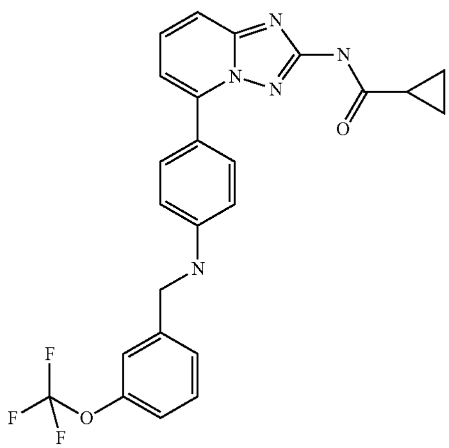 [SMILES: O=C(Nc1nc2cccc(-c3ccc(NCc4cccc(OC(F)(F)F)c4)cc3)n2n1)C1CC1] | N-(5-(4-(3-(trifluoromethoxy)benzyloxy)phenyl)-[1,2,4]triazolo[1,5-a]pyridin-2-yl)cyclopropanecarboxamide | 468.44 | 469.00 |
| 39 | 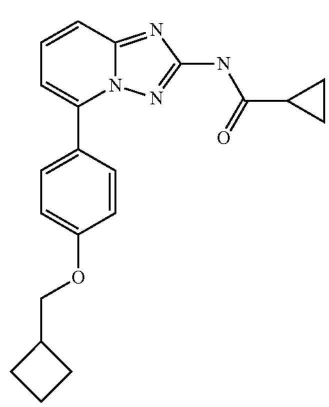 [SMILES: O=C(Nc1nc2cccc(-c3ccc(OCC4CCC4)cc3)n2n1)C1CC1] | N-(5-(4-(cyclobutylmethoxy)phenyl)-[1,2,4]triazolo[1,5-a]pyridin-2-yl)cyclopropanecarboxamide | 362.44 | 363.00 |

TABLE I-continued

| Cpd # | Structures | Name | MW | MS Mes'd |
|---|---|---|---|---|
| 40 | 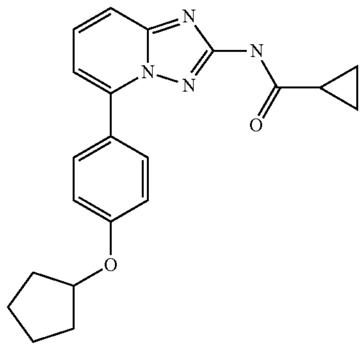 [SMILES: O=C(Nc1nc2cccc(-c3ccc(OC4CCCC4)cc3)n2n1)C1CC1] | N-(5-(4-(cyclopentyloxy)phenyl)-[1,2,4]triazolo[1,5-a]pyridin-2-yl)cyclopropanecarboxamide | 362.44 | 363.10 |
| 41 | 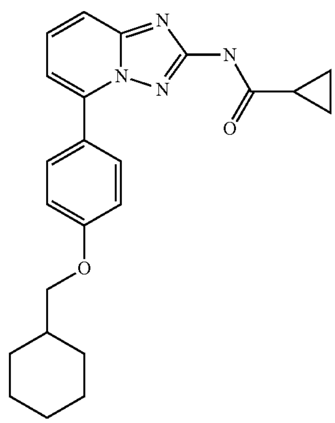 [SMILES: O=C(Nc1nc2cccc(-c3ccc(OCC4CCCCC4)cc3)n2n1)C1CC1] | N-(5-(4-(cyclohexylmethoxy)phenyl)-[1,2,4]triazolo[1,5-a]pyridin-2-yl)cyclopropanecarboxamide | 390.49 | 391.00 |
| 42 | 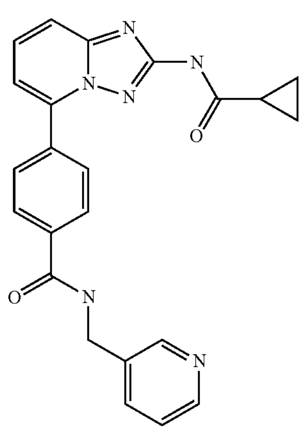 [SMILES: O=C(NCc1cccnc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(pyridin-3-ylmethyl)benzamide | 412.45 | 435.0 (M$^+$ + Na) |

TABLE I-continued

| Cpd # | Structures | Name | MW | MS Mes'd |
|---|---|---|---|---|
| 43 | 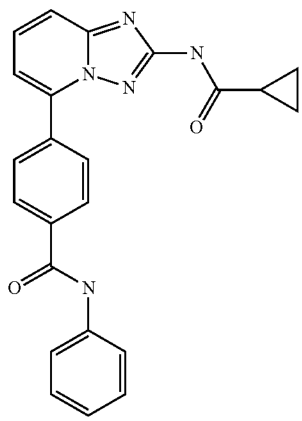 [SMILES: O=C(Nc1ccccc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-phenylbenzamide | 397.44 | 398.00 |
| 44 | 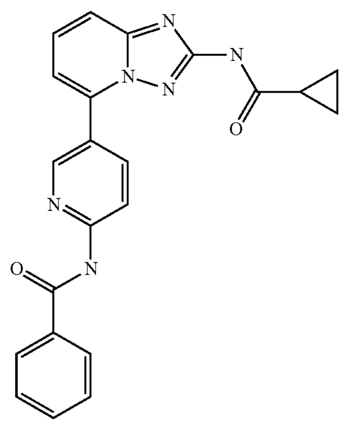 | N-(5-(2-(cyclopropanecarboxamido)-[1,2,4]triazolo[1,5-a]pyridin-5-yl)pyridin-2-yl)benzamide | 398.43 | 399.00 |
| 45 | 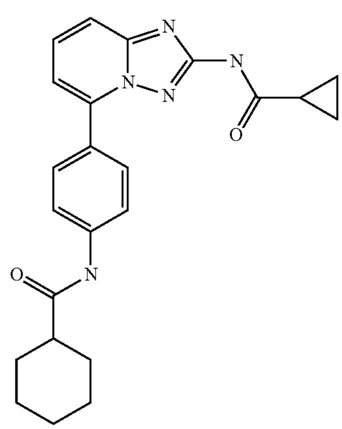 [SMILES: O=C(Nc1ccc(-c2cccc3nc(NC(=O)C4CC4)nn23)cc1)C1CCCCC1] | N-(4-(2-(cyclopropanecarboxamido)-[1,2,4]triazolo[1,5-a]pyridin-5-yl)phenyl)cyclohexanecarboxamide | 403.49 | 404.10 |

TABLE I-continued

| Cpd # | Structures | Name | MW | MS Mes'd |
|---|---|---|---|---|
| 46 | 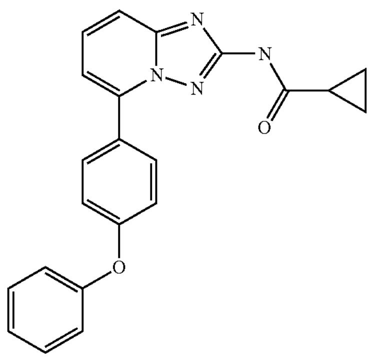 [SMILES: O=C(Nc1nc2cccc(-c3ccc(Oc4ccccc4)cc3)n2n1)C1CC1] | N-(5-(4-phenoxyphenyl)-[1,2,4]triazolo[1,5-a]pyridin-2-yl)cyclopropanecarboxamide | 370.41 | 371.00 |
| 47 | 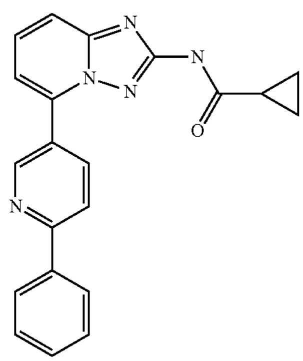 | N-(5-(6-phenylpyridin-3-yl)-[1,2,4]triazolo[1,5-a]pyridin-2-yl)cyclopropanecarboxamide | 355.40 | 356.00 |
| 48 | 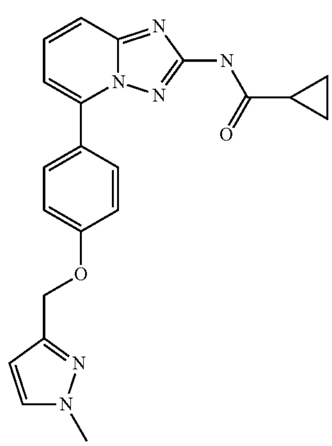 [SMILES: Cn1ccc(COc2ccc(-c3cccc4nc(NC(=O)C5CC5)nn34)cc2)n1] | N-(5-(4-((1-methyl-1H-pyrazol-3-yl)methylmethyl-1H-pyrazol-3-yl)methoxy)phenyl)-[1,2,4]triazolo[1,5-a]pyridin-2-yl)cyclopropanecarboxamide | 388.43 | 389.00 |
| 49 | 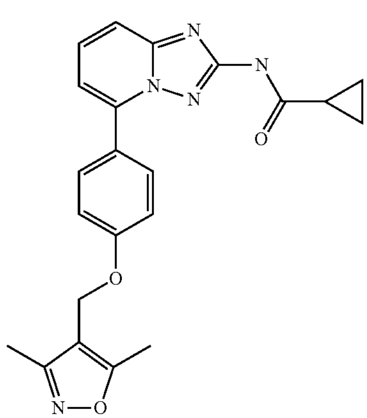 [SMILES: Cc1noc(C)c1COc1ccc(-c2cccc3nc(NC(=O)C4CC4)nn23)cc1] | N-(5-(4-((3,5-dimethylisoxazol-4-yl)methoxy)phenyl)-[1,2,4]triazolo[1,5-a]pyridin-2-yl)cyclopropanecarboxamide | 403.44 | 404.00 |

TABLE I-continued

| Cpd # | Structures | Name | MW | MS Mes'd |
|---|---|---|---|---|
| 50 | 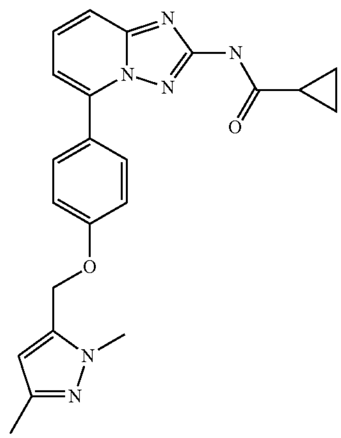 [SMILES: Cc1cc(COc2ccc(-c3cccc4nc(NC(=O)C5CC5)nn34)cc2)n(C)n1] | N-(5-(4-((1,3-dimethyl-1H-pyrazol-5-yl)methyldimethyl-1H-pyrazol-5-yl)methoxy)phenyl)-[1,2,4]triazolo[1,5-a]pyridin-2-yl)cyclopropanecarboxamide | 402.46 | 403.00 |
| 51 | 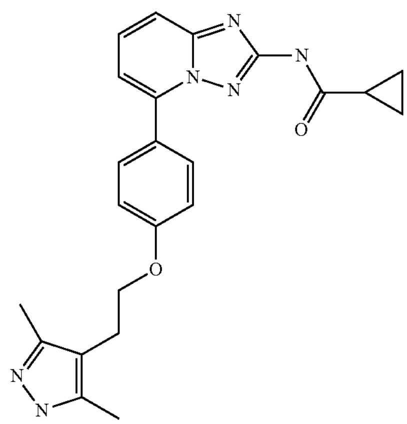 [SMILES: Cc1n[nH]c(C)c1CCOc1ccc(-c2cccc3nc(NC(=O)C4CC4)nn23)cc1] | N-(5-(4-(2-(3,5-dimethyl-1H-pyrazol-4-yl)ethyldimethyl-1H-pyrazol-4-yl)ethoxy)phenyl)-[1,2,4]triazolo[1,5-a]pyridin-2-yl)cyclopropanecarboxamide | 416.49 | 417.10 |
| 52 | 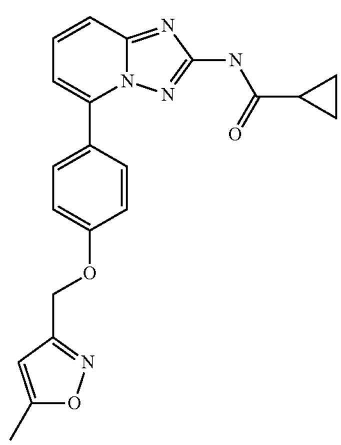 [SMILES: Cc1cc(COc2ccc(-c3cccc4nc(NC(=O)C5CC5)nn34)cc2)no1] | N-(5-(4-((5-methylisoxazol-3-yl)methoxy)phenyl)-[1,2,4]triazolo[1,5-a]pyridin-2-yl)cyclopropanecarboxamide | 389.42 | 390.00 |

TABLE I-continued

| Cpd # | Structures | Name | MW | MS Mes'd |
|---|---|---|---|---|
| 53 | 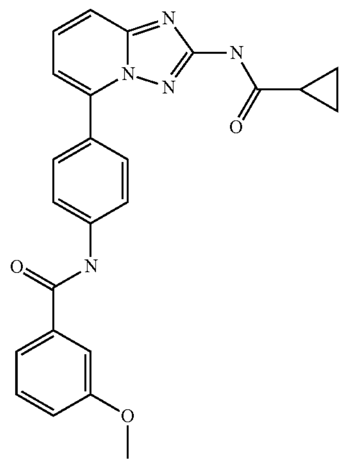 [SMILES: COc1cccc(C(=O)Nc2ccc(-c3cccc4nc(NC(=O)C5CC5)nn34)cc2)c1] | N-(4-(2-(cyclopropanecarboxamido)-[1,2,4]triazolo[1,5-a]pyridin-5-yl)phenyl)-3-methoxybenzamide | 427.47 | 428.00 |
| 54 | 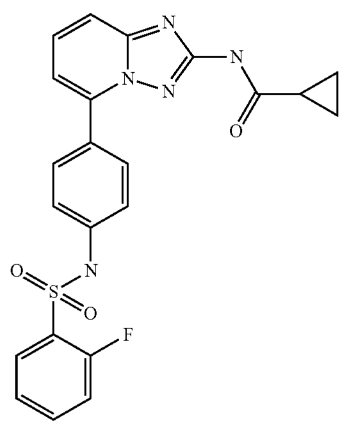 [SMILES: O=C(Nc1nc2cccc(-c3ccc(NS(=O)(=O)c4ccccc4F)cc3)n2n1)C1CC1] | N-(5-(4-(2-fluorophenylsulfonamido)phenyl)-[1,2,4]triazolo[1,5-a]pyridin-2-yl)cyclopropanecarboxamide | 451.48 | 452.00 |
| 55 | 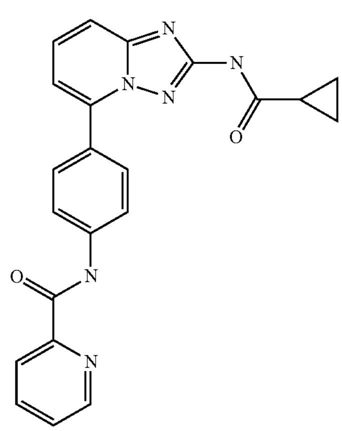 | N-(4-(2-(cyclopropanecarboxamido)-[1,2,4]triazolo[1,5-a]pyridin-5-yl)phenyl)picolinamide | 398.43 | 399.00 |

TABLE I-continued

| Cpd # | Structures | Name | MW | MS Mes'd |
|---|---|---|---|---|
| 56 | 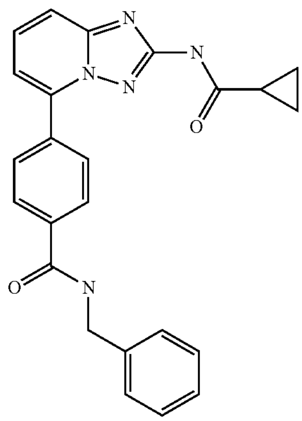 [SMILES: O=C(NCc1ccccc1)c1ccc(-c2cccc3nc(NC(=O)C4CC4)nn23)cc1] | N-benzyl-4-(2-(cyclopropanecarboxamido)-[1,2,4]triazolo[1,5-a]pyridin-5-yl)benzamide | 411.47 | 412.10 |
| 57 | 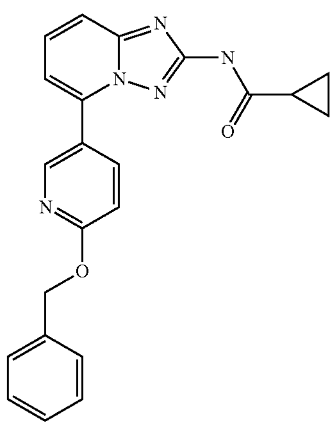 | N-(5-(6-(benzyloxy)pyridin-3-yl)-[1,2,4]triazolo[1,5-a]pyridin-2-yl)cyclopropanecarboxamide | 385.43 | 386.00 |
| 58 | 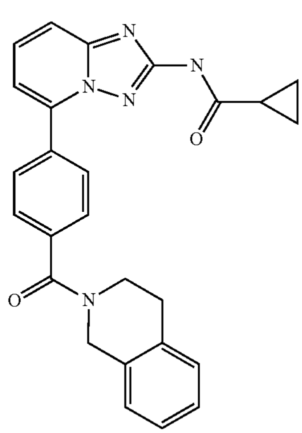 [SMILES: O=C(Nc1nc2cccc(-c3ccc(C(=O)N4CCc5ccccc5C4)cc3)n2n1)C1CC1] | N-(5-(4-(1,2,3,4-tetrahydroisoquinoline-2-carbonyl)phenyl)-[1,2,4]triazolo[1,5-a]pyridin-2-yl)cyclopropanecarboxamide | 437.51 | 438.00 |

| Cpd # | Structures | Name | MW | MS Mes'd |
|---|---|---|---|---|
| 59 | 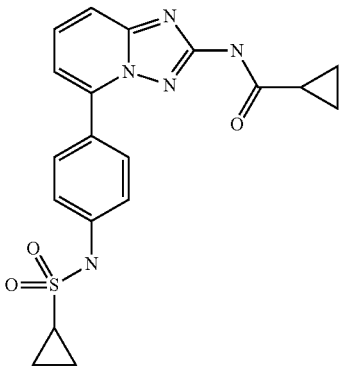 [SMILES: O=C(Nc1nc2cccc(-c3ccc(NS(=O)(=O)C4CC4)cc3)n2n1)C1CC1] | N-(5-(4-(cyclopropanesulfonamido)phenyl)-[1,2,4]triazolo[1,5-a]pyridin-2-yl)cyclopropanecarboxamide | 397.46 | 398.00 |
| 60 | 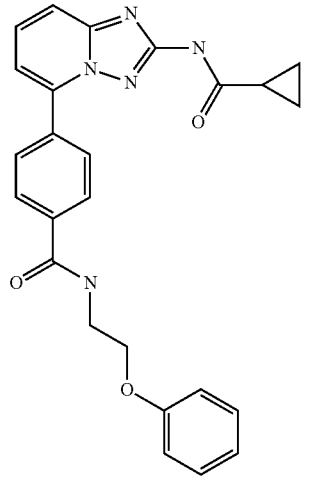 | 4-(2-(cyclopropanecarboxamido)-[1,2,4]triazolo[1,5-a]pyridin-5-yl)-N-(2-phenoxyethyl)benzamide | 441.49 | 442.00 |
| 61 | 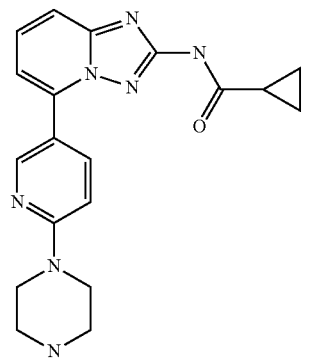 [SMILES: O=C(Nc1nc2cccc(-c3ccc(N4CCNCC4)nc3)n2n1)C1CC1] | N-(5-(6-(piperazin-1-yl)pyridin-3-yl)-[1,2,4]triazolo[1,5-a]pyridin-2-yl)cyclopropanecarboxamide | 363.43 | 364.00 |

TABLE I-continued

| Cpd # | Structures | Name | MW | MS Mes'd |
|---|---|---|---|---|
| 62 | 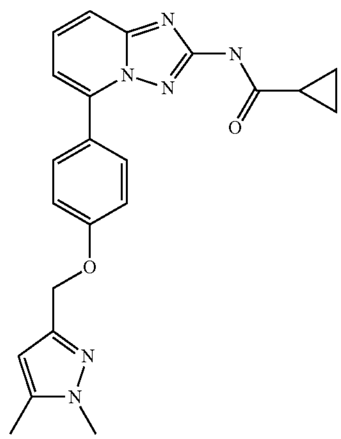 [SMILES: Cc1cc(COc2ccc(-c3cccc4nc(NC(=O)C5CC5)nn34)cc2)nn1C] | N-(5-(4-(((1,5-dimethyl-1H-pyrazol-3-yl)methyldimethyl-1H-pyrazol-3-yl)methoxy)phenyl)-[1,2,4]triazolo[1,5-a]pyridin-2-yl)cyclopropanecarboxamide | 402.46 | 403.10 |
| 63 | 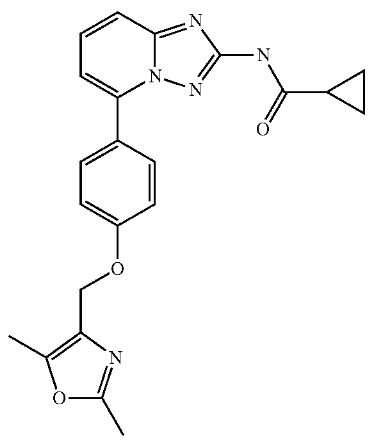 [SMILES: Cc1nc(COc2ccc(-c3cccc4nc(NC(=O)C5CC5)nn34)cc2)c(C)o1] | N-(5-(4-((2,5-dimethyloxazol-4-yl)methoxy)phenyl)-[1,2,4]triazolo[1,5-a]pyridin-2-yl)cyclopropanecarboxamide | 403.44 | 404.00 |
| 64 | 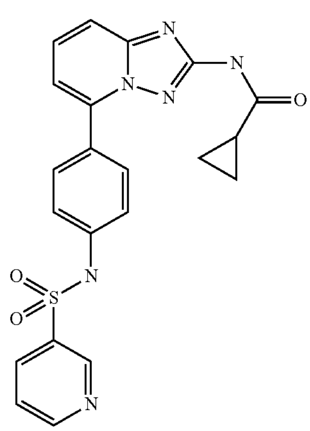 [SMILES: O=C(Nc1nc2cccc(-c3ccc(NS(=O)(=O)c4cccnc4)cc3)n2n1)C1CC1] | N-(5-(4-(pyridine-3-sulfonamido)phenyl)-[1,2,4]triazolo[1,5-a]pyridin-2-yl)cyclopropanecarboxamide | 434.48 | 435.00 |

TABLE I-continued

| Cpd # | Structures | Name | MW | MS Mes'd |
|---|---|---|---|---|
| 65 | 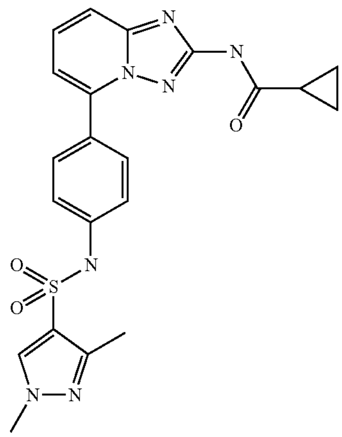 [SMILES: Cc1nn(C)cc1S(=O)(=O)Nc1ccc(-c2cccc3nc(NC(=O)C4CC4)nn23)cc1] | N-(5-(4-(1,3-dimethyl-1H-pyrazole-4-sulfonamido)phenyl)-[1,2,4]triazolo[1,5-a]pyridin-2-yl)cyclopropanecarboxamide | 451.51 | 452.00 |
| 66 | 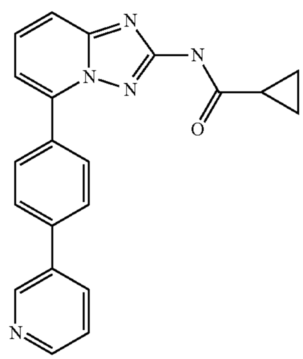 [SMILES: O=C(Nc1nc2cccc(-c3ccc(-c4cccnc4)cc3)n2n1)C1CC1] | N-(5-(4-(pyridin-3-yl)phenyl)-[1,2,4]triazolo[1,5-a]pyridin-2-yl)cyclopropanecarboxamide | 355.40 | 378.0 (M¹ + Na) |
| 67 | 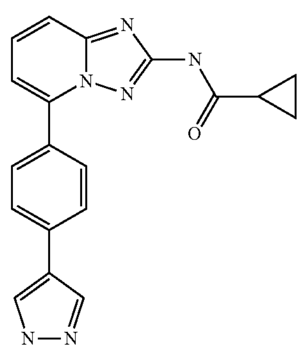 [SMILES: O=C(Nc1nc2cccc(-c3ccc(-c4cn[nH]c4)cc3)n2n1)C1CC1] | N-(5-(4-(1H-pyrazol-4-yl)phenyl)-[1,2,4]triazolo[1,5-a]pyridin-2-yl)cyclopropanecarboxamide | 344.38 | 345.00 |
| 68 | 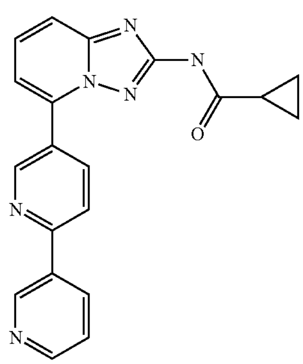 [SMILES: O=C(Nc1nc2cccc(-c3ccc(-c4cccnc4)nc3)n2n1)C1CC1] | N-(5-(2,3'-bipyridin-5-yl)-[1,2,4]triazolo[1,5-a]pyridin-2-yl)cyclopropanecarboxamide | 356.39 | 357.00 |

TABLE I-continued

| Cpd # | Structures | Name | MW | MS Mes'd |
|---|---|---|---|---|
| 69 | 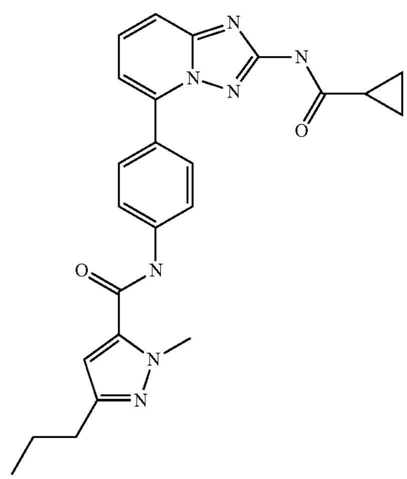 [SMILES: CCCc1cc(C(=O)Nc2ccc(-c3cccc4nc(NC(=O)C5CC5)nn34)cc2)n(C)n1] | N-(4-(2-(cyclopropanecarboxamido)-[1,2,4]triazolo[1,5-a]pyridin-5-yl)phenyl)-1-methyl-3-propyl-1H-pyrazole-5-carboxamide | 443.51 | 444.00 |
| 70 | 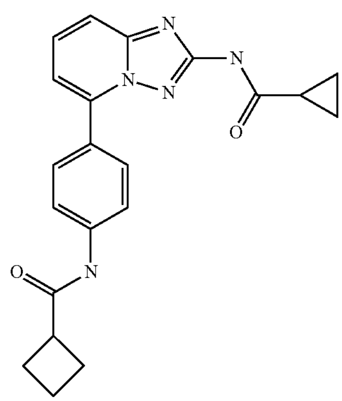 [SMILES: O=C(Nc1ccc(-c2cccc3nc(NC(=O)C4CC4)nn23)cc1)C1CCC1] | N-(4-(2-(cyclopropanecarboxamido)-[1,2,4]triazolo[1,5-a]pyridin-5-yl)phenyl)cyclobutanecarboxamide | 375.43 | 376.00 |
| 71 | 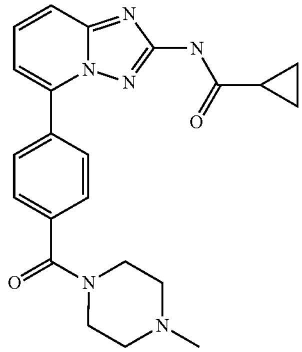 [SMILES: CN1CCN(C(=O)c2ccc(-c3cccc4nc(NC(=O)C5CC5)nn34)cc2)CC1] | N-(5-(4-(4-methylpiperazine-1-carbonyl)phenyl)-[1,2,4]triazolo[1,5-a]pyridin-2-yl)cyclopropanecarboxamide | 404.48 | 405.00 |

TABLE I-continued

| Cpd # | Structures | Name | MW | MS Mes'd |
|---|---|---|---|---|
| 72 | 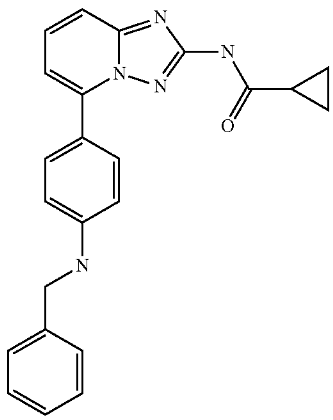 | N-(5-(4-(benzylamino)phenyl)-[1,2,4]triazolo[1,5-a]pyridin-2-yl)cyclopropanecarboxamide | 383.46 | 384.00 |
| 73 | 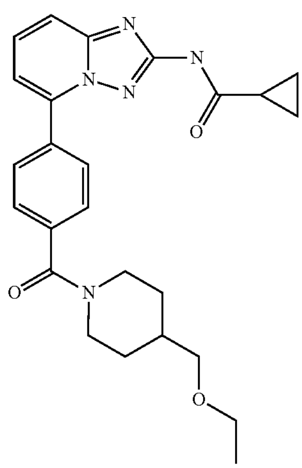 [SMILES: CCOCC1CCN(C(=O)c2ccc(-c3cccc4nc(NC(=O)C5CC5)nn34)cc2)CC1] | N-(5-(4-(4-(ethoxymethyl)piperidine-1-carbonyl)phenyl)-[1,2,4]triazolo[1,5-a]pyridin-2-yl)cyclopropanecarboxamide | 447.54 | 448.10 |
| 74 | 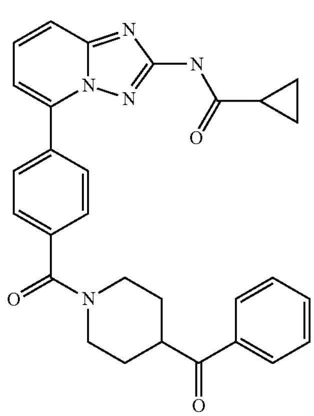 [SMILES: O=C(Nc1nc2cccc(-c3ccc(C(=O)N4CCC(C(=O)c5ccccc5)CC4)cc3)n2n1)C1CC1] | N-(5-(4-(4-benzoylpiperidine-1-carbonyl)phenyl)-[1,2,4]triazolo[1,5-a]pyridin-2-yl)cyclopropanecarboxamide | 493.57 | 494.10 |

TABLE I-continued

| Cpd # | Structures | Name | MW | MS Mes'd |
|---|---|---|---|---|
| 75 | 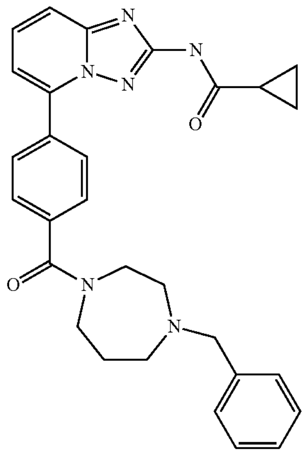 [SMILES: O=C(Nc1nc2cccc(-c3ccc(C(=O)N4CCCN(Cc5ccccc5)CC4)cc3)n2n1)C1CC1] | N-(5-(4-(4-benzyl-1,4-diazepane-1-carbonyl)phenyl)-[1,2,4]triazolo[1,5-a]pyridin-2-yl)cyclopropanecarboxamide | 494.60 | 495.10 |
| 76 | 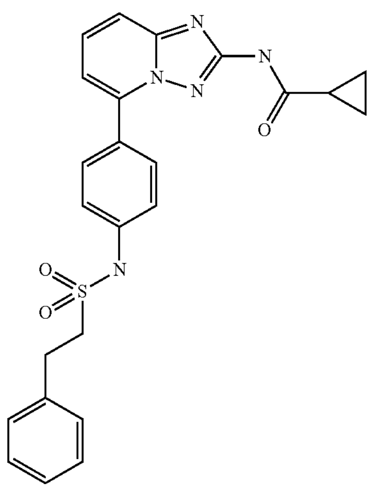 [SMILES: O=C(Nc1nc2cccc(-c3ccc(NS(=O)(=O)CCc4ccccc4)cc3)n2n1)C1CC1] | N-(5-(4-(2-phenylethylsulfonamido)phenyl)-[1,2,4]triazolo[1,5-a]pyridin-2-yl)cyclopropanecarboxamide | 461.55 | 462.10 |
| 77 | 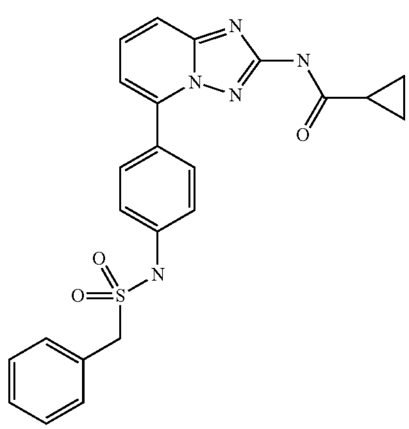 [SMILES: O=C(Nc1nc2cccc(-c3ccc(NS(=O)(=O)Cc4ccccc4)cc3)n2n1)C1CC1] | N-(5-(4-(phenylmethylsulfonamido)phenyl)-[1,2,4]triazolo[1,5-a]pyridin-2-yl)cyclopropanecarboxamide | 447.52 | 448.10 |

TABLE I-continued

| Cpd # | Structures | Name | MW | MS Mes'd |
|---|---|---|---|---|
| 78 | 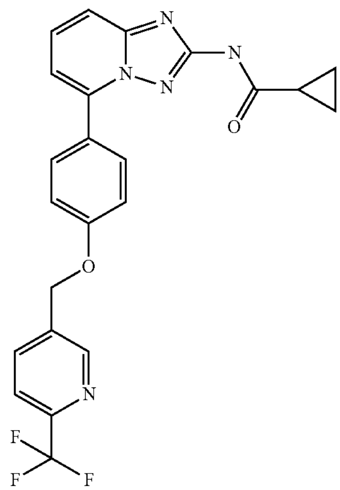 [SMILES: O=C(Nc1nc2cccc(-c3ccc(OCc4ccc(C(F)(F)F)nc4)cc3)n2n1)C1CC1] | N-(5-(4-((6-(trifluoromethyl)pyridin-3-yl)methoxy)phenyl)-[1,2,4]triazolo[1,5-a]pyridin-2-yl)cyclopropanecarboxamide | 453.43 | 454.00 |
| 79 | 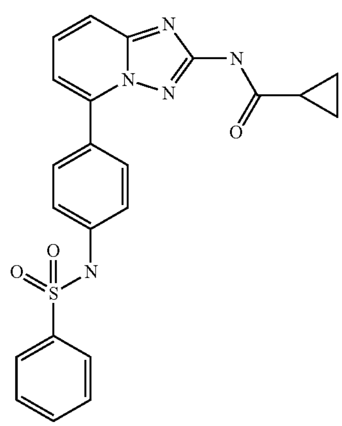 [SMILES: O=C(Nc1nc2cccc(-c3ccc(NS(=O)(=O)c4ccccc4)cc3)n2n1)C1CC1] | N-(5-(4-(phenylsulfonamido)phenyl)-[1,2,4]triazolo[1,5-a]pyridin-2-yl)cyclopropanecarboxamide | 433.49 | 434.00 |
| 80 | 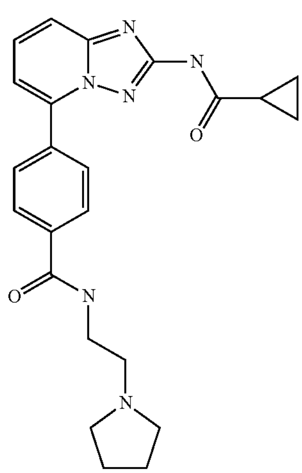 [SMILES: O=C(NCCN1CCCC1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(2-(pyrrolidin-1-yl)ethyl)benzamide | 418.50 | 419.10 |

TABLE I-continued

| Cpd # | Structures | Name | MW | MS Mes'd |
|---|---|---|---|---|
| 81 | 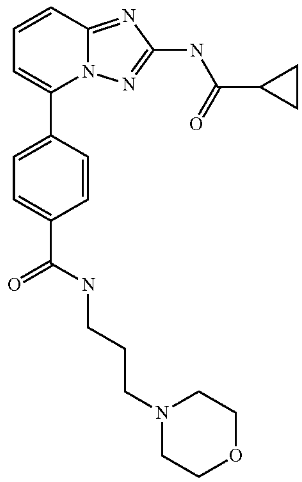 [SMILES: O=C(NCCCN1CCOCC1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(3-morpholinopropyl)benzamide | 448.53 | 449.20 |
| 82 | 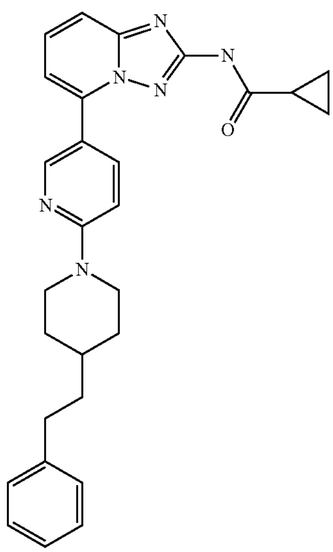 [SMILES: O=C(Nc1nc2cccc(-c3ccc(N4CCC(CCc5ccccc5)CC4)nc3)n2n1)C1CC1] | N-(5-(6-(4-phenethylpiperidin-1-yl)pyridin-3-yl)-[1,2,4]triazolo[1,5-a]pyridin-2-yl)cyclopropanecarboxamide | 466.59 | 467.20 |
| 83 | 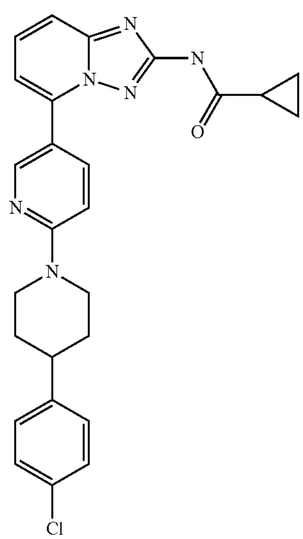 [SMILES: O=C(Nc1nc2cccc(-c3ccc(N4CCC(c5ccc(Cl)cc5)CC4)nc3)n2n1)C1CC1] | N-(5-(6-(4-(4-chlorophenyl)piperidin-1-yl)pyridin-3-yl)-[1,2,4]triazolo[1,5-a]pyridin-2-yl)cyclopropanecarboxamide | 472.98 | 473.10 |

TABLE I-continued

| Cpd # | Structures | Name | MW | MS Mes'd |
|---|---|---|---|---|
| 84 | 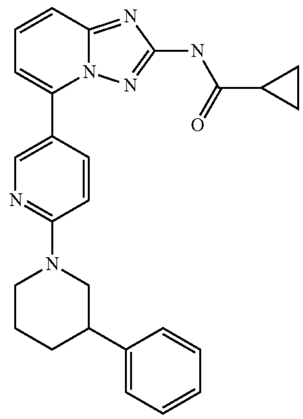 [SMILES: O=C(Nc1nc2cccc(-c3ccc(N4CCCC(c5ccccc5)C4)nc3)n2n1)C1CC1] | N-(5-(6-(3-phenylpiperidin-1-yl)pyridin-3-yl)-[1,2,4]triazolo[1,5-a]pyridin-2-yl)cyclopropanecarboxamide | 438.54 | 439.10 |
| 85 | 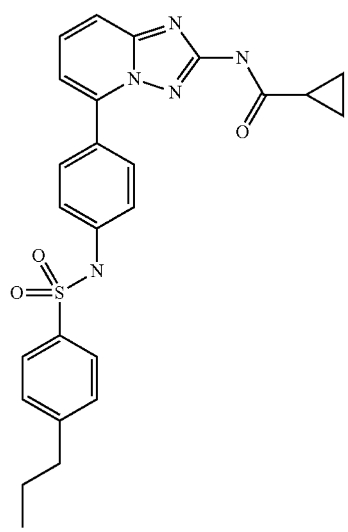 [SMILES: CCCc1ccc(S(=O)(=O)Nc2ccc(-c3cccc4nc(NC(=O)C5CC5)nn34)cc2)cc1] | N-(5-(4-(4-propylphenylsulfonamido)phenyl)-[1,2,4]triazolo[1,5-a]pyridin-2-yl)cyclopropanecarboxamide | 475.57 | 476.00 |
| 86 | 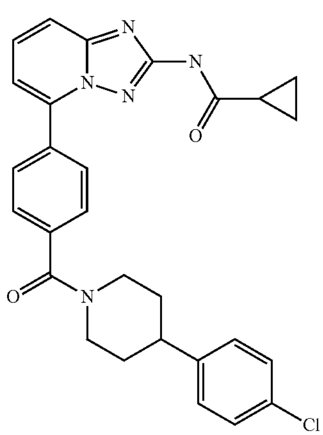 [SMILES: O=C(Nc1nc2cccc(-c3ccc(C(=O)N4CCC(c5ccc(Cl)cc5)CC4)cc3)n2n1)C1CC1] | N-(5-(4-(4-(4-chlorophenyl)piperidine-1-carbonyl)phenyl)-[1,2,4]triazolo[1,5-a]pyridin-2-yl)cyclopropanecarboxamide | 500.00 | 500.10 |

TABLE I-continued

| Cpd # | Structures | Name | MW | MS Mes'd |
|---|---|---|---|---|
| 87 | 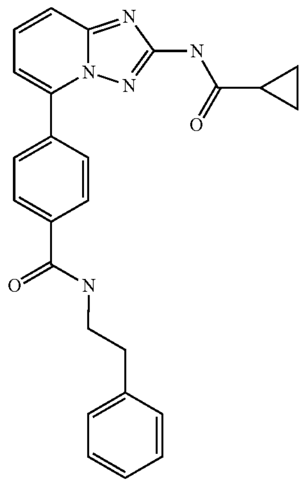 [SMILES: O=C(NCCc1ccccc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-phenethylbenzamide | 425.49 | 426.10 |
| 88 | 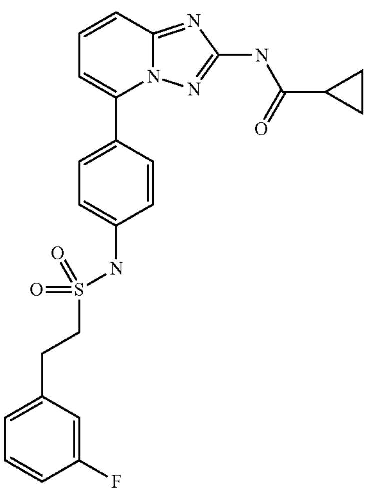 [SMILES: O=C(Nc1nc2cccc(-c3ccc(NS(=O)(=O)CCc4cccc(F)c4)cc3)n2n1)C1CC1] | N-(5-(4-(2-(3-fluorophenyl)ethylsulfonamido)phenyl)-[1,2,4]triazolo[1,5-a]pyridin-2-yl)cyclopropanecarboxamide | 479.54 | 480.00 |
| 89 | 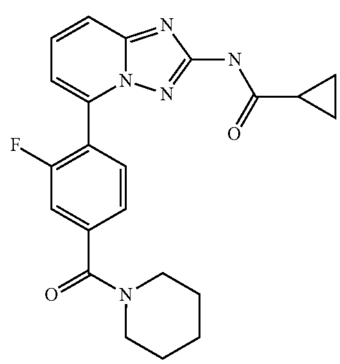 [SMILES: O=C(Nc1nc2cccc(-c3ccc(C(=O)N4CCCCC4)cc3F)n2n1)C1CC1] | N-(5-(2-fluoro-4-(piperidine-1-carbonyl)phenyl)-[1,2,4]triazolo[1,5-a]pyridin-2-yl)cyclopropanecarboxamide | 407.45 | 408.10 |

TABLE I-continued

| Cpd # | Structures | Name | MW | MS Mes'd |
|---|---|---|---|---|
| 90 | 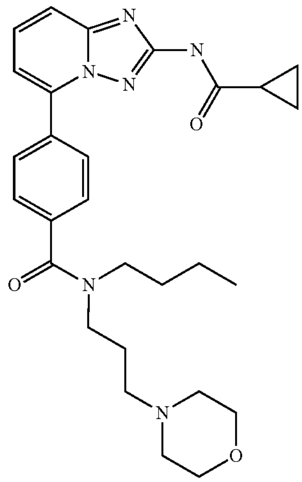 [SMILES: CCCCN(CCCN1CCOCC1)C(=O)c1ccc(-c2cccc3nc(NC(=O)C4CC4)nn23)cc1] | N-butyl-4-(2-(cyclopropanecarboxamido)-[1,2,4]triazolo[1,5-a]pyridin-5-yl)-N-(3-morpholinopropyl)benzamide | 504.64 | 505.20 |
| 91 | 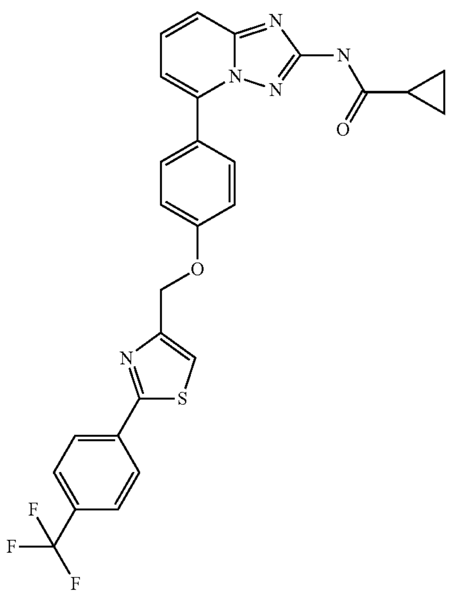 [SMILES: O=C(Nc1nc2cccc(-c3ccc(OCc4csc(-c5ccc(C(F)(F)F)cc5)n4)cc3)n2n1)C1CC1] | N-(5-(4-((2-(4-(trifluoromethyl)phenyl)thiazol-4-yl)methoxy)phenyl)-[1,2,4]triazolo[1,5-a]pyridin-2-yl)cyclopropanecarboxamide | 535.55 | 536.10 |
| 92 | 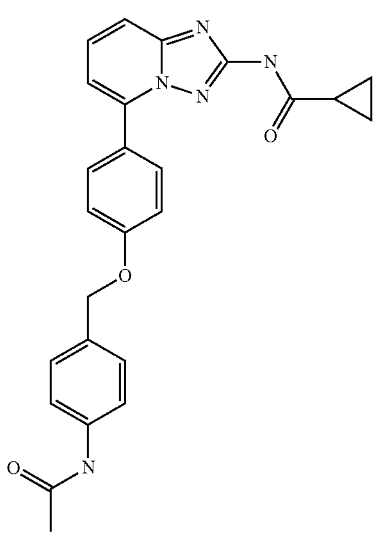 [SMILES: CC(=O)Nc1ccc(COc2ccc(-c3cccc4nc(NC(=O)C5CC5)nn34)cc2)cc1] | N-(5-(4-(4-acetamidobenzyloxy)phenyl)-[1,2,4]triazolo[1,5-a]pyridin-2-yl)cyclopropanecarboxamide | 441.49 | 442.00 |

TABLE I-continued

| Cpd # | Structures | Name | MW | MS Mes'd |
|---|---|---|---|---|
| 93 | 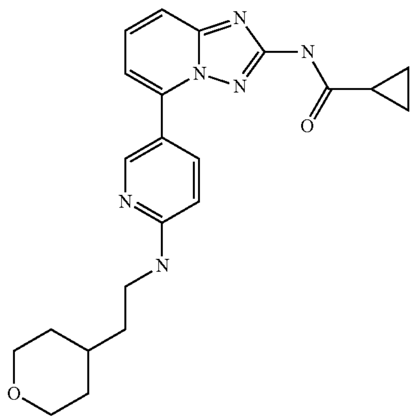 [SMILES: O=C(Nc1nc2cccc(-c3ccc(NCCC4CCOCC4)nc3)n2n1)C1CC1] | N-(5-(6-(2-(tetrahydro-2H-pyran-4-yl)ethylamino)pyridin-3-yl)-[1,2,4]triazolo[1,5-a]pyridin-2-yl)cyclopropanecarboxamide | 406.49 | 407.10 |
| 94 | 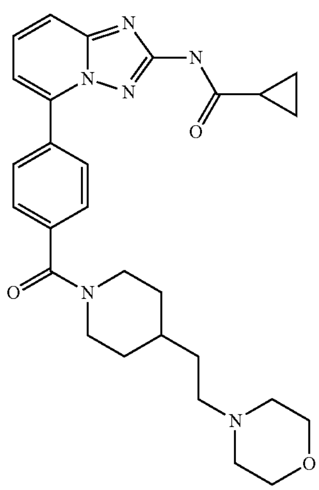 [SMILES: O=C(Nc1nc2cccc(-c3ccc(C(=O)N4CCC(CCN5CCOCC5)CC4)cc3)n2n1)C1CC1] | N-(5-(4-(4-(2-morpholinoethyl)piperidine-1-carbonyl)phenyl)-[1,2,4]triazolo[1,5-a]pyridin-2-yl)cyclopropanecarboxamide | 502.62 | 525.20 |
| 95 | 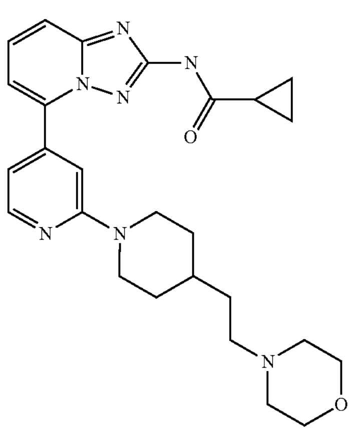 [SMILES: O=C(Nc1nc2cccc(-c3ccnc(N4CCC(CCN5CCOCC5)CC4)c3)n2n1)C1CC1] | N-(5-(2-(4-(2-morpholinoethyl)piperidin-1-yl)pyridin-4-yl)-[1,2,4]triazolo[1,5-a]pyridin-2-yl)cyclopropanecarboxamide | 475.60 | 476.20 |

TABLE I-continued
| Cpd # | Structures | Name | MW | MS Mes'd |
|---|---|---|---|---|
| 96 | 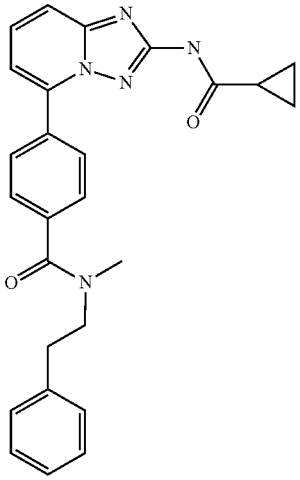 [SMILES: CN(CCc1ccccc1)C(=O)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-methyl-N-phenethylbenzamide | 439.52 | 440.10 |
| 97 | 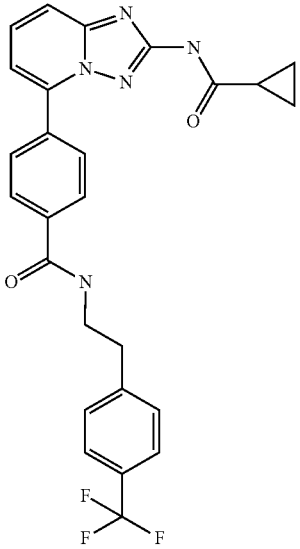 [SMILES: O=C(NCCc1ccc(C(F)(F)F)cc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(4-(trifluoromethyl)phenethyl)benzamide | 493.49 | 494.10 |
| 98 | 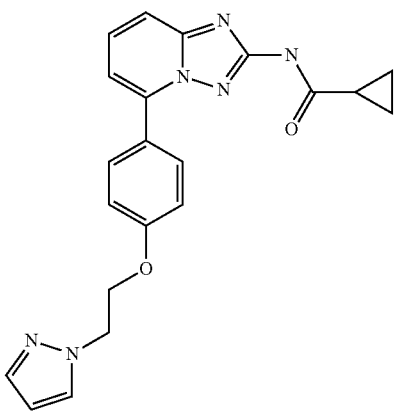 [SMILES: O=C(Nc1nc2cccc(-c3ccc(OCCn4cccn4)cc3)n2n1)C1CC1] | N-(5-(4-(2-(1H-pyrazol-1-yl)ethyl1H-pyrazol-1-yl)ethoxy)phenyl)-[1,2,4]triazolo[1,5-a]pyridin-2-yl)cyclopropanecarboxamide | 388.43 | 389.10 |

TABLE I-continued

| Cpd # | Structures | Name | MW | MS Mes'd |
|---|---|---|---|---|
| 99 | 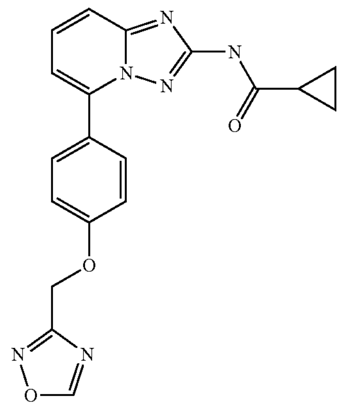 [SMILES: O=C(Nc1nc2cccc(-c3ccc(OCc4ncon4)cc3)n2n1)C1CC1] | N-(5-(4-((1,2,4-oxadiazol-3-yl)methoxy)phenyl)-[1,2,4]triazolo[1,5-a]pyridin-2-yl)cyclopropanecarboxamide | 376.38 | 377.00 |
| 100 | 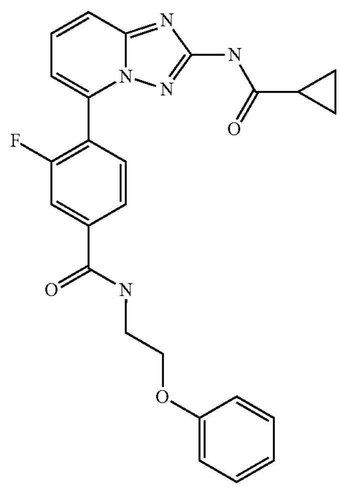 [SMILES: O=C(NCCOc1ccccc1)c1ccc(-c2cccc3nc(NC(=O)C4CC4)nn23)c(F)c1] | 4-(2-(cyclopropanecarboxamido)-[1,2,4]triazolo[1,5-a]pyridin-5-yl)-3-fluoro-N-(2-phenoxyethyl)benzamide | 459.48 | 460.10 |
| 101 | 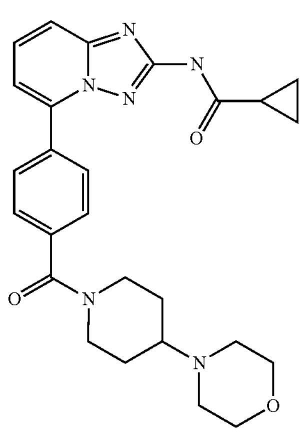 [SMILES: O=C(Nc1nc2cccc(-c3ccc(C(=O)N4CCC(N5CCOCC5)CC4)cc3)n2n1)C1CC1] | N-(5-(4-(4-morpholinopiperidine-1-carbonyl)phenyl)-[1,2,4]triazolo[1,5-a]pyridin-2-yl)cyclopropanecarboxamide | 474.57 | 497.2 (M + 23) |

TABLE I-continued
| Cpd # | Structures | Name | MW | MS Mes'd |
|---|---|---|---|---|
| 102 | 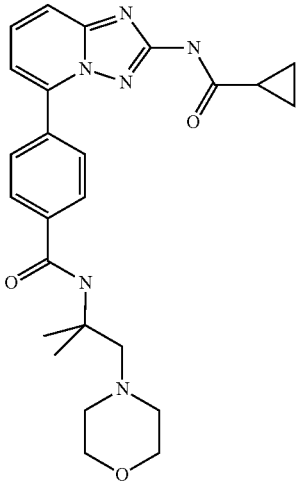 [SMILES: CC(C)(CN1CCOCC1)NC(=O)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(2-methyl-1-morpholinopropan-2-yl)benzamide | 462.56 | 463.20 |
| 103 | 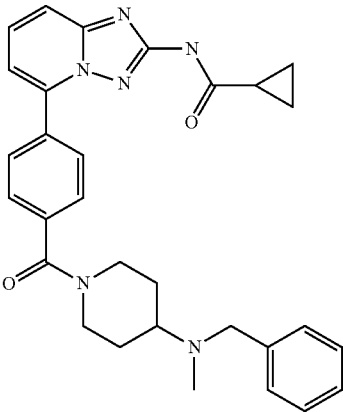 [SMILES: CN(Cc1ccccc1)C1CCN(C(=O)c2ccc(-c3cccc4nc(NC(=O)C5CC5)nn34)cc2)CC1] | N-(5-(4-(4-(benzyl(methyl)amino)piperidine-1-carbonyl)phenyl)-[1,2,4]triazolo[1,5-a]pyridin-2-yl)cyclopropanecarboxamide | 508.63 | 531.2 (M + 23) |
| 104 | 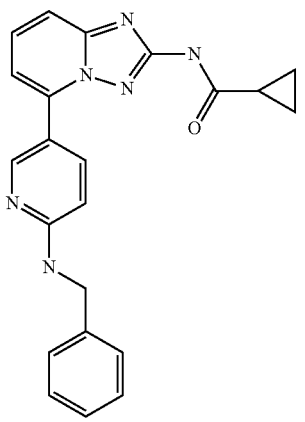 [SMILES: O=C(Nc1nc2cccc(-c3ccc(NCc4ccccc4)nc3)n2n1)C1CC1] | N-(5-(6-(benzylamino)pyridin-3-yl)-[1,2,4]triazolo[1,5-a]pyridin-2-yl)cyclopropanecarboxamide | 384.44 | 385.00 |

TABLE I-continued
| Cpd # | Structures | Name | MW | MS Mes'd |
|---|---|---|---|---|
| 105 | 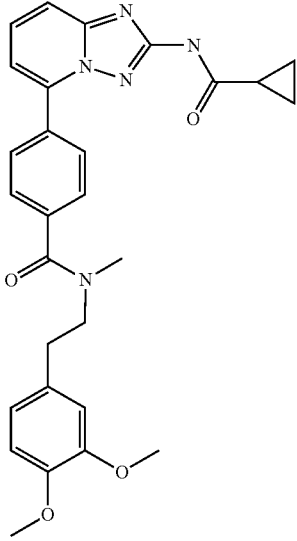 [SMILES: COc1ccc(CCN(C)C(=O)c2ccc(-c3cccc4nc(NC(=O)C5CC5)nn34)cc2)cc1OC] | 4-(2-(cyclopropanecarboxamido)-[1,2,4]triazolo[1,5-a]pyridin-5-yl)-N-(3,4-dimethoxyphenethyl)-N-methylbenzamide | 499.57 | 500.20 |
| 106 | 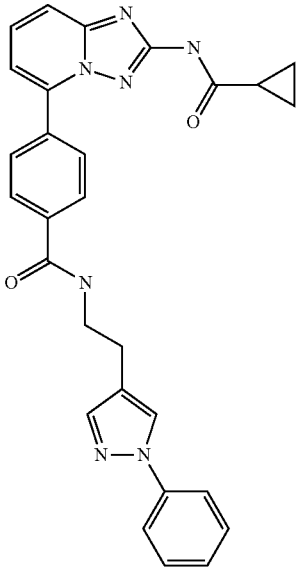 [SMILES: O=C(NCCc1cnn(-c2ccccc2)c1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(2-(1-phenyl-1H-pyrazol-4-yl)ethyl)benzamide | 491.56 | 514.1 (M + 23) |
| 107 | 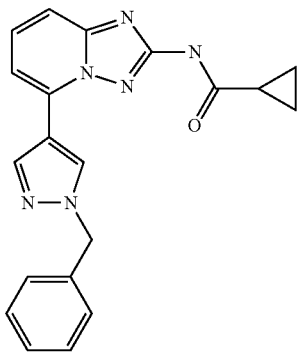 [SMILES: O=C(Nc1nc2cccc(-c3cnn(Cc4ccccc4)c3)n2n1)C1CC1] | N-(5-(1-benzyl-1H-pyrazol-4-yl)-[1,2,4]triazolo[1,5-a]pyridin-2-yl)cyclopropanecarboxamide | 358.41 | 359.00 |

TABLE I-continued

| Cpd # | Structures | Name | MW | MS Mes'd |
|---|---|---|---|---|
| 108 | 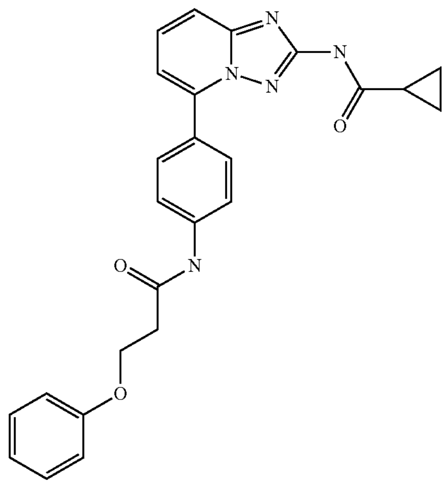 [SMILES: O=C(CCOc1ccccc1)Nc1ccc(-c2cccc3nc(NC(=O)C4CC4)nn23)cc1] | N-(5-(4-(3-phenoxypropanamido)phenyl)-[1,2,4]triazolo[1,5-a]pyridin-2-yl)cyclopropanecarboxamide | 441.49 | 442.00 |
| 109 | 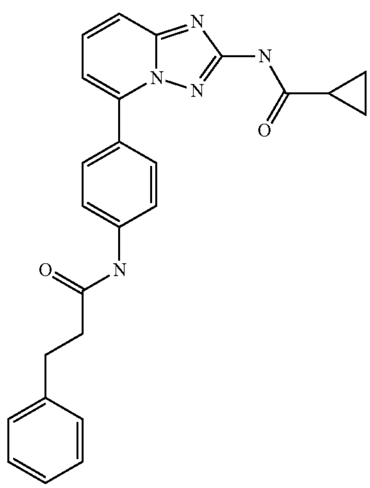 [SMILES: O=C(CCc1ccccc1)Nc1ccc(-c2cccc3nc(NC(=O)C4CC4)nn23)cc1] | N-(5-(4-(3-phenylpropanamido)phenyl)-[1,2,4]triazolo[1,5-a]pyridin-2-yl)cyclopropanecarboxamide | 425.49 | 426.10 |
| 110 | 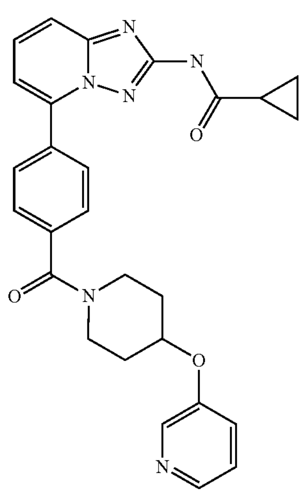 [SMILES: O=C(Nc1nc2cccc(-c3ccc(C(=O)N4CCC(Oc5cccnc5)CC4)cc3)n2n1)C1CC1] | N-(5-(4-(4-(pyridin-3-yloxy)piperidine-1-carbonyl)phenyl)-[1,2,4]triazolo[1,5-a]pyridin-2-yl)cyclopropanecarboxamide | 482.55 | 505.1 (M + 23) |

TABLE I-continued
| Cpd # | Structures | Name | MW | MS Mes'd |
|---|---|---|---|---|
| 111 | 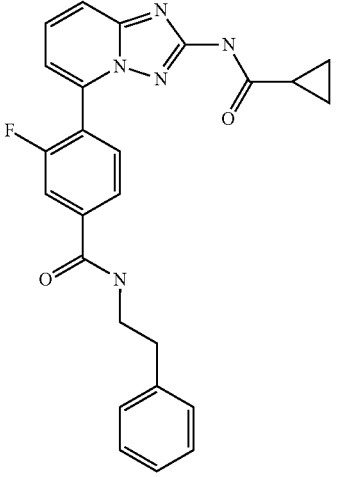 [SMILES: O=C(NCCc1ccccc1)c1ccc(-c2cccc3nc(NC(=O)C4CC4)nn23)c(F)c1] | 4-(2-(cyclopropanecarboxamido)-[1,2,4]triazolo[1,5-a]pyridin-5-yl)-3-fluoro-N-phenethylbenzamide | 443.48 | 444.00 |
| 112 | 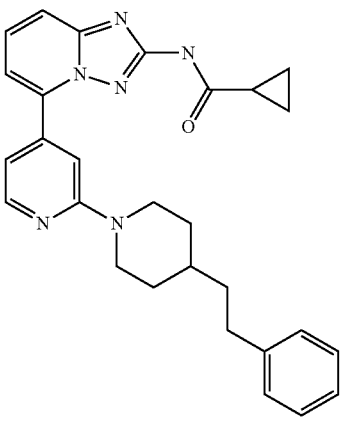 [SMILES: O=C(Nc1nc2cccc(-c3ccnc(N4CCC(CCc5ccccc5)CC4)c3)n2n1)C1CC1] | N-(5-(2-(4-phenethylpiperidin-1-yl)pyridin-4-yl)-[1,2,4]triazolo[1,5-a]pyridin-2-yl)cyclopropanecarboxamide | 466.59 | 467.10 |
| 113 | 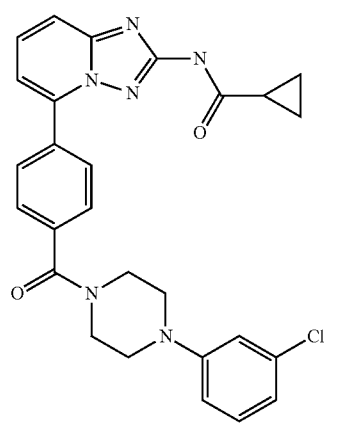 [SMILES: O=C(Nc1nc2cccc(-c3ccc(C(=O)N4CCN(c5cccc(Cl)c5)CC4)cc3)n2n1)C1CC1] | N-(5-(4-(4-(3-chlorophenyl)piperazine-1-carbonyl)phenyl)-[1,2,4]triazolo[1,5-a]pyridin-2-yl)cyclopropanecarboxamide | 500.99 | 501.00 |

TABLE I-continued

| Cpd # | Structures | Name | MW | MS Mes'd |
|---|---|---|---|---|
| 114 | 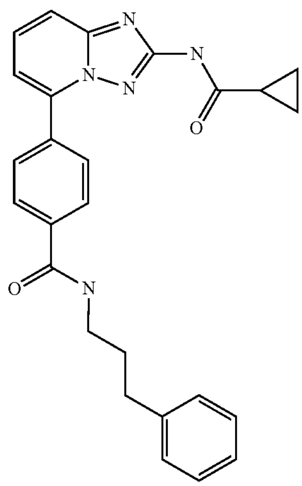 [SMILES: O=C(NCCCc1ccccc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(3-phenylpropyl)benzamide | 439.52 | 440.10 |
| 115 | 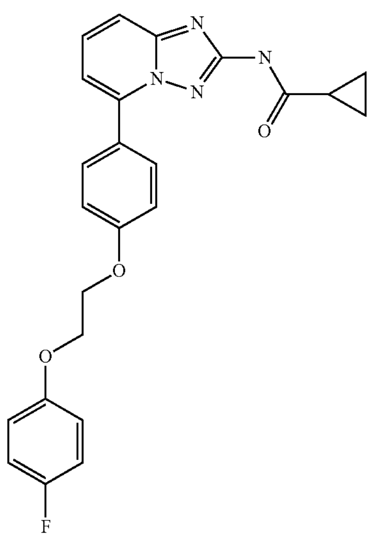 [SMILES: O=C(Nc1nc2cccc(-c3ccc(OCCOc4ccc(F)cc4)cc3)n2n1)C1CC1] | N-(5-(4-(2-(4-fluorophenoxy)ethoxy)phenyl)-[1,2,4]triazolo[1,5-a]pyridin-2-yl)cyclopropanecarboxamide | 432.46 | 433.00 |
| 116 | 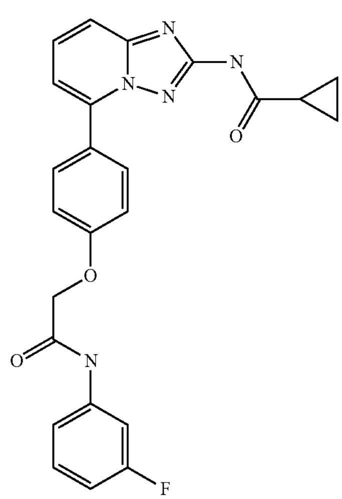 [SMILES: O=C(COc1ccc(-c2cccc3nc(NC(=O)C4CC4)nn23)cc1)Nc1cccc(F)c1] | N-(5-(4-(2-(3-fluorophenylamino)-2-oxoethoxy)phenyl)-[1,2,4]triazolo[1,5-a]pyridin-2-yl)cyclopropanecarboxamide | 445.46 | 446.00 |

TABLE I-continued

| Cpd # | Structures | Name | MW | MS Mes'd |
|---|---|---|---|---|
| 117 | 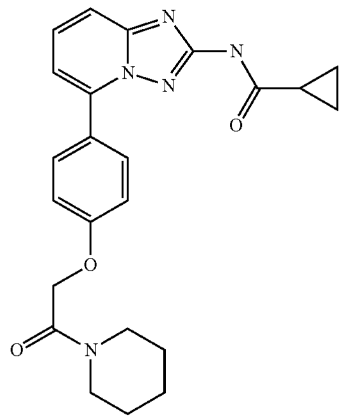 [SMILES: O=C(Nc1nc2cccc(-c3ccc(OCC(=O)N4CCCCC4)cc3)n2n1)C1CC1] | N-(5-(4-(2-oxo-2-(piperidin-1-yl)ethoxy)phenyl)-[1,2,4]triazolo[1,5-a]pyridin-2-yl)cyclopropanecarboxamide | 419.49 | 442 (M + 23) |
| 118 | 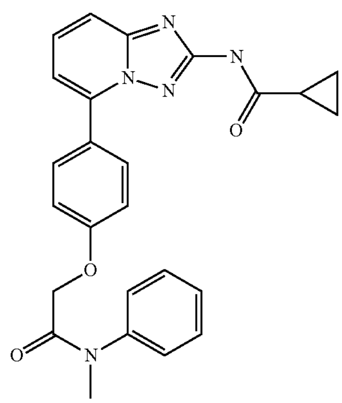 [SMILES: CN(C(=O)COc1ccc(-c2cccc3nc(NC(=O)C4CC4)nn23)cc1)c1ccccc1] | N-(5-(4-(2-(methyl(phenyl)amino)-2-oxoethoxy)phenyl)-[1,2,4]triazolo[1,5-a]pyridin-2-yl)cyclopropanecarboxamide | 441.49 | 442.00 |
| 119 | 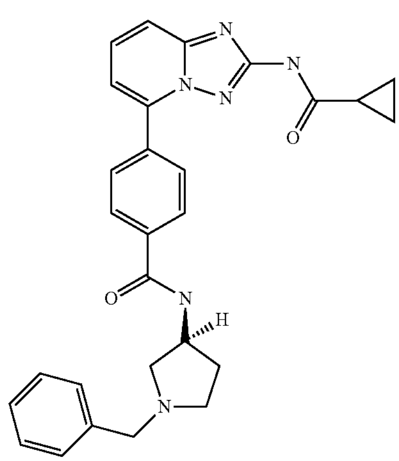 | (S)-N-(1-benzylpyrrolidin-3-yl)-4-(2-(cyclopropanecarboxamido)-[1,2,4]triazolo[1,5-a]pyridin-5-yl)benzamide | 480.57 | 481.20 |

TABLE I-continued

| Cpd # | Structures | Name | MW | MS Mes'd |
|---|---|---|---|---|
| 120 | 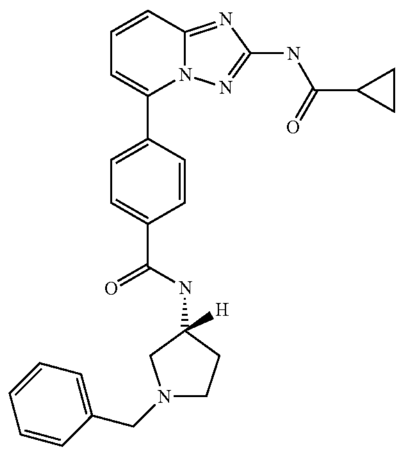 | (R)-N-(1-benzylpyrrolidin-3-yl)-4-(2-(cyclopropanecarboxamido)-[1,2,4]triazolo[1,5-a]pyridin-5-yl)benzamide | 480.57 | 481.10 |
| 121 | 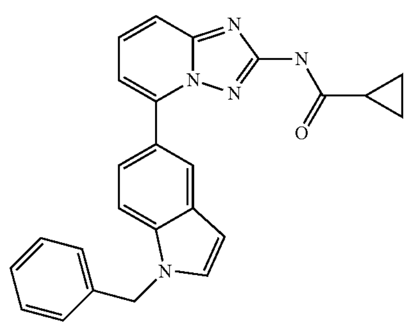 [SMILES: O=C(Nc1nc2cccc(-c3ccc4c(ccn4Cc4ccccc4)c3)n2n1)C1CC1] | N-(5-(1-benzyl-1H-indol-5-yl)-[1,2,4]triazolo[1,5-a]pyridin-2-yl)cyclopropanecarboxamide | 407.48 | 408.00 |
| 122 | 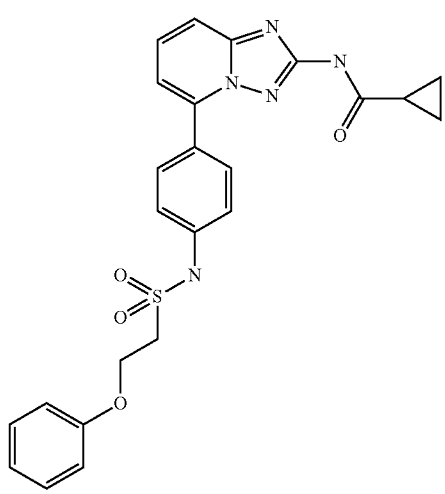 [SMILES: O=C(Nc1nc2cccc(-c3ccc(NS(=O)(=O)CCOc4ccccc4)cc3)n2n1)C1CC1] | N-(5-(4-(2-phenoxyethylsulfanamido)phenyl)-[1,2,4]triazolo[1,5-a]pyridin-2-yl)cyclopropanecarboxamide | 477.55 | 478.00 |

TABLE I-continued
| Cpd # | Structures | Name | MW | MS Mes'd |
|---|---|---|---|---|
| 123 | 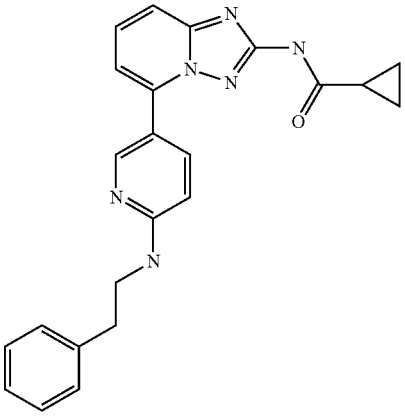 [SMILES: O=C(Nc1nc2cccc(-c3ccc(NCCc4ccccc4)nc3)n2n1)C1CC1] | N-(5-(6-(phenethylamino) pyridin-3-yl)-[1,2,4]triazolo [1,5-a]pyridin-2-yl)cyclopropanecarboxamide | 398.47 | 399.10 |
| 124 | 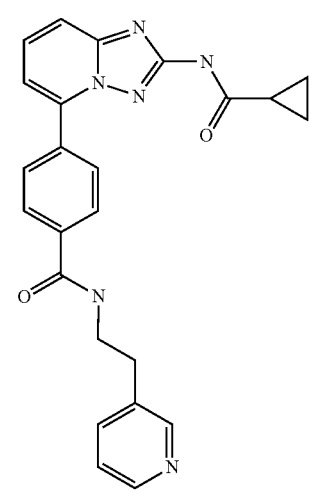 [SMILES: O=C(NCCc1cccnc1)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(2-(pyridin-3-yl)ethyl)benzamide | 425.49 | 427.0 |
| 125 | 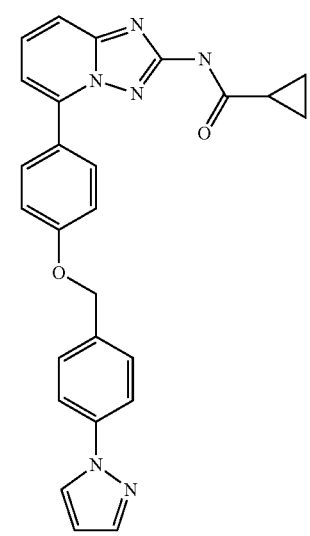 [SMILES: O=C(Nc1nc2cccc(-c3ccc(OCc4ccc(-n5cccn5)cc4)cc3)n2n1)C1CC1] | N-(5-(4-(1H-pyrazol-1-yl)benzyloxy)phenyl)-[1,2,4]triazolo[1,5-a]pyridin-2-yl)cyclopropanecarboxamide | 450.50 | 451.0 |

TABLE I-continued

| Cpd # | Structures | Name | MW | MS Mes'd |
|---|---|---|---|---|
| 126 | 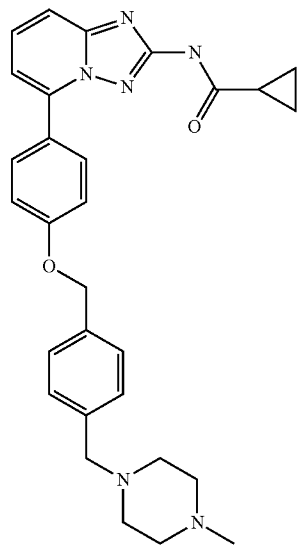 [SMILES: CN1CCN(Cc2ccc(COc3ccc(-c4cccc5nc(NC(=O)C6CC6)nn45)cc3)cc2)CC1] | N-(5-(4-(4-((4-methylpiperazin-1-yl)methyl)benzyloxy)phenyl)-[1,2,4]triazolo[1,5-a]pyridin-2-yl)cyclopropanecarboxamide | 496.61 | 497.1 |
| 127 | 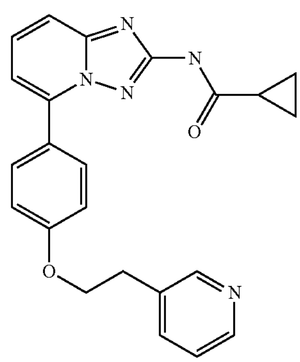 [SMILES: O=C(Nc1nc2cccc(-c3ccc(OCCc4cccnc4)cc3)n2n1)C1CC1] | N-(5-(4-(2-(pyridin-3-yl)ethoxy)phenyl)-[1,2,4]triazolo[1,5-a]pyridin-2-yl)cyclopropanecarboxamide | 399.45 | 400.0 |
| 128 | 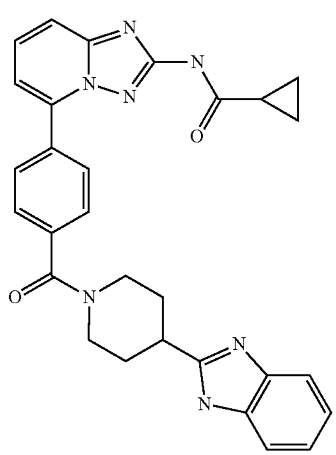 [SMILES: O=C(Nc1nc2cccc(-c3ccc(C(=O)N4CCC(c5nc6ccccc6[nH]5)CC4)cc3)n2n1)C1CC1] | N-(5-(4-(4-(1H-benzo[d]imidazol-2-yl)piperidine-1-carbonyl)phenyl)-[1,2,4]triazolo[1,5-a]pyridin-2-yl)cyclopropanecarboxamide | 505.58 | 506.1 |

TABLE I-continued

| Cpd # | Structures | Name | MW | MS Mes'd |
|---|---|---|---|---|
| 129 | 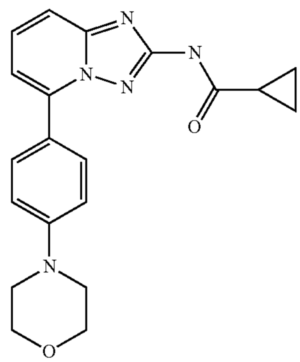 [SMILES: O=C(Nc1nc2cccc(-c3ccc(N4CCOCC4)cc3)n2n1)C1CC1] | N-(5-(4-morpholinophenyl)-[1,2,4]triazolo[1,5-a]pyridin-2-yl)cyclopropanecarboxamide | 363.42 | 364.0 |
| 130 | 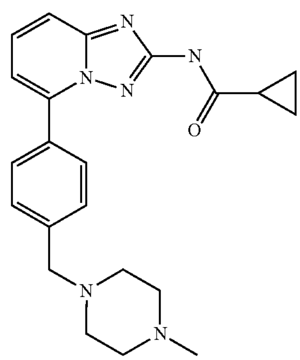 [SMILES: CN1CCN(Cc2ccc(-c3cccc4nc(NC(=O)C5CC5)nn34)cc2)CC1] | N-(5-(4-((4-methylpiperazin-1-yl)methyl)phenyl)-[1,2,4]triazolo[1,5-a]pyridin-2-yl)cyclopropanecarboxamide | 390.49 | 391.1 |
| 131 | 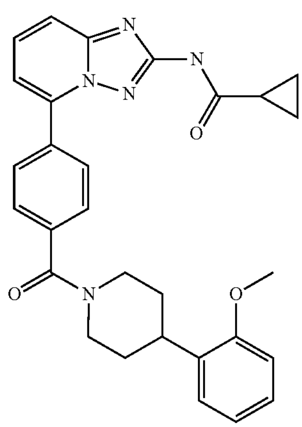 [SMILES: COc1ccccc1C1CCN(C(=O)c2ccc(-c3cccc4nc(NC(=O)C5CC5)nn34)cc2)CC1] | N-(5-(4-(4-(2-methoxyphenyl)piperidine-1-carbonyl)phenyl)-[1,2,4]triazolo[1,5-a]pyridin-2-yl)cyclopropanecarboxamide | 495.59 | 496.1 |
| 132 | 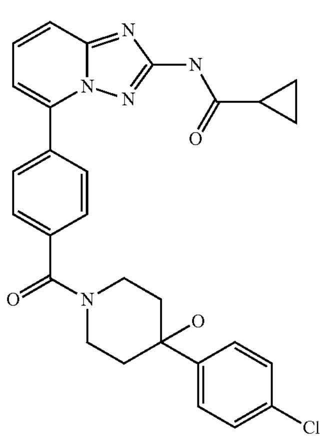 [SMILES: O=C(Nc1nc2cccc(-c3ccc(C(=O)N4CCC(O)(c5ccc(Cl)cc5)CC4)cc3)n2n1)C1CC1] | N-(5-(4-(4-(4-chlorophenyl)-4-hydroxypiperidine-1-carbonyl)phenyl)-[1,2,4]triazolo[1,5-a]pyridin-2-yl)cyclopropanecarboxamide | 516.00 | 516.1 |

TABLE I-continued

| Cpd # | Structures | Name | MW | MS Mes'd |
|---|---|---|---|---|
| 133 | 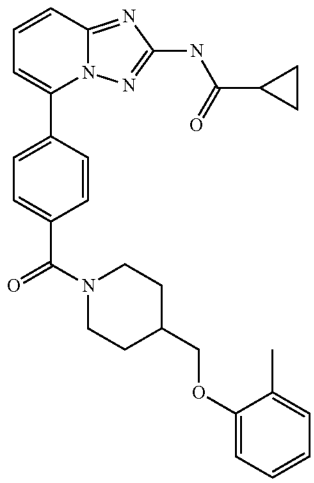 [SMILES: Cc1ccccc1OCC1CCN(C(=O)c2ccc(-c3cccc4nc(NC(=O)C5CC5)nn34)cc2)CC1] | N-(5-(4-(4-(o-tolyloxymethyl)piperidine-1-carbonyl)phenyl)-[1,2,4]triazolo[1,5-a]pyridin-2-yl)cyclopropanecarboxamide | 509.61 | 510.1 |
| 134 | 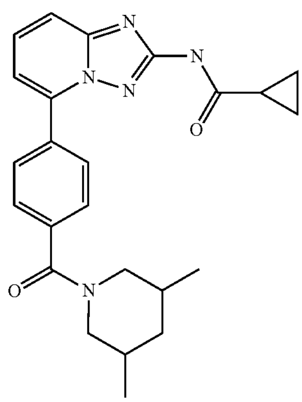 [SMILES: CC1CC(C)CN(C(=O)c2ccc(-c3cccc4nc(NC(=O)C5CC5)nn34)cc2)C1] | N-(5-(4-(3,5-dimethylpiperidine-1-carbonyl)phenyl)-[1,2,4]triazolo[1,5-a]pyridin-2-yl)cyclopropanecarboxamide | 417.52 | 418.1 |
| 135 | 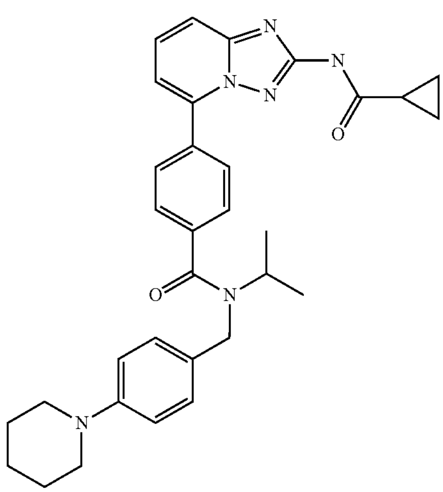 [SMILES: CC(C)N(Cc1ccc(N2CCCCC2)cc1)C(=O)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-isopropyl-N-(4-(piperidin-1-yl)benzyl)benzamide | 536.68 | 539.2 (M$^+$ + Na) |

TABLE I-continued

| Cpd # | Structures | Name | MW | MS Mes'd |
|---|---|---|---|---|
| 136 | 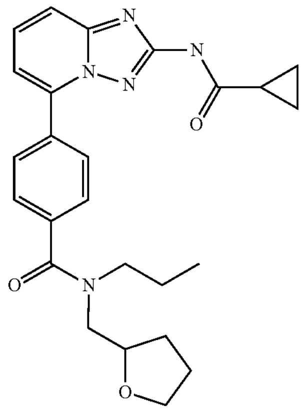 [SMILES: CCCN(CC1CCCO1)C(=O)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-propyl-N-((tetrahydrofuran-2-yl)methyl)benzamide | 447.54 | 448.1 |
| 137 | 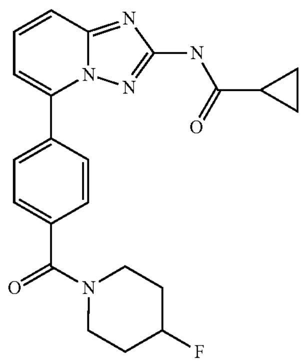 [SMILES: O=C(Nc1nc2cccc(-c3ccc(C(=O)N4CCC(F)CC4)cc3)n2n1)C1CC1] | N-(5-(4-(4-fluoropiperidine-1-carbonyl)phenyl)-[1,2,4]triazolo[1,5-a]pyridin-2-yl)cyclopropanecarboxamide | 407.45 | 408.1 |
| 138 | 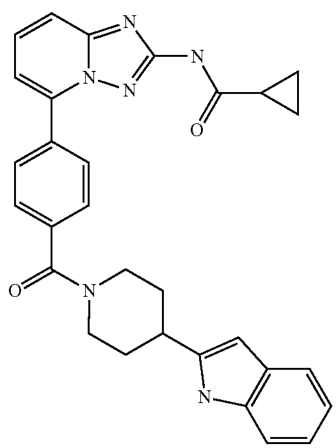 [SMILES: O=C(Nc1nc2cccc(-c3ccc(C(=O)N4CCC(c5cc6ccccc6[nH]5)CC4)cc3)n2n1)C1CC1] | N-(5-(4-(4-(1H-indol-2-yl)piperidine-1-carbonyl)phenyl)-[1,2,4]triazolo[1,5-a]pyridin-2-yl)cyclopropanecarboxamide | 504.60 | 505.1 |
| 139 | 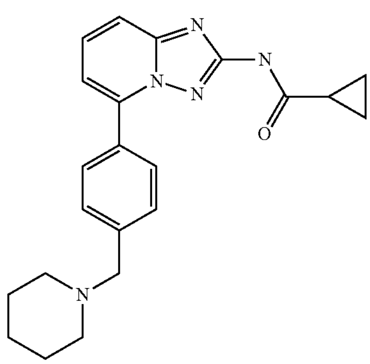 [SMILES: O=C(Nc1nc2cccc(-c3ccc(CN4CCCCC4)cc3)n2n1)C1CC1] | N-(5-(4-(piperidin-1-ylmethyl)phenyl)-[1,2,4]triazolo[1,5-a]pyridin-2-yl)cyclopropanecarboxamide | 375.48 | 376.1 |

TABLE I-continued
| Cpd # | Structures | Name | MW | MS Mes'd |
|---|---|---|---|---|
| 140 | 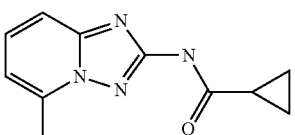 | 1-(cyclopropanecarboxamido)-[1,2,4]triazolo[1,5-a]pyridin-5-yl)benzyl)piperidine-4-carboxamide | 418.5 | 419.1 |
| 141 | 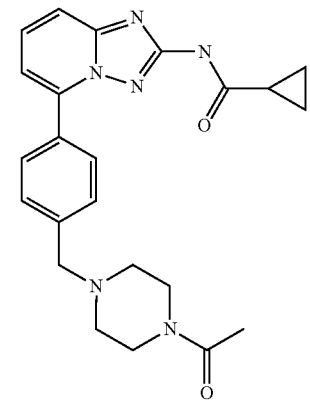 [SMILES: CC(=O)N1CCN(Cc2ccc(-c3cccc4nc(NC(=O)C5CC5)nn34)cc2)CC1] | N-(5-(4-((4-acetoylpiperazin-1-yl)methyl)phenyl)-[1,2,4]triazolo[1,5-a]pyridin-2-yl)cyclopropanecarboxamide | 418.5 | 419.1 |
| 142 | 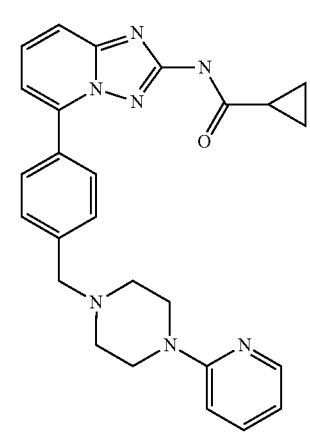 [SMILES: O=C(Nc1nc2cccc(-c3ccc(CN4CCN(c5ccccn5)CC4)cc3)n2n1)C1CC1] | N-(5-(4-((4-(pyridin-2-yl)piperazin-1-yl)methyl)phenyl)-[1,2,4]triazolo[1,5-a]pyridin-2-yl)cyclopropanecarboxamide | 453.55 | 454.1 |

| Cpd # | Structures | Name | MW | MS Mes'd |
|---|---|---|---|---|
| 143 | 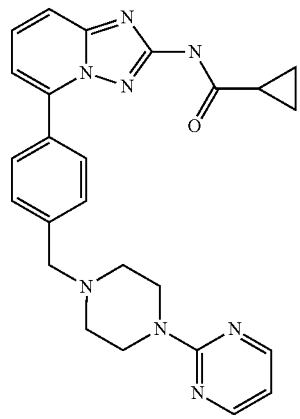 [SMILES: O=C(Nc1nc2cccc(-c3ccc(CN4CCN(c5ncccn5)CC4)cc3)n2n1)C1CC1] | N-(5-(4-((4-(pyrimidin-2-yl)piperazin-1-yl)methyl)phenyl)-[1,2,4]triazolo[1,5-a]pyridin-2-yl)cyclopropanecarboxamide | 454.54 | 477.1 (M$^+$ + Na) |
| 144 | 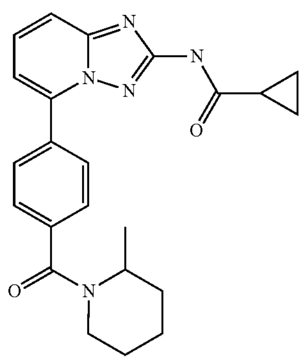 [SMILES: CC1CCCCN1C(=O)c1ccc(-c2cccc3nc(NC(=O)C4CC4)nn23)cc1] | N-(5-(4-(2-methylpiperidine-1-carbonyl)phenyl)-[1,2,4]triazolo[1,5-a]pyridin-2-yl)cyclopropanecarboxamide | 403.49 | 404.1 |
| 145 | 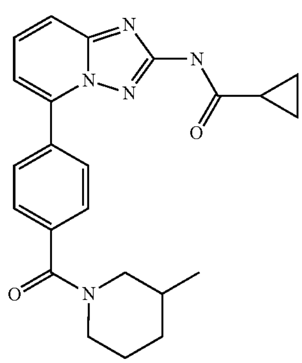 [SMILES: CC1CCCN(C(=O)c2ccc(-c3cccc4nc(NC(=O)C5CC5)nn34)cc2)C1] | N-(5-(4-(3-methylpiperidine-1-carbonyl)phenyl)-[1,2,4]triazolo[1,5-a]pyridin-2-yl)cyclopropanecarboxamide | 403.57 | 404.1 |
| 146 | 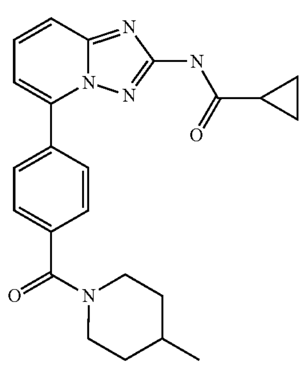 [SMILES: CC1CCN(C(=O)c2ccc(-c3cccc4nc(NC(=O)C5CC5)nn34)cc2)CC1] | N-(5-(4-(4-methylpiperidine-1-carbonyl)phenyl)-[1,2,4]triazolo[1,5-a]pyridin-2-yl)cyclopropanecarboxamide | 403.49 | 404.1 |

TABLE I-continued

| Cpd # | Structures | Name | MW | MS Mes'd |
|---|---|---|---|---|
| 147 | 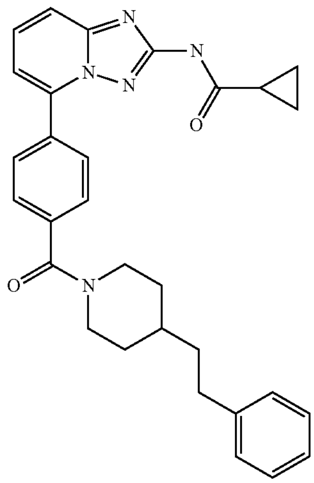 [SMILES: O=C(Nc1nc2cccc(-c3ccc(C(=O)N4CCC(CCc5ccccc5)CC4)cc3)n2n1)C1CC1] | N-(5-(4-(4-phenethylpiperidine-1-carbonyl)phenyl)-[1,2,4]triazolo[1,5-a]pyridin-2-yl)cyclopropanecarboxamide | 493.61 | 494.1 |
| 148 | 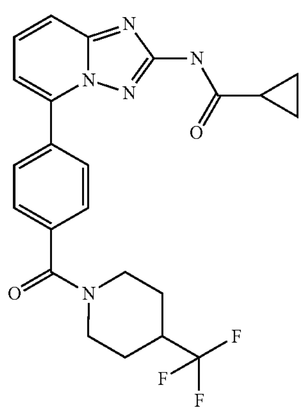 [SMILES: O=C(Nc1nc2cccc(-c3ccc(C(=O)N4CCC(C(F)(F)F)CC4)cc3)n2n1)C1CC1] | N-(5-(4-(4-(trifluoromethyl)piperidine-1-carbonyl)phenyl)-[1,2,4]triazolo[1,5-a]pyridin-2-yl)cyclopropanecarboxamide | 457.46 | 458.0 |
| 149 | 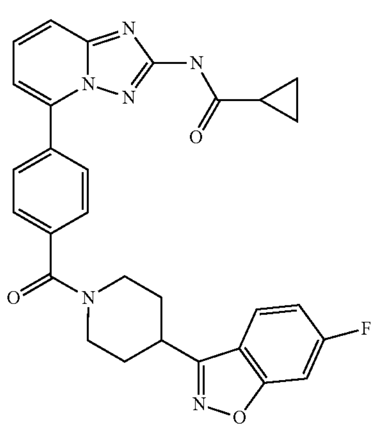 [SMILES: O=C(Nc1nc2cccc(-c3ccc(C(=O)N4CCC(c5noc6cc(F)ccc56)CC4)cc3)n2n1)C1CC1] | N-(5-(4-(4-(6-fluorobenzo[d]isoxazol-3-yl)piperidine-1-carbonyl)phenyl)-[1,2,4]triazolo[1,5-a]pyridin-2-yl)cyclopropanecarboxamide | 524.56 | 525.1 |

TABLE I-continued

| Cpd # | Structures | Name | MW | MS Mes'd |
|---|---|---|---|---|
| 150 | 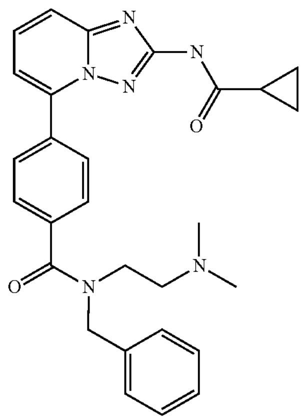 [SMILES: CN(C)CCN(Cc1ccccc1)C(=O)c1ccc(-c2cccc3nc(NC(=O)C4CC4)nn23)cc1] | N-benzyl-4-(2-(cyclopropanecarboxamido)-[1,2,4]triazolo[1,5-a]pyridin-5-yl)-N-(2-(dimethylamino)ethyl)benzamide | 482.59 | 483.1 |
| 151 | 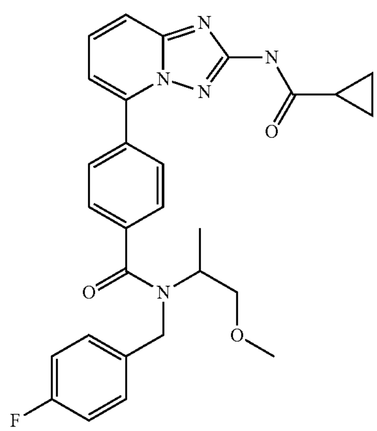 [SMILES: COCC(C)N(Cc1ccc(F)cc1)C(=O)c1ccc(-c2cccc3nc(NC(=O)C4CC4)nn23)cc1] | 4-(2-(cyclopropanecarboxamido)-[1,2,4]triazolo[1,5-a]pyridin-5-yl)-N-(4-fluorobenzyl)-N-(1-methoxypropan-2-yl)benzamide | 501.57 | 502.1 |
| 152 | 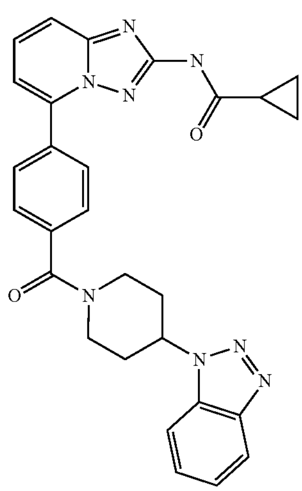 [SMILES: O=C(Nc1nc2cccc(-c3ccc(C(=O)N4CCC(n5nnc6ccccc65)CC4)cc3)n2n1)C1CC1] | N-(5-(4-(4-(1H-benzo[d][1,2,3]triazol-1-yl)piperidine-1-carbonyl)phenyl)-[1,2,4]triazolo[1,5-a]pyridin-2-yl)cyclopropanecarboxamide | 506.57 | 507.1 |

TABLE I-continued

| Cpd # | Structures | Name | MW | MS Mes'd |
|---|---|---|---|---|
| 153 | 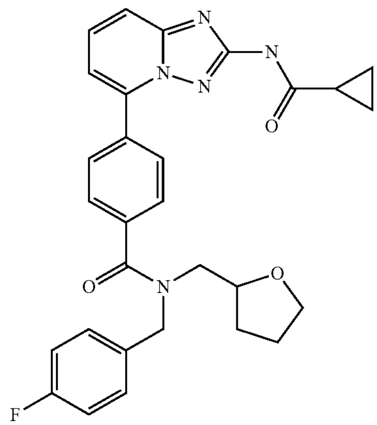 [SMILES: O=C(Nc1nc2cccc(-c3ccc(C(=O)N(Cc4ccc(F)cc4)CC4CCCO4)cc3)n2n1)C1CC1] | 4-(2-(cyclopropanecarboxamido)-[1,2,4]triazolo[1,5-a]pyridin-5-yl)-N-(4-fluorobenzyl)-N-((tetrahydrofuran-2-yl)methyl)benzamide | 513.58 | 514.1 |
| 154 | 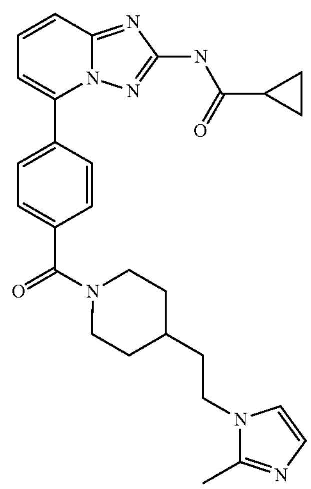 [SMILES: Cc1nccn1CCC1CCN(C(=O)c2ccc(-c3cccc4nc(NC(=O)C5CC5)nn34)cc2)CC1] | N-(5-(4-(imino(4-(2-(2-methyl-1H-imidazol-1-yl)ethyl)piperidin-1-yl)methyl)phenyl)-[1,2,4]triazolo[1,5-a]pyridin-2-yl)cyclopropanecarboxamide | 496.6 | 497.1 |
| 155 | 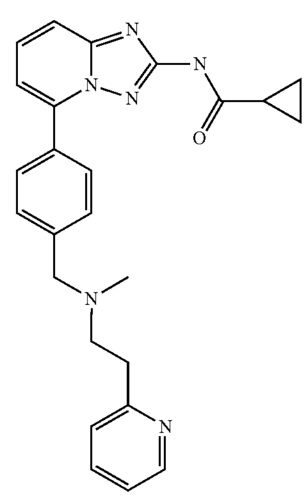 [SMILES: CN(CCc1ccccn1)Cc1ccc(-c2cccc3nc(NC(=O)C4CC4)nn23)cc1] | N-(5-(4-((methyl(2-(pyridin-2-yl)ethyl)amino)methyl)phenyl)-[1,2,4]triazolo[1,5-a]pyridin-2-yl)cyclopropanecarboxamide | 426.52 | 427.1 |

TABLE I-continued

| Cpd # | Structures | Name | MW | MS Mes'd |
|---|---|---|---|---|
| 156 | 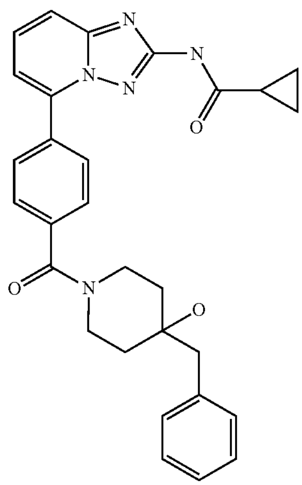 [SMILES: O=C(Nc1nc2cccc(-c3ccc(C(=O)N4CCC(O)(Cc5ccccc5)CC4)cc3)n2n1)C1CC1] | N-(5-(4-(4-benzyl-4-hydroxypiperidine-1-carbonyl)phenyl)-[1,2,4]triazolo[1,5-a]pyridin-2-yl)cyclopropanecarboxamide | 49.59 | 496.1 |
| 157 | 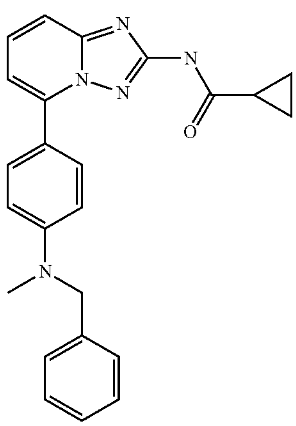 [SMILES: CN(Cc1ccccc1)c1ccc(-c2cccc3nc(NC(=O)C4CC4)nn23)cc1] | N-(5-(4-(benzyl(methyl)amino)phenyl)-[1,2,4]triazolo[1,5-a]pyridin-2-yl)cyclopropanecarboxamide | 397.48 | 398.1 |
| 158 | 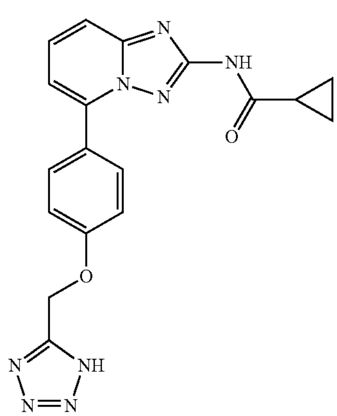 [SMILES: O=C(Nc1nc2cccc(-c3ccc(OCc4nnn[nH]4)cc3)n2n1)C1CC1] | N-(5-(4-((1H-tetrazol-5-yl)methyl1H-tetrazol-5-yl)methoxy)phenyl)-[1,2,4]triazolo[1,5-a]pyridin-2-yl)cyclopropanecarboxamide | 376.38 | 377.1 |

TABLE I-continued

| Cpd # | Structures | Name | MW | MS Mes'd |
|---|---|---|---|---|
| 159 | 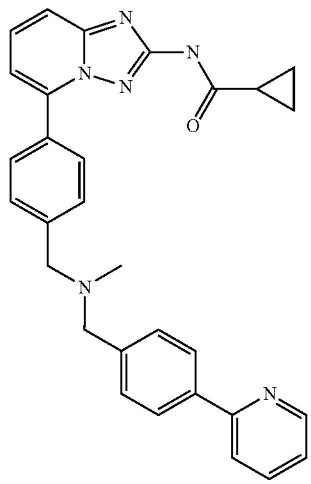 [SMILES: CN(Cc1ccc(-c2ccccn2)cc1)Cc1ccc(-c2cccc3nc(NC(=O)C4CC4)nn23)cc1] | N-(5-(4-((methyl(4-(pyridin-2-yl)benzyl)amino)methyl)phenyl)-[1,2,4]triazolo[1,5-a]pyridin-2-yl)cyclopropanecarboxamide | 488.59 | 511.1 (M⁺ + Na) |
| 160 | 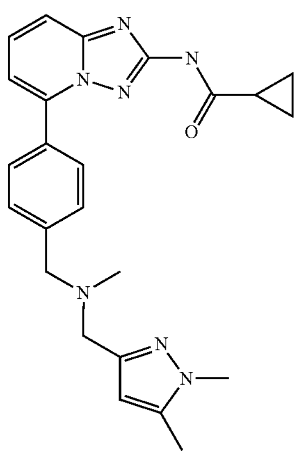 [SMILES: Cc1cc(CN(C)Cc2ccc(-c3cccc4nc(NC(=O)C5CC5)nn34)cc2)nn1C] | N-(5-(4-((((1,5-dimethyl-1H-pyrazol-3-yl)methyl)(methyl)amino)methyl)phenyl)-[1,2,4]triazolo[1,5-a]pyridin-2-yl)cyclopropanecarboxamide | 429.53 | 430.1 |
| 161 | 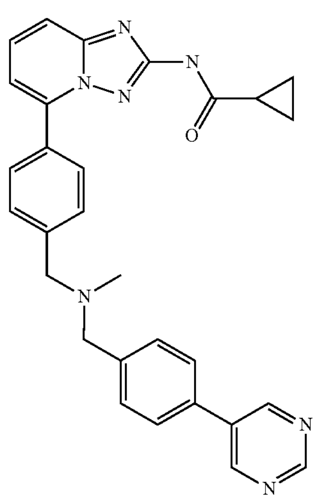 [SMILES: CN(Cc1ccc(-c2cncnc2)cc1)Cc1ccc(-c2cccc3nc(NC(=O)C4CC4)nn23)cc1] | N-(5-(4-((methyl(4-(pyrimidin-5-yl)benzyl)amino)methyl)phenyl)-[1,2,4]triazolo[1,5-a]pyridin-2-yl)cyclopropanecarboxamide | 489.54 | 490.1 |

TABLE I-continued

| Cpd # | Structures | Name | MW | MS Mes'd |
|---|---|---|---|---|
| 162 | 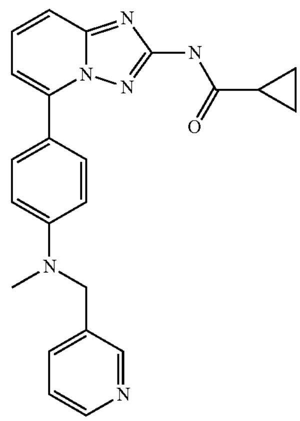 | N-(5-(4-(methyl(pyridin-3-ylmethyl)amino)phenyl)-[1,2,4]triazolo[1,5-a]pyridin-2-yl)cyclopropanecarboxamide | 398.47 | 399.1 |
| 163 | 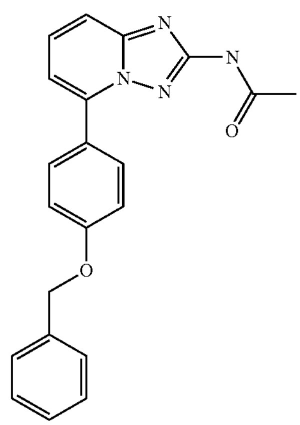 [SMILES: CC(=O)Nc1nc2cccc(-c3ccc(OCc4ccccc4)cc3)n2n1] | N-(5-(4-(benzyloxy)phenyl)-[1,2,4]triazolo[1,5-a]pyridin-2-yl)acetamide | 358.40 | 359.0 |
| 164 | 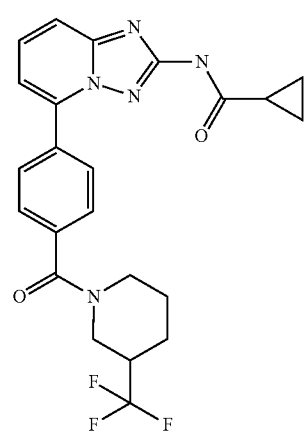 [SMILES: O=C(Nc1nc2cccc(-c3ccc(C(=O)N4CCCC(C(F)(F)F)C4)cc3)n2n1)C1CC1] | N-(5-(4-(3-(trifluoromethyl)piperidine-1-carbonyl)phenyl)-[1,2,4]triazolo[1,5-a]pyridin-2-yl)cyclopropanecarboxamide | 457.46 | 458.0 |

| Cpd # | Structures | Name | MW | MS Mes'd |
|---|---|---|---|---|
| 165 | 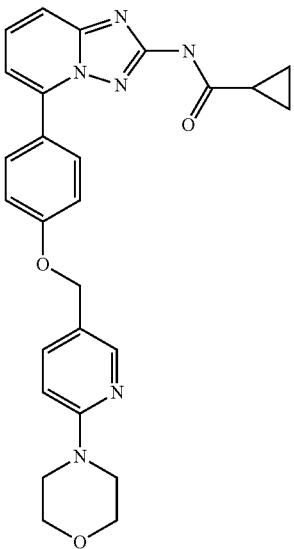 [SMILES: O=C(Nc1nc2cccc(-c3ccc(OCc4ccc(N5CCOCC5)nc4)cc3)n2n1)C1CC1] | N-(5-(4-((6-morpholinopyridin-3-yl)methoxy)phenyl)-[1,2,4]triazolo[1,5-a]pyridin-2-yl)cyclopropanecarboxamide | 470.53 | 471.1 |
| 166 | 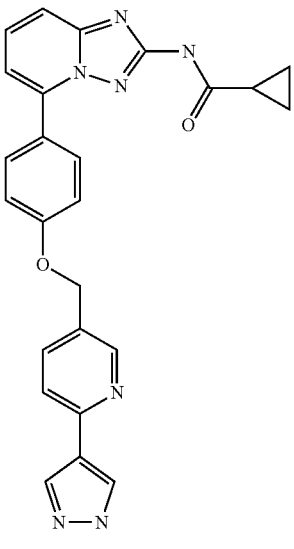 [SMILES: O=C(Nc1nc2cccc(-c3ccc(OCc4ccc(-c5cn[nH]c5)nc4)cc3)n2n1)C1CC1] | N-(5-(4-((6-(1H-pyrazol-4-yl)pyridin-3-yl)methyl1H-pyrazol-4-yl)pyridin-3-yl)methoxy)phenyl)-[1,2,4]triazolo[1,5-a]pyridin-2-yl)cyclopropanecarboxamide | 451.49 | 452.0 |

TABLE I-continued

| Cpd # | Structures | Name | MW | MS Mes'd |
|---|---|---|---|---|
| 167 | 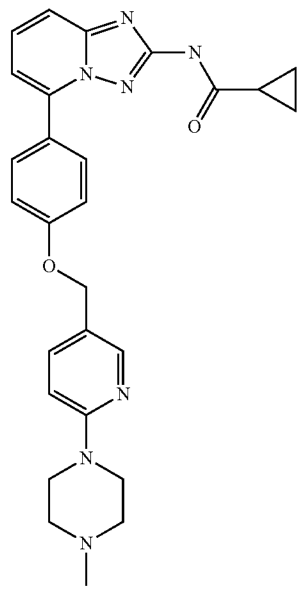 [SMILES: CN1CCN(c2ccc(COc3ccc(-c4cccc5nc(NC(=O)C6CC6)nn45)cc3)cn2)CC1] | N-(5-(4-((6-(4-methylpiperazin-1-yl)pyridin-3-yl)methoxy)phenyl)-[1,2,4]triazolo[1,5-a]pyridin-2-yl)cyclopropanecarboxamide | 483.58 | 484.1 |
| 168 | 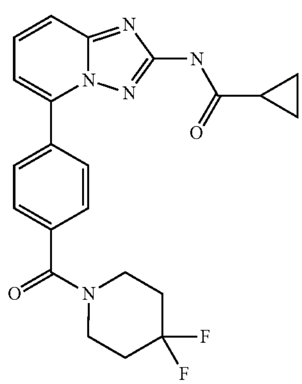 [SMILES: O=C(Nc1nc2cccc(-c3ccc(C(=O)N4CCC(F)(F)CC4)cc3)n2n1)C1CC1] | N-(5-(4-(4,4-difluoropiperidine-1-carbonyl)phenyl)-[1,2,4]triazolo[1,5-a]pyridin-2-yl)cyclopropanecarboxamide | 425.44 | 426.1 |
| 169 | 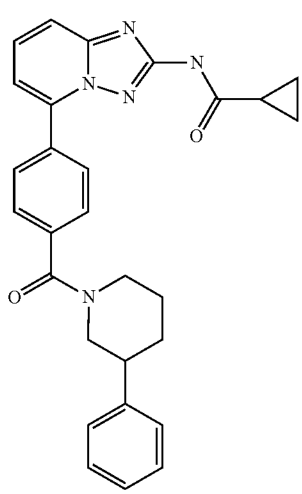 [SMILES: O=C(Nc1nc2cccc(-c3ccc(C(=O)N4CCCC(c5ccccc5)C4)cc3)n2n1)C1CC1] | N-(5-(4-(3-phenylpiperidine-1-carbonyl)phenyl)-[1,2,4]triazolo[1,5-a]pyridin-2-yl)cyclopropanecarboxamide | 465.56 | 466.1 |

TABLE I-continued

| Cpd # | Name | MW | MS Mes'd |
|---|---|---|---|
| 170 | N-(5-(6-(pyridin-3-ylmethylamino)pyridin-3-yl)-[1,2,4]triazolo[1,5-a]pyridin-2-yl)cyclopropanecarboxamide | 385.43 | 386.1 |
| 171 | N-(5-(6-(pyridin-2-ylmethylamino)pyridin-3-yl)-[1,2,4]triazolo[1,5-a]pyridin-2-yl)cyclopropanecarboxamide | 385.43 | 386.1 |
| 172 | N-(5-(6-(2-(pyridin-3-yl)ethylamino)pyridin-3-yl)-[1,2,4]triazolo[1,5-a]pyridin-2-yl)cyclopropanecarboxamide | 399.46 | 400.1 |

TABLE I-continued
| Cpd # | Structures | Name | MW | MS Mes'd |
|---|---|---|---|---|
| 173 | 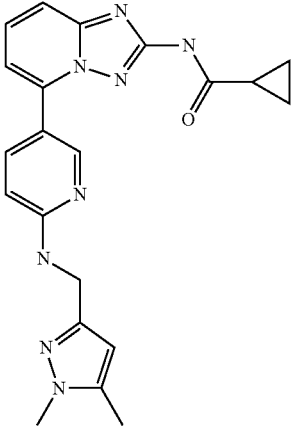 [SMILES: Cc1cc(CNc2ccc(-c3cccc4nc(NC(=O)C5CC5)nn34)cn2)nn1C] | N-(5-(6-((1,5-dimethyl-1H-pyrazol-3-yl)methylamino)pyridin-3-yl)-[1,2,4]triazolo[1,5-a]pyridin-2-yl)cyclopropanecarboxamide | 402.46 | 403.1 |
| 174 | 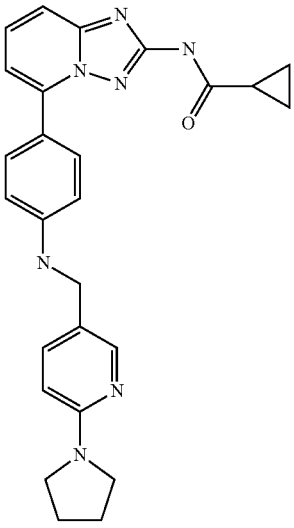 [SMILES: O=C(Nc1nc2cccc(-c3ccc(NCc4ccc(N5CCCC5)nc4)cc3)n2n1)C1CC1] | N-(5-(4-((6-(pyrrolidin-1-yl)pyridin-3-yl)methoxy)phenyl)-[1,2,4]triazolo[1,5-a]pyridin-2-yl)cyclopropanecarboxamide | 454.53 | 455.1 |
| 175 | 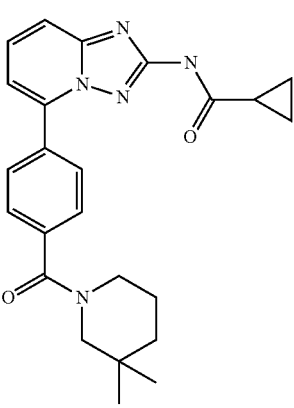 [SMILES: CC1(C)CCCN(C(=O)c2ccc(-c3cccc4nc(NC(=O)C5CC5)nn34)cc2)C1] | N-(5-(4-(3,3-dimethylpiperidine-1-carbonyl)phenyl)-[1,2,4]triazolo[1,5-a]pyridin-2-yl)cyclopropanecarboxamide | 417.52 | 418.1 |

TABLE I-continued

| Cpd # | Structures | Name | MW | MS Mes'd |
|---|---|---|---|---|
| 176 | 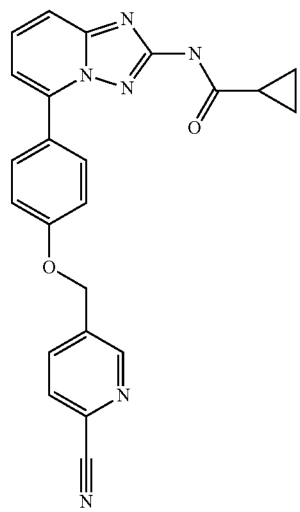 [SMILES: N#Cc1ccc(COc2ccc(-c3cccc4nc(NC(=O)C5CC5)nn34)cc2)cn1] | N-(5-(4-((6-cyanopyridin-3-yl)methoxy)phenyl)-[1,2,4]triazolo[1,5-a]pyridin-2-yl)cyclopropanecarboxamide | 410.44 | 411.0 |
| 177 | 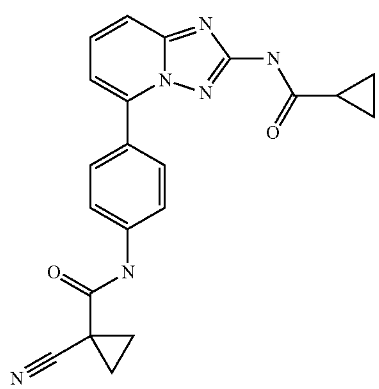 [SMILES: N#CC1(C(=O)Nc2ccc(-c3cccc4nc(NC(=O)C5CC5)nn34)cc2)CC1] | 1-cyano-N-(4-(2-(cyclopropanecarboxamido)-[1,2,4]triazolo[1,5-a]pyridin-5-yl)phenyl)cyclopropanecarboxamide | 386.42 | 387.1 |
| 178 | 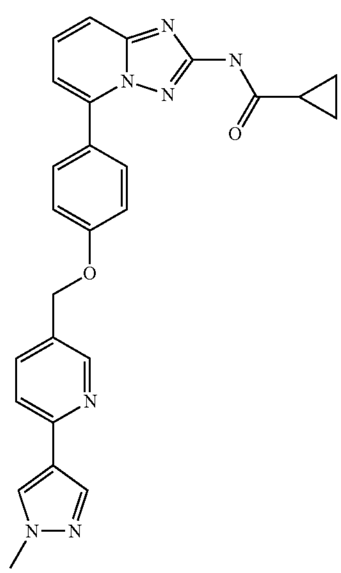 [SMILES: Cn1cc(-c2ccc(COc3ccc(-c4cccc5nc(NC(=O)C6CC6)nn45)cc3)cn2)cn1] | N-(5-(4-((6-(1-methyl-1H-pyrazol-4-yl)pyridin-3-yl)methylmethyl-1H-pyrazol-4-yl)pyridin-3-yl)methoxy)phenyl)-[1,2,4]triazolo[1,5-a]pyridin-2-yl)cyclopropanecarboxamide | 465.52 | 466.0 |

TABLE I-continued

| Cpd # | Structures | Name | MW | MS Mes'd |
|---|---|---|---|---|
| 179 | 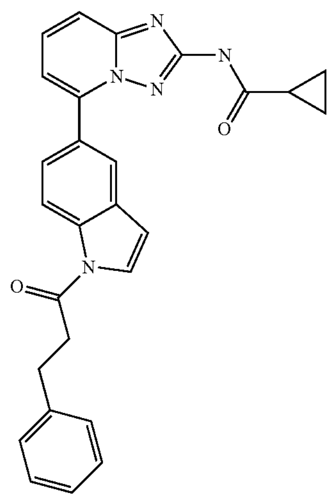 [SMILES: O=C(Nc1nc2cccc(-c3ccc4c(ccn4C(=O)CCc4ccccc4)c3)n2n1)C1CC1] | N-(5-(1-(3-phenylpropanoyl)-1H-indol-5-yl)-[1,2,4]triazolo[1,5-a]pyridin-2-yl)cyclopropanecarboxamide | 449.52 | 450.0 |
| 180 | 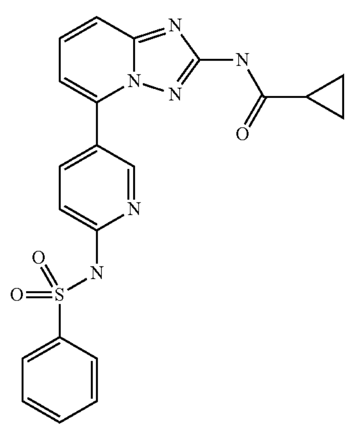 [SMILES: O=C(Nc1nc2cccc(-c3ccc(NS(=O)(=O)c4ccccc4)nc3)n2n1)C1CC1] | N-(5-(6-(phenylsulfonamido)pyridin-3-yl)-[1,2,4]triazolo[1,5-a]pyridin-2-yl)cyclopropanecarboxamide | 434.48 | 435.0 |
| 181 | 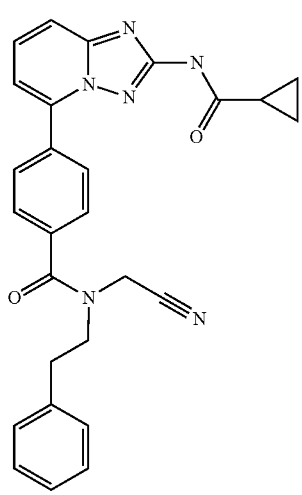 [SMILES: N#CCN(CCc1ccccc1)C(=O)c1ccc(-c2cccc3nc(NC(=O)C4CC4)nn23)cc1] | N-(cyanomethyl)-4-(2-(cyclopropanecarboxamido)-[1,2,4]triazolo[1,5-a]pyridin-5-yl)-N-phenethylbenzamide | 464.63 | 465.0 |

TABLE I-continued
| Cpd # | Structures | Name | MW | MS Mes'd |
|---|---|---|---|---|
| 182 | 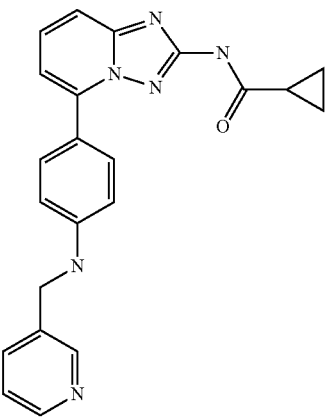 | N-(5-(4-(pyridin-3-ylmethylamino)phenyl)-[1,2,4]triazolo[1,5-a]pyridin-2-yl)cyclopropanecarboxamide | 384.44 | 385.0 |
| 183 | 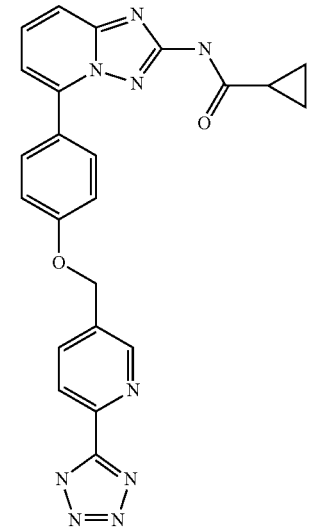 [SMILES: O=C(Nc1nc2cccc(-c3ccc(OCc4ccc(-c5nnn[nH]5)nc4)cc3)n2n1)C1CC1] | N-(5-(4-((6-(1H-tetrazol-5-yl)pyridin-3-yl)methyl1H-tetrazol-5-yl)pyridin-3-yl)methoxy)phenyl)-[1,2,4]triazolo[1,5-a]pyridin-2-yl)cyclopropanecarboxamide | 453.47 | 454.0 |
| 184 | 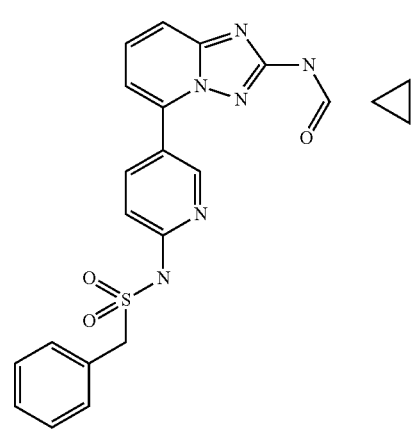 | N-(5-(6-(phenylmethylsulfonamido)pyridin-3-yl)-[1,2,4]triazolo[1,5-a]pyridin-2-yl)cyclopropanecarboxamide | 448.51 | 449.0 |

TABLE I-continued

| Cpd # | Structures | Name | MW | MS Mes'd |
|---|---|---|---|---|
| 185 | 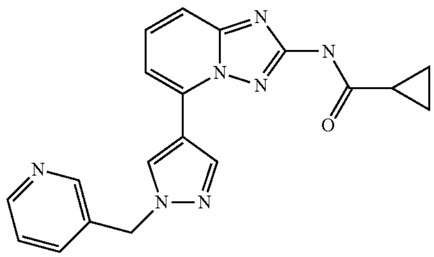 [SMILES: O=C(Nc1nc2cccc(-c3cnn(Cc4cccnc4)c3)n2n1)C1CC1] | N-(5-(1-(pyridin-3-ylmethyl)-1H-pyrazol-4-yl)-[1,2,4]triazolo[1,5-a]pyridin-2-yl)cyclopropanecarboxamide | 359.39 | 360.0 |
| 186 | 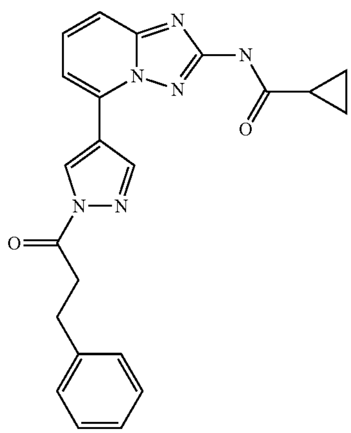 [SMILES: O=C(Nc1nc2cccc(-c3cnn(C(=O)CCc4ccccc4)c3)n2n1)C1CC1] | N-(5-(1-(3-phenylpropanoyl)-1H-pyrazol-4-yl)-[1,2,4]triazolo[1,5-a]pyridin-2-yl)cyclopropanecarboxamide | 400.44 | 401.0 |
| 187 | 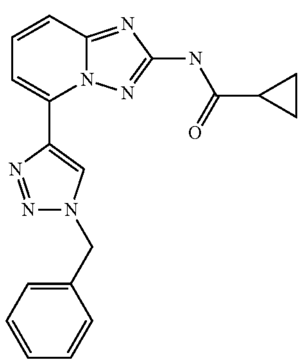 [SMILES: O=C(Nc1nc2cccc(-c3cn(Cc4ccccc4)nn3)n2n1)C1CC1] | N-(5-(1-benzyl-1H-1,2,3-triazol-4-yl)-[1,2,4]triazolo[1,5-a]pyridin-2-yl)cyclopropanecarboxamide | 359.39 | 360.0 |
| 188 | 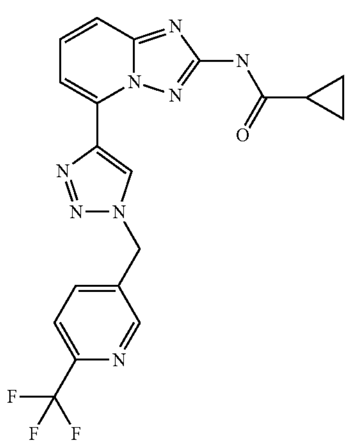 [SMILES: O=C(Nc1nc2cccc(-c3cn(Cc4ccc(C(F)(F)F)nc4)nn3)n2n1)C1CC1] | N-(5-(1-((6-(trifluoromethyl)pyridin-3-yl)methyl)-1H-1,2,3-triazol-4-yl)-[1,2,4]triazolo[1,5-a]pyridin-2-yl)cyclopropanecarboxamide | 428.38 | 451.0 (M$^+$ + Na) |

TABLE I-continued

| Cpd # | Structures | Name | MW | MS Mes'd |
|---|---|---|---|---|
| 189 | 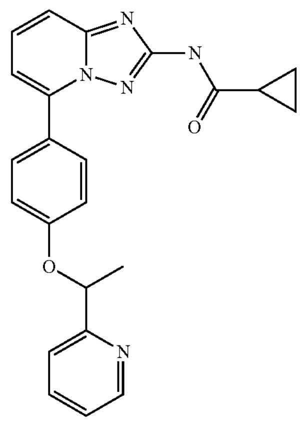 [SMILES: CC(Oc1ccc(-c2cccc3nc(NC(=O)C4CC4)nn23)cc1)c1ccccn1] | N-(5-(4-(1-(pyridin-2-yl)ethoxy)phenyl)-[1,2,4]triazolo[1,5-a]pyridin-2-yl)cyclopropanecarboxamide | 399.45 | 422.0 (M$^+$ + Na) |
| 190 | 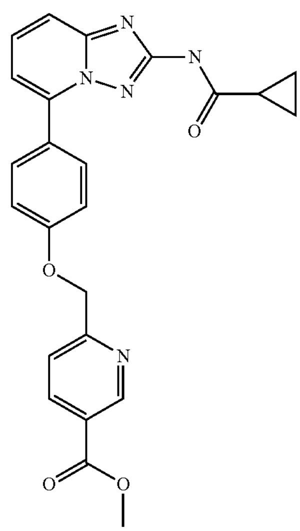 [SMILES: COC(=O)c1ccc(COc2ccc(-c3cccc4nc(NC(=O)C5CC5)nn34)cc2)nc1] | methyl 6-((4-(2-(cyclopropanecarboxamido)-[1,2,4]triazolo[1,5-a]pyridin-5-yl)phenylcyclopropanecarboxamido)-[1,2,4]triazolo[1,5-a]pyridin-5-yl)phenoxy)methyl)nicotinate | 443.47 | 444.0 |
| 191 | 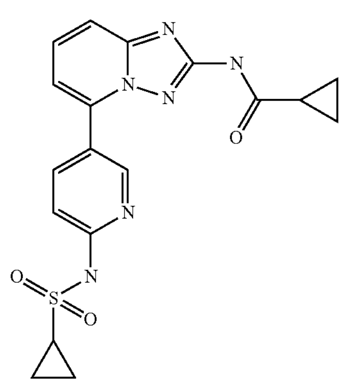 [SMILES: O=C(Nc1nc2cccc(-c3ccc(NS(=O)(=O)C4CC4)nc3)n2n1)C1CC1] | N-(5-(6-(cyclopropanesulfonamido)pyridin-3-yl)-[1,2,4]triazolo[1,5-a]pyridin-2-yl)cyclopropanecarboxamide | 398.46 | 399.0 |

TABLE I-continued

| Cpd # | Structures | Name | MW | MS Mes'd |
|---|---|---|---|---|
| 192 | 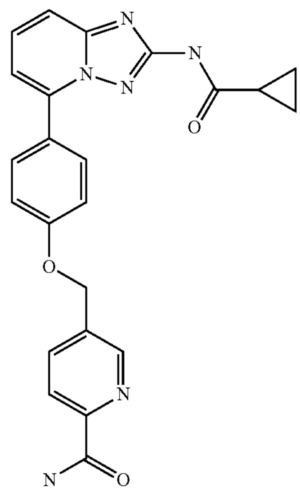 [SMILES: NC(=O)c1ccc(COc2ccc(-c3cccc4nc(NC(=O)C5CC5)nn34)cc2)cn1] | 5-((4-(2-(cyclopropanecarboxamido)-[1,2,4]triazolo[1,5-a]pyridin-5-yl)phenylcyclopropanecarboxamido)-[1,2,4]triazolo[1,5-a]pyridin-5-yl)phenoxy)methyl)picolinamide | 428.45 | 429.1 |
| 193 | 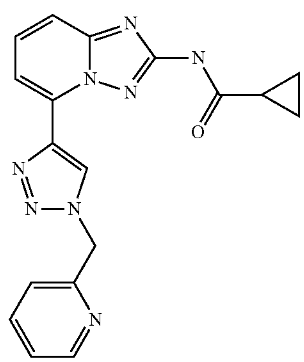 [SMILES: O=C(Nc1nc2cccc(-c3cn(Cc4ccccn4)nn3)n2n1)C1CC1] | N-(5-(1-(pyridin-2-ylmethyl)-1H-1,2,3-triazol-4-yl)-[1,2,4]triazolo[1,5-a]pyridin-2-yl)cyclopropanecarboxamide | 360.38 | 360.0 |
| 194 | 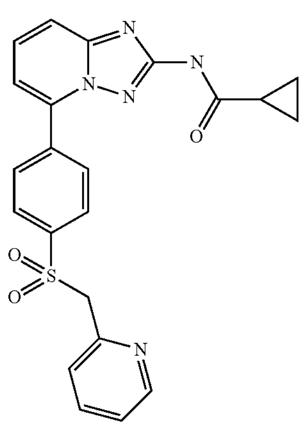 [SMILES: O=C(Nc1nc2cccc(-c3ccc(S(=O)(=O)Cc4ccccn4)cc3)n2n1)C1CC1] | N-(5-(4-(pyridin-2-ylmethylsulfonyl)phenyl)-[1,2,4]triazolo[1,5-a]pyridin-2-yl)cyclopropanecarboxamide | 433.48 | 434.1 |

TABLE I-continued

| Cpd # | Structures | Name | MW | MS Mes'd |
|---|---|---|---|---|
| 195 | 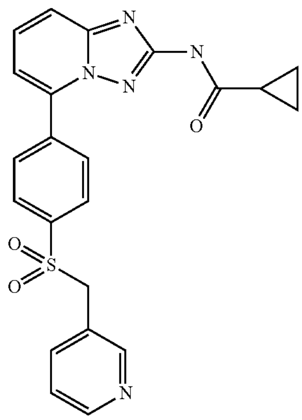 [SMILES: O=C(Nc1nc2cccc(-c3ccc(S(=O)(=O)Cc4cccnc4)cc3)n2n1)C1CC1] | N-(5-(4-(pyridin-3-ylmethylsulfonyl)phenyl)-[1,2,4]triazolo[1,5-a]pyridin-2-yl)cyclopropanecarboxamide | 433.48 | 434.1 |
| 196 | 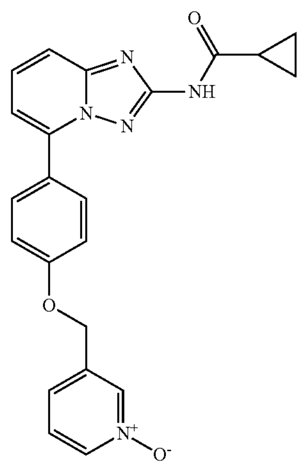 [SMILES: O=C(Nc1nc2cccc(-c3ccc(OCc4ccc[n+]([O-])c4)cc3)n2n1)C1CC1] | Cyclopropanecarboxylic acid {5-[4-(1-hydroxy-pyridin-3-ylmethoxy)-phenyl]-[1,2,4]triazolo[1,5-a]pyridin-2-yl}-amide | 401.43 | 402.0 |
| 197 | 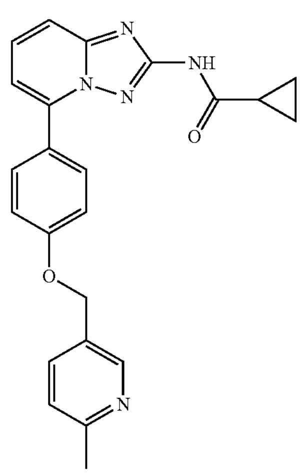 [SMILES: Cc1ccc(COc2ccc(-c3cccc4nc(NC(=O)C5CC5)nn34)cc2)cn1] | Cyclopropanecarboxylic acid {5-[4-(6-methyl-pyridin-3-ylmethoxy)-phenyl]-[1,2,4]triazolo[1,5-a]pyridin-2-yl}-amide | 399.45 | 400.1 |

TABLE I-continued
| Cpd # | Structures | Name | MW | MS Mes'd |
|---|---|---|---|---|
| 198 | 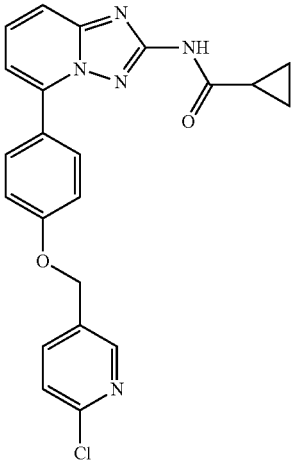 [SMILES: O=C(Nc1nc2cccc(-c3ccc(OCc4ccc(Cl)nc4)cc3)n2n1)C1CC1] | Cyclopropanecarboxylic acid {5-[4-(6-chloro-pyridin-3-ylmethoxy)-phenyl]-[1,2,4]triazolo[1,5-a]pyridin-2-yl}-amide | 419.87 | 420.0 |
| 199 | 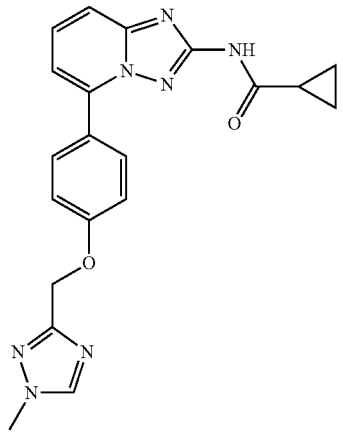 [SMILES: Cn1cnc(COc2ccc(-c3cccc4nc(NC(=O)C5CC5)nn34)cc2)n1] | Cyclopropanecarboxylic acid {5-[4-(1-methyl-1H-[1,2,4]triazol-3-ylmethoxy)-phenyl]-[1,2,4]triazolo[1,5-a]pyridin-2-yl}-amide | 389.42 | 390.1 |
| 200 | 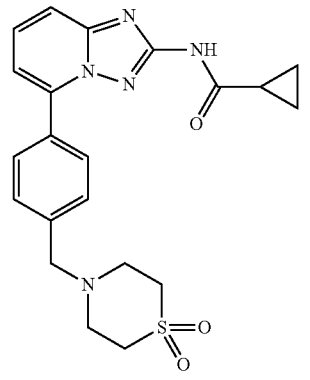 [SMILES: O=C(Nc1nc2cccc(-c3ccc(CN4CCS(=O)(=O)CC4)cc3)n2n1)C1CC1] | Cyclopropanecarboxylic acid {5-[4-(1,1-dioxo-thiomorpholin-4-ylmethyl)-phenyl]-[1,2,4]triazolo[1,5-a]pyridin-2-yl}-amide | 425.51 | 426 |

TABLE I-continued

| Cpd # | Structures | Name | MW | MS Mes'd |
|---|---|---|---|---|
| 201 | 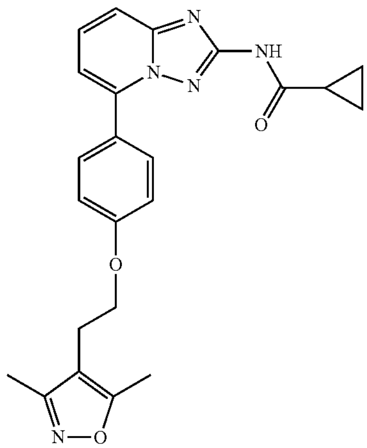 [SMILES: Cc1noc(C)c1CCOc1ccc(-c2cccc3nc(NC(=O)C4CC4)nn23)cc1] | Cyclopropanecarboxylic acid (5-{4-[2-(3,5-dimethyl-isoxazol-4-yl)-ethoxy]-phenyl}-[1,2,4]triazolo[1,5-a]pyridin-2-yl)-amide | 417.47 | 418.1 |
| 202 | 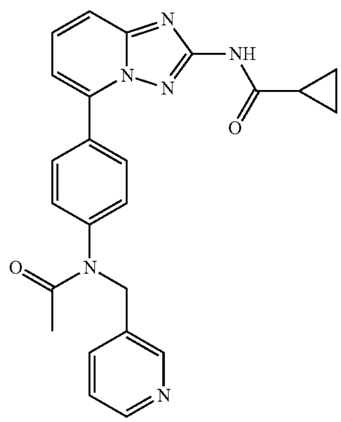 [SMILES: CC(=O)N(Cc1cccnc1)c1ccc(-c2cccc3nc(NC(=O)C4CC4)nn23)cc1] | Cyclopropanecarboxylic acid {5-[4-(acetyl-pyridin-3-ylmethyl-amino)-phenyl]-[1,2,4]triazolo[1,5-a]pyridin-2-yl}-amide | 426.48 | 427.1 |
| 203 | 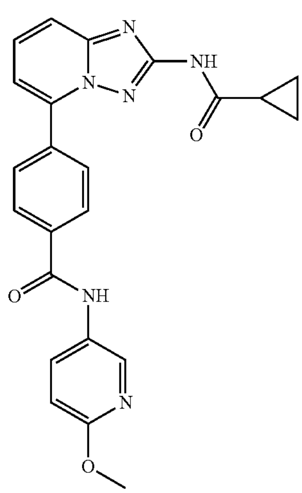 [SMILES: COc1ccc(NC(=O)c2ccc(-c3cccc4nc(NC(=O)C5CC5)nn34)cc2)cn1] | 4-[2-(Cyclopropanecarbonyl-amino)-[1,2,4]triazolo[1,5-a]pyridin-5-yl]-N-(6-methoxy-pyridin-3-yl)-benzamide | 428.45 | 429.0 |

TABLE I-continued
| Cpd # | Structures | Name | MW | MS Mes'd |
|---|---|---|---|---|
| 204 | 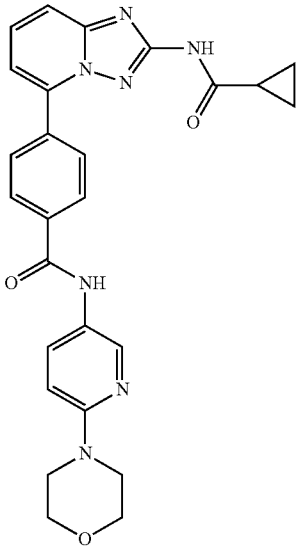 [SMILES: O=C(Nc1ccc(N2CCOCC2)nc1)c1ccc(-c2cccc3nc(NC(=O)C4CC4)nn23)cc1] | 4-[2-(Cyclopropanecarbonyl-amino)-[1,2,4]triazolo[1,5-a]pyridin-5-yl]-N-(6-morpholin-4-yl-pyridin-3-yl)-benzamide | 483.53 | 484.1 |
| 205 | 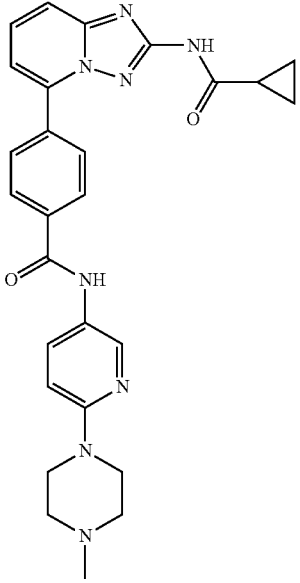 [SMILES: CN1CCN(c2ccc(NC(=O)c3ccc(-c4cccc5nc(NC(=O)C6CC6)nn45)cc3)cn2)CC1] | 4-[2-(Cyclopropanecarbonyl-amino)-[1,2,4]triazolo[1,5-a]pyridin-5-yl]-N-[6-(4-methyl-piperazin-1-yl)-pyridin-3-yl]-benzamide | 496.57 | 497.1 |
| 206 | 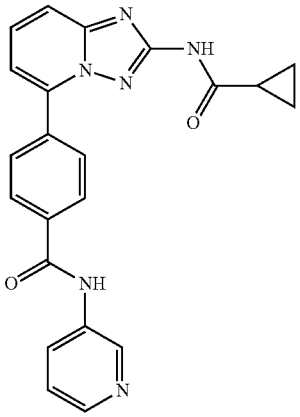 [SMILES: O=C(Nc1cccnc1)c1ccc(-c2cccc3nc(NC(=O)C4CC4)nn23)cc1] | 4-[2-(Cyclopropanecarbonyl-amino)-[1,2,4]triazolo[1,5-a]pyridin-5-yl]-N-pyridin-3-yl-benzamide | 398.43 | 399.1 |

TABLE I-continued

| Cpd # | Structures | Name | MW | MS Mes'd |
|---|---|---|---|---|
| 207 | 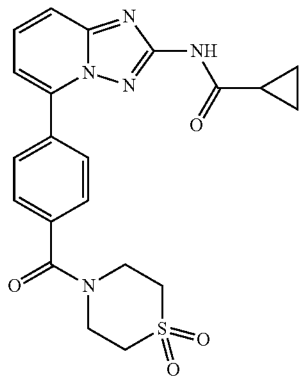 [SMILES: O=C(Nc1nc2cccc(-c3ccc(C(=O)N4CCS(=O)(=O)CC4)cc3)n2n1)C1CC1] | Cyclopropanecarboxylic acid {5-[4-(1,1-dioxo-thiomorpholine-4-carbonyl)-phenyl]-[1,2,4]triazolo[1,5-a]pyridin-2-yl}-amide | 439.49 | 440.0 |
| 208 | 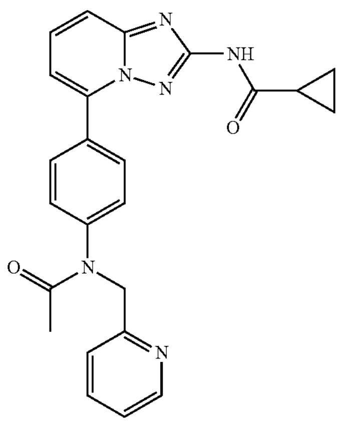 [SMILES: CC(=O)N(Cc1ccccn1)c1ccc(-c2cccc3nc(NC(=O)C4CC4)nn23)cc1] | Cyclopropanecarboxylic acid {5-[4-(acetyl-pyridin-2-ylmethyl-amino)-phenyl]-[1,2,4]triazolo[1,5-a]pyridin-2-yl}-amide | 426.48 | 427.1 |
| 209 | 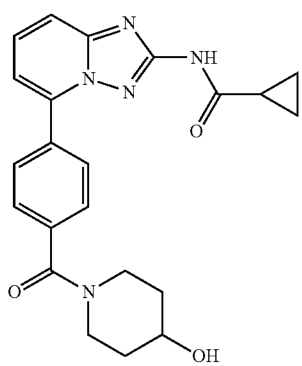 [SMILES: O=C(Nc1nc2cccc(-c3ccc(C(=O)N4CCC(O)CC4)cc3)n2n1)C1CC1] | Cyclopropanecarboxylic acid {5-[4-(4-hydroxy-piperidine-1-carbonyl)-phenyl]-[1,2,4]triazolo[1,5-a]pyridin-2-yl}-amide | 405.46 | 406.1 |
| 210 | 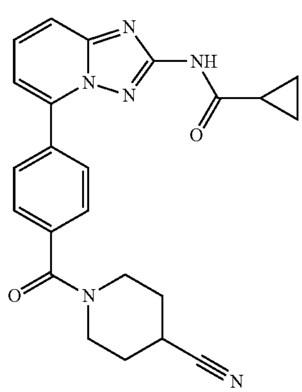 [SMILES: N#CC1CCN(C(=O)c2ccc(-c3cccc4nc(NC(=O)C5CC5)nn34)cc2)CC1] | Cyclopropanecarboxylic acid {5-[4-(4-cyano-piperidine-1-carbonyl)-phenyl]-[1,2,4]triazolo[1,5-a]pyridin-2-yl}-amide | 414.47 | 415.1 |

TABLE I-continued
| Cpd # | Structures | Name | MW | MS Mes'd |
|---|---|---|---|---|
| 211 | 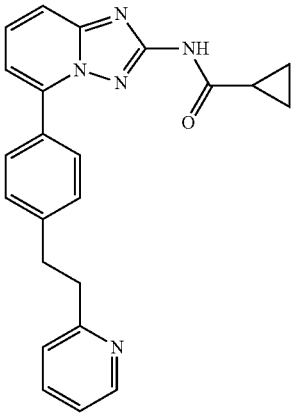 [SMILES: O=C(Nc1nc2cccc(-c3ccc(CCc4ccccn4)cc3)n2n1)C1CC1] | Cyclopropanecarboxylic acid {5-[4-(2-pyridin-2-yl-ethyl)-phenyl]-[1,2,4]triazolo[1,5-a]pyridin-2-yl}-amide | 383.45 | 384.1 |
| 212 | 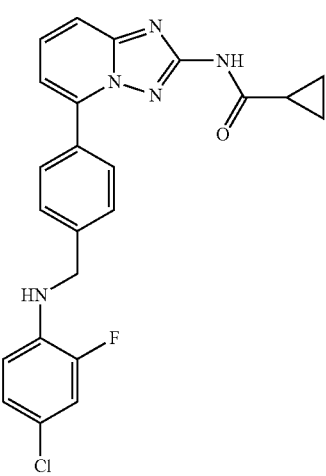 [SMILES: O=C(Nc1nc2cccc(-c3ccc(CNc4ccc(Cl)cc4F)cc3)n2n1)C1CC1] | Cyclopropanecarboxylic acid (5-{4-[(4-chloro-2-fluoro-phenylamino)-methyl]-phenyl}-[1,2,4]triazolo[1,5-a]pyridin-2-yl)-amide | 435.89 | 436 |
| 213 | 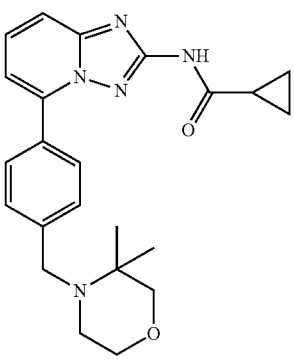 [SMILES: CC1(C)COCCN1Cc1ccc(-c2cccc3nc(NC(=O)C4CC4)nn23)cc1] | Cyclopropanecarboxylic acid {5-[4-(3,3-dimethyl-morpholin-4-ylmethyl)-phenyl]-[1,2,4]triazolo[1,5-a]pyridin-2-yl}-amide | 405.50 | 406.1 |

TABLE I-continued

| Cpd # | Structures | Name | MW | MS Mes'd |
|---|---|---|---|---|
| 214 | 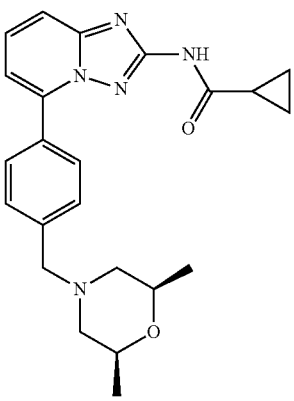 [SMILES: C[C@@H]1CN(Cc2ccc(-c3cccc4nc(NC(=O)C5CC5)nn34)cc2)C[C@H](C)O1] | Cyclopropanecarboxylic acid {5-[4-((2R,6S)-2,6-dimethyl-morpholin-4-ylmethyl)-phenyl]-[1,2,4]triazolo[1,5-a]pyridin-2-yl}-amide | 405.50 | 406.1 |
| 215 | 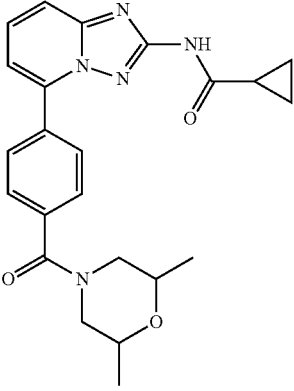 | Cyclopropanecarboxylic acid {5-[4-(2,6-dimethyl-morpholine-4-carbonyl)-phenyl]-[1,2,4]triazolo[1,5-a]pyridin-2-yl}-amide | 419.48 | 420.1 |
| 216 | 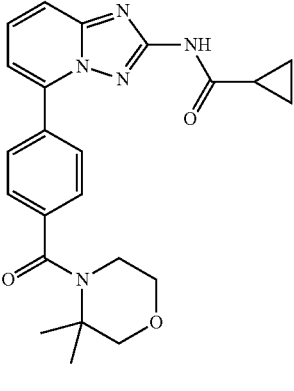 [SMILES: CC1(C)COCCN1C(=O)c1ccc(-c2cccc3nc(NC(=O)C4CC4)nn23)cc1] | Cyclopropanecarboxylic acid {5-[4-(3,3-dimethyl-morpholine-4-carbonyl)-phenyl]-[1,2,4]triazolo[1,5-a]pyridin-2-yl}-amide | 419.48 | 420.1 |
| 217 | 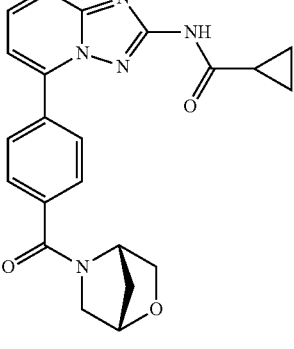 | Cyclopropanecarboxylic acid {5-[4-((1S,4S)-2-oxa-5-aza-bicyclo[2.2.1]heptane-5-carbonyl)-phenyl]-[1,2,4]triazolo[1,5-a]pyridin-2-yl}-amide | 403.44 | 404.1 |

| Cpd # | Structures | Name | MW | MS Mes'd |
|---|---|---|---|---|
| 218 | 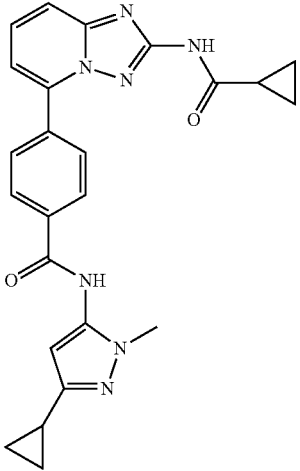 [SMILES: Cn1nc(C2CC2)cc1NC(=O)c1ccc(-c2cccc3nc(NC(=O)C4CC4)nn23)cc1] | 4-[2-(Cyclopropanecarbonyl-amino)-[1,2,4]triazolo[1,5-a]pyridin-5-yl]-N-(5-cyclopropyl-2-methyl-2H-pyrazol-3-yl)-benzamide | 441.49 | 442.1 |
| 219 | 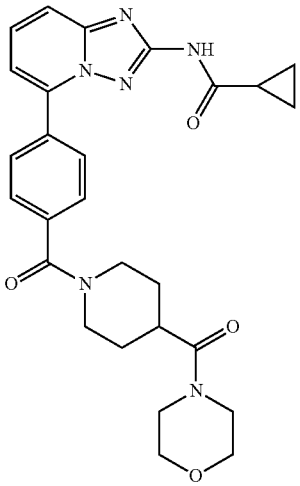 [SMILES: O=C(Nc1nc2cccc(-c3ccc(C(=O)N4CCC(C(=O)N5CCOCC5)CC4)cc3)n2n1)C1CC1] | Cyclopropanecarboxylic acid (5-{4-[4-(morpholine-4-carbonyl)-piperidine-1-carbonyl]-phenyl}-[1,2,4]triazolo[1,5-a]pyridin-2-yl)-amide | 502.57 | 503.1 |
| 220 | 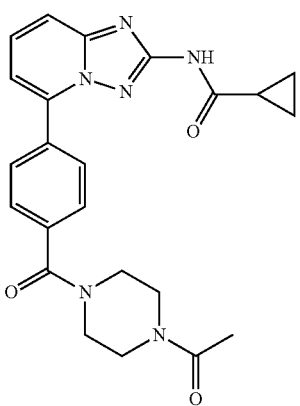 [SMILES: CC(=O)N1CCN(C(=O)c2ccc(-c3cccc4nc(NC(=O)C5CC5)nn34)cc2)CC1] | Cyclopropanecarboxylic acid {5-[4-(4-acetyl-piperazine-1-carbonyl)-phenyl]-[1,2,4]triazolo[1,5-a]pyridin-2-yl}-amide | 432.48 | 433.1 |

TABLE I-continued

| Cpd # | Name | MW | MS Mes'd |
|---|---|---|---|
| 221 | 4-[2-(Cyclopropanecarbonyl-amino)-[1,2,4]triazolo[1,5-a]pyridin-5-yl]-N-pyridazin-3-yl-benzamide | 399.41 | 400.0 |
| 222 | Cyclopropanecarboxylic acid {5-[4-(pyridazin-3-ylaminomethyl)-phenyl]-[1,2,4]triazolo[1,5-a]pyridin-2-yl}-amide | 385.43 | 387 |
| 223 | Cyclopropanecarboxylic acid {5-[4-(pyridin-3-ylaminomethyl)-phenyl]-[1,2,4]triazolo[1,5-a]pyridin-2-yl}-amide | 384.44 | 385.1 |

TABLE I-continued

| Cpd # | Structures | Name | MW | MS Mes'd |
|---|---|---|---|---|
| 224 | 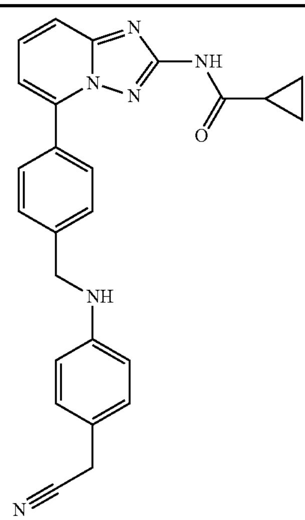 | Cyclopropanecarboxylic acid (5-{4-[(4-cyanomethyl-phenylamino)-methyl]-phenyl}-[1,2,4]triazolo[1,5-a]pyridin-2-yl)-amide | 422.49 | 423.1 |
| 225 | 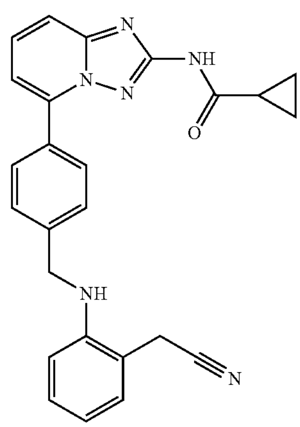 [SMILES: N#CCc1ccccc1NCc1ccc(-c2cccc3nc(NC(=O)C4CC4)nn23)cc1] | Cyclopropanecarboxylic acid (5-{4-[(2-cyanomethyl-phenylamino)-methyl]-phenyl}-[1,2,4]triazolo[1,5-a]pyridin-2-yl)-amide | 422.49 | 423.1 |
| 226 | 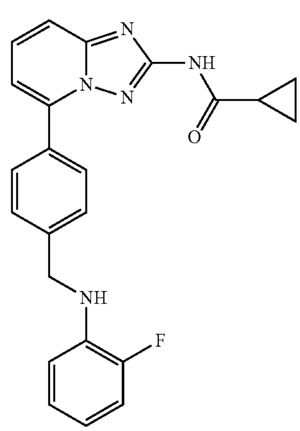 [SMILES: O=C(Nc1nc2cccc(-c3ccc(CNc4ccccc4F)cc3)n2n1)C1CC1] | Cyclopropanecarboxylic acid (5-{4-[(2-fluoro-phenylamino)-methyl]-phenyl}-[1,2,4]triazolo[1,5-a]pyridin-2-yl)-amide | 401.44 | 402.1 |

| Cpd # | Structures | Name | MW | MS Mes'd |
|---|---|---|---|---|
| 227 | 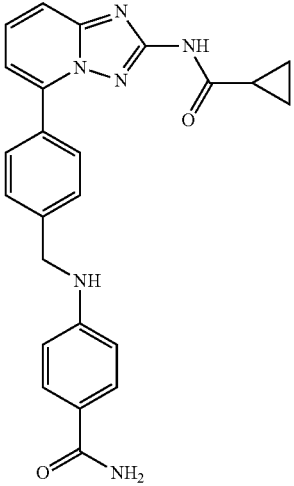 [SMILES: NC(=O)c1ccc(NCc2ccc(-c3cccc4nc(NC(=O)C5CC5)nn34)cc2)cc1] | 4-{4-[2-(Cyclopropanecarbonyl-amino)-[1,2,4]triazolo[1,5-a]pyridin-5-yl]-benzylamino}-benzamide | 426.48 | 428 |
| 228 | 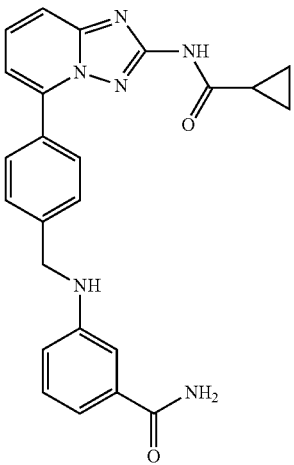 [SMILES: NC(=O)c1cccc(NCc2ccc(-c3cccc4nc(NC(=O)C5CC5)nn34)cc2)c1] | 3-{4-[2-(Cyclopropanecarbonyl-amino)-[1,2,4]triazolo[1,5-a]pyridin-5-yl]-benzylamino}-benzamide | 426.48 | 427.1 |
| 229 | 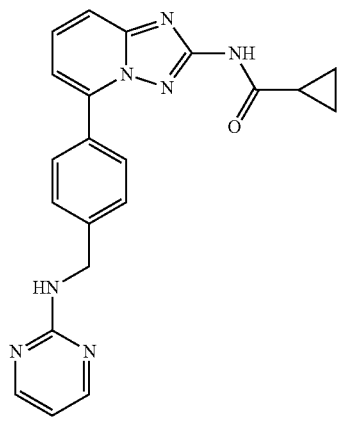 [SMILES: O=C(Nc1nc2cccc(-c3ccc(CNc4ncccn4)cc3)n2n1)C1CC1] | Cyclopropanecarboxylic acid {5-[4-(pyrimidin-2-ylaminomethyl)-phenyl]-[1,2,4]triazolo[1,5-a]pyridin-2-yl}-amide | 385.43 | 386.1 |

TABLE I-continued

| Cpd # | Structures | Name | MW | MS Mes'd |
|---|---|---|---|---|
| 230 | 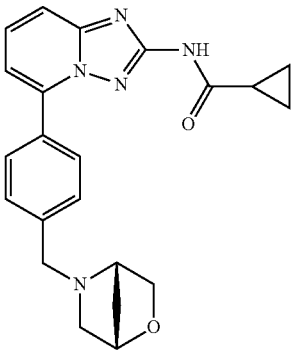 [SMILES: O=C(Nc1nc2cccc(-c3ccc(CN4C[C@@H]5C[C@H]4CO5)cc3)n2n1)C1CC1] | Cyclopropanecarboxylic acid (5-{4-[(1S,4S)-1-(2-oxa-5-aza-bicyclo[2.2.1]hept-5-yl)methyl]-phenyl}-[1,2,4]triazolo[1,5-a]pyridin-2-yl)-amide | 389.46 | 390.1 |
| 231 | 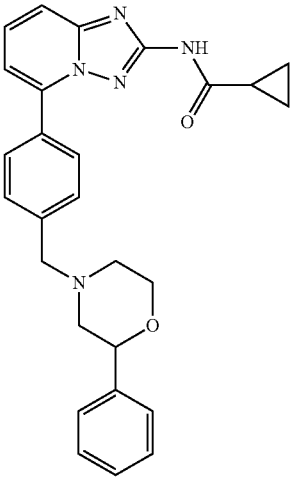 [SMILES: O=C(Nc1nc2cccc(-c3ccc(CN4CCOC(c5ccccc5)C4)cc3)n2n1)C1CC1] | Cyclopropanecarboxylic acid {5-[4-(2-phenyl-morpholin-4-ylmethyl)-phenyl]-[1,2,4]triazolo[1,5-a]pyridin-2-yl}-amide2-phenyl-morpholin-4-ylmethyl)-phenyl]-[1,2,4]triazolo[1,5-a]pyridin-2-yl}-amide | 453.55 | 454.1 |
| 232 | 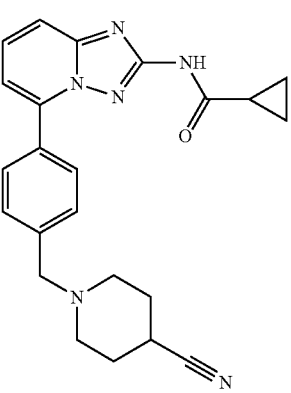 [SMILES: N#CC1CCN(Cc2ccc(-c3cccc4nc(NC(=O)C5CC5)nn34)cc2)CC1] | Cyclopropanecarboxylic acid {5-[4-(4-cyano-piperidin-1-ylmethyl)-phenyl]-[1,2,4]triazolo[1,5-a]pyridin-2-yl}-amide | 400.49 | 401.1 |
| 233 | 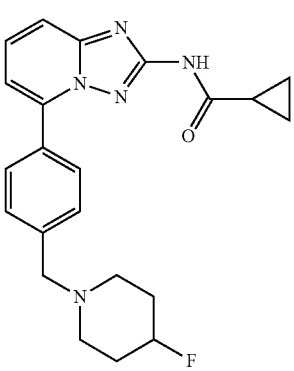 [SMILES: O=C(Nc1nc2cccc(-c3ccc(CN4CCC(F)CC4)cc3)n2n1)C1CC1] | Cyclopropanecarboxylic acid {5-[4-(4-fluoro-piperidin-1-ylmethyl)-phenyl]-[1,2,4]triazolo[1,5-a]pyridin-2-yl}-amide | 393.47 | 394.1 |

TABLE I-continued

| Cpd # | Structures | Name | MW | MS Mes'd |
|---|---|---|---|---|
| 234 | 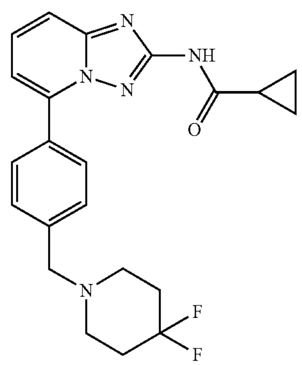 [SMILES: O=C(Nc1nc2cccc(-c3ccc(CN4CCC(F)(F)CC4)cc3)n2n1)C1CC1] | Cyclopropanecarboxylic acid {5-[4-(4,4-difluoro-piperidin-1-ylmethyl)-phenyl]-[1,2,4]triazolo[1,5-a]pyridin-2-yl}-amide | 411.46 | 412.1 |
| 235 | 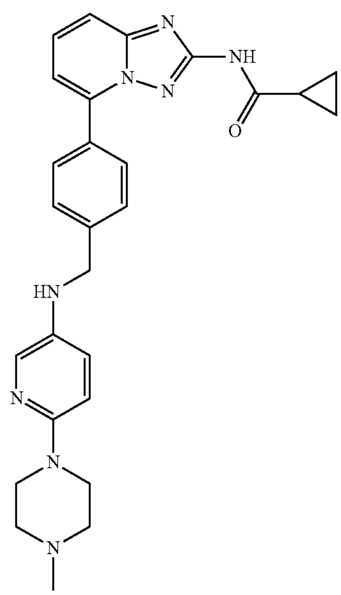 [SMILES: CN1CCN(c2ccc(NCc3ccc(-c4cccc5nc(NC(=O)C6CC6)nn45)cc3)cn2)CC1] | Cyclopropanecarboxylic acid [5-(4-{[6-(4-methyl-piperazin-1-yl)-pyridin-3-ylamino]-methyl}-phenyl)-[1,2,4]triazolo[1,5-a]pyridin-2-yl]-amide | 482.59 | 483.1 |
| 236 | 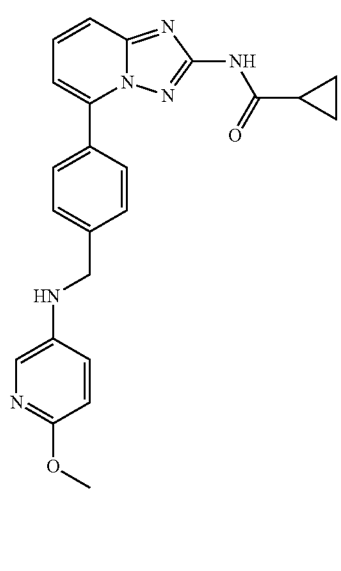 [SMILES: COc1ccc(NCc2ccc(-c3cccc4nc(NC(=O)C5CC5)nn34)cc2)cn1] | Cyclopropanecarboxylic acid (5-{4-[(6-methoxy-pyridin-3-ylamino)-methyl]-phenyl}-[1,2,4]triazolo[1,5-a]pyridin-2-yl)-amide | 414.47 | 415.1 |

TABLE I-continued
| Cpd # | Structures | Name | MW | MS Mes'd |
|---|---|---|---|---|
| 237 | 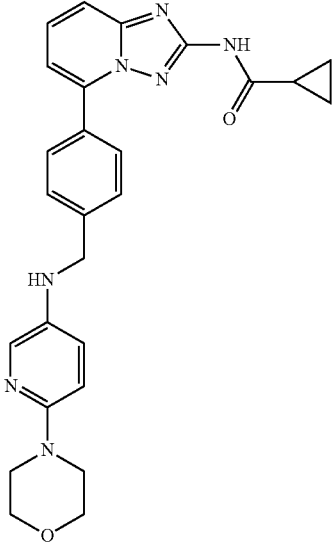 [SMILES: O=C(Nc1nc2cccc(-c3ccc(CNc4ccc(N5CCOCC5)nc4)cc3)n2n1)C1CC1] | Cyclopropanecarboxylic acid (5-{4-[(6-morpholin-4-yl-pyridin-3-ylamino)-methyl]-phenyl}-[1,2,4]triazolo[1,5-a]pyridin-2-yl)-amide | 469.55 | 470 |
| 238 | 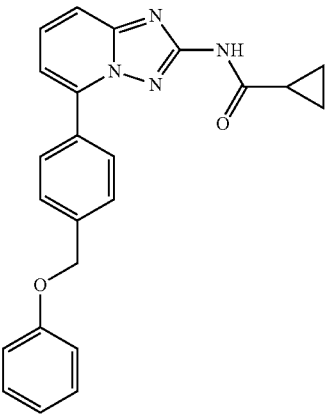 | Cyclopropanecarboxylic acid [5-(4-phenoxymethyl-phenyl)-[1,2,4]triazolo[1,5-a]pyridin-2-yl]-amide | 384.44 | 385.00 |
| 239 | 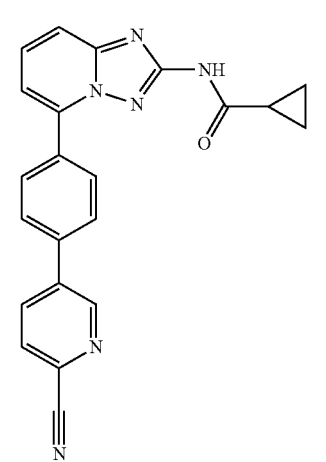 [SMILES: N#Cc1ccc(-c2ccc(-c3cccc4nc(NC(=O)C5CC5)nn34)cc2)cn1] | Cyclopropanecarboxylic acid {5-[4-(6-cyano-pyridin-3-yl)-phenyl]-[1,2,4]triazolo[1,5-a]pyridin-2-yl}-amide | 380.41 | 381.00 |

TABLE I-continued

| Cpd # | Structures | Name | MW | MS Mes'd |
|---|---|---|---|---|
| 240 | 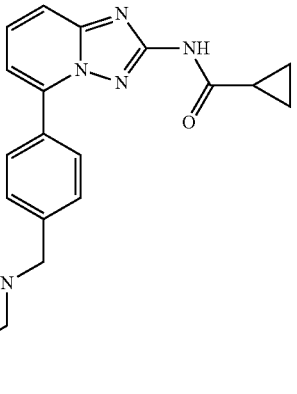 | Cyclopropanecarboxylic acid {5-[4-(4-trifluoromethyl-piperidin-1-ylmethyl)-phenyl]-[1,2,4]triazolo[1,5-a]pyridin-2-yl}-amide | 443.47 | 444.00 |
| 241 | 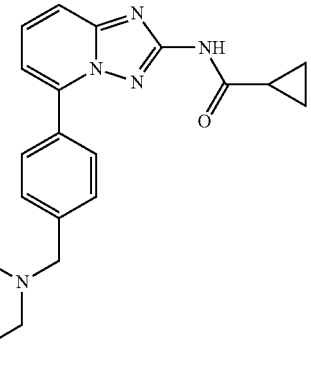 | Cyclopropanecarboxylic acid (5-{4-[4-(2,2,2-trifluoro-ethyl)-piperazin-1-ylmethyl]-phenyl}-[1,2,4]triazolo[1,5-a]pyridin-2-yl)-amide | 458.49 | 459.00 |
| 242 | 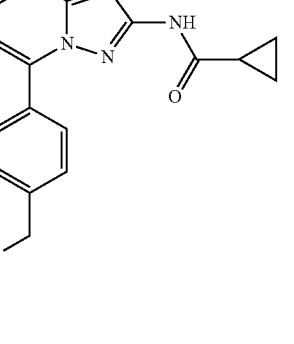 | Cyclopropanecarboxylic acid {5-[4-(4-hydroxy-piperidin-1-ylmethyl)-phenyl]-[1,2,4]triazolo[1,5-a]pyridin-2-yl}-amide | 391.47 | 392 |
| 243 | 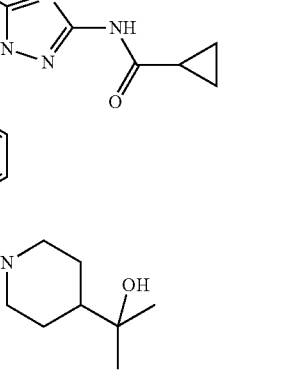 | Cyclopropanecarboxylic acid (5-{4-[4-(1-hydroxy-1-methyl-ethyl)-piperidin-1-ylmethyl]-phenyl}-[1,2,4]triazolo[1,5-a]pyridin-2-yl)-amide | 433.56 | 434.1 |

TABLE I-continued
| Cpd # | Structures | Name | MW | MS Mes'd |
|---|---|---|---|---|
| 244 | 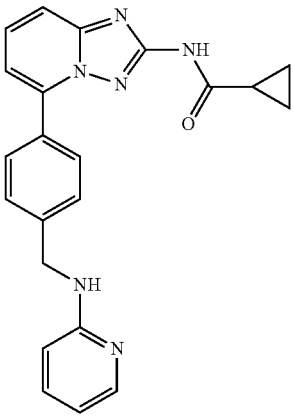 [SMILES: O=C(Nc1nc2cccc(-c3ccc(CNc4ccccn4)cc3)n2n1)C1CC1] | Cyclopropanecarboxylic acid {5-[4-(pyridin-2-ylaminomethyl)-phenyl]-[1,2,4]triazolo[1,5-a]pyridin-2-yl}-amide | 384.44 | 385.1 |
| 245 | 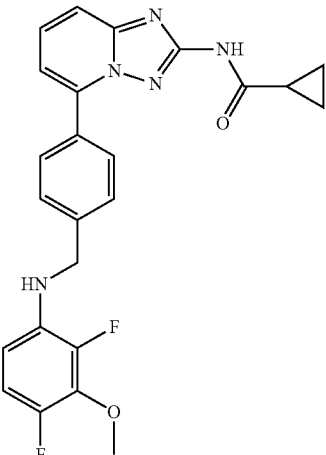 | Cyclopropanecarboxylic acid (5-{4-[(2,4-difluoro-3-methoxy-phenylamino)-methyl]-phenyl}-[1,2,4]triazolo[1,5-a]pyridin-2-yl)-amide | 449.46 | 450 |
| 246 | 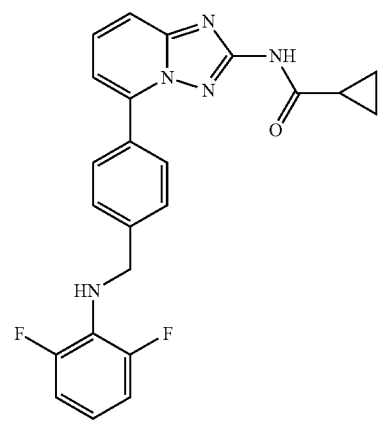 [SMILES: O=C(Nc1nc2cccc(-c3ccc(CNc4c(F)cccc4F)cc3)n2n1)C1CC1] | Cyclopropanecarboxylic acid (5-{4-[(2,6-difluoro-phenylamino)-methyl]-phenyl}-[1,2,4]triazolo[1,5-a]pyridin-2-yl)-amide | 419.43 | 420 |

TABLE I-continued
| Cpd # | Structures | Name | MW | MS Mes'd |
|---|---|---|---|---|
| 247 | 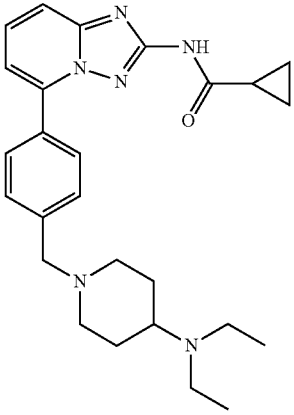 [SMILES: CCN(CC)C1CCN(Cc2ccc(-c3cccc4nc(NC(=O)C5CC5)nn34)cc2)CC1] | Cyclopropanecarboxylic acid {5-[4-(4-diethylamino-piperidin-1-ylmethyl)-phenyl]-[1,2,4]triazolo[1,5-a]pyridin-2-yl}-amide | 446.60 | 447.1 |
| 248 | 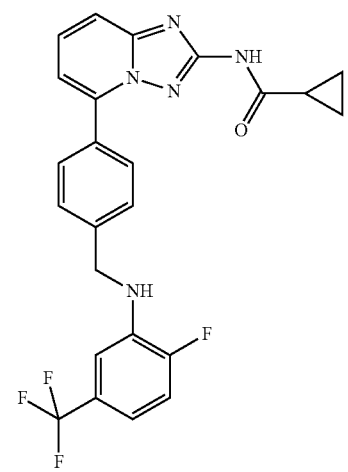 [SMILES: O=C(Nc1nc2cccc(-c3ccc(CNc4cc(C(F)(F)F)ccc4F)cc3)n2n1)C1CC1] | Cyclopropanecarboxylic acid (5-{4-[(2-fluoro-5-trifluoromethyl-phenylamino)-methyl]-phenyl}-[1,2,4]triazolo[1,5-a]pyridin-2-yl)-amide | 469.44 | 447 |
| 249 | 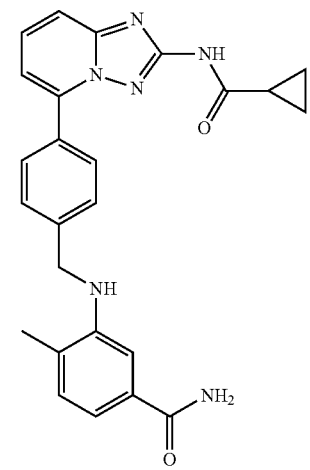 [SMILES: Cc1ccc(C(N)=O)cc1NCc1ccc(-c2cccc3nc(NC(=O)C4CC4)nn23)cc1] | 3-{4-[2-(Cyclopropanecarbonyl-amino)-[1,2,4]triazolo[1,5-a]pyridin-5-yl]-benzylamino}-4-methyl-benzamide | 440.51 | 441.1 |

TABLE I-continued
| Cpd # | Structures | Name | MW | MS Mes'd |
|---|---|---|---|---|
| 250 | 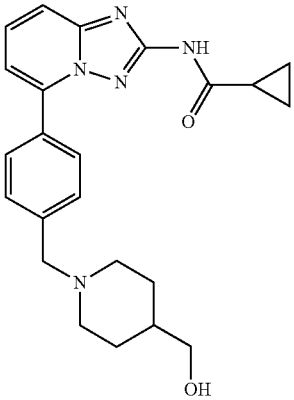 [SMILES: O=C(Nc1nc2cccc(-c3ccc(CN4CCC(CO)CC4)cc3)n2n1)C1CC1] | Cyclopropanecarboxylic acid {5-[4-(4-hydroxymethyl-piperidin-1-ylmethyl)-phenyl]-[1,2,4]triazolo[1,5-a]pyridin-2-yl}-amide | 405.50 | 406.1 |
| 251 | 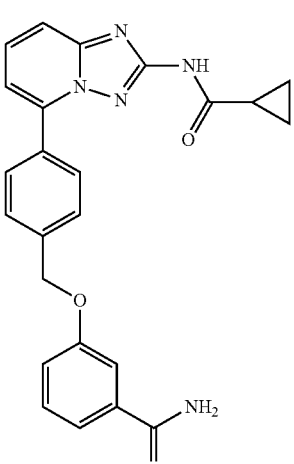 | 3-{4-[2-(Cyclopropanecarbonyl-amino)-[1,2,4]triazolo[1,5-a]pyridin-5-yl]-benzyloxy}-benzamide | 427.46 | 428 |
| 252 | 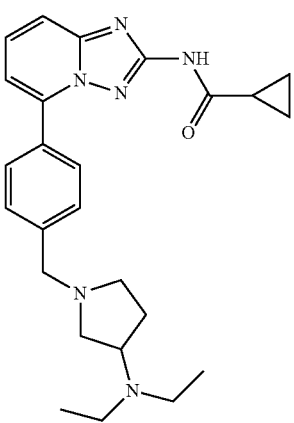 [SMILES: CCN(CC)C1CCN(Cc2ccc(-c3cccc4nc(NC(=O)C5CC5)nn34)cc2)C1] | Cyclopropanecarboxylic acid {5-[4-(3-diethylamino-pyrrolidin-1-ylmethyl)-phenyl]-[1,2,4]triazolo[1,5-a]pyridin-2-yl}-amide | 432.57 | 433.1 |

TABLE I-continued
| Cpd # | Structures | Name | MW | MS Mes'd |
|---|---|---|---|---|
| 253 | 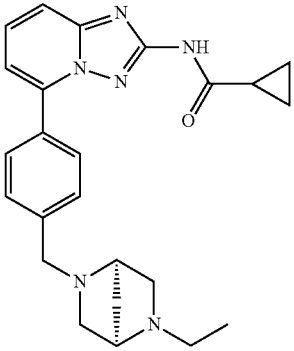 [SMILES: CCN1C[C@H]2C[C@@H]1CN2Cc1ccc(-c2cccc3nc(NC(=O)C4CC4)nn23)cc1] | Cyclopropanecarboxylic acid {5-[4-((1R,4R)-5-ethyl-2,5-diaza-bicyclo[2.2.1]hept-2-ylmethyl)-phenyl]-[1,2,4]triazolo[1,5-a]pyridin-2-yl}-amide | 416.53 | 417.1 |
| 254 | 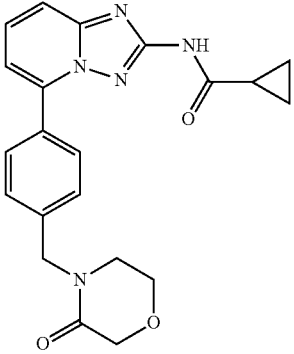 [SMILES: O=C(Nc1nc2cccc(-c3ccc(CN4CCOCC4=O)cc3)n2n1)C1CC1] | Cyclopropanecarboxylic acid {5-[4-(3-oxo-morpholin-4-ylmethyl)-phenyl]-[1,2,4]triazolo[1,5-a]pyridin-2-yl}-amide | 391.43 | 392 |
| 255 | 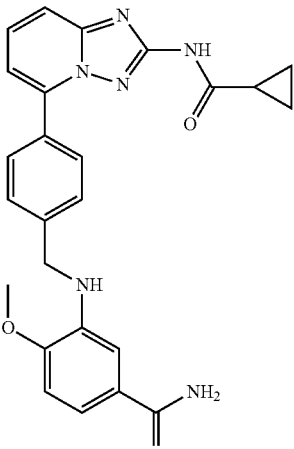 | 3-{4-[2-(Cyclopropanecarbonyl-amino)-[1,2,4]triazolo[1,5-a]pyridin-5-yl]-benzylamino}-4-methoxy-benzamide | 456.51 | 457 |

| Cpd # | Structures | Name | MW | MS Mes'd |
|---|---|---|---|---|
| 256 | 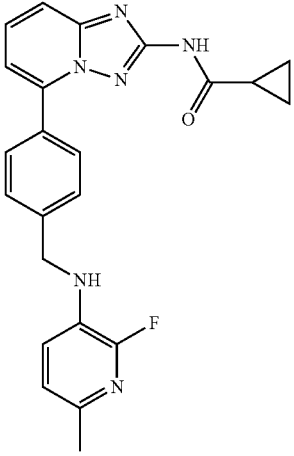 [SMILES: Cc1ccc(NCc2ccc(-c3cccc4nc(NC(=O)C5CC5)nn34)cc2)c(F)n1] | Cyclopropanecarboxylic acid (5-{4-[(2-fluoro-6-methyl-pyridin-3-ylamino)-methyl]-phenyl}-[1,2,4]triazolo[1,5-a]pyridin-2-yl)-amide | 416.46 | 417 |
| 257 | 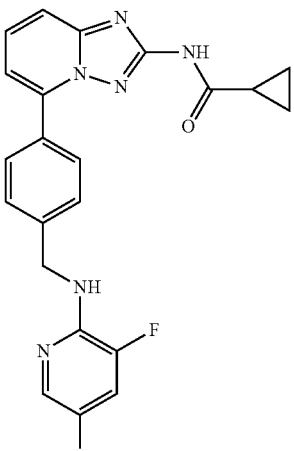 | Cyclopropanecarboxylic acid (5-{4-[(3,5-difluoro-pyridin-2-ylamino)-methyl]-phenyl}-[1,2,4]triazolo[1,5-a]pyridin-2-yl)-amide | 420.42 | 421 |
| 258 | 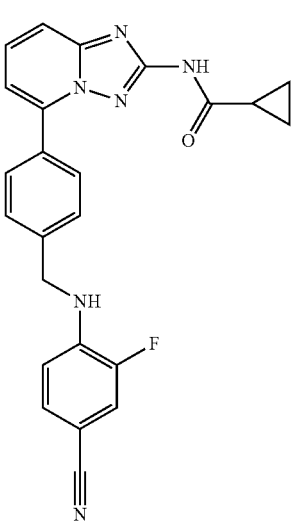 [SMILES: N#Cc1ccc(NCc2ccc(-c3cccc4nc(NC(=O)C5CC5)nn34)cc2)c(F)c1] | Cyclopropanecarboxylic acid (5-{4-[(4-cyano-2-fluoro-phenylamino)-methyl]-phenyl}-[1,2,4]triazolo[1,5-a]pyridin-2-yl)-amide | 426.45 | 427 |

TABLE I-continued
| Cpd # | Structures | Name | MW | MS Mes'd |
|---|---|---|---|---|
| 259 | 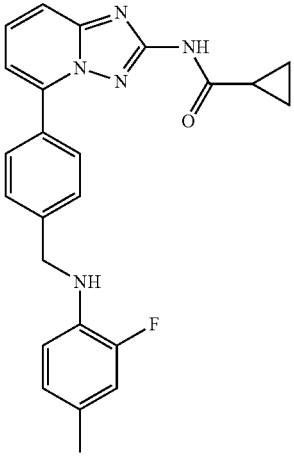 [SMILES: Cc1ccc(NCc2ccc(-c3cccc4nc(NC(=O)C5CC5)nn34)cc2)c(F)c1] | Cyclopropanecarboxylic acid (5-{4-[(2-fluoro-4-methyl-phenylamino)-methyl]-phenyl}-[1,2,4]triazolo[1,5-a]pyridin-2-yl)-amide | 415.47 | 416 |
| 260 | 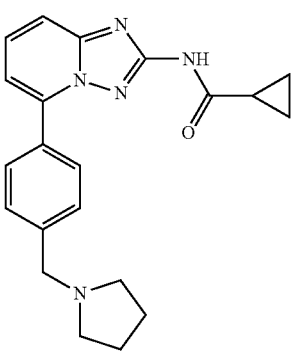 [SMILES: O=C(Nc1nc2cccc(-c3ccc(CN4CCCC4)cc3)n2n1)C1CC1] | Cyclopropanecarboxylic acid [5-(4-pyrrolidin-1-ylmethyl-phenyl)-[1,2,4]triazolo[1,5-a]pyridin-2-yl]-amide | 361.45 | 362.1 |
| 261 | 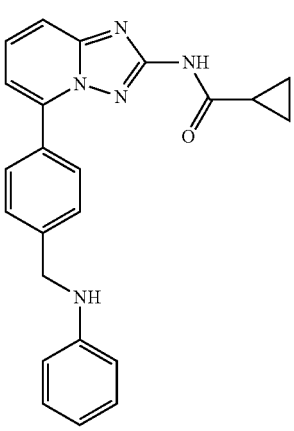 [SMILES: O=C(Nc1nc2cccc(-c3ccc(CNc4ccccc4)cc3)n2n1)C1CC1] | Cyclopropanecarboxylic acid [5-(4-phenylaminomethyl-phenyl)-[1,2,4]triazolo[1,5-a]pyridin-2-yl]-amide | 383.45 | 384 |

TABLE I-continued
| Cpd # | Structures | Name | MW | MS Mes'd |
|---|---|---|---|---|
| 262 | 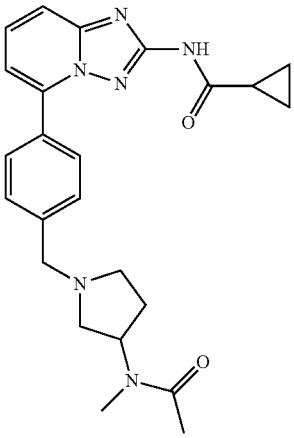 [SMILES: CC(=O)N(C)C1CCN(Cc2ccc(-c3cccc4nc(NC(=O)C5CC5)nn34)cc2)C1] | Cyclopropanecarboxylic acid (5-{4-[3-(acetyl-methyl-amino)-pyrrolidin-1-ylmethyl]-phenyl}-[1,2,4]triazolo[1,5-a]pyridin-2-yl)-amide | 432.53 | 433.1 |
| 263 | 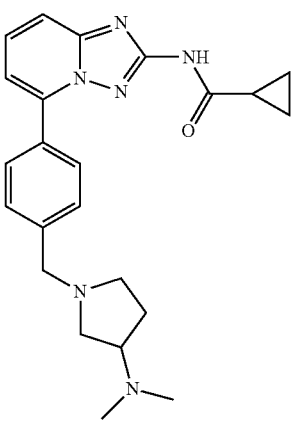 [SMILES: CN(C)C1CCN(Cc2ccc(-c3cccc4nc(NC(=O)C5CC5)nn34)cc2)C1] | Cyclopropanecarboxylic acid {5-[4-(3-dimethylamino-pyrrolidin-1-ylmethyl)-phenyl]-[1,2,4]triazolo[1,5-a]pyridin-2-yl}-amide | 404.52 | 405.1 |
| 264 | 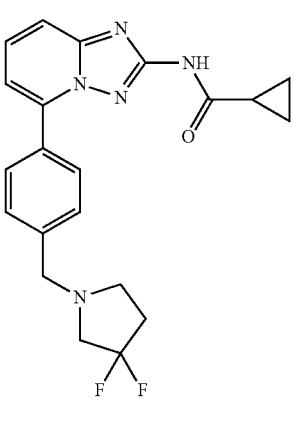 [SMILES: O=C(Nc1nc2cccc(-c3ccc(CN4CCC(F)(F)C4)cc3)n2n1)C1CC1] | Cyclopropanecarboxylic acid {5-[4-(3,3-difluoro-pyrrolidin-1-ylmethyl)-phenyl]-[1,2,4]triazolo[1,5-a]pyridin-2-yl}-amide | 397.43 | 398 |

TABLE I-continued

| Cpd # | Structures | Name | MW | MS Mes'd |
|---|---|---|---|---|
| 265 | 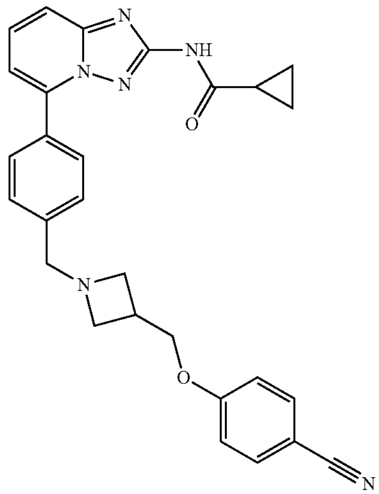 [SMILES: N#Cc1ccc(OCC2CN(Cc3ccc(-c4cccc5nc(NC(=O)C6CC6)nn45)cc3)C2)cc1] | Cyclopropanecarboxylic acid (5-{4-[3-(4-cyano-phenoxymethyl)-azetidin-1-ylmethyl]-phenyl}-[1,2,4]triazolo[1,5-a]pyridin-2-yl)-amide | 478.56 | 479 |
| 266 | 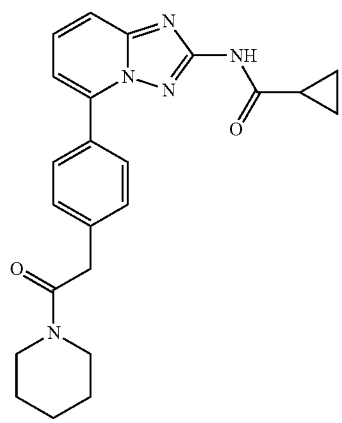 [SMILES: O=C(Nc1nc2cccc(-c3ccc(CC(=O)N4CCCCC4)cc3)n2n1)C1CC1] | Cyclopropanecarboxylic acid {5-[4-(2-oxo-2-piperidin-1-yl-ethyl)-phenyl]-[1,2,4]triazolo[1,5-a]pyridin-2-yl}-amide | 403.49 | 404 |
| 267 | 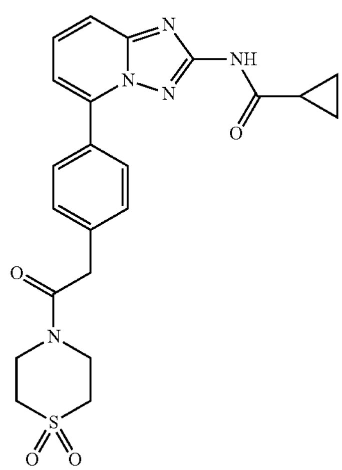 [SMILES: O=C(Nc1nc2cccc(-c3ccc(CC(=O)N4CCS(=O)(=O)CC4)cc3)n2n1)C1CC1] | Cyclopropanecarboxylic acid (5-{4-[2-(1,1-dioxo-thiomorpholin-4-yl)-2-oxo-ethyl]-phenyl}-[1,2,4]triazolo[1,5-a]pyridin-2-yl)-amide | 453.52 | 454 |

TABLE I-continued
| Cpd # | Structures | Name | MW | MS Mes'd |
|---|---|---|---|---|
| 268 | 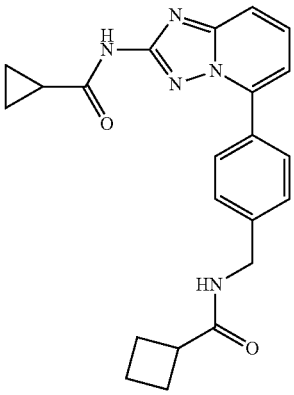 [SMILES: O=C(NCc1ccc(-c2cccc3nc(NC(=O)C4CC4)nn23)cc1)C1CCC1] | Cyclobutanecarboxylic acid 4-[2-(cyclopropanecarbonyl-amino)-[1,2,4]triazolo[1,5-a]pyridin-5-yl]-benzylamide | 389.45 | 390.2 |
| 269 | 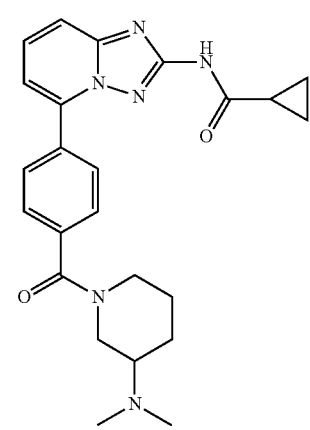 [SMILES: CN(C)C1CCCN(C(=O)c2ccc(-c3cccc4nc(NC(=O)C5CC5)nn34)cc2)C1] | Cyclopropanecarboxylic acid {5-[4-(3-dimethylamino-piperidine-1-carbonyl)-phenyl]-[1,2,4]triazolo[1,5-a]pyridin-2-yl}-amide | 432.55 | 433 |
| 270 | 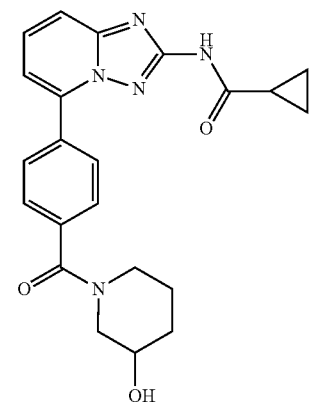 [SMILES: O=C(Nc1nc2cccc(-c3ccc(C(=O)N4CCCC(O)C4)cc3)n2n1)C1CC1] | Cyclopropanecarboxylic acid {5-[4-(3-hydroxy-piperidine-1-carbonyl)-phenyl]-[1,2,4]triazolo[1,5-a]pyridin-2-yl}-amide | 405.46 | 406 |

TABLE I-continued

| Cpd # | Structures | Name | MW | MS Mes'd |
|---|---|---|---|---|
| 271 | 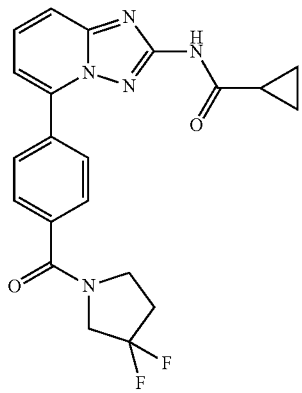 [SMILES: O=C(Nc1nc2cccc(-c3ccc(C(=O)N4CCC(F)(F)C4)cc3)n2n1)C1CC1] | Cyclopropanecarboxylic acid {5-[4-(3,3-difluoro-pyrrolidine-1-carbonyl)-phenyl]-[1,2,4]triazolo[1,5-a]pyridin-2-yl}-amide | 411.41 | 412 |
| 272 | 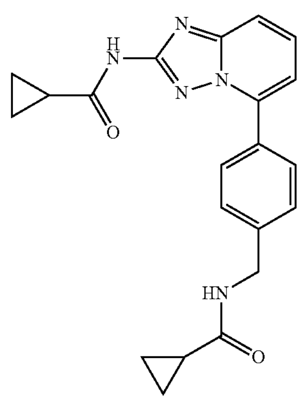 [SMILES: O=C(NCc1ccc(-c2cccc3nc(NC(=O)C4CC4)nn23)cc1)C1CC1] | Cyclopropanecarboxylic acid 4-[2-(cyclopropanecarbonyl-amino)-[1,2,4]triazolo[1,5-a]pyridin-5-yl]-benzylamide | 375.42 | 376.2 |
| 273 | 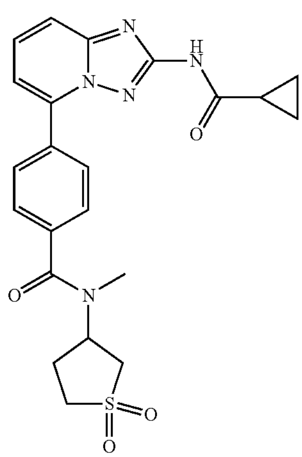 [SMILES: CN(C(=O)c1ccc(-c2cccc3nc(NC(=O)C4CC4)nn23)cc1)C1CCS(=O)(=O)C1] | 4-[2-(Cyclopropanecarbonyl-amino)-[1,2,4]triazolo[1,5-a]pyridin-5-yl]-N-(1,1-dioxo-tetrahydrothiophen-3-yl)-N-methyl-benzamide | 453.52 | 453.9 |

TABLE I-continued

| Cpd # | Structures | Name | MW | MS Mes'd |
|---|---|---|---|---|
| 274 | 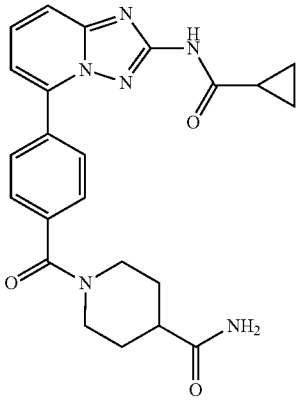 [SMILES: NC(=O)C1CCN(C(=O)c2ccc(-c3cccc4nc(NC(=O)C5CC5)nn34)cc2)CC1] | 1-{4-[2-(Cyclopropanecarbonyl-amino)-[1,2,4]triazolo[1,5-a]pyridin-5-yl]-benzoyl}-piperidine-4-carboxylic acid amide | 432.49 | 433 |
| 275 | 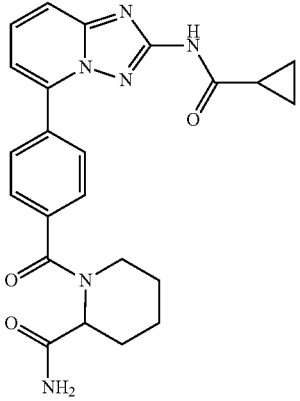 [SMILES: NC(=O)C1CCCCN1C(=O)c1ccc(-c2cccc3nc(NC(=O)C4CC4)nn23)cc1] | 1-{4-[2-(Cyclopropanecarbonyl-amino)-[1,2,4]triazolo[1,5-a]pyridin-5-yl]-benzoyl}-piperidine-2-carboxylic acid amide | 432.49 | 433 |
| 276 | 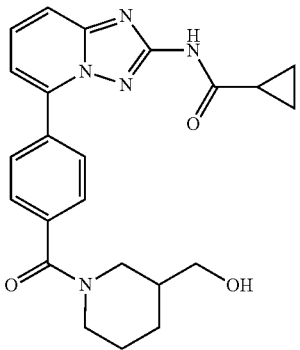 [SMILES: O=C(Nc1nc2cccc(-c3ccc(C(=O)N4CCCC(CO)C4)cc3)n2n1)C1CC1] | Cyclopropanecarboxylic acid {5-[4-(3-hydroxymethyl-piperidine-1-carbonyl)-phenyl]-[1,2,4]triazolo[1,5-a]pyridin-2-yl}-amide | 419.49 | 420 |
| 277 | 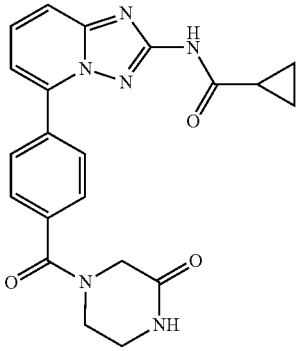 [SMILES: O=C1CN(C(=O)c2ccc(-c3cccc4nc(NC(=O)C5CC5)nn34)cc2)CCN1] | Cyclopropanecarboxylic acid {5-[4-(3-oxo-piperazine-1-carbonyl)-phenyl]-[1,2,4]triazolo[1,5-a]pyridin-2-yl}-amide | 404.43 | 404.9 |

TABLE I-continued

| Cpd # | Structures | Name | MW | MS Mes'd |
|---|---|---|---|---|
| 278 | 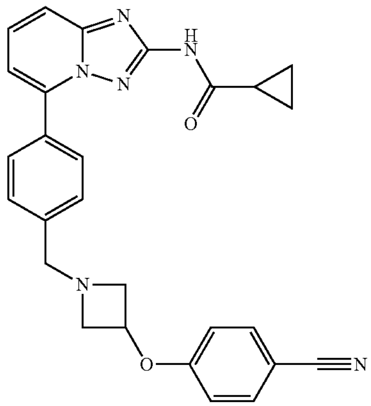 [SMILES: N#Cc1ccc(OC2CN(Cc3ccc(-c4cccc5nc(NC(=O)C6CC6)nn45)cc3)C2)cc1] | Cyclopropanecarboxylic acid (5-{4-[3-(4-cyano-phenoxy)-azetidin-1-ylmethyl]-phenyl}-[1,2,4]triazolo[1,5-a]pyridin-2-yl)-amide | 464.53 | 465 |
| 279 | 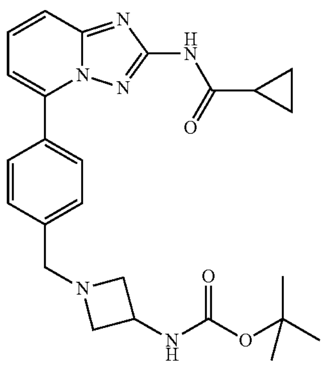 [SMILES: CC(C)(C)OC(=O)NC1CN(Cc2ccc(-c3cccc4nc(NC(=O)C5CC5)nn34)cc2)C1] | (1-{4-[2-(Cyclopropanecarbonyl-amino)-[1,2,4]triazolo[1,5-a]pyridin-5-yl]-benzyl}-azetidin-3-yl)-carbamic acid tert-butyl ester | 462.55 | 463 |
| 280 | 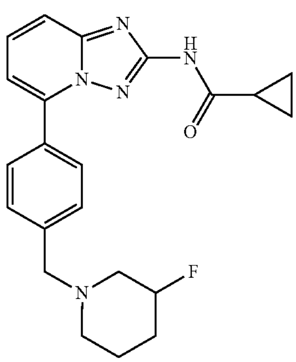 [SMILES: O=C(Nc1nc2cccc(-c3ccc(CN4CCCC(F)C4)cc3)n2n1)C1CC1] | Cyclopropanecarboxylic acid {5-[4-(3-fluoro-piperidin-1-ylmethyl)-phenyl]-[1,2,4]triazolo[1,5-a]pyridin-2-yl}-amide | 393.4 | 395 |
| 281 | 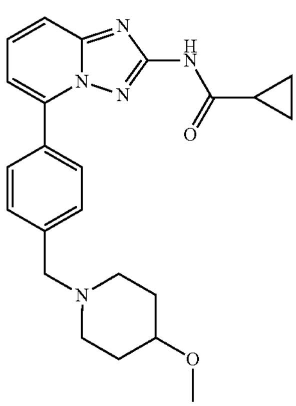 [SMILES: COC1CCN(Cc2ccc(-c3cccc4nc(NC(=O)C5CC5)nn34)cc2)CC1] | Cyclopropanecarboxylic acid {5-[4-(4-methoxy-piperidin-1-ylmethyl)-phenyl]-[1,2,4]triazolo[1,5-a]pyridin-2-yl}-amide | 405.5 | 406.1 |

TABLE I-continued
| Cpd # | Structures | Name | MW | MS Mes'd |
|---|---|---|---|---|
| 282 | 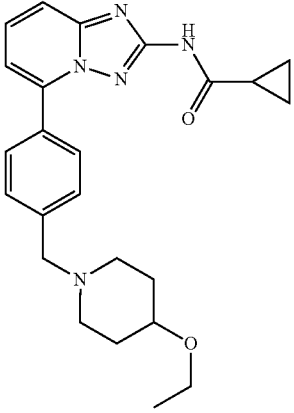 [SMILES: CCOC1CCN(Cc2ccc(-c3cccc4nc(NC(=O)C5CC5)nn34)cc2)CC1] | Cyclopropanecarboxylic acid {5-[4-(4-ethoxy-piperidin-1-ylmethyl)-phenyl]-[1,2,4]triazolo[1,5-a]pyridin-2-yl}-amide | 419.53 | 420 |
| 283 | 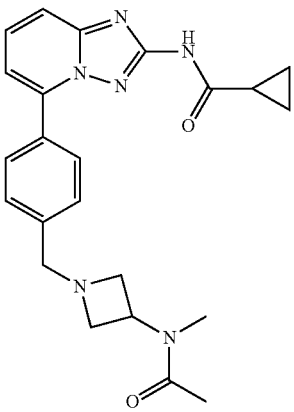 [SMILES: CC(=O)N(C)C1CN(Cc2ccc(-c3cccc4nc(NC(=O)C5CC5)nn34)cc2)C1] | Cyclopropanecarboxylic acid (5-{4-[3-(acetyl-methyl-amino)-azetidin-1-ylmethyl]-phenyl}-[1,2,4]triazolo[1,5-a]pyridin-2-yl)-amide | 418.5 | 419 |
| 284 | 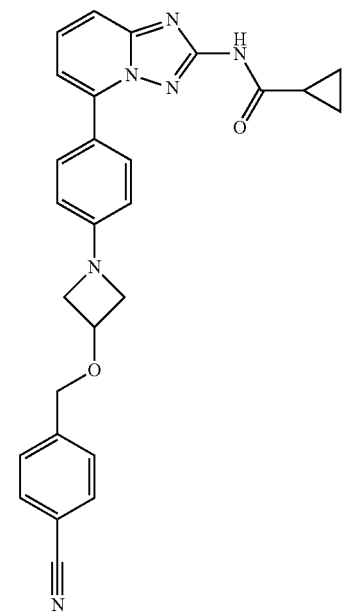 [SMILES: N#Cc1ccc(COC2CN(c3ccc(-c4cccc5nc(NC(=O)C6CC6)nn45)cc3)C2)cc1] | Cyclopropanecarboxylic acid (5-{4-[3-(4-cyano-benzyloxy)-azetidin-1-yl]-phenyl}-[1,2,4]triazolo[1,5-a]pyridin-2-yl)-amide | 464.53 | 465 |

TABLE I-continued
| Cpd # | Structures | Name | MW | MS Mes'd |
|---|---|---|---|---|
| 285 | 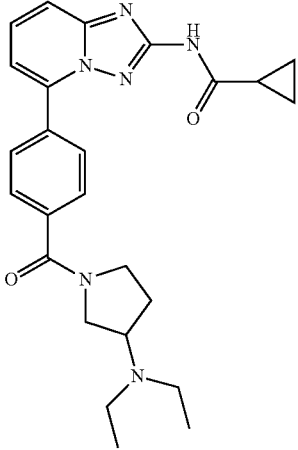 [SMILES: CCN(CC)C1CCN(C(=O)c2ccc(-c3cccc4nc(NC(=O)C5CC5)nn34)cc2)C1] | Cyclopropanecarboxylic acid {5-[4-(3-diethylamino-pyrrolidine-1-carbonyl)-phenyl]-[1,2,4]triazolo[1,5-a]pyridin-2-yl}-amide | 446.55 | 447 |
| 286 | 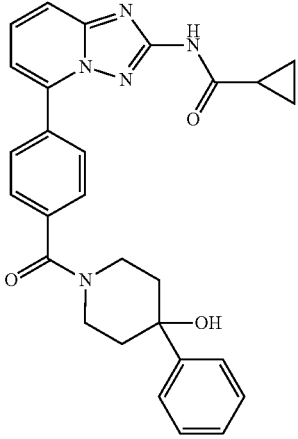 [SMILES: O=C(Nc1nc2cccc(-c3ccc(C(=O)N4CCC(O)(c5ccccc5)CC4)cc3)n2n1)C1CC1] | Cyclopropanecarboxylic acid {5-[4-(4-hydroxy-4-phenyl-piperidine-1-carbonyl)-phenyl]-[1,2,4]triazolo[1,5-a]pyridin-2-yl}-amide | 481.56 | 482 |
| 287 | 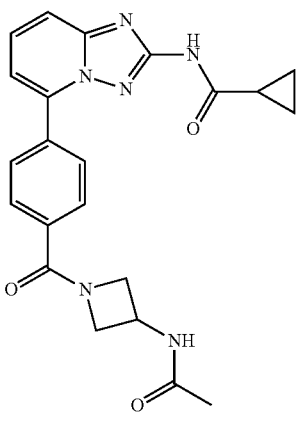 [SMILES: CC(=O)NC1CN(C(=O)c2ccc(-c3cccc4nc(NC(=O)C5CC5)nn34)cc2)C1] | Cyclopropanecarboxylic acid {5-[4-(3-acetylamino-azetidine-1-carbonyl)-phenyl]-[1,2,4]triazolo[1,5-a]pyridin-2-yl}-amide | 418.46 | 419 |

TABLE I-continued

| Cpd # | Structures | Name | MW | MS Mes'd |
|---|---|---|---|---|
| 288 | 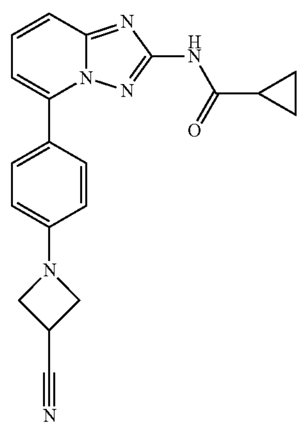 [SMILES: N#CC1CN(c2ccc(-c3cccc4nc(NC(=O)C5CC5)nn34)cc2)C1] | Cyclopropanecarboxylic acid {5-[4-(3-cyano-azetidin-1-yl)-phenyl]-[1,2,4]triazolo[1,5-a]pyridin-2-yl}-amide | 358.40 | 359 |
| 289 | 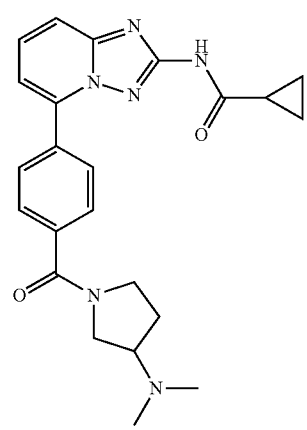 [SMILES: CN(C)C1CCN(C(=O)c2ccc(-c3cccc4nc(NC(=O)C5CC5)nn34)cc2)C1] | Cyclopropanecarboxylic acid {5-[4-(3-dimethylamino-pyrrolidine-1-carbonyl)-phenyl]-[1,2,4]triazolo[1,5-a]pyridin-2-yl}-amide | 418.50 | 419 |
| 290 | 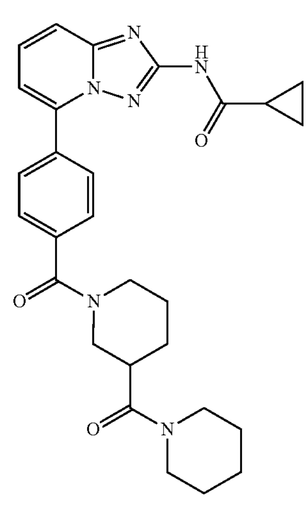 [SMILES: O=C(Nc1nc2cccc(-c3ccc(C(=O)N4CCCC(C(=O)N5CCCCC5)C4)cc3)n2n1)C1CC1] | Cyclopropanecarboxylic acid (5-{4-[3-(piperidine-1-carbonyl)-piperidine-1-carbonyl]-phenyl}-[1,2,4]triazolo[1,5-a]pyridin-2-yl)-amide | 500.60 | 501 |

| Cpd # | Structures | Name | MW | MS Mes'd |
|---|---|---|---|---|
| 291 | 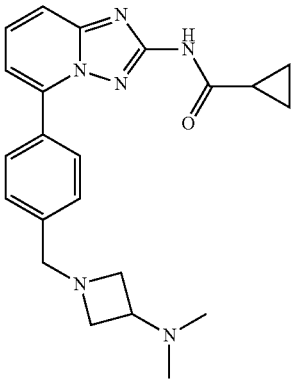 [SMILES: CN(C)C1CN(Cc2ccc(-c3cccc4nc(NC(=O)C5CC5)nn34)cc2)C1] | Cyclopropanecarboxylic acid {5-[4-(3-dimethylamino-azetidin-1-ylmethyl)-phenyl]-[1,2,4]triazolo[1,5-a]pyridin-2-yl}-amide | 390.49 | 391 |
| 292 | 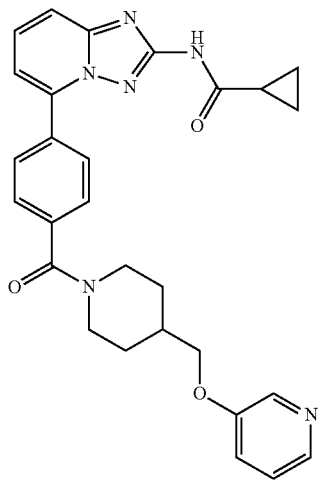 [SMILES: O=C(Nc1nc2cccc(-c3ccc(C(=O)N4CCC(COc5cccnc5)CC4)cc3)n2n1)C1CC1] | Cyclopropanecarboxylic acid (5-{4-[4-(pyridin-3-yloxymethyl)-piperidine-1-carbonyl]-phenyl}-[1,2,4]triazolo[1,5-a]pyridin-2-yl)-amide | 496.57 | 497 |
| 293 | 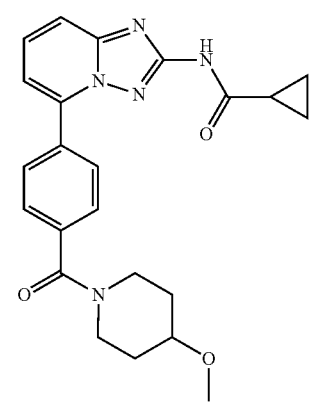 [SMILES: COC1CCN(C(=O)c2ccc(-c3cccc4nc(NC(=O)C5CC5)nn34)cc2)CC1] | Cyclopropanecarboxylic acid {5-[4-(4-methoxy-piperidine-1-carbonyl)-phenyl]-[1,2,4]triazolo[1,5-a]pyridin-2-yl}-amide | 419.48 | 420 |

TABLE I-continued

| Cpd # | Structures | Name | MW | MS Mes'd |
|---|---|---|---|---|
| 294 | 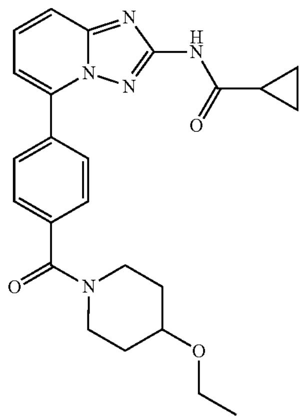 [SMILES: CCOC1CCN(C(=O)c2ccc(-c3cccc4nc(NC(=O)C5CC5)nn34)cc2)CC1] | Cyclopropanecarboxylic acid {5-[4-(4-ethoxy-piperidine-1-carbonyl)-phenyl]-[1,2,4]triazolo[1,5-a]pyridin-2-yl}-amide | 433.51 | 434 |
| 295 | 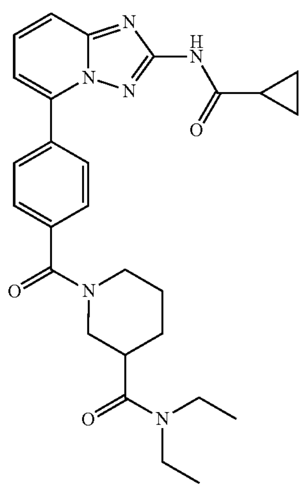 [SMILES: CCN(CC)C(=O)C1CCCN(C(=O)c2ccc(-c3cccc4nc(NC(=O)C5CC5)nn34)cc2)C1] | 1-{4-[2-(Cyclopropanecarbonyl-amino)-[1,2,4]triazolo[1,5-a]pyridin-5-yl]-benzoyl}-piperidine-3-carboxylic acid diethylamide | 488.59 | 489 |
| 296 | 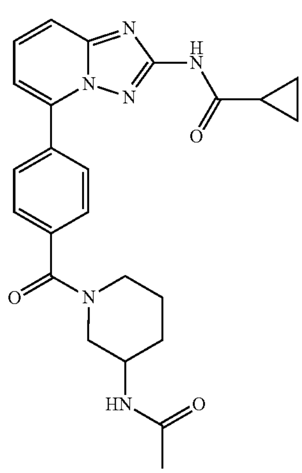 [SMILES: CC(=O)NC1CCCN(C(=O)c2ccc(-c3cccc4nc(NC(=O)C5CC5)nn34)cc2)C1] | Cyclopropanecarboxylic acid {5-[4-(3-acetylamino-piperidine-1-carbonyl)-phenyl]-[1,2,4]triazolo[1,5-a]pyridin-2-yl}-amide | 446.51 | 447 |

| Cpd # | Structures | Name | MW | MS Mes'd |
|---|---|---|---|---|
| 297 | 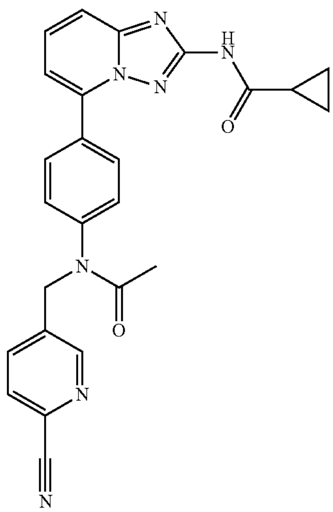 [SMILES: CC(=O)N(Cc1ccc(C#N)nc1)c1ccc(-c2cccc3nc(NC(=O)C4CC4)nn23)cc1] | Cyclopropanecarboxylic acid (5-{4-[acetyl-(6-cyano-pyridin-3-ylmethyl)-amino]-phenyl}-[1,2,4]triazolo[1,5-a]pyridin-2-yl)-amide | 451.49 | 452 |
| 298 | 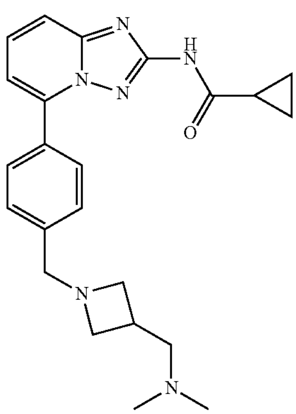 [SMILES: CN(C)CC1CN(Cc2ccc(-c3cccc4nc(NC(=O)C5CC5)nn34)cc2)C1] | Cyclopropanecarboxylic acid {5-[4-(3-dimethylaminomethyl-azetidin-1-ylmethyl)-phenyl]-[1,2,4]triazolo[1,5-a]pyridin-2-yl}-amide | 404.52 | N/A |
| 299 | 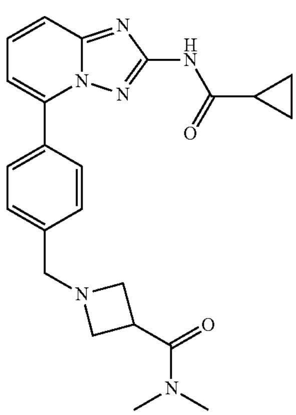 [SMILES: CN(C)C(=O)C1CN(Cc2ccc(-c3cccc4nc(NC(=O)C5CC5)nn34)cc2)C1] | 1-{4-[2-(Cyclopropanecarbonyl-amino)-[1,2,4]triazolo[1,5-a]pyridin-5-yl]-benzyl}-azetidine-3-carboxylic acid dimethylamide | 418.5 | 419 |

TABLE I-continued

| Cpd # | Structures | Name | MW | MS Mes'd |
|---|---|---|---|---|
| 300 | 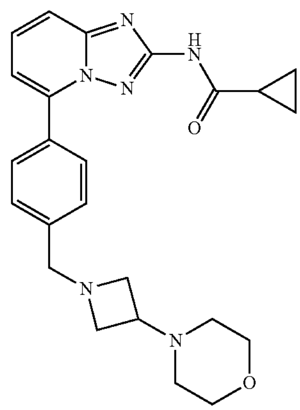 [SMILES: O=C(Nc1nc2cccc(-c3ccc(CN4CC(N5CCOCC5)C4)cc3)n2n1)C1CC1] | Cyclopropanecarboxylic acid {5-[4-(3-morpholin-4-yl-azetidin-1-ylmethyl)-phenyl]-[1,2,4]triazolo[1,5-a]pyridin-2-yl}-amide | 432.53 | 433 |
| 301 | 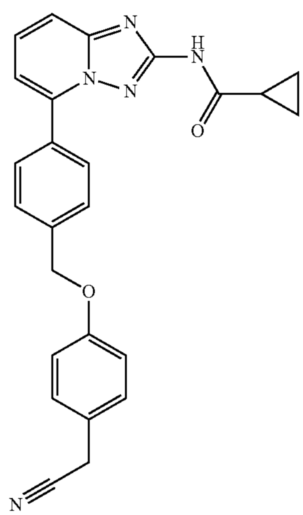 [SMILES: N#CCc1ccc(OCc2ccc(-c3cccc4nc(NC(=O)C5CC5)nn34)cc2)cc1] | Cyclopropanecarboxylic acid {5-[4-(4-cyanomethyl-phenoxymethyl)-phenyl]-[1,2,4]triazolo[1,5-a]pyridin-2-yl}-amide | 423.48 | 424 |
| 302 | 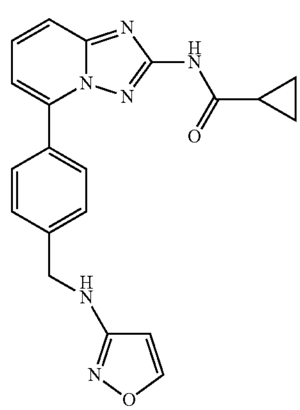 [SMILES: O=C(Nc1nc2cccc(-c3ccc(CNc4ccon4)cc3)n2n1)C1CC1] | Cyclopropanecarboxylic acid {5-[4-(isoxazol-3-ylaminomethyl)-phenyl]-[1,2,4]triazolo[1,5-a]pyridin-2-yl}-amide | 374.40 | 375 |

TABLE I-continued

| Cpd # | Structures | Name | MW | MS Mes'd |
|---|---|---|---|---|
| 303 | 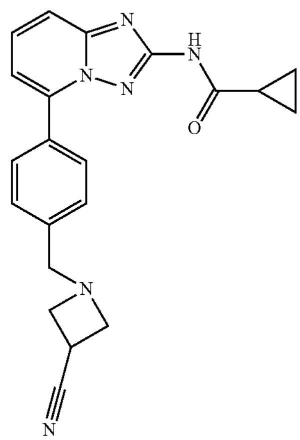 [SMILES: N#CC1CN(Cc2ccc(-c3cccc4nc(NC(=O)C5CC5)nn34)cc2)C1] | Cyclopropanecarboxylic acid {5-[4-(3-cyano-azetidin-1-ylmethyl)-phenyl]-[1,2,4]triazolo[1,5-a]pyridin-2-yl}-amide | 372.43 | 373 |
| 304 | 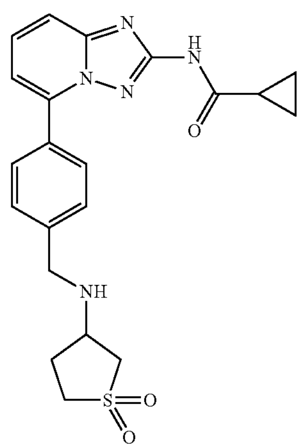 [SMILES: O=C(Nc1nc2cccc(-c3ccc(CNC4CCS(=O)(=O)C4)cc3)n2n1)C1CC1] | Cyclopropanecarboxylic acid (5-{4-[(1,1-dioxo-tetrahydro-thiophen-3-ylamino)-methyl]-phenyl}-[1,2,4]triazolo[1,5-a]pyridin-2-yl)-amide | 425.51 | 426 |
| 305 | 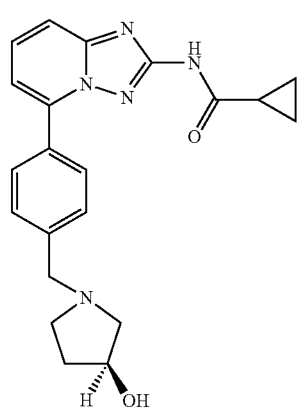 [SMILES: O=C(Nc1nc2cccc(-c3ccc(CN4CC[C@H](O)C4)cc3)n2n1)C1CC1] | Cyclopropanecarboxylic acid {5-[4-((S)-3-hydroxy-pyrrolidin-1-ylmethyl)-phenyl]-[1,2,4]triazolo[1,5-a]pyridin-2-yl}-amide | 377.45 | 378 |

TABLE I-continued
| Cpd # | Structures | Name | MW | MS Mes'd |
|---|---|---|---|---|
| 306 | 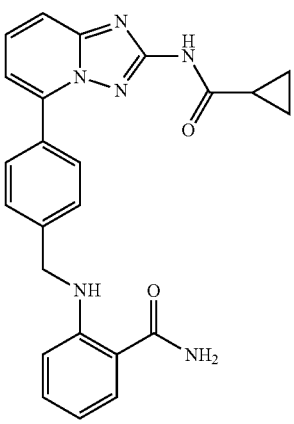 [SMILES: NC(=O)c1ccccc1NCc1ccc(-c2cccc3nc(NC(=O)C4CC4)nn23)cc1] | 2-{4-[2-(Cyclopropanecarbonyl-amino)-[1,2,4]triazolo[1,5-a]pyridin-5-yl]-benzylamino}-benzamide | 426.48 | 427 |
| 307 | 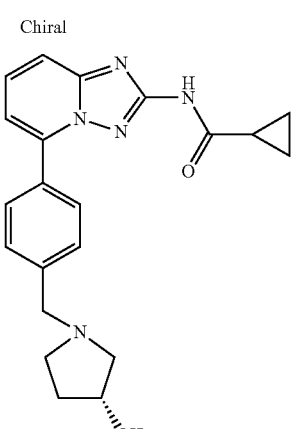 Chiral | Cyclopropanecarboxylic acid {5-[4-((R)-3-hydroxy-pyrrolidin-1-ylmethyl)-phenyl]-[1,2,4]triazolo[1,5-a]pyridin-2-yl}-amide | 377.45 | 378 |
| 308 | 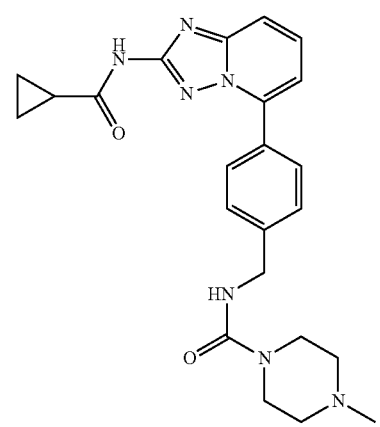 [SMILES: CN1CCN(C(=O)NCc2ccc(-c3cccc4nc(NC(=O)C5CC5)nn34)cc2)CC1] | 4-Methyl-piperazine-1-carboxylic acid 4-[2-(cyclopropanecarbonyl-amino)-[1,2,4]triazolo[1,5-a]pyridin-5-yl]-benzylamide | 433.51 | 434.2 |

TABLE I-continued

| Cpd # | Structures | Name | MW | MS Mes'd |
|---|---|---|---|---|
| 309 | 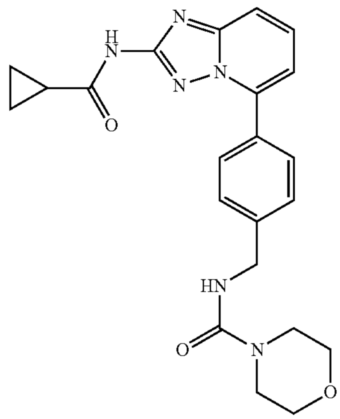 [SMILES: O=C(Nc1nc2cccc(-c3ccc(CNC(=O)N4CCOCC4)cc3)n2n1)C1CC1] | Morpholine-4-carboxylic acid 4-[2-(cyclopropanecarbonyl-amino)-[1,2,4]triazolo[1,5-a]pyridin-5-yl]-benzylamide | 420.46 | 421.3 |
| 310 | 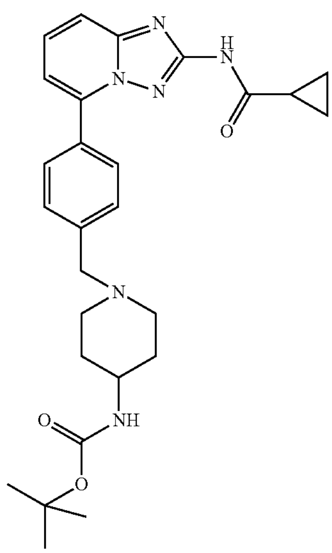 [SMILES: CC(C)(C)OC(=O)NC1CCN(Cc2ccc(-c3cccc4nc(NC(=O)C5CC5)nn34)cc2)CC1] | (1-{4-[2-(Cyclopropanecarbonyl-amino)-[1,2,4]triazolo[1,5-a]pyridin-5-yl]-benzyl}-piperidin-4-yl)-carbamic acid tert-butyl ester | 490.61 | 491.1 |
| 311 | 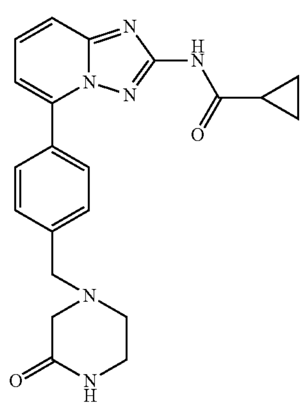 [SMILES: O=C1CN(Cc2ccc(-c3cccc4nc(NC(=O)C5CC5)nn34)cc2)CCN1] | Cyclopropanecarboxylic acid {5-[4-(3-oxo-piperazin-1-ylmethyl)-phenyl]-[1,2,4]triazolo[1,5-a]pyridin-2-yl}-amide | 390.45 | 391 |

TABLE I-continued

| Cpd # | Structures | Name | MW | MS Mes'd |
|---|---|---|---|---|
| 312 | 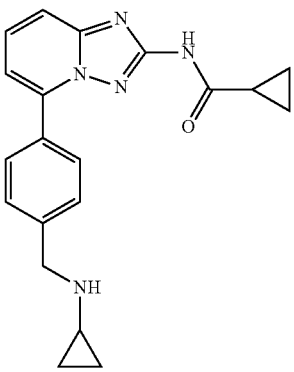 [SMILES: O=C(Nc1nc2cccc(-c3ccc(CNC4CC4)cc3)n2n1)C1CC1] | Cyclopropanecarboxylic acid [5-(4-cyclopropylaminomethyl-phenyl)-[1,2,4]triazolo[1,5-a]pyridin-2-yl]-amide | 347.42 | 348.1 |
| 313 | 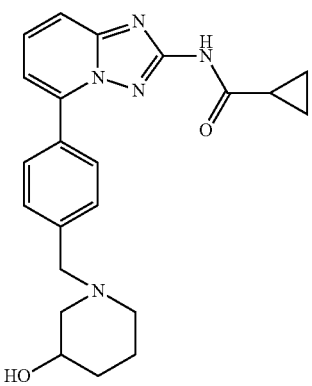 [SMILES: O=C(Nc1nc2cccc(-c3ccc(CN4CCCC(O)C4)cc3)n2n1)C1CC1] | Cyclopropanecarboxylic acid {5-[4-(3-hydroxy-piperidin-1-ylmethyl)-phenyl]-[1,2,4]triazolo[1,5-a]pyridin-2-yl}-amide | 391.48 | 392 |
| 314 | 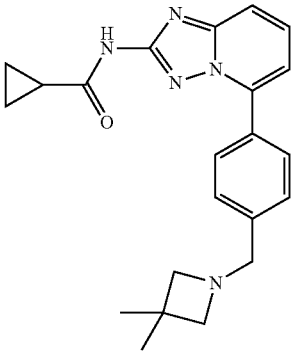 [SMILES: CC1(C)CN(Cc2ccc(-c3cccc4nc(NC(=O)C5CC5)nn34)cc2)C1] | Cyclopropanecarboxylic acid {5-[4-(3,3-dimethyl-azetidin-1-ylmethyl)-phenyl]-[1,2,4]triazolo[1,5-a]pyridin-2-yl}-amide | 375.47 | 376.3 |
| 315 | 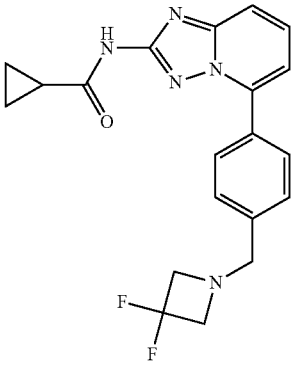 [SMILES: O=C(Nc1nc2cccc(-c3ccc(CN4CC(F)(F)C4)cc3)n2n1)C1CC1] | Cyclopropanecarboxylic acid {5-[4-(3,3-difluoro-azetidin-1-ylmethyl)-phenyl]-[1,2,4]triazolo[1,5-a]pyridin-2-yl}-amide | 383.39 | 384.2 |

TABLE I-continued

| Cpd # | Structures | Name | MW | MS Mes'd |
|---|---|---|---|---|
| 316 | 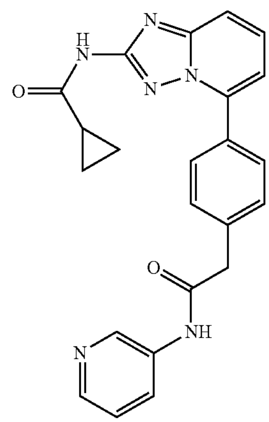 [SMILES: O=C(Cc1ccc(-c2cccc3nc(NC(=O)C4CC4)nn23)cc1)Nc1cccnc1] | Cyclopropanecarboxylic acid {5-[4-(pyridin-3-ylcarbamoylmethyl)-phenyl]-[1,2,4]triazolo[1,5-a]pyridin-2-yl}-amide | 412.44 | 413.3 |
| 317 | 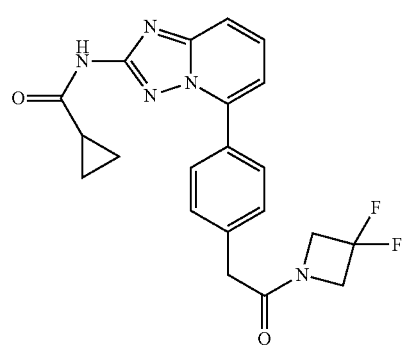 [SMILES: O=C(Nc1nc2cccc(-c3ccc(CC(=O)N4CC(F)(F)C4)cc3)n2n1)C1CC1] | Cyclopropanecarboxylic acid (5-{4-[2-(3,3-difluoro-azetidin-1-yl)-2-oxo-ethyl]-phenyl}-[1,2,4]triazolo[1,5-a]pyridin-2-yl)-amide | 411.4 | 412.2 |
| 318 | 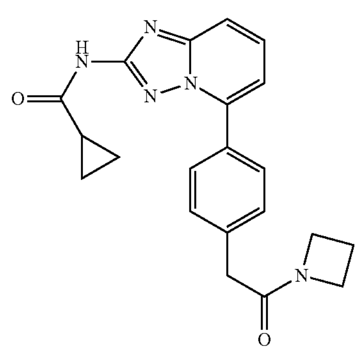 [SMILES: O=C(Nc1nc2cccc(-c3ccc(CC(=O)N4CCC4)cc3)n2n1)C1CC1] | Cyclopropanecarboxylic acid {5-[4-(2-azetidin-1-yl-2-oxo-ethyl)-phenyl]-[1,2,4]triazolo[1,5-a]pyridin-2-yl}-amide | 375.42 | 376.2 |
| 319 | 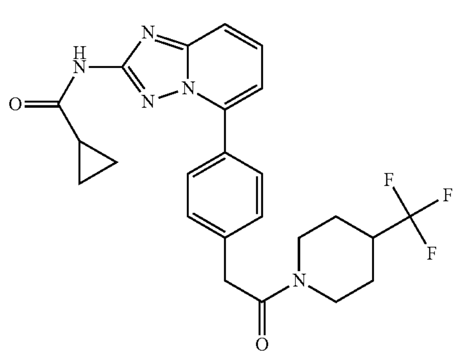 [SMILES: O=C(Nc1nc2cccc(-c3ccc(CC(=O)N4CCC(C(F)(F)F)CC4)cc3)n2n1)C1CC1] | Cyclopropanecarboxylic acid (5-{4-[2-oxo-2-(4-trifluoromethyl-piperidin-1-yl)-ethyl]-phenyl}-[1,2,4]triazolo[1,5-a]pyridin-2-yl)-amide | 471.47 | 472.2 |

TABLE I-continued

| Cpd # | Structures | Name | MW | MS Mes'd |
|---|---|---|---|---|
| 320 | 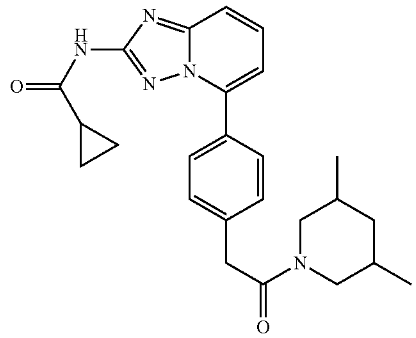 [SMILES: CC1CC(C)CN(C(=O)Cc2ccc(-c3cccc4nc(NC(=O)C5CC5)nn34)cc2)C1] | Cyclopropanecarboxylic acid (5-{4-[2-(3,5-dimethyl-piperidin-1-yl)-2-oxo-ethyl]-phenyl}-[1,2,4]triazolo[1,5-a]pyridin-2-yl)-amide | 431.53 | 432.2 |
| 321 | 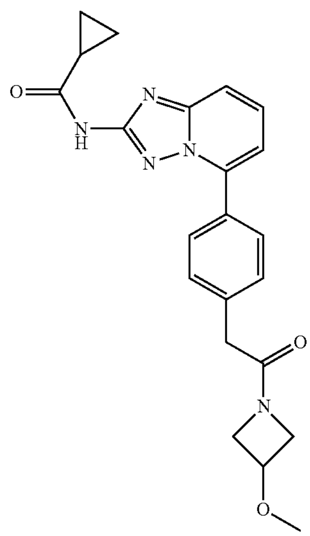 [SMILES: COC1CN(C(=O)Cc2ccc(-c3cccc4nc(NC(=O)C5CC5)nn34)cc2)C1] | Cyclopropanecarboxylic acid (5-{4-[2-(3-methoxy-azetidin-1-yl)-2-oxo-ethyl]-phenyl}-[1,2,4]triazolo[1,5-a]pyridin-2-yl)-amide | 405.45 | 406.2 |
| 322 | 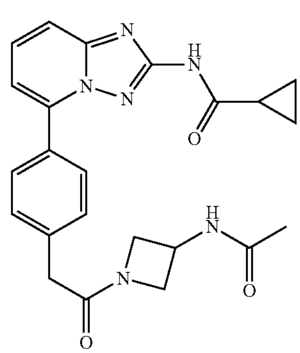 [SMILES: CC(=O)NC1CN(C(=O)Cc2ccc(-c3cccc4nc(NC(=O)C5CC5)nn34)cc2)C1] | Cyclopropanecarboxylic acid (5-{4-[2-(3-acetylamino-azetidin-1-yl)-2-oxo-ethyl]-phenyl}-[1,2,4]triazolo[1,5-a]pyridin-2-yl)-amide | 432.49 | 433.1 |

TABLE I-continued

| Cpd # | Structures | Name | MW | MS Mes'd |
|---|---|---|---|---|
| 323 | 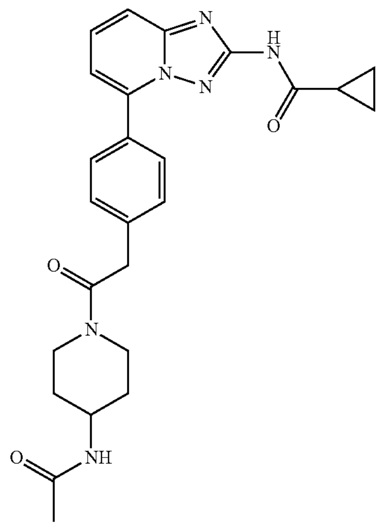 [SMILES: CC(=O)NC1CCN(C(=O)Cc2ccc(-c3cccc4nc(NC(=O)C5CC5)nn34)cc2)CC1] | Cyclopropanecarboxylic acid (5-{4-[2-(4-acetylamino-piperidin-1-yl)-2-oxo-ethyl]-phenyl}-[1,2,4]triazolo[1,5-a]pyridin-2-yl)-amide | 460.54 | 461.1 |
| 324 | 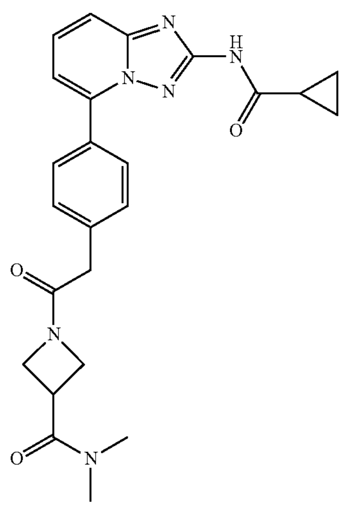 [SMILES: CN(C)C(=O)C1CN(C(=O)Cc2ccc(-c3cccc4nc(NC(=O)C5CC5)nn34)cc2)C1] | 1-(2-{4-[2-(Cyclopropanecarbonyl-amino)-[1,2,4]triazolo[1,5-a]pyridin-5-yl]-phenyl}-acetyl)-azetidine-3-carboxylic acid dimethylamide | 446.51 | 447 |
| 325 | 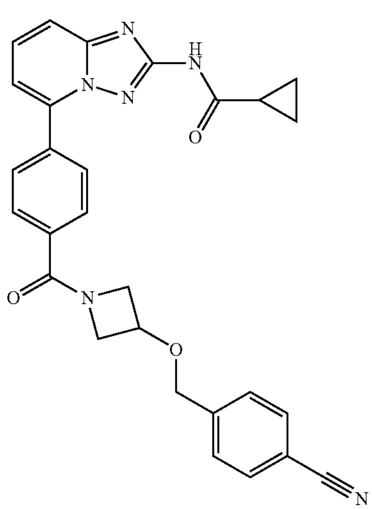 [SMILES: N#Cc1ccc(COC2CN(C(=O)c3ccc(-c4cccc5nc(NC(=O)C6CC6)nn45)cc3)C2)cc1] | Cyclopropanecarboxylic acid (5-{4-[3-(4-cyano-benzyloxy)-azetidine-1-carbonyl]-phenyl}-[1,2,4]triazolo[1,5-a]pyridin-2-yl)-amide | 492.54 | 493.0 |

TABLE I-continued

| Cpd # | Structures | Name | MW | MS Mes'd |
|---|---|---|---|---|
| 326 | 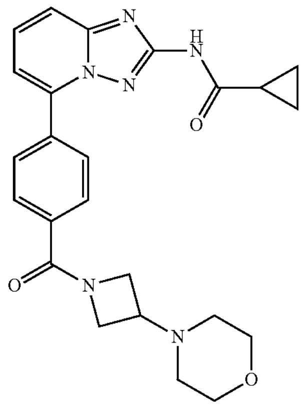 [SMILES: O=C(Nc1nc2cccc(-c3ccc(C(=O)N4CC(N5CCOCC5)C4)cc3)n2n1)C1CC1] | Cyclopropanecarboxylic acid {5-[4-(3-morpholin-4-yl-azetidine-1-carbonyl)-phenyl]-[1,2,4]triazolo[1,5-a]pyridin-2-yl}-amide | 446.51 | 447.0 |
| 327 | 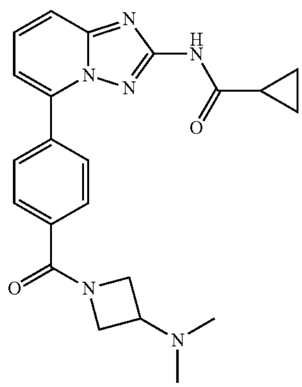 [SMILES: CN(C)C1CN(C(=O)c2ccc(-c3cccc4nc(NC(=O)C5CC5)nn34)cc2)C1] | Cyclopropanecarboxylic acid {5-[4-(3-dimethylamino-azetidine-1-carbonyl)-phenyl]-[1,2,4]triazolo[1,5-a]pyridin-2-yl}-amide | 404.48 | 405.1 |
| 328 | 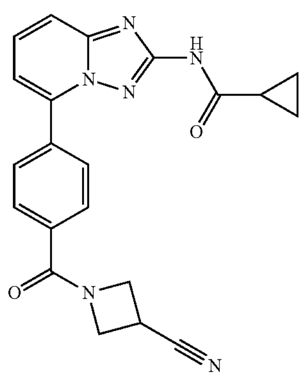 [SMILES: N#CC1CN(C(=O)c2ccc(-c3cccc4nc(NC(=O)C5CC5)nn34)cc2)C1] | Cyclopropanecarboxylic acid {5-[4-(3-cyano-azetidine-1-carbonyl)-phenyl]-[1,2,4]triazolo[1,5-a]pyridin-2-yl}-amide | 386.42 | 387.0 |
| 329 | 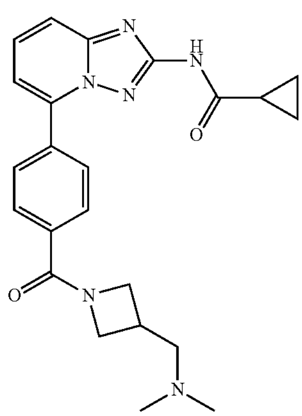 [SMILES: CN(C)CC1CN(C(=O)c2ccc(-c3cccc4nc(NC(=O)C5CC5)nn34)cc2)C1] | Cyclopropanecarboxylic acid {5-[4-(3-dimethylaminomethyl-azetidine-1-carbonyl)-phenyl]-[1,2,4]triazolo[1,5-a]pyridin-2-yl}-amide | 418.50 | 419.1 |

TABLE I-continued

| Cpd # | Structures | Name | MW | MS Mes'd |
|---|---|---|---|---|
| 330 | 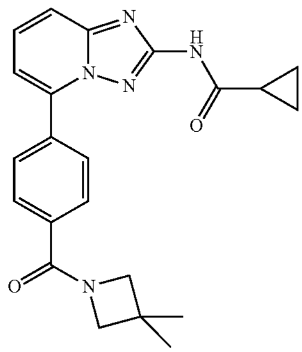 [SMILES: CC1(C)CN(C(=O)c2ccc(-c3cccc4nc(NC(=O)C5CC5)nn34)cc2)C1] | Cyclopropanecarboxylic acid {5-[4-(3,3-dimethyl-azetidine-1-carbonyl)-phenyl]-[1,2,4]triazolo[1,5-a]pyridin-2-yl}-amide | 389.46 | 390.0 |
| 331 | 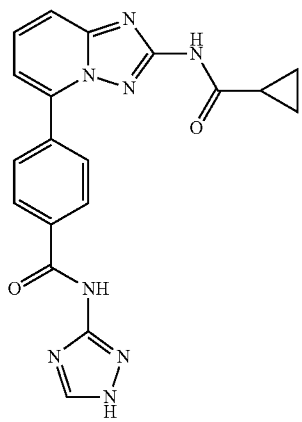 [SMILES: O=C(Nc1nc[nH]n1)c1ccc(-c2cccc3nc(NC(=O)C4CC4)nn23)cc1] | 4-[2-(Cyclopropanecarbonyl-amino)-[1,2,4]triazolo[1,5-a]pyridin-5-yl]-N-(1H-1,2,4-triazol-3-yl)-benzamide | 388.39 | 389.0 |

TABLE II

NMR Data of Representative Compounds of the Invention

| Cpd # | (δ) NMR data |
|---|---|
| 2 | ($^1$H, CDCl$_3$) 8.32 (1H, s, ArH), 7.96 (1H, m, ArH), 7.79 (1H, m, ArH), 7.66 (3H, m, ArH), 7.32 (1H, d, ArH), 4.31 (2H, s, CH$_2$), 4.05 (4H, b, 2 × CH$_2$), 3.6 (2H, br, CH$_2$), 3.06 (2H, br, CH$_2$), 1.85 (1H, br, CH), 1.12 (2H, m, CH$_2$), 0.98 (2H, m, CH$_2$) |
| 3 | ($^1$H, CDCl$_3$) 10.50 (1H, br, NH), 8.85 (1H, s, ArH), 8.72 (1H, d, ArH), 7.72 (2H, m, ArH), 7.34 (1H, m, ArH), 7.09 (1H, d, ArH), 3.79 (4H, br, 2 × CH$_2$), 1.90 (1H, br, CH), 1.80 (6H, br, 3 × CH$_2$), 1.19 (2H, m, CH$_2$), 0.99 (2H, m, CH$_2$) |
| 4 | ($^1$H, CDCl$_3$) 9.13 (2H, s, 2 × CH), 7.79 (1H, m, ArH), 7.63 (1H, d, ArH), 7.28 (1H, under CDCl$_3$ peak, ArH), 3.72 (4H, m, 2 × CH$_2$), 2.09 (5H, m, 2 × CH$_2$, CH), 1.20 (2H, m, CH$_2$), 1.00 (2H, m, CH$_2$) |
| 5 | ($^1$H, CDCl$_3$) 11.0 (1H, b, NH), 8.73 (1H, s, ArH), 8.41 (1H, d, ArH), 7.80 (1H, m, ArH), 7.65 (1H, d, ArH), 7.28 (1H, under CDCl$_3$, ArH), 6.87 (1H, d, ArH), 4.50 (2H, b, CH$_2$), 3.60 (4H, br, 2 × CH$_2$), 2.90 (2H, br, CH$_2$), 2.89 (3H, s, CH$_3$), 1.91 (1H, br, CH), 1.18 (2H, m, CH$_2$), 0.99 (2H, m, CH$_2$) |
| 6 | ($^1$H, CDCl$_3$) 8.71 (1H, s, NH), 8.35 (1H, m, ArH), 8.27 (1H, br, ArH), 7.57 (2H, d, ArH), 7.07 (1H, m, ArH), 6.78 (1H, d, ArH), 3.86 (4H, m, 2 × CH$_2$), 3.66 (4H, m, 2 × CH$_2$), 1.6 (1H, br, CH), 1.22 (2H, m, CH$_2$), 0.95 (2H, m, CH$_2$) |
| 7 | ($^1$H, CDCl$_3$) 8.24 (1H, b, NH), 8.07 (2H, d, ArH), 7.80 (2H, d, ArH), 7.69-7.60 (4H, m, ArH), 7.51 (2H, m, ArH), 7.42 (1H, m, ArH), 7.16 (1H, d, ArH), 1.6 (1H, b, CH), 1.23 (2H, m, CH$_2$), 0.97 (2H, m, CH$_2$) |
| 8 | ($^1$H, CDCl$_3$) 9.00 (2H, s, ArH), 8.66 (1H, br, NH), 7.60 (2H, m, ArH), 7.05 (1H, m, ArH), 3.95 (4H, m, 2 × CH$_2$), 3.81 (4H, m, 2 × CH$_2$), 2.10 (1H, br, CH), 1.22 (2H, m, CH2), 0.97 (2H, m, CH$_2$) |
| 9 | ($^1$H, CDCl$_3$) 8.97 (2H, s, ArH), 8.47 (1H, br, NH), 7.57 (2H, m, ArH), 7.03 (1H, dd, ArH), 3.91 (4H, m, 2 × CH$_2$), 1.66 (9H, under water peak, 3 × CH$_2$), 1.22 (2H, m, CH$_2$), 0.97 (2H, m, CH$_2$). |
| 10 | ($^1$H, CDCl$_3$) 8.95 (1H, b, NH), 8.15 (2H, d, ArH), 8.00 (2H, d, ArH), 7.88 (2H, d, ArH), 7.70 (3H, m, ArH), 7.54 (2H, m, ArH), 7.24 (1H, d, ArH), 2.10 (1H, under peak of water, CH), 1.22 (2H, m, CH$_2$), 0.96 (2H, m, CH$_2$) |
| 11 | ($^1$H, DMSO-d6) 11.03 (1H, s, NH), 8.58 (1H, d, NH), 8.11 (2H, d, ArH), 7.98 (2H, d, ArH), 7.72 (2H, m, ArH), 7.36 (1H, dd, ArH), 2.90 (1H, m, CH), 2.04 (1H, br, CH), 0.82 (4H, m, 2 × CH$_2$), 0.72 (2H, m, CH$_2$), 0.62 (2H, m, CH$_2$) |
| 12 | ($^1$H, CDCl$_3$) 8.70 (1H, b, NH), 7.97 (2H, d, ArH), 7.60-7.30 (7H, m, ArH), 7.15 (2H, m, ArH), 7.07 (1H, m, ArH), 5.17 (2H, s, CH$_2$), 1.60 (1H, under water peak, CH), 1.21 (2H, m, CH$_2$), 0.94 (2H, m, CH$_2$) |
| 13 | ($^1$H, CDCl$_3$) 9.23 (1H, b, NH), 8.18 (2H, d, ArH), 8.09 (2H, d, ArH), 7.70 (2H, m, ArH), 7.19 (1H, d, ArH), 7.29 (1H, b, NH), 2.33 (2H, br, 2 × CH), 1.20 (2H, m, CH$_2$), 0.95 (2H, m, CH$_2$), 0.71 (4H, m, 2 × CH$_2$) |
| 15 | ($^1$H, DMSO-d6) 11.04 (1H, br, NH), 8.08 (1H, d, ArH), 7.88 (1H, d, ArH), 7.68 (2H, m, ArH), 7.51 (2H, d, ArH), 2.48-7.30 (5H, m, ArH), 5.32 (2H, s, CH$_2$), 2.02 (1H, br, CH), 0.83 (4H, m, 2 × CH$_2$) |
| 17 | ($^1$H, CDCl$_3$) 9.09 (1H, b, NH), 8.05 (2H, d, ArH), 7.58 (4H, m, ArH), 7.12 (1H, d, ArH), 3.76 (2H, br, CH$_2$), 3.44 (2H, b, CH$_2$), 1.86 (3H, b, CH$_2$, CH), 1.72 (4H, b, 2 × CH$_2$), 1.57 (2H, b, CH$_2$), 1.21 (2H, m, CH$_2$), 0.94 (2H, m, CH$_2$) |
| 18 | ($^1$H, CDCl$_3$) 10.20 (1H, b, NH), 8.06 (2H, d, ArH), 7.72 (2H, m, ArH), 7.63 (2H, d, ArH), 7.23 (1H, d, ArH), 4.27 (2H, s, CH$_2$), 3.99 |

TABLE II-continued

NMR Data of Representative Compounds of the Invention

| Cpd # | (δ) NMR data |
|---|---|
| | (4H, m, 2 × CH$_2$), 3.50 (2H, br, CH$_2$), 2.95 (2H, br, CH$_2$), 1.97 (1H, br, CH), 1.17 (2H, m, CH$_2$), 0.95 (2H, m, CH$_2$) |
| 19 | ($^1$H, CDCl$_3$) 10.50 (1H, b, NH), 8.08 (2H, d, ArH), 7.72 (4H, m, ArH), 7.28 (1H, m, ArH), 3.70 (2H, t, CH$_2$), 3.52 (2H, t, CH$_2$), 2.01-1.80 (4H, m, 2 × CH$_2$), 1.50 (1H, br, CH), 1.19 (2H, m, CH$_2$), 0.98 (2H, m, CH$_2$). |
| 20 | ($^1$H, CDCl$_3$) 7.94 (2H, d, ArH), 7.70 (2H, d, ArH), 7.54 (2H, m, ArH), 7.35 (1H, m, ArH), 7.28 (1H, d, ArH), 7.06 (2H, m, ArH), 1.45 (1H, br, CH), 1.12 (2H, m, CH$_2$), 0.85 (2H, m, CH$_2$) |
| 21 | ($^1$H, DMSO-d6) 11.04 (1H, b, NH), 10.51 (1H, s, NH), 8.07 (2H, d, ArH), 8.00 (4H, m, ArH), 7.80-7.50 (5H, m, ArH), 7.33 (1H, d, ArH), 2.03 (1H, br, CH), 0.84 (4H, m, 2 × CH$_2$) |
| 22 | ($^1$H, DMSO-d6) 11.07 (1H, br, NH), 10.75 (1H, s, NH), 8.19 (2H, d, ArH), 8.09 (2H, d, ArH), 7.96 (4H, m, ArH), 7.69 (2H, m, ArH), 7.32 (1H, m, ArH), 2.02 (1H, br, CH), 0.84 (4H, m, 2 × CH$_2$) |
| 23 | ($^1$H, DMSO-d6) 11.01 (1H, br, NH), 10.44 (1H, s, NH), 8.01 (2H, d, ArH), 7.78 (2H, d, ArH), 7.67 (2H, m, ArH), 7.36 (4H, m, ArH), 7.28 (2H, m, ArH), 3.70 (2H, s, CH$_2$), 2.03 (1H, br, CH), 0.83 (4H, m, 2 × CH$_2$) |
| 24 | ($^1$H, CDCl$_3$) 8.49 (1H, s, ArH), 8.08 (2H, d, ArH), 7.61 (4H, m, ArH), 7.12 (1H, d, ArH), 3.90-3.50 (8H, b, 4 × CH$_2$), 1.60 (1H, under water peak, CH), 1.21 (2H, CH$_2$), 0.96 (2H, m, CH$_2$). |
| 27 | ($^1$H, CDCl$_3$), 9.20 (1H, b, NH), 8.06 (2H, d, ArH), 7.68 (2H, m, ArH), 7.59 (2H, d, ArH), 7.18 (1H, m, ArH), 4.84 (1H, br, CH), 3.93 (1H, br, CH), 3.1-2.6 (5H, b, 2 × CH$_2$, CH), 1.85 (1H, b, CH), 1.72 (1H, b, CH), 1.31 (1H, br, CH), 1.21 (2H, m, CH$_2$), 0.96 (2H, m, CH$_2$), 0.91 (9H, s, 3 × CH$_3$) |
| 28 | ($^1$H, DMSO-d6) 11.06 (1H, b, NH), 8.11 (2H, d, ArH), 7.73 (2H, m, ArH), 7.65 (2H, d, ArH), 7.37 (1H, m, ArH), 4.0-3.2 (8H, m, 4 × CH$_2$), 1.97 (3H, m, CH$_2$, CH), 0.81 (4H, m, 2 × CH$_2$) |
| 29 | ($^1$H, DMSO-d6) 11.05 (1H, br, NH), 9.25 (1H, t, NH), 8.13 (2H, d, ArH), 8.08 (2H, d, ArH), 7.74 (2H, m, ArH), 7.38 (2H, m, ArH), 7.20 (3H, m, ArH), 4.55 (2H, d, CH$_2$), 2.03 (1H, br, CH), 0.82 (4H, m, 2 × CH$_2$) |
| 30 | ($^1$H, DMSO-d6) 11.02 (1H, br, NH), 7.93 (2H, d, ArH), 7.69 (2H, m, ArH), 7.44 (2H, d, ArH), 7.28 (5H, m, ArH), 1.20 (1H, m, ArH), 3.19 (3H, s, CH$_3$), 2.06 (1H, br, CH), 0.82 (4H, m, 2 × CH$_2$) |
| 31 | ($^1$H, CDCl$_3$) 8.75 (1H, b, NH), 8.06 (2H, br, ArH), 7.65 (4H, m, ArH), 7.33 (1H, m, ArH), 7.14 (2H, m, ArH), 6.94 (2H, d, ArH), 4.74 (1H, br, CH), 4.54 (1H, b, CH), 3.84 (3H, s, CH$_3$), 3.03 (3H, br, CH$_3$), 1.20 (1H, m, CH), 1.33 (2H, br, CH$_2$), 0.94 (2H, m, CH$_2$) |
| 33 | ($^1$H, DMSO-d6) 11.04 (1H, s, NH), 10.56 (1H, s, NH), 8.07 (2H, d, ArH), 7.98 (2H, d, ArH), 7.85 (2H, m, ArH), 7.68 (3H, m, ArH), 7.49 (1H, m, ArH), 7.33 (1H, d, ArH), 2.08 (1H, br, CH), 0.84 (4H, m, 2 × CH$_2$) |
| 34 | ($^1$H, DMSO-d6) 11.03 (1H, b, 2 × NH), 9.35 (1H, s, ArH), 8.97 (1H, s, ArH), 8.86 (1H, m, H, ArH), 8.11 (4H, m, ArH), 7.70 (2H, m, ArH), 7.35 (1H, d, ArH), 2.07 (1H, br, CH), 0.84 (4H, m, 2 × CH$_2$). |
| 35 | ($^1$H, DMSO-d6) 10.98 (1H, b, NH), 8.72 (1H, s, ArH), 8.57 (1H, m, ArH), 8.02 (2H, d, ArH), 7.92 (1H, m, ArH), 7.65 (2H, m, ArH), 7.45 (1H, dd, ArH), 7.26 (1H, d, ArH), 7.22 (2H, d, ArH), 5.28 (2H, s, CH$_2$), 2.03 (1H, br, CH), 0.82 (4H, m, 2 × CH$_2$) |
| 36 | ($^1$H, DMSO-d6) 11.03 (1H, br, NH), 8.62 (1H, m, ArH), 8.02 (2H, d, ArH), 7.89 (1H, m, ArH), 7.66 (2H, m, ArH), 7.58 (1H, d, ArH), 7.40 (1H, dd, ArH), 7.27 (1H, d, ArH), 7.21 (2H, d, ArH), 5.31 (2H, s, CH$_2$), 2.02 (1H, br, CH), 0.83 (4H, m, 2 × CH$_2$) |
| 37 | ($^1$H, DMSO-d6) 11.01 (1H, br, NH), 8.04 (2H, d, ArH), 7;68 (2H, m, ArH), 7.55 (2H, m, ArH), 7.50 (1H, s, ArH), 7.38 (1H, d, ArH), 7.28 (1H, d, ArH), 7.20 (2H, d, ArH), 5.30 (2H, s, CH$_2$), 2.02 (1H, br, CH), 0.82 (4H, m, 2 × CH$_2$) |
| 38 | ($^1$H, DMSO-d6) 11.01 (1H, br, NH), 8.00 (2H, d, ArH), 7.69 (2H, d, ArH), 7.69 (1H, dd, ArH), 7.64 (1H, d, ArH), 7.26 (1H, d, ArH), 7.11 (2H, d, ArH), 4.07 (2H, d, CH$_2$), 2.78 (1H, m, CH), 2.2-1.8 (7H, m, CH, 3 × CH$_2$), 0.83 (4H, m, 2 × CH$_2$) |
| 39 | ($^1$H, DMSO-d6) 11.04 (1H, s, NH), 10.56 (1H, s, NH), 8.07 (2H, d, ArH), 7.98 (2H, d, ArH), 7.85 (2H, m, ArH), 7.68 (3H, m, ArH), 7.49 (1H, m, ArH), 7.33 (1H, d, ArH), 2.08 (1H, br, CH), 0.84 (4H, m, 2 × CH$_2$) |
| 40 | ($^1$H, DMSO-d6) 11.01 (1H, b, NH), 7.99 (2H, d, ArH), 7.69 (1H, dd, ArH), 7.63 (1H, d, ArH), 7.26 (1H, d, ArH), 7.07 (2H, d, ArH), 4.95 (1H, m, CH), 1.98 (3H, m, CH, CH$_2$), 1.62 (6H, 3 × CH$_2$), 1.11 (4H, m, 2 × CH$_2$) |
| 41 | ($^1$H, DMSO-d6) 11.01 (1H, br NH), 7.99 (2H, d, ArH), 7.67 (1H, dd, ArH), 7.64 (1H, d, ArH), 7.25 (1H, d, ArH), 7.10 (2H, d, ArH), 3.89 (2H, d, CH$_2$), 2.02 (1H, br, CH), 1.90-1.60 (5H, m, CH, 2 × CH$_2$), 1.20-1.00 (6H, m, 2 × CH$_2$), 1.09 (4H, m, 2 × CH$_2$) |
| 42 | ($^1$H, DMSO-d6) 11.08 (1H, br, NH), 9.35 (1H, m, ArH), 8.79 (1H, s, ArH), 8.69 (1H, d, ArH), 8.21 (1H, d, ArH), 8.14 (2H, d, ArH), 8.07 (2H, d, ArH), 7.74 (3H, m, ArH), 7.38 (1H, m, ArH), 4.65 (2H, d, CH$_2$), 2.07 (1H, br, CH), 0.81 (4H, m, 2 × CH$_2$) |
| 43 | ($^1$H, DMSO-d6) 11.08 (1H, br, NH), 10.41 (1H, s, NH), 8.15 (4H, m, ArH), 7.78 (4H, m, ArH), 7.37 (3H, m, ArH), 7.12 (1H, m, ArH), 2.07 (1H, br, CH), 0.83 (4H, m, 2 × CH$_2$) |
| 44 | ($^1$H, DMSO-d6) 11.08 (1H, s, NH), 9.09 (1H, d, ArH), 8.54 (1H, dd, ArH), 8.37 (1H, d, ArH), 8.08 (1H, d, ArH), 7.75 (2H, m, ArH), 7.63 (2H, m, ArH), 7.63 (1H, m, ArH), 7.55 (2H, m, ArH), 7.45 (1H, dd, ArH), 2.02 (1H, br, CH), 0.83 (4H, m, 2 × CH$_2$) |
| 45 | ($^1$H, DMSO-d6) 11.01 (1H, br, NH), 10.06 (1H, s, NH), 8.00 (2H, d, ArH), 7.78 (2H, m, ArH), 7.67 (2H, m, ArH), 7.28 (1H, m, ArH), 2.36 (1H, m, CH), 2.03 (1H, m, CH), 1.83-1.26 (10H, m, 5 × CH$_2$), 0.82 (4H, m, 2 × CH$_2$) |
| 46 | ($^1$H, DMSO-d6) 11.05 (1H, br, NH), 8.05 (2H, d, ArH), 7.69 (2H, m, ArH), 7.46 (2H, m, ArH), 7.25 (2H, m, ArH), 7.14 (4H, d, ArH), 2.02 (1H, br, CH), 0.81 (4H, m, 2 × CH$_2$) |
| 47 | ($^1$H, DMSO-d6) 11.13 (1H, br, NH), 9.32 (1H, d, ArH), 8.59 (1H, dd, ArH), 8.22 (3H, m, ArH), 7.77 (2H, m, ArH), 7.54 (4H, m, ArH), 2.01 (1H, m, CH), 0.84 (4H, m, 2 × CH$_2$) |
| 49 | ($^1$H, DMSO-d6) 11.06 (1H, br, NH), 8.03 (2H, d, ArH), 7.69 (2H, m, ArH), 7.28 (1H, d, ArH), 7.20 (2H, d, ArH), 5.04 (2H, s, CH$_2$), 2.45 (3H, s, CH$_3$), 2.25 (3H, s, CH$_3$), 2.03 (1H, br, CH), 0.83 (4H, m, 2 × CH$_2$) |
| 50 | ($^1$H, DMSO-d6) 11.18 (1H, b, NH), 8.01 (2H, d, ArH), 7.68 (2H, m, ArH), 7.26 (1H, d, ArH), 7.09 (2H, d, ArH), 4.12 (2H, t, CH$_2$), 2.86 (2H, t, CH$_2$), 2.28 (6H, s, 2 × CH$_3$), 2.02 (1H, br, CH), 0.81 (4H, m, 2 × CH$_2$). |
| 51 | ($^1$H, DMSO-d6) 11.05 (1H, br, NH), 8.02 (2H, d, ArH), 7.68 (2H, m, ArH), 7.28 (1H, d, ArH), 7.21 (2H, d, ArH), 6.38 (1H, s, ArH), 5.27 (2H, s, CH$_2$), 2.42 (3H, s, CH$_3$), 2.05 (1H, br, CH), 0.82 (4H, m, 2 × CH$_2$) |
| 52 | ($^1$H, DMSO-d6) 11.04 (1H, br, NH), 10.47 (1H, s, NH), 8.07 (2H, d, ArH), 7.97 (2H, d, ArH), 7.74-7.66 (2H, m, ArH), 7.58 (1H, d, ArH), 7.48 (2H, m, ArH), 7.33 (1H, dd, ArH), 7.20 (1H, dd, ArH), 3.86 (3H, s, CH$_3$), 2.02 (1H, br, CH), 0.82 (4H, m, 2 × CH$_2$) |
| 53 | ($^1$H, DMSO-d6) 11.05 (2H, br, 2 × NH), 7.96 (3H, m, ArH), 7.70-7.60 (3H, m, ArH), 7.50-7.40 (2H, m, ArH), 7.27 (2H, d, ArH), 7.21 (1H, d, ArH), 2.01 (1H, br, CH), 0.82 (4H, m, 2 × CH$_2$) |
| 54 | ($^1$H, DMSO-d6) 11.06 (1H, br, NH), 10.93 (1H, s, NH), 8.78 (1H, d, ArH), 8.20 (1H, d, ArH), 8.12 (5H, m, ArH), 7.70 (3H, m, ArH), 7.34 (1H, d, ArH), 2.07 (1H, br, CH), 0.84 (4H, m, 2 × CH$_2$) |
| 55 | ($^1$H, DMSO-d6) 11.06 (1H, br, NH), 9.22 (1H, t, NH), 8.14 (2H, d, ArH), 8.07 (2H, d, ArH), 7.74 (2H, m, ArH), 7.38 (5H, m, ArH), 7.26 (1H, m, ArH), 4.54 (2H, d, CH$_2$), 2.02 (1H, br, CH), 0.82 (4H, m, 2 × CH$_2$) |
| 56 | ($^1$H, DMSO-d6) 11.08 (1H, br, NH), 8.89 (1H, d, ArH), 8.42 (1H, dd, ArH), 7.70 (2H, m, ArH), 7.49 (2H, d, ArH), 7.40 (4H, m, ArH), 7.10 (1H, d, ArH), 5.47 (2H, s, CH$_2$), 2.03 (1H, br, CH), 0.82 (4H, m, 2 × CH$_2$) |
| 57 | ($^1$H, DMSO-d6) 11.18 (1H, br, NH), 8.01 (2H, d, ArH), 7.68 (2H, m, ArH), 7.26 (1H, d, ArH), 7.09 (2H, d, ArH), 4.12 (2H, t, CH$_2$), 2.86 (2H, t, CH$_2$), 2.28 (6H, s, 2 × CH$_3$), 2.02 (1H, br, CH), 0.81 (4H, m, 2 × CH$_2$). |
| 58 | ($^1$H, DMSO-d6) 11.18 (1H, br, NH), 8.01 (2H, d, ArH), 7.68 (2H, m, ArH), 7.26 (1H, d, ArH), 7.09 (2H, d, ArH), 4.12 (2H, t, CH$_2$), 2.86 (2H, t, CH$_2$), 2.28 (6H, s, 2 × CH$_3$), 2.02 (1H, br, CH), 0.81 (4H, m, 2 × CH$_2$). |
| 59 | ($^1$H, DMSO-d6) 11.05 (1H, br, NH), 8.02 (2H, d, ArH), 7.68 (2H, m, ArH), 7.28 (1H, d, ArH), 7.21 (2H, d, ArH), 6.38 (1H, s, ArH), 5.27 (2H, s, CH$_2$), 2.42 (3H, s, CH$_3$), 2.05 (1H, br, CH), 0.82 (4H, m, 2 × CH$_2$) |
| 60 | ($^1$H, DMSO-d6) 11.04 (1H, br, NH), 10.47 (1H, s, NH), 8.07 (2H, d, ArH), 7.97 (2H, d, ArH), 7.74-7.66 (2H, m, ArH), 7.58 (1H, d, ArH), |

TABLE II-continued

NMR Data of Representative Compounds of the Invention

| Cpd # | (δ) NMR data |
|---|---|
| | 7.48 (2H, m, ArH), 7.33 (1H, dd, ArH), 7.20 (1H, dd, ArH), 3.86 (3H, s, CH$_3$), 2.02 (1H, br, CH), 0.82 (4H, m, 2 × CH$_2$) |
| 61 | ($^1$H, DMSO-d6) 11.05 (2H, br, 2 × NH), 7.96 (3H, m, ArH), 7.70-7.60 (3H, m, ArH), 7.50-7.40 (2H, m, ArH), 7.27 (2H, d, ArH), 7.21 (1H, d, ArH), 2.01 (1H, br, CH), 0.82 (4H, m, 2 × CH$_2$) |
| 62 | ($^1$H, DMSO-d6) 11.06 (1H, s, NH), 10.93 (1H, s, NH), 8.78 (1H, d, ArH), 8.20 (1H, d, ArH), 8.12 (5H, m, ArH), 7.70 (3H, m, ArH), 7.34 (1H, d, ArH), 2.07 (1H, br, CH), 0.84 (4H, m, 2 × CH$_2$) |
| 63 | ($^1$H, DMSO-d6) 11.12 (1H, br, NH), 8.02 (2H, d, ArH), 7.70 (2H, m, ArH), 7.31 (1H, d, ArH), 7.19 (2H, d, ArH), 4.99 (2H, s, CH$_2$), 2.36 (3H, s, CH$_3$), 2.34 (3H, s, CH$_3$), 2.02 (1H, br, CH), 0.83 (4H, m, 2 × CH$_2$) |
| 64 | ($^1$H, DMSO-d6) 11.01 (1H, br, NH), 10.95 (1H, br, NH), 9.00 (1H, d, ArH), 8.83 (1H, m, ArH), 8.24 (1H, m, ArH), 7.95 (2H, d, ArH), 7.65 (3H, m, ArH), 7.28 (2H, d, ArH), 7.23 (1H, dd, ArH), 2.02 (1H, br, CH), 0.81 (4H, m, 2 × CH$_2$) |
| 65 | ($^1$H, DMSO-d6) 11.07 (1H, br, NH), 10.11 (1H, s, NH), 8.31 (1H, s, ArH), 7.94 (2H, d, ArH), 7.66 (2H, m, ArH), 7.26 (3H, m, ArH), 3.75 (3H, s, CH$_3$), 2.26 (3H, s, CH$_3$), 2.02 (1H, br, CH), 0.82 (4H, m, 2 × CH$_2$) |
| 66 | ($^1$H, DMSO-d6) 11.11 (1H, br, NH), 9.13 (1H, s, ArH), 8.73 (1H, d, ArH), 8.44 (1H, b, ArH), 8.20 (2H, d, ArH), 8.01 (2H, d, ArH), 7.75 (3H, m, ArH), 7.41 (1H, dd, ArH), 2.03 (1H, br, CH), 0.82 (4H, m, 2 × CH$_2$) |
| 67 | (1H, DMSO-d6) 11.07 (1H, s, NH), 8.20 (2H, s, ArH), 8.06 (2H, d, ArH), 7.80 (2H, d, ArH), 7.75-7.66 (2H, m, ArH), 7.35 (1H, dd, ArH), 2.02 (1H, br, CH), 0.84 (4H, m, 2 × CH$_2$) |
| 68 | ($^1$H, DMSO-d6) 11.16 (1H, s, NH), 9.46 (1H, s, ArH), 9.38 (1H, s, ArH), 8.77 (2H, m, ArH), 8.67 (1H, dd, ArH), 7.77 (3H, m, ArH), 7.54 (1H, m, ArH), 2.01 (1H, m, CH), 0.84 (4H, m, 2 × CH$_2$) |
| 69 | ($^1$H, DMSO-d6) 8.06 (2H, d, ArH), 7.93 (2H, d, ArH), 7.74-7.66 (2H, m, ArH), 7.32 (1H, d, ArH), 6.92 (1H, s, ArH), 4.04 (3H, s, CH$_3$), 2.55 (2H, t, CH$_2$), 2.02 (1H, br, CH), 1.65 (2H, m, CH$_2$), 0.95 (3H, t, CH$_3$), 0.82 (4H, m, 2 × CH$_2$) |
| 70 | ($^1$H, DMSO-d6), 9.99 (1H, s, NH), 8.00 (2H, d, ArH), 7.78 (2H, d, ArH), 7.70-7.63 (2H, m, d, ArH), 2.25-1.80 (8H, m, 2 × CH, 3 × CH$_2$), 0.82 (4H, m, 2 × CH$_2$) |
| 71 | ($^1$H, DMSO-d6) 11.07 (1H, br, NH), 9.95 (1H, br, NH), 8.14 (2H, d, ArH), 7.75 (2H, m, ArH), 7.65 (2H, d, ArH), 7.36 (1H, dd, ArH), 4.5 (1H, b, CH), 3.80 (1H, b, CH), 3.5 (2H, under water peak, 2 × CH), 3.08 (4H, br, 2 × CH$_2$), 2.84 (3H, s, CH$_3$), 2.02 (1H, br, CH), 0.83 (4H, m, 2 × CH$_2$). |
| 72 | ($^1$H, DMSO-d6) 10.95 (1H, br, NH), 7.85 (2H, d, ArH), 7.61 (1H, dd, ArH), 7.51 (1H, d, ArH), 7.40 (4H, m, ArH), 7.36 (1H, m, ArH), 7.24 (1H, d, ArH), 7.09 (4H, m, ArH), 6.88 (1H, m, ArH), 6.70 (2H, d, ArH), 4.37 (2H, d, CH$_2$), 2.02 (1H, br, CH), 0.81 (4H, m, 2 × CH$_2$) |
| 73 | ($^1$H, DMSO-d6) 11.05 (1H, s, NH), 8.09 (4H, m, ArH), 8.02 (2H, d, ArH), 7.3-7.56 (7H, m, ArH), 7.36 (1H, m, ArH), 4.54 (1H, b, CH), 3.80 (2H, m, CH$_2$), 3.06 (1H, br, CH), 2.02-1.80 (4H, br, 2 × CH, CH$_2$), 1.58 (2H, m, CH$_2$), 0.81 (4H, m, 2 × CH$_2$) |
| 74 | ($^1$H, DMSO-d6) 11.05 (1H, br, NH), 8.08 (2H, m, ArH), 7.72 (2H, m, ArH), 7.58 (2H, m, ArH), 7.30 (6H, m, ArH), 3.67 (4H, b, 2 × CH$_2$), 3.45 (2H, br, CH$_2$), 2.65 (3H, br, CH, CH$_2$), 2.04 (1H, b, r CH), 1.89 (1H, b, CH), 1.77 (1H, br, CH), 0.82 (4H, m, 2 × CH$_2$) |
| 75 | ($^1$H, DMSO-d6) 11.04 (1H, br, NH), 10.27 (1H, s, NH), 8.03 (2H, d, ArH), 7.68 (2H, m, ArH), 7.39 (2H, d, ArH), 7.26 (6H, m, ArH), 3.49 (2H, m, CH$_2$), 3.04 (2H, m, CH$_2$), 2.02 (1H, br, CH), 0.82 (4H, m, 2 × CH$_2$) |
| 76 | ($^1$H, DMSO-d6) 11.05 (1H, br, NH), 10.21 (1H, br, NH), 8.04 (2H, d, ArH), 7.68 (2H, m, ArH), 7.35 (8H, m, ArH), 4.59 (2H, s, CH$_2$), 2.02 (1H, br, CH), 0.83 (4H, m, 2 × CH$_2$) |
| 77 | ($^1$H, DMSO-d6) 11.03 (1H, br, NH), 8.92 (1H, s, ArH), 8.20 (1H, d, ArH), 8.04 (2H, d, ArH), 7.98 (1H, d, ArH), 7.68 (2H, m, ArH), 7.26 (1H, d, ArH), 7.24 (2H, d, ArH), 5.42 (2H, s, CH$_2$), 2.03 (1H, br, CH), 0.82 (4H, m, 2 × CH$_2$) |
| 78 | ($^1$H, DMSO-d6) 11.05 (1H, s, NH), 8.09 (2H, d, ArH), 8.02 (2H, d, ArH), 7.3-7.56 (7H, m, ArH), 7.36 (1H, m, ArH), 4.54 (1H, b, CH), 3.80 (2H, m, CH$_2$), 3.06 (1H, br, CH), 2.02-1.80 (4H, br, 2 × CH, CH$_2$), 1.58 (2H, m, CH$_2$), 0.81 (4H, m, 2 × CH$_2$) |
| 79 | ($^1$H, DMSO-d6) 10.99 (1H, s, NH), 7.92 (2H, d, ArH), 7.86 (2H, d, ArH), 7.69-7.55 (5H, m, ArH), 7.22 (3H, m, ArH), 2.01 (1H, br, CH), 0.80 (4H, m, 2 × CH$_2$) |
| 80 | ($^1$H, DMSO-d6) 11.06 (1H, br, NH), 8.60 (1H, t, NH), 8.12 (2H, d, ArH), 8.12 (2H, d, ArH), 7.74 (2H, m, ArH), 7.37 (1H, dd, ArH), 3.43 (6H, under water peak, 3 × CH$_3$), 2.60 (2H, t, CH$_2$), 2.02 (1H, br, CH), 1.69 (4H, m, 2 × CH$_2$), 0.82 (4H, m, 2 × CH$_2$) |
| 81 | ($^1$H, DMSO-d6) 11.06 (1H, br, NH), 8.66 (1H, m, ArH), 8.12 (2H, d, ArH), 7.88 (2H, d, ArH), 7.73 (2H, m, ArH), 7.49 (AH, m, ArH), 6.57 (1H, b, NH), 3.57 (4H, m, 2 × CH$_2$), 3.20 (2H, under water peak, CH$_2$), 2.35 (6H, m, 3 × CH$_2$), 2.02 (1H, br, CH), 1.73 (2H, m, CH$_2$), 0.82 (4H, m, 2 × CH$_2$). |
| 82 | ($^1$H, DMSO-d6) 11.07 (1H, s, NH), 8.87 (1H, s, ArH), 8.27 (1H, dd, ArH), 7.68 (1H, dd, ArH), 7.60 (1H, d, ArH), 7.33-7.00 (7H, m, ArH), 4.46 (2H, d, CH$_2$), 2.29 (2H, m, CH$_2$), 2.63 (2H, m, CH$_2$), 2.02 (1H, br, CH), 1.82 (2H, d, CH$_2$), 1.55 (3H, m CH$_2$, CH), 1.18 (2H, m, CH$_2$), 0.84 (4H, m, 2 × CH$_2$). |
| 83 | ($^1$H, DMSO-d6), 11.06 (1H, br, NH), 8.89 (1H, s, ArH), 8.28 (1H, d, ArH), 7.69 (1H, dd, ArH), 7.60 (1H, dd, ArH), 7.35 (5H, m, ArH), 7.05 (1H, d, ArH), 4.62 (2H, d, CH$_2$), 3.02 (2H, t, CH$_2$), 2.89 (1H, m, CH), 2.02 (1H, m, CH), 1.88 (2H, d, CH$_2$), 1.62 (2H, m, CH$_2$), 0.84 (4H, m, 2 × CH$_2$) |
| 84 | ($^1$H, DMSO-d6) 11.05 (1H, s, NH), 8.87 (1H, s, ArH), 8.27 (1H, dd, ArH), 7.68 (1H, m, ArH), 7.60 (1H, dd, ArH), 7.34 (5H, m, ArH), 7.26 (1H, m, ArH), 7.60 (1H, d, ArH), 4.52 (2H, t, CH$_2$), 3.04 (2H, m, CH$_2$), 2;75 (1H, m, CH), 2.01 (2H, m, 2 × CH), 1.82 (2H, d, CH$_2$), 1.63 (1H, m, CH), 0.82 (4H, m, 2 × CH$_2$) |
| 85 | ($^1$H, DMSO-d6) 11.00 (1H, br, NH), 10.69 (1H, br, NH), 7.93 (2H, d, ArH), 7.79 (2H, d, ArH), 7.65 (2H, m, ArH), 7.41 (2H, d, ArH), 7.23 (3H, m, ArH), 2.60 (2H, t, CH$_2$), 2.01 (1H, br, CH), 1.58 (2H, m, CH$_2$), 0.84 (7H, m, 2 × CH$_2$, CH$_3$) |
| 87 | ($^1$H, DMSO-d6) 11.08 (1H, br, NH), 8.12 (1H, t, NH), 7.99 (2H, d, ArH), 7.74 (2H, d, ArH), 7.74 (2H, m, ArH), 7.40-7.22 (6H, m, ArH), 3.53 (2H, m, CH$_2$), 2.88 (2H, t, CH$_2$), 2.01 (1H, br, CH), 0.82 (4H, m, 2 × CH$_2$). |
| 88 | ($^1$H, DMSO-d6) 11.03 (1H, br, NH), 10.27 (1H, s, NH), 8.02 (2H, d, ArH), 7.68 (2H, m, ArH), 7.39-6.97 (7H, m, ArH), 3.54 (2H, m, CH$_2$), 3.07 (2H, m, CH$_2$), 2.01 (1H, m, CH), 0.81 (4H, m, 2 × CH$_2$). |
| 89 | ($^1$H, DMSO-d6), 7.78 (3H, m, ArH), 7.47 (1H, d, ArH), 7.39 (1H, d, ArH), 7.29 (1H, d, ArH), 3.62 (2H, br, CH$_2$), 2.01 (1H, br, CH), 1.64 (6H, 3 × CH$_2$), 0.79 (4H, m, 2 × CH$_2$) |
| 91 | ($^1$H, DMSO-d6) 11.04 (1H, br, NH), 8.19 (2H, d, ArH), 8.04 (2H, d, ArH), 7.98 (1H, s, ArH), 7.90 (2H, d, ArH), 7.66 (2H, m, ArH), 7.27 (3H, m, ArH), 5.39 (2H, s, CH$_2$), 2.02 (1H, br, CH), 0.83 (4H, m, 2 × CH$_2$) |
| 92 | ($^1$H, DMSO-d6) 11.03 (1H, br, NH), 10.01 (1H, br, NH), 8.00 (2H, d, ArH), 7.65 (4H, m, ArH), 7.41 (2H, d, ArH), 7.27 (1H, m, ArH), 7.17 (2H, d, ArH), 5.15 (2H, s, CH$_2$), 2.04 (4H, m, CH$_3$, CH), 0.82 (4H, m, 2 × CH$_2$). |
| 96 | ($^1$H, DMSO-d6) 11.08 (1H, br, NH), 8.07 (1H, d, ArH), 8.01 (1H, d, ArH), 7.73 (2H, m, ArH), 7.48 (1H, d, ArH), 7.37-7.10 (6H, m, ArH), 7.05 (1H, m, ArH), 3.72 (1H, m, CH), 3.46 (1H, m, CH), 3.06 (1H, m, CH), 2.89 (4H, m, CH, CH$_3$), 2.03 (1H, br, CH), 0.82 (4H, m, 2 × CH$_2$) |
| 97 | ($^1$H, DMSO-d6) 11.06 (1H, br, NH), 8.74 (1H, t, NH), 8.12 (2H, d, ArH), 7.98 (2H, d, ArH), 7.74 (2H, m, ArH), 7.67 (2H, d, ArH), 7.49 (2H, d, ArH), 7.37 (1H, dd, ArH), 3.59 (2H, m, CH$_2$), 2.99 (2H, t, CH$_2$), 2.02 (1H, br, CH), 0.82 (4H, m, 2 × CH$_2$) |
| 98 | ($^1$H, CDCl$_3$) 7.88 (2H, d, ArH), 7.62 (1H, m, ArH), 7.53 (1H, d, ArH), 7.49 (m, ArH), 7.12 (1H, d, ArH), 6.95 (2H, d, ArH), 6.21 (1H, m, ArH), 4.51 (2H, t, CH$_2$), 4.35 (2H, t, CH$_2$), 1.90 (1H, br, CH), 1.11 (2H, m, CH$_2$), 0.87 (2H, m, CH$_2$) |
| 99 | ($^1$H, CDCl$_3$) 8.73 (1H, s, ArH), 8.20 (1H, br, NH), 7.89 (2H, d, ArH), 7.51 (2H, m, ArH), 7.10 (2H, d, ArH), 6.98 (1H, m, ArH), 5.28 (2H, s, CH$_2$), 2.0 (1H, br, CH), 1.12 (2H, m, CH$_2$), 0.87 (2H, m, CH$_2$) |
| 100 | ($^1$H, DMSO-d6) 11.03 (1H, br, NH), 8.96 (1H, t, NH), 7.90-7.70 (5H, m, ArH), 7.30 (3H, m, ArH), 6.96 (2H, m, ArH), 4.15 (2H, t, CH$_2$), 3.69 (2H, m, CH$_2$), 2.0 (1H, br, CH), 0.80 (4H, m, 2 × CH$_2$) |

TABLE II-continued

NMR Data of Representative Compounds of the Invention

| Cpd # | (δ) NMR data |
|---|---|
| 102 | ($^1$H, DMSO-d6), 11.07 (1H, s, NH), 9.70 (1H, br, NH), 8.13 (2H, m, ArH), 8.02 (2H, m, ArH), 7.75 (2H, m, ArH), 7.36 (1H, m, ArH), 4-3.6 (6H, m, 3 × CH$_2$), 3.1 (2H, br, CH2), 2.01 (1H, br, CH), 1.50 (6H, br, 2 × CH$_3$), 0.81 (4H, m, 2 × CH$_2$) |
| 104 | ($^1$H, DMSO-d6) 11.06 (1H, b, NH), 8.82 (1H, s, ArH), 8.22 (1H, d, NH), 7.68 (1H, m, ArH), 7.60 (1H, d, ArH), 7.37-7.20 (7H, m, ArH), 6.79 (1H, d, ArH), 4.61 (2H, s, CH$_2$), 2;03 (1H, br, CH), 0.84 (4H, m, 2 × CH$_2$) |
| 105 | ($^1$H, DMSO-d6) 11.08 (1H, b, NH), 8.08 (1H, d, ArH), 8.00 (1H, d, ArH), 7.74 (2H, m, ArH), 7.49 (1H, d, ArH), 7.35 (1H, b, ArH), 7.25 (1H, d, ArH), 6.92 (1H, m, ArH), 6.82 (1H, d, ArH), 6.55 (1H, br, ArH), 3.6 (9H, under water peak, 3 × CH$_3$), 3.06 (2H, m, CH$_2$), 2.89 (2H, m, CH$_2$), 2.02 (1H, br, CH), 0.83 (4H, m, 2 × CH$_2$) |
| 106 | ($^1$H, DMSO-d6) 11.04 (1H, br, NH), 8.79 (1H, m, NH), 8.38 (1H, s, ArH), 8.12 (1H, d, ArH), 8.08 (2H, d, ArH), 7.79 (2H, d, ArH), 7.73 (2H, m, ArH), 7.65 (1H, s, ArH), 7.48 (2H, m, ArH), 7.37 (1H, m, ArH), 3.55 (2H, m, CH$_2$), 2.81 (2H, m, CH$_2$), 2.02 (1H, m, CH), 0.82 (4H, m, 2 × CH$_2$) |
| 107 | ($^1$H, DMSO-d6) 11.10 (1H, br, NH), 8.98 (1H, s, ArH), 8.56 (1H, s, ArH), 7.67 (1H, m, ArH), 7.59 (1H, d, ArH), 7.54 (1H, d, ArH), 7.39-7.27 (5H, m, ArH), 5.48 (2H, s, CH$_2$), 2.05 (1H, br, CH), 0.86 (4H, m, 2 × CH$_2$) |
| 108 | ($^1$H, DMSO-d6) 11.01 (1H, br, NH), 10.35 (1H, br, NH), 8.03 (2H, d, ArH), 7.79 (2H, d, ArH), 7.69 (2H, m, ArH), 7.29 (3H, m, ArH), 6.95 (3H, m, ArH), 4.29 (2H, t, CH$_2$), 2.86 (2H, t, CH$_2$), 2.02 (1H, br, CH), 0.82 (4H, m, 2 × CH$_2$) |
| 109 | ($^1$H, DMSO-d6) 11.02 (1H, br, NH), 10.18 (1H, s, NH), 8.00 (2H, d, ArH), 7.77 (2H, d, ArH), 7.68 (2H, m, ArH), 7.28 (5H, m, ArH), 7.19 (1H, m, ArH), 2.95 (2H, t, CH$_2$), 2.69 (2H, t, CH$_2$), 2.02 (1H, br, CH), 0.82 (4H, m, 2 × CH$_2$) |
| 112 | ($^1$H, DMSO-d6) 11.09 (1H, br, NH), 8.23 (1H, d, ArH), 7.75 (2H, m, ArH), 7.66 (1H, br, ArH), 7.47 (1H, d, ArH), 7.27-7.19 (5H, m, ArH), 4.38 (2H, d, CH$_2$), 2.89 (2H, t, CH$_2$), 2.63 (2H, m, CH$_2$), 2.02 (1H, m, CH), 1.80 (2H, d, CH$_2$), 1.55 (3H, m, CH$_3$), 1.21 (2H, m, CH$_2$), 0.83 (4H, m, 2 × CH$_2$) |
| 113 | ($^1$H, DMSO-d6) 11.05 (1H, br, NH), 8.11 (2H, d, ArH), 7.74 (2H, m, ArH), 7.63 (2H, m, ArH), 7.37 (1H, dd, ArH), 7.24 (1H, m, ArH), 6.99 (1H, m, ArH), 6.94 (1H, dd, ArH), 6.82 (1H, dd, ArH), 3.8-3.2 (8H, under water peak, 4 × CH$_2$), 2.02 (1H, br, CH), 0.82 (4H, m, 2 × CH$_2$) |
| 114 | ($^1$H, DMSO-d6) 11.03 (1H, br, NH), 8.63 (1H, m, ArH), 8.12 (2H, d, ArH), 8.02 (2H, m, ArH), 7.73 (2H, m, ArH), 7.38-7.18 (5H, m, ArH), 3.25 (2H, under water peak, CH$_2$), 2.66 (2H, t, CH$_2$), 2.03 (1H, br, CH), 1.87 (4H, m, CH$_2$), 0.82 (4H, m, 2 × CH$_2$) |
| 115 | ($^1$H, DMSO-d6) 10.98 (1H, b, NH), 8.02 (2H, d, ArH), 7.66 (2H, m, ArH), 7.26 (1H, m, ArH), 7.14 (4H, dd, ArH), 7.02 (2H, dd, ArH), 4.40 (2H, m, CH$_2$), 4.34 (2H, m, CH$_2$), 2.03 (1H, br, CH), 0.82 (4H, m, 2 × CH$_2$) |
| 116 | ($^1$H, DMSO-d6) 10.99 (1H, br, NH), 10.37 (1H, br, NH), 8.02 (2H, d, ArH), 7.68 (3H, m, ArH), 7.40 (3H, m, ArH), 7.26 (1H, m, ArH), 7.17 (2H, d, ArH), 6.93 (1H, m, ArH), 4.84 (2H, s, CH$_2$), 2.02 (1H, br, CH), 0.82 (4H, m, 2 × CH$_2$) |
| 117 | ($^1$H, CDCl$_3$) 9.60 (1H, br, NH), 7.95 (2H, d, ArH), 7.61 (2H, m, ArH), 7.10 (3H, m, ArH), 4.76 (2H, s, CH$_2$), 3.58 (4H, m, CH$_2$), 3.49 (4H, m, CH$_2$), 2.02 (1H, br, CH), 1.70-1.50 (6H, m, 3 × CH$_2$), 1.17 (2H, m, CH$_2$), 0.92 (2H, m, CH$_2$) |
| 119 | ($^1$H, DMSO-d6) 11.07 (1H, br, NH), 8.63 (1H, d, NH), 8.12 (2H, d, ArH), 8.02 (2H, d, ArH), 7.74 (2H, m, ArH), 7.34 (5H, m, ArH), 7.25 (1H, m, ArH), 4.41 (1H, m, CH), 3.61 (2H, s, CH$_2$), 2.84 (1H, m, CH), 2.65 (1H, m, CH), 2.50 (2H, under DMSO-d6 peak, CH$_2$), 2.19 (1H, m, CH), 2.02 (1H, br, CH), 1.84 (1H, m, CH), 0.83 (4H, m, 2 × CH$_2$) |
| 120 | ($^1$H, DMSO-d6) 11.04 (1H, br, NH), 8.68 (1H, br, NH), 8.12 (2H, d, ArH), 8.02 (2H, m, ArH), 7.77 (2H, m, ArH), 7.37 (6H, m, ArH), 4.46 (1H, m, CH), 3.74 (2H, br, CH$_2$), 3-2 (7H, m, 3 × CH$_2$, CH), 0.82 (4H, m, 2 × CH$_2$) |
| 121 | ($^1$H, DMSO-d6) 10.96 (1H, br, NH), 8.24 (1H, s, ArH), 7.70 (2H, m, ArH), 7.63 (3H, m, ArH), 7.26 (6H, m, ArH), 6.63 (1H, d, ArH), 5.51 (2H, s, CH$_2$), 2.02 (1H, br, CH), 0.81 (4H, m, 2 × CH$_2$) |
| 122 | ($^1$H, DMSO-d6) 11.01 (1H, br, NH), 8.05 (2H, d, ArH), 7.69 (2H, m, ArH), 7.40 (2H, d, ArH), 7.29 (3H, m, ArH), 6.92 (3H, m, ArH), 4.36 (3H, t, CH$_2$), 3.69 (2H, t, CH$_2$), 2.02 (1H, br, CH), 0.82 (4H, m, 2 × CH$_2$) |
| 123 | ($^1$H, DMSO-d6) 11.11 (1H, br, NH), 8.93 (1H, br, ArH), 8.31 (1H, d, ArH), 7.70 (2H, m, ArH), 7.32-6.91 (6H, m, ArH), 6.92 (1H, d, ArH), 3.64 (2H, t, CH$_2$), 2.93 (2H, t, CH$_2$), 2.04 (1H, br, CH), 0.84 (4H, m, 2 × CH$_2$) |
| 124 | ($^1$H, DMSO-d6) 11..06 (1H, br, NH), 8.77 (2H, m, ArH), 8.68 (1H, m, ArH), 8.23 (1H, d, NH), 8.10 (2H, d, ArH), 7.95 (2H, d, ArH), 7.78 (3H, m, ArH), 7.36 (1H, m, ArH), 3.64 (2H, m, CH$_2$), 3.06 (2H, m, CH$_2$), 2.04 (1H, br, CH), 0.83 (4H, m, 2 × CH$_2$). |
| 125 | (($^1$H, DMSO-d6) 10.99 (1H, s, NH), 8.50 (1H, s, ArH), 8.02 (2H, d, ArH), 7.88 (2H, d, ArH), 7.70 (4H, m, ArH), 7.26 (1H, d, ArH), 7.21 (2H, d, ArH), 6.55 (1H, s, ArH), 5.27 (2H, s, CH$_2$), 2.04 (1H, b, CH), 0.81 (4H, m, 2 × CH$_2$). |
| 127 | ($^1$H, DMSO-d6), 10.98 (1H, s, NH), 8.63 (1H, s, ArH), 8.51 (1H, m, ArH), 8.00 (2h, d, ArH), 7.91 (1H, d, ArH), 7.64 (2H, m, ArH), 7.46 (1H, m, ArH), 7.24 (1H, m, ArH), 7.13 (2H, m, ArH), 4.36 (2H, t, CH$_2$), 3.14 (2H, t, CH$_2$), 2.04 (1H, br, CH), 0.82 (4H, m, 2 × CH$_2$). |
| 129 | (1H, DMSO-d6) 11.06 (1H, br, NH), 7.98 (2H, d, ArH), 7.67 (1H, m, ArH), 7.59 (1H, d, ArH), 7.25 (1H, m, ArH), 7.08 (2H, m, ArH), 3.67 (4H, m, 2 × CH$_2$), 3.25 (4H, m, 2 × CH$_2$), 2.02 (1H, br, CH), 0.82 (4H, m, 2 × CH$_2$) |
| 131 | ($^1$H, DMSO-d6), 11.08 (1H, b, NH), 8.08 (2H, d, ArH), 7.72 (2H, m, ArH), 7.61 (2H, d, ArH), 7.36 (1H, m, ArH), 7.19 (2H, m, ArH), 6.95 (2H, m, ArH), 4.65 (1H, b, CH), 3.79 (3H, s, CH$_3$), 3.75 (1H, br, CH), 3.20 (2H, br, CH$_2$), 3.90 (1H, br, CH), 2.03 (1H, br, CH), 1.80 (1H, br, CH), 1.65 (3H, br, CH, CH$_2$), 0.82 (4H, m, 2 × CH$_2$). |
| 132 | ($^1$H, DMSO-d6) 11.07 (1H, br, NH), 8.08 (2H, d, ArH), 7.73 (2H, m, ArH), 7.64 (2H, d, ArH), 7.57 (2H, d, ArH), 7.37 (3H, m, ArH), 4.48 (1H, br, CH), 3.53 (2H, b, CH$_2$), 3.20 (1H, br, CH), 1.97 (3H, CH, CH$_2$), 1.71 (1H, br, CH), 1.57 (1H, br, CH), 0.82 (4H, m, 2 × CH$_2$) |
| 133 | ($^1$H, DMSO-d6), 11.42 (1H, br, NH), 8.42 (2H, d, ArH), 8.08 (2H, m, ArH), 7.91 (2H, d, ArH), 7.70 (1H, m, ArH), 7.48 (2H, m, ArH), 7.25 (1H, d, ArH), 7.17 (1H, m, ArH), 4.91 (1H, br, CH), 4.22 (2H, b, CH2), 4.02 (1H, b, CH), 3.51 (1H, br, CH), 3.22 (1H, br, CH), 2.50 (3H, s, CH$_3$), 2.45-2.14 (4H, b, 2 × CH, CH$_2$), 1.68 (2H, br, CH$_2$), 1.17 (4H, m, 2 × CH$_2$) |
| 134 | ($^1$H, DMSO-d6), 11..09 (1H, br, NH), 8.09 (2H, d, ArH), 7.73 (2H, m, ArH), 7.54 (2H, d, ArH), 7.37 (1H, m, ArH), 4.48 (1H, br, CH), 3.51 (1H, br, CH), 3.35 (1H, under water peak, CH), 2.67 (1H, br, CH), 2.26 (1H, br, CH), 2.04 (1H, br, CH), 1.82 (1H, m, CH), 1.62 (2H, br, CH$_2$), 0.93-0.75 (10H, m, 2 × CH$_2$, 2 × CH$_3$) |
| 137 | ($^1$H, DMSO-d6) 11.08 (1H, br, NH), 8.08 (2H, d, ArH), 7.73 (2H, m, ArH), 7.59 (2H, d, ArH), 7.35 (1H, m, ArH), 5.00 (1h, m, CH), 4.88 (1H, m, CH), 3.8-3.2 (3H, br, 3 × CH), 2.1-1.8 (5H, br, CH, 2 × CH$_2$), 0.82 (4H, m, 2 × CH$_2$) |
| 138 | ($^1$H, DMSO-d6) 11.11 (1H, b, NH), 10.84 (1H, s, NH), 8.09 (2H, d, ArH), 7.73 (2H, m, ArH), 7.62 (3H, m, ArH), 7.32 (2H, m, ArH), 7.15 (1H, s, ArH), 7.06 (1H, m, ArH), 6.97 (1H, m, ArH).4.64 (1H, br, CH), 3.74 (1H, br, CH), 3.31 (1H, br, CH), 3.11 (1H, br, CH), 3.11 (1H, m, CH), 2.99 (1H, br, CH), 3.1 (3H, br, CH, CH$_2$), 1.68 (2H, m, CH$_2$), 0.82 (4H, m, 2 × CH$_2$) |
| 142 | ($^1$H, DMSO-d6), 11.06 (1H, br, NH), 8.15 (3H, ArH), 7.74 (4H, m, ArH), 7.65 (1H, m, ArH)7.35 (1H, m, ArH), 6.97 (1H, d, ArH), 6.77 (1H, m, ArH), 4.49 (2H, s, CH$_2$), 3.6-3.2 (8H, br, 2 × CH$_2$), 2.02 (1H, br, CH), 0.83 (4H, m, 2 × CH$_2$) |
| 144 | (1H, DMSO-d6), 11.10 (1H, s, NH), 8.06 (2H, d, ArH), 7.72 (2H, m, ArH), 7.52 (2H, d, ArH), 7.35 (1H, m, ArH), 4.1 (3H, b, 3 × CH), 3.0 (1H, br, CH), 2.01 (1H, br, CH), 1.7-1.3 (6H, br, 3 × CH$_2$), 1.21 (3H, d, CH$_3$), 0.82 (4H, m, 2 × CH$_2$) |
| 145 | ($^1$H, DMSO-d6), 11.11 (1H, br, NH), 8.07 (2H, d, ArH), 7.73 (2H, m, ArH), 7.55 (2H, d, ArH), 7.36 (1H, m, ArH), 4.34 (1H, b, CH), 3.52 (1H, br, CH), 3.04 (1H, b, CH), 2.77 (1H, m, CH), 2.02 (1H, br, CH), 1.82 (1H, br, CH), 1.61 (2H, br, CH$_2$), 1.45 (1H, br, CH), 1.19 (1H, m, CH), 1.0-0.75 (7H, CH$_3$, 2 × CH$_2$) |
| 146 | ($^1$H, DMSO-d6), 11.11 (1H, br, NH), 8.06 (2H, d, ArH), 7.72 (2H, m, ArH), 7.55 (2H, d, ArH), 7.35 (1H, m, ArH), 4.46 (1H, br, CH), 3.58 (1H, b, CH), 3.07 (1H, br, CH), 2.78 (1H, b, CH), 2.01 (1H, b, CH), |

TABLE II-continued

NMR Data of Representative Compounds of the Invention

| Cpd # | (δ) NMR data |
|---|---|
| | 1.61 (3H, br, CH$_2$, CH), 1.10 (2H, br, CH$_2$), 0.94 (3H, d, CH$_3$), 0.82 (4H, m, 2 × CH$_2$) |
| 147 | ($^1$H, DMSO-d6) 11.09 (1H, br, NH), 8.07 (2H, d, ArH), 7.73 (2H, m, ArH), 7.55 (2H, d, ArH), 7.35 (1H, dd, ArH), 7.25 (3H, m, arh), 7.19 (6H, m, ArH), 4.48 (1H, br, CH), 3.62 (1H, b, CH), 3.06 (1H, b, CH), 2.76 (1H, br, CH), 2.61 (2H, m, CH$_2$), 2.01 (1H, br, CH), 1.82 (1H, b, CH), 1.71 (1H, br, CH), 1.54 (3H, br, CH, CH$_2$), 1.16 (2H, br, CH$_2$), 0.82 (4H, m, 2 × CH$_2$) |
| 148 | ($^1$H, DMSO-d6), 11.11 (1H, br, NH), 8.08 (2H, d, ArH), 7.74 (2H, m, ArH), 7.59 (2H, d, ArH), 7.36 (1H, m, ArH), 4.60 (1H, br, CH), 3.71 (1H, br, CH), 3.16 (1H, b, CH), 2.87 (1H, br, CH), 2.67 (1H, b, CH), 1.81 (3H, br, CH, CH$_2$), 1.47 (2H, m, CH$_2$), 0.81 (4H, m, 2 × CH$_2$) |
| 149 | ($^1$H, DMSO-d6) 11.09 (1H, br, NH), 8.12 (3H, m, ArH), 7.71 (3H, m, ArH), 7.63 (2H, d, ArH), 7.31 (2H, m, ArH), 4.61 (1H, br, CH), 3.75 (1H, b, CH), 3.53 (1H, b, CH), 3.4 (1H, under water peak, CH) 3.09 (1H, br, CH), 2.16 (1H, br, CH), 2.03 (2H, br, 2 × CH), 1.88 (2H, CH$_2$), 0.82 (4H, m, 2 × CH$_2$) |
| 156 | ($^1$H, DMSO-d6) 11.01 (1H, s, NH), 8.81 (2H, d, ArH), 7.72 (2H, s, ArH), 7.54 (2H, d, ArH), 7.34 (1H, m, ArH), 7.32 (3H, m, ArH), 7.21 (2H, m, ArH), 4.44 (1, b, CH), 4.23 (1H, br, CH), 2.72 (2H, s, CH$_2$), 2.03 (1H, b, CH), 1.51 (3H, br, 3 × CH), 1.36 (1H, br, CH), 0.81 (4H, m, 2 × CH$_2$) |
| 157 | ($^1$H, DMSO-d6), 1095 (1H, br, NH), 7.95 (2H, d, ArH), 7.64 (1H, m, ArH), 7.53 (1H, d, ArH), 7.38 (1H, dd, ArH), 7.22 (3H, m, ArH), 6.84 (2h, d, ArH), 4.67 (2H, s, CH$_2$), 3.14 (3H, s, CH$_3$), 2.04 (2H, br, CH), 0.81 (4H, m, 2 × CH$_2$). |
| 158 | ($^1$H, DMSO-d6) 11.02 (1H, br, NH), 7.9 (2H, d, ArH), 7.68 (1H, dd, ArH), 7.62 (1H, d, ArH), 7.26 (1H, m, ArH), 7.23 (2H, d, ArH), 7.07 (1H, br, NH), 5.31 (2H, s, CH$_2$), 2.04 (1H, br, CH), 0.82 (4H, m, 2 × CH$_2$) |
| 160 | (1H, DMSO-d6) 10.99 (1H, br, NH), 7.99 (2H, d, ArH), 7.71 (2H, m, ArH), 7.48 (2H, d, ArH), 7.28 (1H, d, ArH), 5.98 (1H, s, ArH), 3.74 (3H, s, CH$_3$), 3.58 (1H, s, CH$_2$), 3.55 (2H, s, CH$_2$), 2.10 (6H, s, 2 × CH$_3$), 2.02 (1H, br, CH), 0.81 (4H, m, 2 × CH$_2$) |
| 161 | ($^1$H, DMSO-d6) 10.99 (1H, br, NH), 9.16 (3H, d, ArH), 8.00 (2H, d, ArH), 7.80 (1H, d, ArH), 7.69 (2H, m, ArH), 7.56 (4H, d, ArH), 7.30 (1H, d, ArH), 3.64 (4H, s, CH2), 2.18 (3H, s, CH3), 2.01 (1H, br, CH), 0.81 (4H, m, 2 × CH$_2$) |
| 163 | ($^1$H, DMSO-d6) 10.72 (1H, br, NH), 7.99 (2H, m, ArH), 7.65 (2H, b, ArH), 7.48 (4H, b, ArH), 7.18 (2H, m, ArH), 5.21 (2H, d, CH$_2$), 2.12 (3H, br, CH$_3$) |
| 164 | ($^1$H, DMSO-d6) 11.10 (1H, b, NH), 8.11 (2H, br, ArH), 7.75 (2H, br, ArH), 7.59 (2H, br, ArH), 7.37 (1H, m, ArH), 4.57 (1H, b, CH), 3.59 (1H, br, CH), 3.16 (1H, br, CH), 2.99 (1H, br, CH$_2$), 2.60 (1h, br, CH), 2.01 (2H, br, 2 × CH), 1.59 (3H, br, CH$_2$), 0.83 (4H, m, 2 × CH$_2$) |
| 165 | ($^1$H, DMSO-d6) 8.26 (1H, d, ArH), 8.01 (2H, d, ArH), 7.68 (2H, m, ArH), 7.62 (1H, d, ArH), 7.26 (1H, d, ArH), 7.17 (2H, d, ArH), 6.87 (1H, d, ArH), 5.10 (2H, s, CH$_2$), 3.69 (4H, t, 2 × CH$_2$), 3.46 (4H, t, 2 × CH$_2$), 2.07 (1H, br, CH), 0.81 (4H, m, 2 × CH$_2$) |
| 166 | ($^1$H, DMSO-d6) 8.64 (1H, d, ArH), 8.12 (1H, s, ArH), 8.03 (2H, d, ArH), 7.87 (1H, d, ArH), 7.73 (1H, d, ArH), 7.69 (1H, m, ArH), 7.63 (1H, q, ArH), 7.27 (1H, d, ArH), 7.22 (2H, d, ArH), 5.25 (2H, s, CH$_2$), 2.04 (1H, br, CH), 0.81 (4H, m, 2 × CH$_2$) |
| 167 | ($^1$H, DMSO-d6) 11.00 (1H, br, NH), 10.03 (1H, br, NH), 8.31 (1H, d, ArH), 8.03 (2H, d, ArH), 7.76 (1H, d, ArH), 7.69 (1H, m, ArH), 7.63 (1H, d, ArH), 7.26 (1H, m, ArH), 7.18 (2H, m, ArH), 7.00 (1H, d, ArH), 5.12 (2H, s, CH$_2$), 4.41 (1H, br, CH$_2$), 3.49 (2H, br, CH$_2$), 3.15 (4H, br, 2 × CH$_2$), 2.84 (3H, s, CH$_3$), 2.04 (1H, br, CH), 0.82 (4H, m, 2 × CH$_2$) |
| 168 | ($^1$H, DMSO-d6) 11.03 (1H, br, NH), 8.10 (2H, dd, ArH), 7.73 (2H, dd, ArH), 7.64 (2H, dd, ArH), 7.36 (1H, m, ArH), 3.74 (1H, br, CH), 2.08 (5H, br, 2 × CH$_2$, CH), 0.82 (4H, m, 2 × CH$_2$) |
| 169 | ($^1$H, DMSO-d6) 11.02 (1H, b, NH), 8.09 (2H, br, ArH), 7.71 (2H, br, ArH), 7.60 (2H, d, ArH), 7.25 (6H, br, ArH), 4.57 (1H, br, CH), 3.65 (1H, b, CH), 3.21 (1H, br, CH), 2.91 (1H, br, CH$_2$), 2.80 (1H, b, CH), 1.98 (2H, br, 2 × CH), 1.77 (3H, br, CH$_2$ and CH), 0.82 (4H, m, 2 × CH$_2$) |
| 170 | ($^1$H, DMSO-d6) 11.10 (1H, br, NH), 8.86 (1H, s, ArH), 8.82 (1H, d, ArH), 8.76 (1H, d, ArH), 8.39 (1H, d, ArH), 8.27 (1H, br, NH), 8.26 (1H, d, ArH), 7.91 (1H, dd, ArH), 7.70 (1H, q, ArH), 7.62 (1H, dd, ArH), 7.33 (1H, d, ArH), 6.90 (1H, d, ArH), 4.78 (2H, s, CH2), 2.02 (1H, br, CH), 0.83 (4H, m, 2 × CH$_2$). |
| 171 | ($^1$H, DMSO-d6) 11.04 (1H, br, NH), 8.83 (1H, s, ArH), 8.68 (1H, d, ArH), 8.52 (1H, br, NH), 8.32 (1H, d, ArH), 8.13 (1H, m, ArH), 7.70 (1H, m, ArH), 7.68 (1H, m, ArH), 7.64 (1H, m, ArH), 7.60 (1H, m, ArH), 7.36 (1H, d, ArH), 7.01 (1H, d, ArH), 4.85 (2H, s, CH2), 2.02 (1H, br, CH), 0.83 (4H, m, 2 × CH$_2$). |
| 172 | ($^1$H, DMSO-d6) 11.16 (1H, br, NH), 8.94 (1H, s, ArH), 8.85 (1H, s, ArH), 8.77 (1H, d, ArH), 8.49 (1H, br, NH), 8.43 (1H, m, ArH), 8.37 (1H, d, ArH), 7.94 (1H, dd, ArH), 7.73 (1H, dd, ArH), 7.67 (1H, d, ArH), 7.41 (1H, d, ArH), 6.99 (1H, d, ArH), 3.76 (2H, t, CH$_2$), 3.13 (2H, t, CH$_2$), 2.03 (1H, br, CH), 0.85 (4H, m, 2 × CH$_2$) |
| 173 | ($^1$H, DMSO-d6) 11.17 (1H, br, NH), 9.00 (1H, s, ArH), 8.45 (1H, d, ArH), 7.72 (2H, m, ArH), 7.46 (1H, d, ArH), 7.12 (1H, d, ArH), 6.06 (1H, s, ArH), 4.52 (2H, s, CH$_2$), 3.69 (3H, s, CH$_3$), 2.23 (3H, s, CH$_3$), 2.04 (1H, br, CH), 0.84 (4H, m, 2 × CH$_2$). |
| 174 | ($^1$H, DMSO-d6) 11.02 (1H, br, NH), 8.14 (1H, s, ArH), 8.03 (3H, m, ArH), 7.66 (2H, m, ArH), 7.27 (1H, d, ArH), 7.20 (2H, dd, ArH), 7.10 (1H, d, ArH), 5.17 (2H, s, CH$_2$), 3.53 (4H, t, 2 × CH$_2$), 2.02 (5H, t, 2 × CH$_2$, CH), 0.82 (4H, m, 2 × CH$_2$) |
| 175 | ($^1$H, DMSO-d6) 11.04 (1H, b, NH), 8.09 (2H, d, ArH), 7.72 (2H, dd, ArH), 7.53 (2H, br, ArH), 7.36 (1H, dd, ArH), 3.09 (1H, b, CH), 2.08 (1H, br, CH), 1.56 (2H, br, CH$_2$), 1.43 (2H, br, CH$_2$), 0.97 (4H, m, 2 × CH$_2$), 0.81 (6H, m, 2 × CH$_3$) |
| 176 | ($^1$H, DMSO-d6) 11.01 (1H, br, NH), 8.89 (1H, s, ArH), 8.16 (1H, d, ArH), 8.09 (1H, d, ArH), 8.04 (2H, d, ArH), 7.67 (2H, m, ArH), 7.27 (1H, d, ArH), 7.23 (2H, d, ArH), 5.41 (2H, s, CH$_2$), 2.04 (1H, br, CH), 0.81 (4H, m, 2 × CH$_2$). |
| 177 | ($^1$H, DMSO-d6) 11.00 (1H, br, NH), 10.24 (1H, b, NH), 8.02 (2H, d, ArH), 7.76 (2H, d, ArH), 7.68 (2H, m, ArH), 7.30 (1H, dd, ArH), 2.03 (1H, br, CH), 1.71 (4H, m, 2 × CH$_2$), 0.82 (4H, m, 2 × CH$_2$) |
| 178 | ($^1$H, DMSO-d6) 11.00 (1H, b, NH), 8.63 (1H, d, ArH), 8.29 (1H, s, ArH), 8.02 (3H, m, ArH), 7.88 (1H, d, ArH), 7.69 (2H, m, ArH), 7.63 (1H, d, ArH), 7.27 (1H, d, ArH), 7.22 (2H, m, ArH), 5.24 (2H, s, CH$_2$), 3.89 (3H, s, CH$_3$), 2.03 (1H, br, CH), 0.81 (4H, m, 2 × CH$_2$). |
| 179 | ($^1$H, DMSO-d6) 10.99 (1H, b, NH), 8.49 (1H, d, ArH), 8.30 (1H, d, ArH), 8.07 (1H, d, ArH), 7.93 (1H, dd, ArH), 7.69 (2H, m, ArH), 7.39 (5H, m, ArH), 7.21 (1H, m, ArH), 6.84 (1H, d, ArH), 3.45 (2H, t, CH$_2$), 3.06 (2H, t, CH$_2$), 2.05 (1H, br, CH), 0.81 (4H, m, 2 × CH$_2$) |
| 180 | ($^1$H, DMSO-d6) 11.03 (1H, br, NH), 8.82 (1H, d, ArH), 8.36 (1H, dd, ArH), 7.96 (2H, m, ArH), 7.66 (5H, m, ArH), 7.34 (1H, dd, ArH), 7.26 (1H, m, ArH), 2.01 (1H, br, CH), 0.81 (4H, m, 2 × CH$_2$) |
| 181 | ($^1$H, DMSO-d6) 11.01 (1H, b, NH), 8.06 (2H, b, ArH), 7.73 (2H, br, ArH), 7.36 (3H, m, ArH), 7.25 (3H, m, ArH), 7.10 (2H, b, ArH), 4.63 (2H, b, CH$_2$), 3.59 (2H, br, CH$_2$), 2.92 (2H, t, CH$_2$), 2.03 (1H, br, CH), 0.81 (4H, m, 2 × CH$_2$) |
| 182 | ($^1$H, DMSO-d6) 10.94 (1H, b, NH), 8.62 (1H, s, ArH), 8.46 (1H, d, ArH), 7.86 (2H, d, ArH), 7.78 (1H, d, ArH), 7.62 (1H, dd, ArH), 7.51 (1H, d, ArH), 7.37 (1H, m, ArH), 6.89 (1H, m, NH), 6.73 (2H, d, ArH), 6.57 (1H, s, ArH), 4.42 (2H, d, CH$_2$), 2.05 (1H, br, CH), 0.81 (4H, m, 2 × CH$_2$). |
| 183 | ($^1$H, DMSO-d6) 10.99 (1H, b, NH), 8.93 (1H, s, ArH), 8.28 (1H, d, ArH), 8.20 (1H, d, ArH), 8.05 (2H, d, ArH), 7.65 (2H, m, ArH), 7.27 (1H, d, ArH), 7.25 (2H, d, ArH), 5.41 (2H, s, CH$_2$), 2.03 (1H, br, CH), 0.81 (4H, m, 2 × CH$_2$). |
| 184 | ($^1$H, DMSO-d6) 11.07 (1H, br, NH), 10.83 (1H, br, NH), 9.04 (1H, b, ArH), 8.41 (1H, br, ArH), 7.72 (2H, m, ArH), 7.42 (6H, m, ArH), 7.05 (1H, br, ArH), 4.90 (2H, br, CH$_2$), 2.04 (1H, br, CH), 0.83 (4H, m, 2 × CH$_2$). |
| 185 | ($^1$H, DMSO-d6) 11.08 (1H, br, NH), 9.01 (1H, s, ArH), 8.60 (3H, m, ArH), 7.83 (1H, d, ArH), 7.67 (1H, m, ArH), 7.55 (3H, m, ArH), 5.58 (2H, s, CH$_2$), 2.07 (1H, br, CH), 0.86 (4H, m, 2 × CH$_2$) |
| 186 | ($^1$H, DMSO-d6) 11.19 (1H, br, NH), 9.59 (1H, s, ArH), 9.86 (1H, s, ArH), 7.73 (3H, m, ArH), 7.30 (4H, m, ArH), 7.20 (1H, m, ArH), 3.52 (2H, t, CH$_2$), 3.06 (2H, t, CH$_2$), 2.09 (1H, br, CH), 0.87 (4H, m, 2 × CH$_2$). |
| 187 | ($^1$H, DMSO-d6) 11.14 (1H, s, NH), 9.12 (1H, s, ArH), 7.97 (1H, d, ArH), 7.79 (1H, m, ArH), 7.71 (1H, m, ArH), 7.36 (5H, m, ArH), 5.84 (2H, s, CH$_2$), 2.07 (1H, br, CH), 0.86 (4H, m, 2 × CH$_2$). |
| 189 | (1H, DMSO-d6) 11.05 (1H, br, NH), 8.60 (1H, d, ArH), 7.93 (2H, d, ArH), 7.86 (1H, m, ArH), 7.69 (1H, dd, ArH), 7.63 (1H, d, ArH), 7.52 (1H, d, ArH), 7.37 (1H, m, ArH), 7.24 (1H, m, ArH), 7.08 (2H, m, ArH), 5.63 (1H, q, CH), 2.02 (1H, br, CH), 1.64 (3H, d, CH$_3$), 0.82 (4H, m, 2 × CH$_2$) |

TABLE II-continued

NMR Data of Representative Compounds of the Invention

| Cpd # | (δ) NMR data |
|---|---|
| 190 | ($^1$H, DMSO-d6) 11.04 (1H, br, NH), 9.11 (1H, s, ArH), 8.38 (1H, d, ArH), 8.02 (2H, d, ArH), 7.69 (3H, m, ArH), 7.22 (3H, m, ArH), 5.41 (2H, s, ArH), 3.90 (3H, s, ArH), 2.04 (1H, br, CH), 0.81 (4H, m, 2 × $CH_2$). |
| 191 | ($^1$H, DMSO-d6) 11.06 (1H, br, NH), 8.95 (1H, d, ArH), 8.39 (1H, dd, ArH), 7.70 (2H, m, ArH), 7.38 (1H, dd, ArH), 7.19 (1H, dd, ArH), 3.11 (1H, br, CH), 2.03 (1H, br, CH), 1.08 (4H, m, 2 × $CH_2$), 0.82 (4H, m, 2 × $CH_2$). |
| 192 | ($^1$H, DMSO-d6) 11.07 (1H, b, NH), 8.76 (1H, s, ArH), 8.16 (1H, br, ArH), 8.09 (2H, s, ArH), 8.03 (2H, d, ArH), 7.68 (3H, m, ArH), 7.28 (1H, d, ArH), 7.23 (2H, d, ArH), 5.38 (2H, s, $CH_2$), 2.02 (1H, br, CH), 0.81 (4H, m, 2 × $CH_2$). |
| 193 | ($^1$H, DMSO-d6) 9.18 (1H, s, ArH), 8.53 (1H, m, ArH), 7.99 (1H, d, ArH), 7.82 (2H, m, ArH), 7.71 (1H, d, ArH), 7.42 (1H, d, ArH), 7.37 (1H, d, ArH), 5.95 (2H, s, $CH_2$), 2.06 (1H, br, CH), 0.86 (4H, m, 2 × $CH_2$). |
| 194 | ($^1$H, DMSO-d6) 11.12 (1H, br, NH), 8.51 (1H, d, ArH), 8.41 (1H, s, ArH), 8.28 (2H, d, ArH), 7.95 (1H, d, ArH), 7.77 (3H, m, ArH), 7.42 (2H, m ArH), 4.90 (2H, s, $CH_2$), 2.02 (1H, br, CH), 0.82 (4H, m, $CH_2$) |
| 195 | ($^1$H, DMSO-d6) 11.15 (1H, br, NH), 8.43 (1H, d, ArH), 8.23 (2H, d, ArH), 7.86 (5H, m, ArH), 7.42 (3H, m, ArH), 4.93 (2H, s, $CH_2$), 2.01 (1H, br, CH), 0.83 (4H, m, 2 × $CH_2$) |
| 196 | ($^1$H, DMSO-d6) 10.99 (1H, b, NH), 8.37 (1H, b, ArH), 8.20 (1H, m, ArH), 8.03 (2H, d, ArH), 7.69 (1H, dd, ArH), 7.63 (1H, dd, ArH), 7.46 (2H, m, ArH), 7.26 (1H, dd, ArH), 7.20 (2H, dd, ArH), 5.25 (2H, s, $CH_2$), 2.04 (1H, b, CH), 0.82 (4H, m, $CH_2$). |
| 197 | ($^1$H, DMSO-d6) 10.99 (1H, b, NH), 8.57 (1H, d, ArH), 8.02 (2H, d, ArH), 7.79 (1H, dd, ArH), 7.69 (1H, dd, ArH), 7.63 (1H, dd, ArH), 7.29 (1H, d, ArH), 7.26 (1H, dd, ArH), 7.20 (2H, d, ArH), 5.22 (2H, s, $CH_2$), 2.50 (3H, s, $CH_3$), 2.03 (1H, b, CH), 0.81 (4H, m, $CH_2$). |
| 198 | ($^1$H, DMSO-d6) 10.99 (1H, b, NH), 8.56 (1H, m, ArH), 8.03 (2H, d, ArH), 7.99 (1H, dd, ArH), 7.69 (1H, dd, ArH), 7.63 (1H, dd, ArH), 7.58 (1H, d, ArH), 7.27 (1H, dd, ArH), 7.21 (1H, dd, ArH), 5.29 (2H, s, $CH_2$), 2.04 (1H, b, CH), 0.81 (4H, m, $CH_2$). |
| 199 | ($^1$H, DMSO-d6) 10.97 (1H, b, NH) 8.47 (1H, s, ArH) 8.01 (2H, d, 2 × ArH) 7.66 (2H, m, 2 × ArH) 7.23 (3H, m, 3 × ArH) 5.17 (2H, s, $CH_2$) 3.87 (1H, s, $CH_3$) 2.03 (1H, b, CH) 0.81 (4H, m, 2 × $CH_2$) |
| 200 | ($^1$H, DMSO-d6) 11.00 (1H, b, NH) 7.99 (2H, d, 2 × ArH) 7.70 (2H, m, 2 × ArH) 7.53 (2H, d, 2 × ArH) 7.30 (1H, dd, ArH) 3.78 (2H, s, $CH_2$) 3.14 (4H, b, 4 × CH) 2.93 (4H, b, 4 × CH) 2.03 (1H, b, CH) 0.82 (4H, m, 2 × $CH_2$) |
| 201 | ($^1$H, DMSO-d6) 10.97 (1H, b, NH), 8.38 (1H, b, ArNH), 8.01 (2H, d, ArH), 7.68 (1H, dd, ArH), 7.62 (1H, dd, ArH), 7.25 (1H, dd, ArH), 7.09 (2H, d, ArH), 4.15 (2H, t, $CH_2$), 2.81 (2H, t, $CH_2$), 2.36 (3H, s, $CH_3$), 2.23 (3H, s, $CH_3$), 2.04 (1H, b, CH), 0.81 (4H, m, $CH_2$). |
| 202 | ($^1$H, DMSO-d6) 11.02 (1H, b, NH), 8.44 (2H, m, ArH), 8.08 (2H, d, ArH), 7.70 (3H, m, ArH), 7.47 (2H, d, ArH), 7.34 (2H, m, ArH), 5.0 (2H, s, $CH_2$), 2.04 (1H, b, CH), 1.97 (3H, b, $CH_3$), 0.81 (4H, m, $CH_2$). |
| 203 | ($^1$H, DMSO-d6) 11.04 (1H, b, NH), 10.44 (1H, b, NH), 8.56 (1H, d, ArH), 8.20 (2H, d, ArH), 8.12 (2H, d, ArH), 8.09 (1H, dd, ArH), 7.76 (1H, d, ArH), 7.75 (1H, s, ArH), 7.41 (1H, dd, ArH), 6.87 (1H, dd, ArH), 3.86 (3H, s, $CH_3$), 2.04 (1H, b, CH), 0.82 (4H, m, $CH_2$). |
| 204 | ($^1$H, DMSO-d6) 11.04 (1H, b, NH), 10.31 (1H, b, NH), 8.53 (1H, d, ArH), 8.19 (2H, d, ArH), 8.12 (2H, d, ArH), 7.98 (1H, dd, ArH), 7.75 (1H, d, ArH), 7.74 (1H, s, ArH), 7.40 (1H, dd, ArH), 6.88 (1H, dd, ArH), 3.71 (4H, t, 2 × $CH_2$), 3.41 (4H, t, 2 × $CH_2$), 2.04 (1H, b, CH), 0.82 (4H, m, $CH_2$). |
| 205 | ($^1$H, DMSO-d6) 10.35 (1H, b, NH), 8.50 (1H, d, ArH), 8.18 (2H, d, ArH), 8.12 (2H, d, ArH), 7.94 (1H, dd, ArH), 7.75 (1H, d, ArH), 7.74 (1H, s, ArH), 7.40 (1H, dd, ArH), 6.88 (1H, dd, ArH), 3.45 (4H, t, 2 × $CH_2$), 2.41 (4H, t, 2 × $CH_2$), 2.22 (3H, s, $CH_3$), 2.05 (1H, b, CH), 0.82 (4H, m, $CH_2$). |
| 206 | ($^1$H, DMSO-d6) 11.05 (1H, b, NH), 10.61 (1H, b, NH), 8.97 (1H, d, ArH), 8.34 (1H, dd, ArH), 8.25 (1H, dd, ArH), 8.24 (2H, d, ArH), 8.14 (1H, dd, ArH), 7.76 (1H, d, ArH), 7.75 (1H, s, ArH), 7.42 (1H, ddd, ArH), 7.41 (1H, dd, ArH), 2.04 (1H, b, CH), 0.82 (4H, m, $CH_2$). |
| 207 | ($^1$H, DMSO-d6) 11.03 (1H, b, NH), 8.11 (2H, d, ArH), 7.73 (1H, d, ArH), 7.72 (1H, s, ArH), 7.68 (2H, d, ArH), 7.36 (1H, dd, ArH), 4.01 (2H, b, $CH_2$), 3.81 (2H, b, $CH_2$), 3.31 (4H, b under water peak, 2 × $CH_2$), 2.03 (1H, b, CH), 0.81 (4H, m, $CH_2$). |
| 208 | ($^1$H, DMSO-d6) 11.02 (1H, b, NH), 8.56 (1H, d, ArH), 8.06 (1H, d, ArH), 7.77 (1H, ddd, ArH), 7.70 (1H, d, ArH), 7.69 (1H, s, ArH), 7.57 (1H, d, ArH), 7.42 (1H, d, ArH), 7.31 (1H, dd, ArH), 7.26 (1H, d, ArH), 5.03 (2H, s, $CH_2$), 2.03 (1H, b, CH), 2.00 (3H, b, $CH_3$), 0.81 (4H, m, $CH_2$). |
| 209 | ($^1$H, DMSO-d6) 11.02 (1H, b, NH), 8.07 (2H, d, ArH), 7.73 (1H, d, ArH), 7.72 (1H, s, ArH), 7.55 (2H, d, ArH), 7.35 (1H, dd, ArH), 4.79 (1H, b, CH), 4.02 (1H, b, CH), 3.76 (1H, m, CH), 3.54 (1H, b, CH), 2.03 (1H, b, CH), 1.75 (2H, b, $CH_2$), 1.39 (2H, b, $CH_2$), 0.81 (4H, m, $CH_2$). |
| 210 | ($^1$H, DMSO-d6) 11.03 (1H, b, NH), 8.09 (2H, d, ArH), 7.73 (1H, d, ArH), 7.72 (1H, s, ArH), 7.59 (2H, d, ArH), 7.35 (1H, dd, ArH), 3.93 (2H, b, $CH_2$), 3.93 (3H, b under water peak, 3 × CH), 2.03 (1H, b, CH), 1.94 (2H, b, CH2), 1.77 (2H, b, $CH_2$), 0.81 (4H, m, $CH_2$). |
| 211 | ($^1$H, DMSO-d6) 10.29 (1H, b, NH), 8.99 (1H, m, ArH), 8.46 (2H, d, ArH), 8.14 (1H, dd, ArH), 8.11 (1H, dd, ArH), 8.03 (1H, dd, ArH), 7.88 (2H, d, ArH), 7.73 (1H, m, ArH), 7.71 (1H, m, ArH), 7.69 (1H, d, ArH), 7.63 (1H, ddd, ArH), 3.61 (4H, b, 2 × $CH_2$), 2.80 (1H, b, CH), 1.41 (2H, m, $CH_2$), 1.29 (2H, m, $CH_2$). |
| 212 | ($^1$H, DMSO-d6) 10.96 (1H, b, NH) 7.95 (2H, d, 2 × ArH) 7.67 (2H, m, 2 × ArH) 7.51 (2H, d, 2 × ArH) 7.25 (1H, dd, ArH) 7.19 (1H, dd, ArH) 7.95 (1H, d, ArH) 6.60 (1H, t, NH) 6.50 (1H, m, ArH) 4.40 (2H, d, $CH_2$) 2.01 (1H, b, CH) 0.80 (4H, m, 2 × $CH_2$) |
| 213 | ($^1$H, DMSO-d6) 10.98 (1H, b, NH) 7.95 (2H, d, 2 × ArH) 7.69 (2H, m, 2 × ArH) 7.50 (2H, d, 2 × ArH) 7.27 (1H, dd, ArH) 3.55 (4H, m, 4 × CH) 3.31 (2H, s, $CH_2$) 2.37 (2H, m, 2 × $CH_2$) 2.02 (1H, b, CH) 1.09 (6H, s, 2 × $CH_3$) 0.81 (4H, m, 2 × $CH_2$) |
| 214 | ($^1$H, DMSO-d6) 10.98 (1H, b, NH) 7.98 (2H, d, 2 × ArH) 7.69 (2H, m, 2 × ArH) 7.48 (2H, d, 2 × ArH) 7.29 (1H, dd, ArH) 3.60 (2H, m, 2 × CH) 3.53 (2H, s, $CH_2$) 2.72 (2H, d, 2 × CH) 2.03 (1H, b, CH) 1.70 (2H, m, 2 × CH) 1.04 (6H, d, 2 × $CH_3$) 0.81 (4H, m, 2 × $CH_2$) |
| 215 | ($^1$H, DMSO-d6) 10.34 (1H, b, NH), 8.62 (2H, d, ArH), 8.18 (1H, dd, ArH), 8.08 (1H, dd, ArH), 8.05 (2H, d, ArH), 7.88 (1H, m, ArH), 7.78 (1H, dd, ArH), 4.91 (1H, b, CH), 4.08 (3H, m, CH + $CH_2$), 2.98 (2H, b, $CH_2$), 2.75 (H, b, CH), 1.58 (3H, b, 2 × $CH_3$), 1.40 (2H, m, $CH_2$), 1.31 (2H, m, $CH_2$). |
| 216 | ($^1$H, DMSO-d6) 8.60 (2H, d, ArH), 8.17 (1H, dd, ArH), 8.07 (2H, d, ArH), 8.06 (1H, dd, ArH), 7.77 (1H, dd, ArH), 4.21 (2H, t, $CH_2$), 3.92 (2H, s, $CH_2$), 3.87 (2H, t, $CH_2$), 3.36 (1H, b, CH), 1.96 (6H, s, 2 × $CH_3$), 1.41 (2H, m, $CH_2$), 1.31 (2H, m, $CH_2$). |
| 217 | ($^1$H, DMSO-d6) 8.63 (3H, b, NH, ArH), 8.19 (3H, m, ArH), 8.09 (1H, dd, ArH), 7.78 (1H, dd, ArH), 5.26 (1H, d, CH), 5.02 (1H, d, CH), 4.41 (1H, dd, CH), 4.27 (1H, dd, CH), 4.12 (1H, m, CH), 3.87 (1H, d, $CH_2$), 2.76 (1H, b, CH), 2.36 (2H, m, $CH_2$), 1.40 (2H, m, $CH_2$), 1.31 (2H, m, $CH_2$). |
| 218 | ($^1$H, DMSO-d6) 10.35 (1H, b, NH), 10.08 (1H, b, NH), 8.70 (2H, d, ArH), 8.60 (2H, d, ArH), 8.45 (1H, dd, ArH), 8.19 (1H, dd, ArH), 8.09 (1H, dd, ArH), 8.05 (1H, m, ArH), 7.97 (1H, m, ArH), 7.82 (1H, dd, ArH), 4.17 (3H, s, $CH_3$), 4.12 (1H, s, CH), 2.73 (H, b, CH), 1.41 (2H, m, $CH_2$), 1.28 (4H, m, 2 × $CH_2$), 1.12 (2H, m, $CH_2$). |
| 219 | (1H, DMSO-d6) 8.64 (1H, b, NH), 8.61 (2H, d, ArH), 8.18 (1H, dd, ArH), 8.09 (1H, dd, ArH), 8.04 (2H, d, ArH), 7.78 (1H, dd, ArH), 5.03 (1H, b, CH), 3.98 (9H, b, 4 × $CH_2$ + CH), 3.48 (2H, m, $CH_2$), 2.77 (H, b, CH), 2.17 (4H, m, 2 × $CH_2$), 1.41 (2H, m, $CH_2$), 1.30 (2H, m, $CH_2$). |
| 220 | ($^1$H, DMSO-d6) 8.64 (2H, d, ArH), 8.18 (1H, dd, ArH), 8.08 (1H, d, ArH), 8.07 (2H, d, ArH), 7.80 (1H, dd, ArH), 4.07 (10H, b, CH and $CH_2$), 3.65 (1H, b, CH), 2.77 (1H, b, CH), 1.41 (2H, m, $CH_2$), 1.32 (2H, m, $CH_2$). |
| 221 | ($^1$H, DMSO-d6) 11.04 (1H, b, NH), 9.04 (1H, dd, ArH), 8.44 (1H, dd, ArH), 8.25 (2H, d, ArH), 8.19 (2H, d, ArH), 7.76 (1H, dd, ArH), 7.75 (2H, d, ArH), 7.41 (1H, dd, ArH), 2.77 (1H, b, CH), 0.82 (4H, m, 2 × $CH_2$). |
| 222 | ($^1$H, DMSO-d6) 10.99 (1H, b, NH) 8.38 (1H, s, NH) 7.98 (1H, dd, ArH) 7.96 (2H, d, 2 × ArH) 7.69 (2H, m, 2 × ArH) 7.46 (3H, m, 3 × ArH) 7.26 (1H, dd, ArH) 7.01 (1H, dd, ArH) 5.35 (2H, s, $CH_2$) 2.01 (1H, b, CH) 0.80 (4H, m, 2 × $CH_2$) |
| 223 | ($^1$H, DMSO-d6) 11.06 (1H, b, NH)) 8.54 (1H, s, ArH) 8.36 (1H, d, ArH) 8.30 (1H, s, ArH) 8.08 (2H, d, 2 × ArH) 7.74 (3H, m, 3 × ArH) 7.64 (3H, m, 3 × ArH) 7.30 (1H, m, NH) 6.79 (2H, s, $CH_2$) 2.01 (1H, b, CH) 0.81 (4H, m, 2 × $CH_2$) |

TABLE II-continued

NMR Data of Representative Compounds of the Invention

| Cpd # | (δ) NMR data |
|---|---|
| 224 | (¹H, DMSO-d6) 10.98 (1H, b, NH) 7.95 (2H, d, 2 × Ar) 7.68 (3H, m, 3 × ArH) 7.52 (2H, d, 2 × ArH) 7.27 (1H, dd, ArH) 7.02 (2H, d, 2 × ArH) 6.61 (2H, d, 2 × ArH) 6.47 (1H, m, ArH) 4.38 (2H, d, CH₂) 3.77 (2H, s, CH₂) 2.03 (1H, b, CH) 0.81 (4H, m, 2 × CH₂) |
| 225 | (¹H, DMSO-d6) 10.98 (1H, b, NH) 7.96 (2H, d, 2 × ArH) 7.68 (2H, m, 2 × ArH) 7.56 (2H, d, 2 × ArH) 7.27 (1H, dd, ArH) 7.19 (1H, d, ArH) 7.07 (1H, m, ArH) 6.60 (1H, m, ArH) 6.52 (1H, d, ArH) 6.11 (1H, t, NH) 4.48 (2H, d, CH₂) 3.93 (2H, s, CH₂) 2.02 (1H, b, CH) 0.80 (4H, m, 2 × CH₂) |
| 226 | (¹H, DMSO-d6) 10.98 (1H, b, NH) 7.95 (2H, d, 2 × ArH) 7.67 (2H, m, 2 × ArH) 7.26 (2H, d, 2 × ArH) 7.02 (1H, m, ArH) 6.88 (1H, m, ArH) 6.61 (1H, m, ArH) 6.52 (1H, m, ArH) 6.30 (1H, t, NH) 4.45 (2H, d, CH₂) 2.01 (1H, b, CH) 0.80 (4H, m, 2 × CH₂) |
| 227 | (¹H, DMSO-d6) 10.98 (1H, b, NH) 7.96 (1H, d, 2 × ArH) 7.69 (2H, m, 2 × ArH) 7.62 (2H, d, 2 × ArH) 7.52 (2H, d, 2 × ArH) 7.27 (1H, dd, ArH) 6.89 (1H, t, NH) 6.82 (2H, b, NH₂) 6.59 (2H, d, 2 × ArH) 4.43 (2H, d, CH₂) 2.01 (1H, b, CH) 0.81 (4H, m, 2 × CH₂) |
| 228 | (¹H, DMSO-d6) 10.99 (1H, b, NH) 7.96 (2H, d, 2 × ArH) 7.74 (1H, b, NH) 7.68 (2H, m, 2 × ArH) 7.53 (2H, d, 2 × ArH) 7.27 (1H, dd, ArH) 7.14 (1H, b, NH) 7.11 (2H, m, 2 × ArH) 7.02 (1H, d, ArH) 6.74 (1H, dd, ArH) 6.52 (1H, t, NH) 4.42 (2H, d, CH₂) 2.02 (1H, b, CH) 0.80 (4H, m, 2 × CH₂) |
| 229 | (¹H, DMSO-d6) 10.98 (1H, b, NH) 8.28 (2H, d, 2 × ArH) 7.93 (2H, d, 2 × ArH) 7.78 (1H, t, NH) 7.68 (2H, m, 2 × ArH) 7.47 (2H, d, 2 × ArH) 4.25 (1H, dd, ArH) 6.59 (1H, m, ArH) 7.58 (2H, d, CH₂) 2.02 (1H, b, CH) 0.80 (4H, m, 2 × CH₂) |
| 230 | (¹H, DMSO-d6) 10.99 (1H, b, NH) 7.95 (2H, d, 2 × ArH) 7.69 (2H, m, 2 × ArH) 7.52 (2H, d, 2 × ArH) 7.28 (1H, dd, ArH) 4.37 (1H, b, CH) 3.96 (1H, d, CH) 3.81 (2H, m, 2 × CH) 3.55 (1H, dd, CH) 3.49 (1H, b, CH) 3.78 (1H, dd, CH) 3.46 (1H, d, CH) 2.02 (1H, b, CH) 1.84 (1H, dd, CH) 1.62 (1H, d, CH) 0.81 (4H, m, 2 × CH₂) |
| 231 | (¹H, DMSO-d6) 10.99 (1H, b, NH) 7.98 (1H, d, 2 × ArH) 7.69 (2H, m, 2 × ArH) 7.51 (2H, d, 2 × ArH) 7.30 (6H, m, 6 × ArH) 4.53 (1H, dd, CH) 3.95 (1H, dd, CH) 3.71 (1H, m, CH) 3.62 (2H, m, 2 × CH) 2.89 (1H, d, CH) 2.76 (1H, d, CH) 2.23 (1H, m, CH) 2.05 (2H, m, 2 × CH) 0.81 (4H, m, 2 × CH₂) |
| 232 | (¹H, DMSO-d6) 10.99 (1H, b, NH) 7.97 (2H, d, 2 × ArH) 7.70 (2H, m, 2 × ArH) 7.47 (2H, d, 2 × ArH) 7.29 (1H, m, ArH) 3.57 (2H, s, CH₂) 2.89 (2H, b, 2 × CH) 2.57 (2H, m, 2 × CH) 2.33 (1H, b, CH) 2.02 (1H, b, CH) 1.87 (2H, b, 2 × CH) 1.73 (2H, b, 2 × CH) 0.81 (4H, m, 2 × CH₂) |
| 233 | (¹H, DMSO-d6) 10.99 (1H, b, NH) 7.97 (2H, d, 2 × ArH) 7.70 (2H, m, 2 × ArH) 7.48 (2H, d, 2 × ArH) 7.29 (1H, dd, ArH) 4.70 (1H, b d, CH) 3.57 (2H, s, CH₂) 2.57 (2H, b, 2 × CH) 2.35 (2H, b, 2 × CH) 2.03 (1H, b, CH) 1.88 (2H, b, 2 × CH) 1.74 (2H, b, 2 × CH) 0.81 (4H, m, 2 × CH₂) |
| 234 | (¹H, DMSO-d6) 10.99 (1H, b, NH) 7.98 (1H, d, 2 × ArH) 7.70 (2H, m, 2 × ArH) 7.50 (2H, d, 2 × ArH) 7.29 (1H, dd, ArH) 3.65 (2H, s, CH₂) 2.54 (4H, b, 4 × CH) 1.98 (5H, b, 5 × CH) 0.81 (4H, m, 2 × CH₂) |
| 235 | (¹H, DMSO-d6) 10.98 (1H, b, NH) 7.95 (2H, d, 2 × ArH) 7.67 (2H, m, 2 × ArH) 7.60 (1H, d, ArH) 7.53 (2H, d, 2 × ArH) 7.26 (1H, dd, 2 × ArH) 6.96 (1H, dd, ArH) 6.66 (1H, d, ArH) 5.90 (1H, t, NH) 4.33 (2H, d, CH₂) 3.21 (4H, b m, 2 × CH₂) 2.37 (4H, b m, 2 × CH₂) 2.18 (3H, s, CH₃) 2.02 (1H, b, CH) 0.81 (4H, m, 2 × CH₂) |
| 236 | (¹H, DMSO-d6) 10.98 (1H, b, NH) 7.96 (2H, d, 2 × ArH) 7.68 (2H, m, 2 × ArH) 7.54 (2H, d, ArH) 7.48 (1H, d, ArH) 7.27 (1H, dd, ArH) 7.09 (1H, dd, ArH) 6.59 (1H, d, ArH) 6.09 (1H, t, NH) 4.35 (2H, d, CH₂) 3.70 (3H, s, CH₃) 2.02 (1H, b, CH) 0.80 (4H, 2 × CH₂) |
| 237 | (¹H, DMSO-d6) 10.98 (1H, b, NH) 7.95 (2H, d, 2 × ArH) 7.68 (2H, m, 2 × ArH) 7.62 (1H, d, ArH) 7.53 (2H, d, 2 ArH) 7.26 (1H, dd, ArH) 6.99 (1H, dd, ArH) 6.67 (1H, d, ArH) 5.95 (1H, t, NH) 4.34 (2H, d, CH₂) 3.66 (4H, m, 2 × CH₂) 3.17 (4H, m, 2 × CH₂) 2.02 (1H, b, CH) 0.81 (4H, m, 2 × CH₂) |
| 238 | (¹H, DMSO-d6) 11.00 (1H, b, NH) 8.02 (1H, d, 2 × ArH) 7.70 (2H, m, 2 × ArH) 7.62 (2H, d, 2 × ArH) 7.31 (3H, m, 3 × ArH) 7.05 (2H, d, 2 × ArH) 9.56 (1H, m, ArH) 5.23 (2H, s, CH₂) 2.02 1H, b, CH) 0.81 (4H, m, 2 × CH₂) |
| 239 | (¹H, DMSO-d6) 11.04 (1H, b, NH) 9.23 (1H, dd, ArH) 8.48 (1H, dd, ArH) 8.22 (2H, d, 2 × ArH) 8.18 (1H, dd, ArH) 8.06 (2H, d, 2 × ArH) 7.75 (2H, m, 2 × ArH) 7.42 (1H, dd, ArH) 2.05 (1H, b, CH) 0.82 (4H, m, 2 × CH₂) |
| 240 | (¹H, DMSO-d6) 10.99 (1H, b, NH) 7.97 (2H, d, 2 × ArH) 7.70 (2H, m, 2 × ArH) 7.48 (2H, d, 2 × ArH) 7.29 (1H, dd, ArH) 3.58 (2H, s, CH₂) 2.93 (2H, m, 2 × CH) 2.28 (1H, m, CH) 2.02 (3H, m, 3 × CH) 1.80 (2H, m, 2 × CH) 1.49 (2H, m, 2 × CH) 0.82 (4H, m, 2 × CH₂) |
| 241 | (¹H, DMSO-d6) 10.99 (1H, b, NH) 7.97 (2H, d, 2 × ArH) 7.70 (2H, m, 2 × ArH) 7.47 (2H, d, 2 × ArH) 7.28 (1H, m, ArH) 3.56 (2H, s, CH₂) 3.15 (2H, m, CH₂) 2.65 (4H, m, 4 × CH) 2.44 (4H, b, 4 × CH) 2.02 (1H, b, CH) 0.81 (4H, m, 2 × CH₂) |
| 242 | (¹H, DMSO-d6) 10.99 (1H, b, NH) 7.96 (2H, d, 2 × ArH) 7.69 (2H, m, 2 × ArH) 7.46 (2H, d, 2 × ArH) 7.29 (1H, m, ArH) 4.53 (1H, s, OH) 3.53 (2H, s, CH₂) 3.47 (1H, m, CH) 2.70 (2H, m, 2 × CH) 2.09 (2H, m, 2 × CH) 2.03 (1H, b, CH) 1.72 (2H, m, 2 × CH) 1.38 (2H, m, 2 × CH) 0.80 (4H, m, 2 × CH₂) |
| 243 | (¹H, DMSO-d6) 10.99 (1H, b, NH) 7.96 (2H, d, 2 × ArH) 7.69 (2H, m, 2 × ArH) 7.47 (2H, d, 2 × ArH) 7.28 (1H, m, ArH) 4.02 (1H, s, OH) 3.52 (2H, s, CH₂) 2.91 (2H, b, 2 × CH) 2.02 (1H, b, CH) 1.90 (2H, b, 2 × CH) 1.66 (2H, b, 2 × CH) 1.25 (3H, b, 3 × CH) 1.03 (6H, s, 2 × CH₃) 0.81 (4H, m, 2 × CH₂) |
| 244 | (¹H, DMSO-d6) 11.03 (1H, b, NH) 7.94 (3H, m, 3 × ArH) 7.69 (2H, m, 2 × ArH) 7.49 (2H, d, 2 × ArH) 7.38 (1H, m, ArH) 7.26 (1H, m, ArH) 7.17 (1H, t, NH) 6.54 (1H, d, ArH) 6.48 (1H, m, ArH) 4.56 (2H, d, CH₂) 2.00 (1H, b, CH) 0.81 (4H, m, 2 × CH₂) |
| 245 | (¹H, DMSO-d6) 11.04 (1H, b, NH) 7.97 (2H, m, 2 × ArH) 7.69 (2H, m, 2 × ArH) 7.52 (2H, d, 2 × ArH) 7.28 (1H, m, ArH) 6.74 (1H, t, NH) 6.31 (2H, d, 2 × ArH) 4.34 (2H, d, CH₂) 2.00 (1H, b, CH) 0.80 (4H, m, 2 × CH₂) |
| 246 | (¹H, DMSO-d6) 11.04 (1H, b, NH) 7.94 (2H, d, 2 × ArH) 7.67 (2H, m, 2 × ArH) 7.47 (2H, d, 2 × ArH) 7.26 (1H, d, ArH) 6.89 (2H, m, 2 × ArH) 6.62 (1H, m, ArH) 6.06 (1H, b, NH) 4.49 (2H, d, CH₂) 2.00 (1H, b, CH) 0.80 (4H, m, 2 × CH₂) |
| 247 | (¹H, DMSO-d6) 11.05 (1H, b, NH) 7.96 (2H, d, 2 × ArH) 7.70 (2H, m, 2 × ArH) 7.46 (2H, d, 2 × ArH) 7.29 (1H, dd, ArH) 3.32 (2H, s, CH2) 2.87 (2H, b, d, 2 × CH) 2.47 (4H, q, under DMSO-d6 peak, 2 × CH₂) 1.97 (3H, m, 3 × CH) 1.61 (3H, b m, 3 × CH) 1.43 (2H, m, 2 × CH) 0.93 (6H, t, 2 × CH₃) 0.81 (4H, m, 2 × CH₂) |
| 248 | (¹H, DMSO-d6) 11.03 (1H, b, NH) 7.98 (2H, d, 2 × ArH) 7.69 (2H, m, 2 × ArH) 7.55 (2H, d, 2 × ArH) 7.26 (2H, m, 2 × ArH) 6.87 (3H, b m, 2 × ArH + NH) 4.52 (2H, d, CH₂) 1.99 (1H, b, CH) 0.80 (4H, 2 × CH₂) |
| 249 | (¹H, DMSO-d6) 11.05 (1H, b, NH) 7.95 (2H, d, 2 × ArH) 7.72 (1H, b, NH) 7.68 (2H, m, 2 × ArH) 7.52 (2H, d, 2 × ArH) 7.27 (1H, dd, ArH) 7.10 (1H, b, NH) 7.03 (2H, m, 2 × ArH) 6.96 (1H, s, ArH) 5.89 (1H, t, NH) 4.51 (2H, d, CH₂) 2.22 (3H, s, CH₃) 2.00 (1H, b, CH) 0.80 (4H, m, 2 × CH₂) |
| 251 | (¹H, DMSO-d6) 11.05 (1H, b, NH) 8.03 (2H, d, 2 × ArH) 7.99 (1H, s, NH) 7.69 (2H, m, 2 × ArH) 7.64 (2H, d, 2 × ArH) 7.56 (1H, m, ArH) 7.48 (1H, d, ArH) 7.38 (2H, m, NH + ArH) 7.30 (1H, dd, ArH) 7.21 (1H, ddd, ArH) 5.27 (2H, s, CH₂) 1.98 (1H, b, CH) 0.79 (4H, m, 2 × CH₂) |
| 252 | (¹H, CDCl₃) 9.86 (1H, b, NH) 7.92 (2H, d, 2 × ArH) 7.55 (2H, m, 2 × ArH) 7.46 (2H, d, 2 × ArH) 7.06 (1H, dd, ArH) 3.85 (1H, m, CH) 3.77 (2H, s, CH₂) 3.09 (5H, m, 5 × CH) 2.93 (2H, m, 2 × CH) 2.75 (1H, q, CH) 2.21 (2H, q, 2 × CH) 1.28 (6H, t, 2 × CH₃) 1.21 (1H, s, CH) 1.12 (2H, m, 2 × CH) 0.87 (2H, m, 2 × CH) |
| 253 | (¹H, DMSO-d6) 9.4 (1H, b, NH) 7.95 (2H, d, 2 × ArH) 7.57 (2H, m, 2 × ArH) 7.49 (2H, d, 2 × ArH) 7.08 (1H, dd, ArH) 4.10 (1H, s, CH) 3.91 (1H, d, CH) 3.78 (1H, d, CH) 3.55 (1H, s, CH) 3.38 (1H, b, CH) 3.22 (3H, m, 3 × CH) 3.02 (1H, m, CH) 2.81 (1H, dd, CH) 2.10 (2H, s, CH₂) 1.37 (3H, t, CH₃) 1.18 (3H, m, 3 × CH) 0.91 (2H, m, 2 × CH) |
| 254 | (¹H, DMSO-d6) 11.07 (1H, b, NH) 7.99 (2H, d, 2 × ArH) 7.70 (2H, m, 2 × ArH) 7.44 (2H, d, 2 × ArH) 7.29 (1H, dd, ArH) 4.64 (2H, s, CH₂) 4.15 (2H, s, CH₂) 3.86 (2H, dd, t, CH₂) 3.34 (2H, t, CH₂) 2.01 (1H, b, CH) 0.81 (4H, m, 2 × CH₂) |
| 255 | (¹H, DMSO-d6) 11.05 (1H, b, NH) 7.94 (2H, d, 2 × ArH) 7.69 (3H, m, 2 × ArH + NH) 7.50 (2H, d, 2 × ArH) 7.27 (1H, dd, ArH) 7.14 (1H, dd, ArH) 7.03 (1H, b, NH) 7.00 (1H, d, ArH) 6.85 (1H, d, ArH) 5.84 (1H, t, NH) 4.47 (2H, d, CH₂) 2.00 (1H, b, CH) 0.80 (4H, m, 2 × CH₂). |
| 256 | (¹H, DMSO-d6) 11.03 (1H, b, NH) 7.95 (2H, d, 2 × ArH) 7.69 (2H, m, 2 × ArH) 7.52 (2H, d, 2 × ArH) 6.88 (2H, m, 2 × ArH) 6.45 (1H, t, |

TABLE II-continued

NMR Data of Representative Compounds of the Invention

| Cpd # | (δ) NMR data |
|---|---|
| | NH) 4.43 (2H, d, CH₂) 2.21 (3H, s, CH₃) 2.00 (1H, b, CH) 0.80 (4H, m, 2 × CH₂) |
| 257 | (¹H, DMSO-d6) 11.03 (1H, b, NH) 7.92 (2H, d, 2 × ArH) 7.87 (1H, d, ArH) 7.66 (3H, m, 3 × ArH) 7.47 (2H, d, 2 × ArH) 7.40 (1H, t, NH) 7.25 (1H, dd, ArH) 4.62 (2H, d, CH₂) 1.99 (1H, b, CH) 0.80 (4H, m, 2 × CH₂) |
| 258 | (¹H, DMSO-d6) 11.03 (1H, b, NH) 7.96 (2H, d, 2 × ArH) 7.69 (2H, m, 2 × ArH) 7.57 (1H, dd, ArH) 7.51 (2H, d, 2 × ArH) 7.45 (1H, m, ArH) 7.37 (1H, dd, ArH) 7.27 (1H, dd, ArH) 6.70 (1H, t, NH) 4.53 (2H, d, CH₂) 1.99 (1H, b, CH) 0.80 (4H, m, 2 × CH₂) |
| 259 | (¹H, DMSO-d6) 11.03 (1H, b, NH) 7.94 (2H, d, 2 × ArH) 7.68 (2H, m, 2 × ArH) 7.52 (2H, d, 2 × ArH) 7.26 (1H, dd, ArH) 6.86 (1H, dd, ArH) 6.69 (1H, d, ArH) 6.50 (1H, m, ArH) 6.13 (1H, t, NH) 4.41 (2H, d, CH₂) 2.13 (3H, s, CH₃) 2.00 (1H, b, CH) 0.80 (4H, m, 2 × CH₂) |
| 260 | (¹H, DMSO-d6) 11.06 (1H, b, NH) 7.98 (2H, d, 2 × ArH) 7.70 (2H, m, 2 × ArH) 7.52 (2H, d, 2 × ArH) 7.30 (1H, dd, ArH) 3081 (2H, s, CH₂) 2.62 (4H, s, 2 × CH₂) 2.01 (1H, b, CH) 1.76 (4H, s, 2 × CH₂) 0.81 (4H, m, 2 × CH₂) |
| 261 | (¹H, DMSO-d6) 11.04 (1H, b, NH) 7.95 (2H, d, 2 × ArH) 7.68 (2H, m, 2 × ArH) 7.53 (2H, d, 2 × ArH) 7.27 (1H, dd, ArH) 7.05 (2H, m, 2 × ArH) 6.59 (2H, dd, 2 × ArH) 6.51 (1H, m, ArH) 6.39 (1H, t, NH) 4.36 (2H, d, CH₂) 2.00 (1H, b, CH) 0.80 (4H, m, 2 × CH₂) |
| 263 | (¹H, DMSO-d6) 11.05 (1H, b, NH) 7.97 (2H, d, 2 × ArH) 7.69 (2H, m, 2 × ArH) 7.48 (2H, d, 2 × ArH) 7.29 (1H, dd, ArH) 4.11 (2H, b, CH2) 2.88 (1H, m, CH) 2.70 (1H, m, CH) 2.59 (1H, m, CH) 2.52 (1H, m, CH) 2.38 (1H, m, CH) 2.18 (6H, s, 2 × CH₃) 2.01 (1H, b, CH) 1.90 (1H, m, CH) 1.68 (1H, m, CH) 0.81 (4H, m, 2 × CH₂) |
| 264 | (¹H, DMSO-d6) 11.05 (1H, b, NH) 7.98 (1H, d, 2 × ArH) 7.70 (2H, m, 2 × ArH) 7.49 (2H, d, 2 × ArH) 7.29 (1H, dd, ArH) 3.72 (2H, s, CH2) 2.91 (2H, t, CH₂) 2.74 (2H, t, CH₂) 2.27 (2H, m, CH₂) 2.01 (1H, b, CH) 0.81 (4H, m, 2 × CH₂) |
| 265 | (¹H, DMSO-d6) 11.05 (1H, b, NH) 7.94 (2H, d, 2 × ArH) 7.77 (2H, d, 2 × ArH) 7.69 (2H, m, 2 × ArH) 7.45 (2H, d, 2 × ArH) 7.27 (1H, dd, ArH) 7.13 (2H, d, ArH) 7.24 (2H, d, CH₂) 3.67 (2H, s, CH₂) 3.37 (2H, b, 2 × CH, under NH+ peak) 3.07 (2H, m, 2 × CH) 2.85 (1H, m, CH) 2.00 (1H, b, CH) 0.81 (4H, m, 2 × CH₂) |
| 266 | (¹H, DMSO-d6) 11.06 (1H, b, NH); 7.95 (2H, d, 2 × ArH) 7.69 (2H, m, 2 × ArH) 7.41 (2H, d, 2 × ArH) 7.29 (1H, dd, ArH) 3.80 (2H, s, CH₂) 3.48 (4H, m, 2 × CH₂) 2.01 (1H, b, CH) 1.56 (2H, m, CH₂) 1.43 (4H, m, 2 × CH₂) 0.81 (4H, m, 2 × CH₂) |
| 267 | (¹H, DMSO-d6) 11.06 (1H, b, NH) 7.94 (2H, d, ArH) 7.69 (2H, m, ArH), 7.29 (2H, d, ArH) 7.27 (1H, dd, ArH) 3.92 (6H, m, 3 × CH₂), 3.26 (2H, b, CH₂) 3.17 (2H, b, CH₂) 2.01 (1H, b, CH) 0.81 (4H, m, 2 × CH₂) |
| 278 | (¹H, DMSO-d6) 11.06 (1H, b, NH) 7.95 (2H, d, 2 × ArH) 7.76 (2H, d, 2 × ArH) 7.70 (2H, m, 2 × ArH) 7.47 (2H, d, 2 × ArH) 7.28 (1H, dd, ArH) 7.03 (2H, d, 2 × ArH) 4.96 (1H, m, CH) 3.80 (2H, t, 2 × CH) 3.74 (2H, s, CH₂) 3.13 (2H, t, 2 × CH) 2.02 (1H, b, CH) 0.81 (4H, m, 2 × CH₂) |
| 279 | (¹H, DMSO-d6) 11.05 (1H, b, NH) 7.94 (2H, d, 2 × ArH) 7.69 (2H, m, 2 × ArH) 7.43 (2H, d, 2 × ArH) 7.37 (1H, d, NH) 7.28 (1H, dd, ArH) 4.08 (1H, m, CH) 3.63 (2H, s, CH₂) 3.51 (2H, m, 2 × CH) 2.88 (2H, m, 2 × CH) 2.00 (1H, b, CH) 1.37 (9H, s, 3 × CH₃) 0.81 (4H, m, 2 × CH₂) |
| 280 | (¹H, DMSO-d6) 11.06 (1H, b, NH) 7.97 (2H, d, 2 × ArH) 7.70 (2H, m, 2 × ArH) 7.47 (2H, d, 2 × ArH) 7.29 (1H, dd, ArH) 4.72 (1H, m, Ch) 4.60 (1H, m, CH) 3.60 (2H, s, CH₂) 2.72 (1H, m, CH) 2.43 (1H, m, CH) 2.29 (1H, m, CH) 2.01 (1H, b, CH) 1.77 (1H, m, CH) 1.51 (1H, m, CH) 0.81 (4H, m, 2 × CH₂) |
| 281 | (¹H, DMSO-d6) 11.06 (1H, b, NH) 7.96 (2H, d, 2 × ArH) 7.68 (2H, m, 2 × ArH) 7.47 (2H, d, 2 × ArH) 7.29 (1H, dd, ArH) 3.54 (2H, s, CH₂) 3.22 (3H, s, CH₃) 2.67 (2H, m, 2 × CH) 2.14 (2H, m, 2 × CH) 2.01 (1H, b, CH) 1.84 (2H, m, 2 × CH) 1.44 (2H, m, 2 × CH) 0.81 (4H, m, 2 × CH₂) |
| 282 | (¹H, DMSO-d6) 11.06 (1H, b, NH) 7.96 (2H, d, 2 × ArH) 7.70 (2H, m, 2 × ArH) 7.47 (2H, d, 2 × ArH) 7.29 (1H, dd, ArH) 3.55 (2H, s, CH₂) 3.43 (2H, q, CH₂) 3.28 (1H, m, CH) 2.71 (2H, m, 2 × CH) 2.12 (2H, m, 2 × CH) 2.01 (1H, b, CH) 1.83 (2H, m, 2 × CH) 1.44 (2H, m, 2 × CH) 1.09 (3H, t, CH₃) 0.81 (4H, m, 2 × CH₂) |
| 283 | (¹H, DMSO-d6) 11.14 (1H, b, NH) 8.06 (2H, d, 2 × ArH) 7.72 (2H, m, 2 × ArH) 7.53 (2H, d, 2 × ArH) 7.31 (1H, dd, ArH) 4.83 (2H, q, CH2) 4.15 (1H, m, CH) 3.87 (1H, m, CH) 3.79 (1H, m, CH) 3.66 (1H, m, CH) 3.44 (1H, m, CH) 3.12 (3H, s, CH₃) 2.40 (3H, s, CH₃) 2.00 (1H, b, CH) 0.81 (4H, m, 2 × CH₂) |
| 284 | 1H-NMR (¹H, DMSO-d6): 11.02 (1H, b, NH), 7.95 (2H, d, ArH), 7.78 (2H, d, ArH), 7.65 (1H, dd, ArH), 7.55 (1H, d, ArH), 7.21 (1H, d, ArH), 7.15 (2H, d, ArH), 6.58 (2H, d, ArH), 4.34 (2H, d, CH₂), 4.08 (3H, m, 2 × CH + CH), 3.78 (2H, t, 2 × CH), 3.16 (2H, d, 2 × CH), 2.01 (1H, b, CH), 0.81 (4H, m, 2 × CH₂) |
| 291 | (¹H, CDCl3) 9.39 (1H, b, NH) 7.95 (2H, d, 2 × ArH) 7.58 (2H, m, 2 × ArH) 7.48 (2H, d, 2 × ArH) 7.06 (1H, dd, ArH) 3.90 (2H, s, CH₂) 3.76 (2H, m, 2 × CH) 3.28 (2H, m, 2 × CH) 3.18 (1H, m, CH) 2.21 (7H, b, s, 2 × CH₃ + CH) 1.16 (2H, m, 2 × CH) 0.90 (2H, m, 2 × CH) |
| 298 | (¹H, CDCl3) 8.82 (1H, b, NH) 7.96 (2H, d, 2 × ArH) 7.59 (2H, m, 2 × ArH) 7.52 (2H, d, 2 × ArH) 7.07 (1H, dd, ArH) 3.90 (2H, s, CH2) 3.78 (2H, m, 2 × CH) 3.53 (2H, m, 2 × CH) 3.08 (1H, m, CH) 2.99 (2H, d, CH₂) 2.50 (6H, s, 2 × CH₃) 2.02 (1H, b, CH) 1.17 (2H, m, 2 × CH) 0.91 (2H, m, 2 × CH) |
| 299 | (¹H, DMSO-d6) 10.99 (1H, b, NH) 7.95 (2H, d, 2 × ArH) 7.69 (2H, m, 2 × ArH) 7.44 (2H, d, 2 × ArH) 7.27 (1H, dd, ArH) 3.62 (2H, s, CH₂) 3.48 (2H, b, 2 × CH) 3.39 (1H, b, NH) 3.19 (2H, b, 2 × CH) 2.83 (3H, s, CH₃) 2.81 (3H, s, CH₃) 2.02 (1H, b, NH) 0.81 (4H, m, 2 × CH₂) |
| 300 | (¹H, DMSO-d6) 10.99 (1H, b, NH) 7.95 (2H, d, 2 × ArH) 7.70 (2H, m, 2 × ArH) 7.45 (2H, d, 2 × ArH) 7.27 (1H, dd, ArH) 3.66 (2H, s, CH₂) 3.57 (4H, m, 2 × CH₂) 3.39 (1H, m, CH) 2.90 (4H, m, 2 × CH₂) 2.24 (4H, m, 2 × CH₂) 2.02 (1H, b, CH) 0.81 (4H, m, 2 × CH₂) |
| 301 | (¹H, DMSO-d6) 11.00 (1H, b, NH) 8.02 (2H, d, 2 × ArH) 7.71 (2H, m, 2 × ArH) 7.62 (2H, d, 2 × ArH) 7.31 (1H, dd, ArH) 7.29 (2H, d, 2 × ArH) 7.07 (2H, d, 2 × ArH) 5.23 (2H, s, CH₂) 3.94 (2H, s, CH₂) 2.03 (1H, b, CH) 0.81 (4H, m, 2 × CH₂) |
| 302 | (¹H, DMSO-d6) 11.00 (1H, b, NH) 8.37 (1H, d, ArH) 7.95 (2H, d, 2 × ArH) 7.69 (2H, m, 2 × ArH) 7.51 (2H, d, 2 × ArH) 7.27 (1H, dd, ArH) 6.79 (1H, t, NH) 6.02 (1H, dArH) 4.37 (2H, d, CH₂) 2.02 (1H, b, CH) 0.81 (4H, m, 2 × CH₂) |
| 303 | (¹H, DMSO-d6) 10.99 (1H, b, NH) 7.96 (2H, d, 2 × ArH) 7.69 (2H, m, 2 × ArH) 7.45 (2H, d, 2 × ArH) 7.28 (1H, dd, ArH) 3.68 (2H, s, CH₂) 3.51 (2H, m, 2 × CH) 3.33 (2H, m, 2 × CH) 2.03 (1H, b, CH) 0.81 (4H, m, 2 × CH₂) |
| 304 | (¹H, DMSO-d6) 10.99 (1H, b, NH) 7.97 (2H, d, 2 × ArH) 7.69 (2H, m, 2 × ArH) 7.53 (2H, d, 2 × ArH) 7.28 (1H, dd, ArH) 3.90 (1H, b, NH) 3.83 (2H, m, CH₂) 3.48 (1H, m, CH) 3.34 (1H, m, CH) 3.26 (1H, m, CH) 3.05 (1H, m, CH) 2.94 (1H, m, CH) 2.28 (1H, m, CH) 2.03 (2H, b + m, 2 × CH) 0.81 (4H, m, 2 × CH₂) |
| 305 | (¹H, DMSO-d6) 10.99 (1H, b, NH) 7.96 (2H, d, 2 × ArH) 7.70 (2H, m, 2 × ArH) 7.48 (2H, d, 2 × ArH) 7.29 (1H, d, ArH) 4.68 (1H, b, OH) 4.22 (1H, m, CH) 3.66 (2H, m, CH2) 2.72 (1H, m, CH) 2.64 (1H, m, CH) 2.46 (1H, m, CH) 2.37 (1H, m, CH) 2.02 (2H, b + m, 2 × CH) 1.58 (1H, m, CH) 0.81 (4H, m, 2 × CH₂) |
| 306 | (¹H, DMSO-d6) 10.99 (1H, b, NH) 8.68 (1H, m, NH) 7.97 (2H, d, 2 × ArH) 7.86 (1H, b, NH) 7.69 (2H, m, 2 × ArH) 7.63 (1H, d, ArH) 7.51 (2H, d, 2 × ArH) 7.27 (1H, d, ArH) 7.22 (1H, m, ArH) 7.20 (1H, b, NH) 6.65 (1H, d, ArH) 6.54 (1H, m, ArH) 4.51 (2H, d, CH₂) 2.02 (1H, b, CH) 0.80 (4H, m, 2 × CH₂) |
| 307 | (¹H, DMSO-d6) 10.99 (1H, b, NH) 7.96 (2H, d, 2 × ArH) 7.70 (2H, m, 2 × ArH) 7.48 (2H, d, 2 × ArH) 7.29 (1H, d, ArH) 4.68 (1H, b, OH) 4.22 (1H, m, CH) 3.66 (2H, m, CH₂) 2.72 (1H, m, CH) 2.64 (1H, m, CH) 2.46 (1H, m, CH) 2.37 (1H, m, CH) 2.02 (2H, b + m, 2 × CH) 1.58 (1H, m, CH) 0.81 (4H, m, 2 × CH₂) |
| 310 | (¹H, DMSO-d6) 10.99 (1H, b, NH) 7.96 (2H, d, 2 × ArH) 7.69 (2H, m, 2 × ArH) 7.46 (2H, d, 2 × ArH) 7.28 (1H, dd, ArH) 6.74 (1H, d, NH) 3.53 (2H, s, CH₂) 2.79 (2H, m, 2 × CH) 2.02 (3H, m, 3 × CH) 1.70 (2H, m, 2 × CH) 1.42 (2H, m, 2 × CH) 1.37 (9H, s, 3 × CH₃) 0.81 (4H, m, 2 × CH₂) |

TABLE II-continued

NMR Data of Representative Compounds of the Invention

| Cpd # | (δ) NMR data |
|---|---|
| 311 | (¹H, DMSO-d6) 10.99 (1H, b, NH) 7.99 (2H, d, 2 × ArH) 7.70 (3H, m, 2 × ArH + NH) 7.51 (2H, d, 2 × ArH) 7.30 (1H, dd, ArH) 3.64 (2H, s, CH$_2$) 3.18 (2H, m, CH$_2$) 2.96 (2H, s, CH$_2$) 2.60 (2H, m, CH$_2$) 2.03 (1H, b, CH) 0.81 (4H, m, 2 × CH$_2$) |
| 312 | (¹H, DMSO-d6) 10.98 (1H, b, NH) 7.95 (2H, d, 2 × ArH) 7.69 (3H, m, 2 × ArH + NH) 7.50 (2H, d, 2 × ArH) 7.27 (1H, dd, ArH) 3.81 (2H, s, CH$_2$) 2.08 (1H, m, CH$_2$) 2.02 (1H, b, CH) 0.81 (4H, m, 2 × CH$_2$) 0.37 (2H, m, 2 × CH) 0.28 (2H, m, 2 × CH) |
| 325 | (¹H, DMSO-d6) 11.08 (1H, b, NH), 8.09 (2H, d, ArH), 7.82 (2H, d, ArH), 7.79 (2H, d, ArH), 7.74 (1H, d, ArH), 7.73 (1H, s, ArH), 7.35 (1H, dd, ArH), 7.13 (2H, d, ArH), 4.52 (1H, t, CH), 4.30 (2H, d, CH$_2$), 4.23 (2H, m, 2 × CH), 3.92 (1H, m, CH), 3.12 (1H, m, CH), 2.01 (1H, b, CH), 0.80 (4H, m, 2 × CH$_2$). |
| 326 | (¹H, DMSO-d6) 11.08 (1H, b, NH), 8.09 (2H, d, ArH), 7.81 (2H, d, ArH), 7.74 (2H, d, ArH), 7.35 (1H, dd, ArH), 4.38 (1H, t, CH), 4.21 (1H, m, CH), 4.10 (1H, m, CH), 3.92 (1H, m, CH), 3.59 (4H, t, 2 × CH$_2$), 3.17 (1H, m, CH), 2.33 (4H, b, 2 × CH$_2$), 1.99 (1H, b, CH), 0.82 (4H, m, 2 × CH$_2$). |
| 327 | (¹H, DMSO-d6) 11.08 (1H, b, NH), 8.10 (2H, d, ArH), 7.80 (2H, d, ArH), 7.74 (1H, d, ArH), 7.73 (1H, s, ArH), 7.35 (1H, dd, ArH), 4.37 (1H, t, CH), 4.15 (1H, m, CH), 4.09 (1H, m, CH), 3.86 (1H, m, CH), 3.10 (1H, m, CH), 2.10 (6H, s, 2 × CH$_3$), 2.01 (1H, b, CH), 0.82 (4H, m, 2 × CH$_2$). |
| 328 | (¹H, DMSO-d6) 11.09 (1H, b, NH), 8.10 (2H, d, ArH), 7.81 (2H, d, ArH), 7.74 (2H, d, ArH), 7.37 (1H, dd, ArH), 4.66 (1H, t, CH), 4.58 (1H, t, CH), 4.39 (1H, t, CH), 4.23 (1H, t, CH), 3.88 (1H, m, CH), 2.01 (1H, b, CH), 0.81 (4H, m, 2 × CH$_2$). |
| 329 | (¹H, DMSO-d6) 11.01 (1H, b, NH), 8.08 (2H, d, ArH), 7.79 (2H, d, ArH), 7.73 (1H, d, ArH), 7.72 (1H, s, ArH), 7.35 (1H, dd, ArH), 4.43 (1H, t, CH), 4.15 (1H, t, CH), 4.07 (1H, m, CH), 4.00 (1H, m, CH), 3.71 (1H, m, CH), 3.17 (2H, d, CH$_2$), 2.15 (6H, s, 2 × CH$_3$), 2.03 (1H, b, CH), 0.81 (4H, m, 2 × CH$_2$). |
| 330 | (¹H, DMSO-d6) 11.01 (1H, b, NH), 8.08 (2H, d, ArH), 7.79 (2H, d, ArH), 7.73 (1H, d, ArH), 7.72 (1H, s, ArH), 7.35 (1H, dd, ArH), 4.04 (2H, b, CH$_2$), 3.77 (2H, b, CH$_2$), 2.02 (1H, b, CH), 1.27 (6H, s, 2 × CH$_3$), 0.81 (4H, m, 2 × CH$_2$). |
| 331 | (¹H, DMSO-d6) 11.06 (1H, b, NH), 8.18 (3H, d, ArH), 7.76 (1H, d, ArH), 7.75 (2H, d, ArH), 7.66 (1H, s, ArH), 7.41 (1H, dd, ArH), 2.03 (1H, b, CH), 0.82 (4H, m, 2 × CH$_2$). |

BIOLOGICAL EXAMPLES

Example 1

In Vitro Assays

Example 1.1

JAK1 Inhibition Assay

Recombinant human JAK1 catalytic domain (amino acids 850-1154; catalog number 08-144) was purchased from Carna Biosciences. 10 ng of JAK1 was incubated with 12.5 μg polyGT substrate (Sigma catalog number P0275) in kinase reaction buffer (15 mM Tris-HCl pH 7.5, 1 mM DTT, 0.01% Tween-20, 10 mM MgCl$_2$, 2 μM non-radioactive ATP, 0.25 μCi 33P-gamma-ATP (GE Healthcare, catalog number AH9968) final concentrations) with or without 5 μL containing test compound or vehicle (DMSO, 1% final concentration), in a total volume of 25 μL, in a polypropylene 96-well plate (Greiner, V-bottom). After 45 min at 30° C., reactions were stopped by adding of 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 μM staurosporine) from cpm obtained in the presence of vehicle. The ability of a test compound to inhibit this activity was determined as:

Percentage inhibition=((cpm determined for sample with test compound present–cpm determined for sample with positive control inhibitor) divided by (cpm determined in the presence of vehicle–cpm determined for sample with positive control inhibitor))*100%.

Dose dilution series were prepared for the compounds enabling the testing of dose-response effects in the JAK1 assay and the calculation of the IC$_{50}$ for each compound. Each compound was routinely tested at concentration of 20 μM followed by a ⅓ serial dilution, 8 points (20 μM-6.67 μM-2.22 μM-740 nM-247 nM-82 nM-27 nM-9 nM) in a final concentration of 1% DMSO. When potency of compound series increased, more dilutions were prepared and/or the top concentration were lowered (e.g. 5 μM, 1 μM).

Semi-Quantitative Score:

TABLE III

JAK1 IC$_{50}$ Values of Compounds

| Cpd # | JAK1 |
|---|---|
| 1 | *** |
| 2 | *** |
| 3 | *** |
| 4 | ** |
| 5 | * |
| 6 | * |
| 7 | **** |
| 8 | * |
| 9 | * |
| 10 | **** |
| 11 | *** |
| 12 | **** |
| 13 | **** |
| 14 | *** |
| 15 | **** |
| 17 | **** |
| 18 | **** |
| 19 | **** |
| 20 | *** |
| 21 | **** |
| 22 | *** |
| 23 | **** |
| 24 | *** |
| 25 | **** |
| 26 | *** |
| 27 | *** |
| 28 | *** |
| 29 | **** |
| 30 | **** |
| 31 | **** |
| 32 | ** |
| 33 | **** |
| 34 | *** |
| 35 | *** |
| 36 | **** |
| 37 | **** |
| 38 | *** |
| 39 | **** |
| 40 | **** |
| 41 | **** |
| 42 | *** |
| 43 | *** |
| 44 | ** |
| 45 | *** |

TABLE III-continued

JAK1 IC$_{50}$ Values of Compounds

| Cpd # | JAK1 |
|---|---|
| 46 | **** |
| 47 | *** |
| 48 | **** |
| 49 | **** |
| 50 | **** |
| 51 | **** |
| 52 | **** |
| 53 | *** |
| 54 | **** |
| 55 | *** |
| 56 | **** |
| 57 | **** |
| 58 | **** |
| 59 | **** |
| 60 | **** |
| 61 | * |
| 62 | **** |
| 63 | *** |
| 64 | **** |
| 65 | *** |
| 66 | **** |
| 67 | *** |
| 68 | *** |
| 69 | *** |
| 70 | *** |
| 71 | **** |
| 72 | **** |
| 73 | *** |
| 74 | **** |
| 75 | **** |
| 76 | **** |
| 77 | **** |
| 78 | **** |
| 79 | **** |
| 80 | *** |
| 81 | *** |
| 85 | **** |
| 86 | **** |
| 87 | **** |
| 88 | **** |
| 89 | **** |
| 90 | **** |
| 92 | **** |
| 93 | *** |
| 94 | *** |
| 95 | * |
| 96 | **** |
| 97 | **** |
| 98 | **** |
| 99 | **** |
| 100 | **** |
| 101 | *** |
| 102 | *** |
| 103 | * |
| 104 | **** |
| 105 | *** |
| 106 | **** |
| 107 | **** |
| 108 | **** |
| 109 | **** |
| 110 | *** |
| 111 | **** |
| 112 | * |
| 113 | **** |
| 114 | **** |
| 115 | **** |
| 116 | **** |
| 117 | * |
| 118 | **** |
| 119 | **** |
| 120 | **** |
| 121 | **** |
| 122 | **** |
| 123 | **** |
| 124 | **** |
| 125 | **** |

TABLE III-continued

JAK1 IC$_{50}$ Values of Compounds

| Cpd # | JAK1 |
|---|---|
| 126 | *** |
| 127 | *** |
| 128 | ** |
| 129 | * |
| 130 | * |
| 131 | *** |
| 132 | *** |
| 133 | *** |
| 134 | **** |
| 135 | *** |
| 136 | *** |
| 137 | **** |
| 138 | **** |
| 139 | ** |
| 140 | *** |
| 141 | *** |
| 142 | *** |
| 143 | *** |
| 144 | **** |
| 145 | **** |
| 146 | **** |
| 147 | *** |
| 148 | **** |
| 149 | *** |
| 150 | **** |
| 151 | *** |
| 152 | *** |
| 153 | *** |
| 154 | *** |
| 155 | * |
| 156 | **** |
| 157 | **** |
| 158 | *** |
| 159 | *** |
| 160 | *** |
| 161 | ** |
| 162 | * |
| 163 | **** |
| 164 | **** |
| 165 | *** |
| 166 | **** |
| 167 | *** |
| 168 | **** |
| 169 | **** |
| 170 | ** |
| 171 | *** |
| 172 | ** |
| 173 | * |
| 174 | * |
| 175 | **** |
| 176 | **** |
| 177 | **** |
| 178 | **** |
| 179 | **** |
| 180 | *** |
| 181 | *** |
| 182 | **** |
| 183 | **** |
| 184 | * |
| 185 | **** |
| 187 | ** |
| 188 | * |
| 189 | **** |
| 190 | **** |
| 191 | * |
| 192 | **** |
| 193 | * |
| 194 | *** |
| 195 | *** |
| 196 | **** |
| 197 | **** |
| 198 | **** |
| 199 | **** |
| 200 | **** |
| 201 | **** |
| 202 | **** |

TABLE III-continued

JAK1 IC$_{50}$ Values of Compounds

| Cpd # | JAK1 |
|---|---|
| 203 | **** |
| 204 | **** |
| 205 | *** |
| 206 | **** |
| 207 | **** |
| 208 | **** |
| 209 | **** |
| 210 | **** |
| 211 | **** |
| 212 | **** |
| 213 | *** |
| 214 | *** |
| 215 | **** |
| 216 | *** |
| 217 | *** |
| 218 | *** |
| 219 | * |
| 220 | *** |
| 221 | **** |
| 222 | **** |
| 223 | **** |
| 224 | **** |
| 225 | **** |
| 226 | **** |
| 227 | **** |
| 228 | **** |
| 229 | **** |
| 230 | *** |
| 231 | **** |
| 232 | **** |
| 233 | **** |
| 234 | **** |
| 235 | **** |
| 236 | **** |
| 237 | *** |
| 238 | **** |
| 239 | **** |
| 240 | **** |
| 241 | **** |
| 242 | *** |
| 243 | *** |
| 244 | **** |
| 245 | **** |
| 246 | **** |
| 247 | * |
| 248 | *** |
| 249 | **** |
| 250 | *** |
| 266 | **** |
| 267 | **** |
| 268 | **** |
| 269 | *** |
| 270 | **** |
| 271 | **** |
| 272 | **** |
| 273 | **** |
| 274 | *** |
| 275 | **** |
| 276 | **** |
| 277 | **** |
| 278 | **** |
| 279 | *** |
| 280 | **** |
| 281 | **** |
| 282 | *** |
| 283 | * |
| 284 | **** |
| 285 | *** |
| 286 | *** |
| 287 | **** |
| 288 | **** |
| 289 | **** |
| 290 | *** |
| 292 | **** |
| 293 | **** |
| 294 | *** |
| 295 | *** |
| 296 | *** |
| 297 | **** |
| 298 | * |
| 299 | ** |
| 300 | * |
| 301 | **** |
| 302 | **** |
| 303 | **** |
| 304 | **** |
| 305 | *** |
| 306 | **** |
| 307 | *** |
| 308 | *** |
| 309 | *** |
| 310 | **** |
| 311 | *** |
| 312 | *** |
| 313 | **** |
| 314 | *** |
| 315 | *** |
| 316 | **** |
| 317 | **** |
| 318 | *** |
| 319 | **** |
| 320 | *** |
| 321 | **** |
| 322 | * |
| 323 | ** |
| 324 | * |
| 325 | **** |
| 326 | *** |
| 327 | *** |
| 328 | **** |
| 329 | *** |
| 330 | **** |
| 331 | *** |

\* >1000 nM  
\*\* 501-1000 nM  
\*\*\* 101-500 nM  
\*\*\*\* <100 nM

Example 1.2

JAK2 Inhibition Assay

Recombinant human JAK2 catalytic domain (amino acids 808-1132; catalog number PV4210) was purchased from Invitrogen. 0.025 mU of JAK2 was incubated with 2.5 μg polyGT substrate (Sigma catalog number P0275) in kinase reaction buffer (5 mM MOPS pH 7.5, 9 mM MgAc, 0.3 mM EDTA, 0.06% Brij and 0.6 mM DTT, 1 μM non-radioactive ATP, 0.25 μCi 33P-gamma-ATP (GE Healthcare, catalog number AH9968) final concentrations) with or without 5 μL containing test compound or vehicle (DMSO, 1% final concentration), in a total volume of 25 μL, in a polypropylene 96-well plate (Greiner, V-bottom). After 90 min at 30° C., reactions were stopped by adding of 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 μM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100%.

Dose dilution series were prepared for the compounds enabling the testing of dose-response effects in the JAK2 assay and the calculation of the $IC_{50}$ for each compound. Each compound was routinely tested at concentration of 20 µM followed by a ⅓ serial dilution, 8 points (20 µM–6.67 µM-2.22 µM-740 nM-247 nM-82 nM-27 nM-9 nM) in a final concentration of 1% DMSO. When potency of compound series increased, more dilutions were prepared and/or the top concentration was lowered (e.g. 5 µM, 1 µM).

TABLE IV

JAK2 $IC_{50}$ Values of Compounds

| Cpd # | JAK2 |
|---|---|
| 1 | ## |
| 3 | # |
| 7 | ### |
| 10 | ### |
| 12 | #### |
| 13 | #### |
| 14 | ## |
| 15 | #### |
| 17 | ### |
| 18 | # |
| 19 | ### |
| 20 | ## |
| 21 | ### |
| 22 | ### |
| 23 | ### |
| 24 | ### |
| 25 | ### |
| 26 | ### |
| 27 | ## |
| 28 | # |
| 29 | ### |
| 30 | #### |
| 31 | ### |
| 32 | # |
| 33 | #### |
| 36 | #### |
| 37 | #### |
| 39 | #### |
| 40 | #### |
| 41 | ### |
| 46 | ### |
| 48 | ### |
| 49 | ### |
| 50 | #### |
| 51 | #### |
| 52 | #### |
| 54 | #### |
| 56 | ### |
| 57 | #### |
| 58 | ### |
| 59 | #### |
| 60 | #### |
| 62 | #### |
| 66 | ### |
| 71 | ## |
| 72 | #### |
| 74 | ### |
| 75 | ### |
| 76 | #### |
| 77 | ### |
| 78 | #### |
| 85 | ### |
| 87 | #### |
| 88 | ### |
| 90 | ## |
| 92 | ### |
| 96 | #### |
| 97 | #### |
| 98 | ### |
| 99 | #### |
| 100 | #### |
| 104 | ### |
| 107 | #### |
| 108 | #### |
| 109 | #### |
| 111 | ### |
| 114 | ### |
| 115 | ### |
| 116 | ### |
| 119 | ### |
| 121 | #### |
| 156 | #### |
| 163 | #### |
| 176 | #### |
| 196 | ### |
| 197 | #### |
| 198 | #### |
| 199 | ### |
| 200 | #### |
| 201 | ### |
| 202 | #### |
| 203 | ### |
| 204 | ### |
| 205 | ## |
| 206 | ### |
| 207 | #### |
| 208 | #### |
| 209 | ### |
| 210 | ### |
| 211 | #### |
| 212 | #### |
| 213 | ### |
| 214 | ### |
| 215 | ### |
| 216 | ### |
| 217 | ## |
| 218 | ### |
| 219 | # |
| 220 | ## |
| 221 | ### |
| 222 | ### |
| 223 | ## |
| 224 | #### |
| 225 | #### |
| 226 | #### |
| 227 | #### |
| 228 | #### |
| 229 | #### |
| 230 | ### |
| 231 | ### |
| 232 | ### |
| 233 | #### |
| 234 | #### |
| 235 | ### |
| 236 | #### |
| 237 | ## |
| 238 | #### |
| 239 | ### |
| 240 | #### |
| 241 | ### |
| 242 | ## |
| 243 | ## |
| 244 | #### |
| 245 | #### |
| 246 | #### |
| 247 | # |
| 248 | ### |
| 249 | ### |

TABLE IV-continued

JAK2 IC$_{50}$ Values of Compounds

| Cpd # | JAK2 |
|---|---|
| 250 | ## |
| 251 | ### |
| 253 | ## |
| 254 | ## |
| 255 | ## |
| 256 | ### |
| 257 | #### |
| 258 | #### |
| 259 | ### |
| 260 | ### |
| 261 | ### |
| 262 | ### |
| 263 | ### |
| 264 | ### |
| 265 | ### |
| 266 | ### |
| 267 | ### |
| 268 | ### |
| 269 | # |
| 270 | ### |
| 271 | #### |
| 272 | ### |
| 273 | #### |
| 274 | ## |
| 275 | ### |
| 276 | ### |
| 277 | ### |
| 278 | ### |
| 279 | # |
| 280 | #### |
| 281 | # |
| 282 | # |
| 283 | # |
| 284 | ## |
| 285 | # |
| 286 | ## |
| 287 | ## |
| 288 | ### |
| 289 | ## |
| 290 | # |
| 292 | ### |
| 293 | # |
| 294 | # |
| 295 | # |
| 296 | ## |
| 297 | #### |
| 298 | # |
| 299 | # |
| 300 | # |
| 301 | #### |
| 302 | #### |
| 303 | ### |
| 304 | #### |
| 305 | # |
| 306 | #### |
| 307 | # |
| 308 | # |
| 309 | ## |
| 310 | # |
| 311 | ### |
| 312 | ### |
| 313 | ### |
| 314 | # |
| 315 | ### |
| 316 | ### |
| 317 | #### |
| 318 | ### |
| 319 | ### |
| 320 | ### |
| 321 | ### |
| 322 | # |
| 323 | ## |
| 324 | # |
| 325 | ### |
| 326 | # |
| 327 | # |
| 328 | #### |
| 329 | # |
| 330 | ### |
| 331 | #### |

Semi-quantitative score:
>1000 nM
501-1000 nM
101-500 nM
<100 nM

Example 1.3

JAK3 Inhibition Assay

Recombinant human JAK3 catalytic domain (amino acids 781-1124; catalog number PV3855) was purchased from Invitrogen. 0.025mU of JAK3 was incubated with 2.5 g polyGT substrate (Sigma catalog number P0275) in kinase reaction buffer (25 mM Tris pH 7.5, 0.5 mM EGTA, 0.5 mM Na3VO4, 5 mM b-glycerolphosphate, 0.01% Triton X-100, 1 µM non-radioactive ATP, 0.25 µCi 33P-gamma-ATP (GE Healthcare, catalog number AH9968) final concentrations) with or without 5 µL containing test compound or vehicle (DMSO, 1% final concentration), in a total volume of 25 µL, in a polypropylene 96-well plate (Greiner, V-bottom). After 105 min at 30° C., reactions were stopped by adding of 25 µL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 µL per well of a 75 mM phosphoric acid solution and the bottom of the plates was sealed. 40 µL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 µM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100%.

Dose dilution series were prepared for the compounds enabling the testing of dose-response effects in the JAK3 assay and the calculation of the IC$_{50}$ for each compound. Each compound was routinely tested at concentration of 20 µM followed by a ⅓ serial dilution, 8 points (20 µM-6.67 µM-2.22 µM-740 nM-247 nM-82 nM-27 nM-9 nM) in a final concentration of 1% DMSO. When potency of compound series increased, more dilutions were prepared and/or the top concentration was lowered (e.g. 5 µM, 1 µM).

TABLE V

JAK3 IC$_{50}$ Values of Compounds

| Cpd # | JAK3 |
|---|---|
| 1 | + |
| 3 | + |

TABLE V-continued

JAK3 IC$_{50}$ Values of Compounds

| Cpd # | JAK3 |
|---|---|
| 10 | + |
| 12 | ++++ |
| 13 | + |
| 15 | +++ |
| 17 | + |
| 18 | + |
| 19 | + |
| 29 | + |
| 30 | + |
| 33 | + |
| 36 | +++ |
| 37 | ++ |
| 39 | + |
| 40 | ++ |
| 42 | + |
| 43 | + |
| 46 | + |
| 48 | + |
| 49 | + |
| 50 | +++ |
| 51 | ++ |
| 52 | ++ |
| 54 | + |
| 56 | + |
| 57 | ++ |
| 58 | + |
| 59 | + |
| 60 | +++ |
| 62 | +++ |
| 66 | + |
| 71 | + |
| 72 | ++ |
| 74 | + |
| 75 | + |
| 76 | +++ |
| 77 | + |
| 78 | +++ |
| 85 | + |
| 87 | +++ |
| 88 | + |
| 90 | + |
| 92 | ++ |
| 96 | + |
| 97 | +++ |
| 98 | + |
| 99 | +++ |
| 100 | + |
| 104 | + |
| 107 | + |
| 108 | + |
| 109 | ++ |
| 111 | ++ |
| 114 | + |
| 116 | ++ |
| 119 | + |
| 121 | ++ |
| 125 | ++++ |
| 156 | +++ |
| 163 | +++ |
| 176 | ++++ |
| 189 | ++ |
| 192 | +++ |
| 200 | +++ |
| 215 | ++++ |
| 234 | +++ |
| 240 | ++ |
| 271 | +++ |
| 302 | +++ |
| 306 | ++++ |
| 317 | + |
| 319 | +++ |
| 325 | ++ |
| 328 | +++ |
| 330 | +++ |

Semi-quantitative score:
+ >1000 nM
++ 501-1000 nM
+++ 101-500 nM
++++ <100 nM
N/A—not available

Example 1.4

TYK2 Inhibition Assay

Recombinant human TYK2 catalytic domain (amino acids 871-1187; catalog number 08-147) was purchased from Carna biosciences. 5 ng of TYK2 was incubated with 12.5 μg polyGT substrate (Sigma catalog number P0275) in kinase reaction buffer (25 mM Hepes pH 7.5, 100 mM NaCl, 0.2 mM Na3VO4, 0.1% NP-40, 0.1 μM non-radioactive ATP, 0.125 μCi 33P-gamma-ATP (GE Healthcare, catalog number AH9968) final concentrations) with or without 5 μL containing test compound or vehicle (DMSO, 1% final concentration), in a total volume of 25 μL, in a polypropylene 96-well plate (Greiner, V-bottom). After 90 min at 30 OC, reactions were stopped by adding of 25 μL/well of 150 mM phosphoric acid. All of the terminated kinase reaction was transferred to prewashed (75 mM phosphoric acid) 96 well filter plates (Perkin Elmer catalog number 6005177) using a cell harvester (Perkin Elmer). Plates were washed 6 times with 300 μL per well of a 75 mM phosphoric acid solution and the bottom of the plates was sealed. 40 μL/well of Microscint-20 was added, the top of the plates was sealed and readout was performed using the Topcount (Perkin Elmer). Kinase activity was calculated by subtracting counts per minute (cpm) obtained in the presence of a positive control inhibitor (10 μM staurosporine) from cpm obtained in the presence of vehicle. The ability of a test compound to inhibit this activity was determined as:

Percentage inhibition=((cpm determined for sample with test compound present−cpm determined for sample with positive control inhibitor) divided by (cpm determined in the presence of vehicle−cpm determined for sample with positive control inhibitor))*100%.

Dose dilution series were prepared for the compounds enabling the testing of dose-response effects in the TYK2 assay and the calculation of the IC$_{50}$ for each compound. Each compound was routinely tested at concentration of 20 μM followed by a ⅓ serial dilution, 8 points (20 μM-6.67 μM-2.22 μM-740 nM-247 nM-82 nM-27 nM-9 nM) in a final concentration of 1% DMSO. When potency of compound series increased, more dilutions were prepared and/or the top concentration was lowered (e.g. 5 μM, 1 μM).

TABLE VI

TYK2 IC$_{50}$ Values of Compounds

| Cpd # | TYK2 |
|---|---|
| 1 | − |
| 13 | −− |
| 15 | − |

TABLE VI-continued

TYK2 IC$_{50}$ Values of Compounds

| Cpd # | TYK2 |
|---|---|
| 17 | -- |
| 18 | - |
| 33 | --- |
| 36 | --- |
| 37 | -- |
| 39 | - |
| 40 | -- |
| 41 | - |
| 42 | - |
| 43 | - |
| 46 | - |
| 48 | - |
| 49 | - |
| 50 | - |
| 51 | -- |
| 52 | -- |
| 54 | --- |
| 56 | - |
| 57 | - |
| 58 | - |
| 59 | --- |
| 60 | -- |
| 62 | - |
| 66 | -- |
| 109 | - |
| 111 | - |
| 116 | - |
| 119 | - |
| 121 | - |
| 156 | --- |
| 163 | - |
| 176 | ---- |
| 271 | ---- |
| 302 | ---- |
| 306 | ---- |
| 317 | --- |
| 319 | --- |

Semi-quantitative score:
- >1000 nM
-- 501-1000 nM
--- 101-500 nM
---- <100 nM
N/A—not available Example 2

Cellular Assays

Example 2.1

JAK-STAT Signalling Assay

HeLa cells were maintained in Dulbecco's Modified Eagle's Medium (DMEM) containing 10% heat inactivated fetal calf serum, 100 U/mL penicillin and 100 µg/mL streptomycin. HeLa cells were used at 70% confluence for transfection. 20,000 cells in 87 µL cell culture medium were transiently transfected with 40 ng pSTAT1(2)-luciferase reporter (Panomics), 8 ng of LacZ reporter as internal control reporter and 52 ng of pBSK using 0.32 µL Jet-PEI (Polyplus) as transfection reagent per well in 96-well plate format. After overnight incubation at 37° C., 10% $CO_2$, transfection medium was removed. 75 µL of DMEM+1.5% heat inactivated fetal calf serum was added. 15 µL of compound at 6.7× concentration was added for 60 min and then 10 µL of human OSM (Peprotech) at 33 ng/mL final concentration.

All compounds were tested in duplicate starting from 20 µM followed by a ⅓ serial dilution, 8 doses in total (20 µM-6.6 µM-2.2 µM-740 nM-250 nM-82 nM-27 nM-9 nM) in a final concentration of 0.2% DMSO.

After overnight incubation at 37° C., 10% $CO_2$ cells were lysed in 100 µL lysis buffer/well (PBS, 0.9 mM $CaCl_2$, 0.5 mM $MgCl_2$, 5% Trehalose, 0.025% Tergitol NP9, 0.15% BSA).

40 µL of cell lysate was used to read β-galactosidase activity by adding 180 µL βGal solution (30 µl ONPG 4 mg/mL+ 150 µL P-Galactosidase buffer (0.06 M $Na_2HPO_4$, 0.04 M $NaH_2PO_4$, 1 mM $MgCl_2$)) for 20 min. The reaction was stopped by addition of 50 µL $Na_2CO_3$ 1 M. Absorbance was read at 405 nm.

Luciferase activity was measured using 40 µL cell lysate plus 40 µl of Steadylite® as described by the manufacturer (Perkin Elmer), on the Envision (Perkin Elmer).

10 µM of a pan-JAK inhibitor was used as a positive control (100% inhibition). As negative control 0.5% DMSO (0% inhibition) was used. The positive and negative controls were used to calculate z' and 'percent inhibition' (PIN) values.

Percentage inhibition=((fluorescence determined in the presence of vehicle−fluorescence determined for sample with test compound present) divided by (fluorescence determined in the presence of vehicle−fluorescence determined for sample without trigger))*100%.

PIN values were plotted for compounds tested in dose-response and EC$_{50}$ values were derived.

TABLE VII

STAT signalling EC$_{50}$ Values of Compounds

| Cpd # | EC$_{50}$ |
|---|---|
| 7 | * |
| 10 | * |
| 12 | *** |
| 13 | * |
| 14 | * |
| 15 | *** |
| 17 | * |
| 18 | * |
| 19 | * |
| 20 | ** |
| 21 | * |
| 22 | * |
| 23 | * |
| 25 | * |
| 26 | * |
| 27 | * |
| 28 | * |
| 29 | *** |
| 30 | ** |
| 31 | * |
| 33 | * |
| 36 | *** |
| 37 | ** |
| 39 | * |
| 40 | *** |
| 41 | ** |
| 46 | * |
| 48 | * |
| 49 | * |
| 50 | * |
| 51 | *** |
| 52 | ** |
| 54 | * |
| 56 | * |
| 57 | * |
| 58 | * |
| 59 | * |
| 60 | *** |
| 62 | * |
| 64 | * |
| 66 | * |

TABLE VII-continued

STAT signalling $EC_{50}$ Values of Compounds

| Cpd # | $EC_{50}$ |
|---|---|
| 71 | * |
| 72 | * |
| 74 | * |
| 75 | * |
| 76 | ** |
| 77 | * |
| 78 | * |
| 79 | * |
| 85 | * |
| 87 | *** |
| 88 | * |
| 89 | * |
| 90 | * |
| 92 | * |
| 96 | * |
| 97 | *** |
| 98 | * |
| 99 | *** |
| 100 | * |
| 104 | * |
| 106 | *** |
| 107 | * |
| 108 | ** |
| 109 | ** |
| 111 | ** |
| 113 | * |
| 114 | * |
| 115 | * |
| 116 | * |
| 118 | * |
| 119 | * |
| 120 | * |
| 121 | ** |
| 122 | * |
| 123 | * |
| 124 | * |
| 125 | * |
| 134 | ** |
| 137 | ** |
| 138 | *** |
| 144 | * |
| 145 | ** |
| 146 | * |
| 148 | * |
| 150 | * |
| 156 | *** |
| 157 | * |
| 163 | * |
| 164 | * |
| 166 | * |
| 168 | * |
| 169 | * |
| 175 | ** |
| 176 | *** |
| 177 | * |
| 178 | * |
| 179 | * |
| 182 | * |
| 183 | * |
| 189 | *** |
| 190 | * |
| 192 | *** |
| 196 | * |
| 197 | *** |
| 198 | *** |
| 199 | * |
| 200 | ** |
| 201 | *** |
| 202 | * |
| 203 | * |
| 204 | * |
| 206 | * |
| 207 | * |
| 208 | * |
| 209 | * |
| 210 | * |
| 211 | ** |
| 212 | *** |
| 215 | *** |
| 221 | * |
| 222 | * |
| 223 | * |
| 224 | *** |
| 225 | *** |
| 226 | *** |
| 227 | * |
| 228 | ** |
| 229 | ** |
| 231 | * |
| 232 | * |
| 233 | * |
| 234 | ** |
| 235 | * |
| 236 | ** |
| 238 | ** |
| 239 | * |
| 240 | *** |
| 241 | ** |
| 244 | ** |
| 245 | *** |
| 246 | *** |
| 249 | * |
| 266 | ** |
| 267 | * |
| 268 | * |
| 269 | * |
| 270 | * |
| 271 | *** |
| 272 | * |
| 273 | * |
| 275 | * |
| 276 | * |
| 277 | * |
| 278 | * |
| 280 | ** |
| 281 | * |
| 284 | * |
| 287 | * |
| 288 | * |
| 289 | * |
| 292 | * |
| 293 | * |
| 297 | * |
| 301 | *** |
| 302 | *** |
| 303 | ** |
| 304 | * |
| 306 | *** |
| 310 | * |
| 313 | * |
| 316 | * |
| 317 | ** |
| 319 | ** |
| 321 | * |
| 325 | ** |
| 326 | * |
| 327 | * |
| 328 | ** |
| 329 | * |
| 330 | **** |

\* >1000 nM
\*\* 501-1000 nM
\*\*\* 101-500 nM
\*\*\*\* 1-100 nM

Example 2.2

OSM/IL-1β Signaling Assay

OSM and IL-10 were shown to synergistically upregulate MMP13 levels in the human chondrosarcoma cell line SW1353. The cells were seeded in 96 well plates at 15,000 cells/well in a volume of 120 µL DMEM (Invitrogen) containing 10% (v/v) FBS and 1% penicillin/streptomycin (InVitrogen) incubated at 37° C. 5% $CO_2$. Cells were preincubated with 15 µL compound in M199 medium with 2% DMSO 1 hr before triggering with 15 µL OSM and IL-1β to reach 25 ng/mL OSM and 1 ng/mL IL-1β, and MMP13 levels were measured in conditioned medium 48 hours after triggering. MMP13 activity was measured using an antibody capture activity assay. For this purpose, 384 well plates (NUNC, 460518, MaxiSorb black) were coated with 35 µL of a 1.5 µg/mL anti-human MMP13 antibody (R&D Systems, MAB511) solution for 24 hours at 4° C. After washing the wells 2 times with PBS+0.05% Tween, the remaining binding sites were blocked with 100 µL 5% non-fat dry milk (Santa Cruz, sc-2325, Blotto) in PBS for 24 hours at 4° C. Next, the wells were washed 2 times with PBS+0.05% Tween and 35 µL of ⅒ dilution of culture supernatant containing MMP13 in 100-fold diluted blocking buffer was added and incubated for 4 hours at room temperature. Next the wells were washed twice with PBS+0.05% Tween followed by MMP13 activation by addition of 35 µL of a 1.5 mM 4-Aminophenylmercuric acetate (APMA) (Sigma, A9563) solution and incubation at 37° C. for 1 hour. The wells were washed again with PBS+0.05% Tween and 35 µL MMP13 substrate (Biomol, P-126, OmniMMP fluorogenic substrate) was added. After incubation for 24 hours at 37° C. fluorescence of the converted substrate was measured in a Perkin Elmer Wallac EnVision 2102 Multilabel Reader (wavelength excitation: 320 nm, wavelength emission: 405 nm).

Percentage inhibition=((fluorescence determined in the presence of vehicle−fluorescence determined for sample with test compound present) divided by (fluorescence determined in the presence of vehicle−fluorescence determined for sample without trigger))*100%.

TABLE VIII

MMP13 $EC_{50}$ Values of Compounds

| Cpd # | $EC_{50}$ |
|---|---|
| 7 | * |
| 10 | * |
| 12 | * |
| 13 | * |
| 15 | * |
| 17 | * |
| 18 | * |
| 19 | * |
| 21 | * |
| 22 | * |
| 23 | * |
| 24 | * |
| 25 | * |
| 26 | * |
| 27 | * |
| 28 | * |
| 29 | * |
| 30 | * |
| 31 | * |
| 32 | * |
| 33 | * |
| 36 | ** |
| 37 | * |
| 39 | * |
| 40 | *** |
| 41 | ** |
| 46 | * |
| 48 | * |
| 49 | * |
| 50 | * |
| 51 | * |
| 52 | * |
| 54 | * |
| 56 | * |
| 57 | * |
| 58 | ** |
| 59 | * |
| 60 | ** |
| 62 | * |
| 64 | * |
| 66 | * |
| 71 | * |
| 72 | ** |
| 74 | * |
| 75 | ** |
| 76 | *** |
| 77 | *** |
| 78 | ** |
| 79 | ** |
| 85 | * |
| 87 | ** |
| 88 | * |
| 89 | * |
| 90 | * |
| 92 | * |
| 96 | * |
| 97 | ** |
| 98 | * |
| 99 | *** |
| 100 | * |
| 104 | * |
| 106 | *** |
| 107 | * |
| 108 | ** |
| 109 | ** |
| 111 | * |
| 113 | * |
| 114 | ** |
| 115 | * |
| 116 | * |
| 118 | * |
| 119 | * |
| 120 | * |
| 121 | * |
| 122 | * |
| 123 | * |
| 124 | * |
| 125 | * |
| 134 | * |
| 137 | * |
| 138 | * |
| 144 | * |
| 145 | * |
| 146 | * |
| 148 | * |
| 150 | * |
| 163 | * |
| 164 | * |
| 166 | * |
| 168 | * |
| 169 | * |
| 175 | *** |
| 176 | *** |
| 177 | * |
| 178 | * |
| 182 | * |
| 183 | * |
| 189 | * |

TABLE VIII-continued

MMP13 $EC_{50}$ Values of Compounds

| Cpd # | $EC_{50}$ |
|---|---|
| 190 | * |
| 192 | ** |
| 196 | * |
| 197 | * |
| 198 | * |
| 199 | * |
| 200 | * |
| 201 | ** |
| 202 | * |
| 207 | * |
| 208 | * |
| 209 | * |
| 210 | *** |
| 211 | ** |
| 212 | *** |
| 215 | * |
| 221 | * |
| 222 | * |
| 223 | * |
| 224 | * |
| 225 | *** |
| 226 | ** |
| 227 | ** |
| 228 | *** |
| 229 | ** |
| 231 | *** |
| 233 | ** |
| 234 | *** |
| 236 | *** |
| 238 | * |
| 240 | * |
| 241 | * |
| 244 | ** |
| 245 | * |
| 246 | ** |
| 266 | * |
| 267 | * |
| 270 | * |
| 271 | ** |
| 273 | * |
| 275 | * |
| 276 | * |
| 280 | * |
| 287 | * |
| 289 | * |
| 292 | * |
| 297 | * |
| 301 | * |
| 302 | * |
| 304 | * |
| 306 | ** |
| 316 | * |
| 317 | * |
| 319 | * |
| 325 | ** |
| 328 | * |
| 330 | ** |

\* >1000 nM
\*\* 501-1000 nM
\*\*\* 1-500 nM

Example 2.3

PBL Proliferation Assay

Human peripheral blood lymphocytes (PBL) were stimulated with IL-2 and proliferation measured using a BrdU incorporation assay. The PBL were first stimulated for 72 hrs with PHA to induce IL-2 receptor, fasted for 24 hrs to stop cell proliferation followed by IL-2 stimulation for another 72 hrs (including 24 hr BrdU labeling). Cells were preincubated with test compounds 1 hr before IL-2 addition. Cells were cultured in RPMI 1640 containing 10% (v/v) FBS.

Example 3

In Vivo Models

Example 3.1

CIA Model 3.1.1 Materials

Completed Freund's adjuvant (CFA) and incomplete Freund's adjuvant (IFA) were purchased from Difco. Bovine collagen type II (CII), lipopolysaccharide (LPS), and Enbrel were obtained from Chondrex (Isle d'Abeau, France); Sigma (P4252, L'Isle d'Abeau, France), Whyett (25 mg injectable syringe, France) Acros Organics (Palo Alto, Calif.), respectively. All other reagents used were of reagent grade and all solvents were of analytical grade.

3.1.2 Animals

Dark Agouti rats (male, 7-8 weeks old) were obtained from Harlan Laboratories (Maison-Alfort, France). Rats were kept on a 12 hours light/dark cycle (0700-1900). The temperature was maintained at 22° C., and food and water were provided ad libitum.

3.1.3 Collagen Induced Arthritis (CIA)

One day before the experiment, CII solution (2 mg/mL) was prepared with 0.05 M acetic acid and stored at 4° C. Just before the immunization, equal volumes of adjuvant (IFA) and CII were mixed by a homogenizer in a pre-cooled glass bottle in an ice water bath. Extra adjuvant and prolonged homogenization might be required if an emulsion is not formed. 0.2 mL of the emulsion was injected intradermally at the base of the tail of each rat on day 1, a second booster intradermal injection (CII solution at 2 mg/mL in CFA 0.1 mL saline) was performed on day 9. This immunization method was modified from published methods (Sims N A et al., (2004) Targeting osteoclasts with zoledronic acid prevents bone destruction in collagen-induced arthritis, Arthritis Rheum. 50 2338-2346; Jou et al., 2005).

3.1.4 Study Design

The therapeutic effects of the test compounds were tested in the rat CIA model. Rats were randomly divided into equal groups and each group contained 10 rats. All rats were immunized on day 1 and boosted on day 9. Therapeutic dosing lasted from day 16 to day 30. The negative control group was treated with vehicle (MC 0.5%) and the positive control group with Enbrel (10 mg/kg, 3× week., s.c.). A compound of interest was typically tested at 3 doses, e.g. 3, 10, 30 mg/kg, p.o.

3.1.5 Clinical Assessment of Arthritis

Arthritis was scored according the method of Khachigian 2006, Lin et al 2007 and Nishida et al. 2004. The swelling of each of the four paws was ranked with the arthritic score as follows: 0—no symptoms; 1—mild, but definite redness and swelling of one type of joint such as the ankle or wrist, or apparent redness and swelling limited to individual digits, regardless of the number of affected digits; 2—moderate redness and swelling of two or more types of joints; 3—severe redness and swelling of the entire paw including digits; 4—maximally inflamed limb with involvement of multiple joints (maximum cumulative clinical arthritis score 16 per animal) (Nishida et al., 2004).

3.1.6 Change in Body Weight (%) after Onset of Arthritis

Clinically, body weight loss is associated with arthritis (Shelton et al., 2005; Argiles et al., 1998; Rall, 2004; Walsmith et al., 2004). Hence, changes in body weight after onset of arthritis could be used as a non-specific endpoint to evaluate the effect of therapeutics in the rat model. The change in body weight (%) after onset of arthritis was calculated as follows:

$$\text{Mice: } \frac{\text{Body Weight}_{(week\,6)} - \text{Body Weight}_{(week\,5)}}{\text{Body Weight}_{(week\,5)}} \times 100\%$$

$$\text{Rats: } \frac{\text{Body Weight}_{(week\,4)} - \text{Body Weight}_{(week\,3)}}{\text{Body Weight}_{(week\,3)}} \times 100\%$$

3.1.7 Radiology

X-ray photos were taken of the hind paws of each individual animal. A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5—mutilating abnormality without bony outlines. This scoring system is a modification from Salvemini et al., 2001; Bush et al., 2002; Sims et al., 2004; Jou et al., 2005.

3.1.8 Histology

After radiological analysis, the hind paws of mice were fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 m thick) were cut and each series of sections were 100 µm in between. The sections were stained with hematoxylin and eosin (H&E). Histologic examinations for synovial inflammation and bone and cartilage damage were performed double blind. In each paw, four parameters were assessed using a four-point scale. The parameters were cell infiltration, pannus severity, cartilage erosion and bone erosion. Scoring was performed as follows: 1-normal, 2-mild, 3-moderate, 4-marked. These four scores were summed together and represented as an additional score, namely the 'RA total score'.

3.1.9 Micro-Computed Tomography (pCT) Analysis of Calcaneus

Heel Bone

Bone degradation observed in RA occurs especially at the cortical bone and can be revealed by µCT analysis (Sims N A et al., 2004; Oste L et al., ECTC Montreal 2007). After scanning and 3D volume reconstruction of the calcaneus bone, bone degradation was measured as the number of discrete objects present per slide, isolated in silico perpendicular to the longitudinal axis of the bone. The more the bone that was degraded, the more discrete objects that were measured. 1000 slices, evenly distributed along the calcaneus (spaced by about 10.8 µm), are analyzed.

3.1.10 Results

The following compounds were efficacious in all readouts performed in the rat CIA study, with statistical significance in several of the readouts: 18, 37, 145, 176, 200, 215, and 330.

Example 3.2

Septic Shock Model

Injection of lipopolysaccharide (LPS) induces a rapid release of soluble tumour necrosis factor (TNF-alpha) into the periphery. This model is used to analyse prospective blockers of TNF release in vivo.

Six BALB/cJ female mice (20 g) per group were treated at the intended dosing once, po. Thirty minutes later, LPS (15 µg/kg; E. Coli serotype 0111:B4) was injected ip. Ninety minutes later, mice were euthanized and blood was collected. Circulating TNF alpha levels were determined using commercially available ELISA kits. Dexamethasone (5 µg/kg) was used as a reference anti-inflammatory compound. Selected compounds are tested at one or multiple doses, e.g. 3 and/or 10 and/or 30 mg/kg, po.

The following compounds exhibited a statistically significant reduction in the TNF release (>50%) at 30 mg/kg po: 12, 18, 36, 37, 52, 60, 74, 125, 148, 176, 197, 200, 207, 208, 215, and 229.

Example 3.3

MAB Model

The MAB model allows a rapid assessment of the modulation of an RA-like inflammatory response by therapeutics (Kachigian L M. Nature Protocols (2006) 2512-2516: Collagen antibody-induced arthritis). DBA/J mice were injected i.v. with a cocktail of mAbs directed against collagen II. One day later, compound treatment was initiated (vehicle: 10% (v/v) HPβCD). Three days later, mice received an i.p. LPS injection (50 µg/mouse), resulting in a fast onset of inflammation. Compound treatment was continued until 10 days after the mAb injection. Inflammation was read by measuring paw swelling and recording the clinical score of each paw. The cumulative clinical arthritis score of four limbs was presented to show the severity of inflammation. A scoring system is applied to each limb using a scale of 0-4, with 4 being the most severe inflammation.

0 Symptom free
1 Mild, but definite redness and swelling of one type of joint such as the ankle or wrist, or apparent redness and swelling limited to individual digits, regardless of the number of affected digits
2 Moderate redness and swelling of two or more types of joints
3 Severe redness and swelling of the entire paw including digits
4 Maximally inflamed limb with involvement of multiple joints The following compound, dosed p.o. at 30 mg/kg reduced the clinical score with statistical significance at 30 mg/kg and significantly reduced inflammation at 30 mg/kg doses: 36, 37, 176

Example 3.4

Oncology Models

In vitro and in vivo models to validate efficacy of small molecules towards JAK2-driven myeloproliferative diseases are described by Wernig et al. Cancer Cell 13, 311, 2008 and Geron et al. Cancer Cell 13, 321, 2008.

Example 3.5

Mouse IBD Model

In vitro and in vivo models to validate efficacy of small molecules towards IBD are described by Wirtz et al. 2007.

Example 3.6

Mouse Asthma Model

In vitro and in vivo models to validate efficacy of small molecules towards asthma are described by Nials et al., 2008; Ip et al. 2006; Pernis et al., 2002; Kudlacz et al., 2008)

Example 4

Toxicity, DMPK and Safety Models

Example 4.1

Thermodynamic Solubility

A solution of 1 mg/mL of the test compound is prepared in a 0.2M phosphate buffer pH7.4 or a 0.1M citrate buffer pH3.0 at room temperature in a glass vial.

The samples are rotated in a Rotator drive STR 4 (Stuart Scientific, Bibby) at speed 3.0 at room temperature for 24 hours.

After 24 hours, 800 µL of the sample is transferred to an eppendorf tube and centrifuged 5 min at 14000 rpm. 200 µL of the supernatant of the sample is then transferred to a Multiscreen® Solubility Plate (Millipore, MSSLBPC50) and the supernatant is filtered (10-12" Hg) with the aid of a vacuum manifold into a clean Greiner polypropylene V-bottom 96 well plate (Cat no. 651201). 5 µL of the filtrate is diluted into 95 µL (F20) of the same buffer used to incubate in the plate containing the standard curve (Greiner, Cat no. 651201).

The standard curve for the compound is prepared freshly in DMSO starting from a 10 mM DMSO stock solution diluted factor 2 in DMSO (5000 µM) and then further diluted in DMSO up to 19.5 µM. 3 µl of the dilution series as from 5000 µM is then transferred to a 97 µl acetonitrile-buffer mixture (50/50). The final concentration range was 2.5 to 150 µM.

The plate is sealed with sealing mats (MA96RD-04S, www.kinesis.co.uk) and samples are measured at room temperature on LCMS (ZQ 1525 from Waters) under optimized conditions using Quanoptimize to determine the appropriate mass of the molecule.

The samples are analyzed on LCMS with a flow rate of 1 ml/min. Solvent A is 15 mM ammonia and solvent B is acetonitrile. The sample is run under positive ion spray on an XBridge C18 3.5 µM (2.1×30 mm) column, from Waters. The solvent gradient has a total run time of 2 minutes and ranges from 5% B to 95% B.

Peak areas are analyzed with the aid of Masslynx software package and peak areas of the samples are plotted against the standard curve to obtain the solubility of the compound.

Solubility values are reported in µM or µg/mL.

Example 4.2

Aqueous Solubility

Starting from a 10 mM stock in DMSO, a serial dilution of the compound is prepared in DMSO. The dilution series is transferred to a 96 NUNC Maxisorb plate F-bottom (Cat no. 442404) and 0.2M phosphate buffer pH7.4 or 0.1M citrate buffer pH3.0 at room temperature is added.

The final concentration ranges from 200 µM to 2.5 µM in 5 equal dilution steps. The final DMSO concentration does not exceed 2%. 200 µM Pyrene is added to the corner points of each 96 well plate and serves as a reference point for calibration of Z-axis on the microscope.

The assay plates are sealed and incubated for 1 hour at 37° C. while shaking at 230 rpm. The plates are then scanned under a white light microscope, yielding individual pictures of the precipitate per concentration. The precipitate is analyzed and converted into a number which was plotted onto a graph. The first concentration at which the compound appears completely dissolved is the concentration is reported, however the true concentration lies somewhere between this concentration and one dilution step higher.

Solubility values are reported in µg/mL.

Example 4.3

Plasma Protein Binding

Equilibrium Dialysis

A 10 mM stock solution of the compound in DMSO is diluted with a factor 5 in DMSO. This solution is further diluted in freshly thawed human, rat, mouse or dog plasma (BioReclamation INC) with a final concentration of 10 µM and final DMSO concentration of 0.5% (5.5 µl in 1094.5 µl plasma in a PP-Masterblock 96 well (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 hours at 37° C. while shaking at 230 rpm. After incubation, 120 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200 rcf at 4° C. and the supernatant is transferred to a 96 v-bottom PP plate (Greiner, 651201) for analysis on LCMS.

The plate is sealed with sealing mats (MA96RD-04S) of www.kinesis.co.uk and samples are measured at room temperature on LCMS (ZQ 1525 from Waters) under optimized conditions using Quanoptimize to determine the appropriate mass of the molecule.

The samples are analyzed on LCMS with a flow rate of 1 mL/min. Solvent A was 15 mM ammonia and solvent B was acetonitrile. The sample was run under positive ion spray on an XBridge C18 3.5 µM (2.1×30 mm) column, from Waters. The solvent gradient has a total run time of 2 minutes and ranges from 5% B to 95% B.

Peak area from the compound in the buffer chamber and the plasma chamber are considered to be 100% compound. The percentage bound to plasma is derived from these results and is reported to the LIMS as percentage bound to plasma.

The solubility of the compound in the final test concentration in PBS is inspected by microscope to indicate whether precipitation is observed or not.

Example 4.4

Liability for QT Prolongation

Potential for QT prolongation is assessed in the hERG patch clamp assay.

4.4.1 Conventional Whole-Cell Patch-Clamp

Whole-cell patch-clamp recordings are performed using an EPC10 amplifier controlled by Pulse v8.77 software (HEKA). Series resistance is typically less than 10 MΩ and compensated by greater than 60%, recordings are not leak subtracted. Electrodes are manufactured from GC150TF pipette glass (Harvard), resistance is between 2 and 3 MΩ.

The external bathing solution contains: 135 mM NaCl, 5 mM KCl, 1.8 mM $CaCl_2$, 5 mM Glucose, 10 mM HEPES, pH 7.4.

The internal patch pipette solution contains: 100 mM Kgluconate, 20 mM KCl, 1 mM $CaCl_2$, 1 mM $MgCl_2$, 5 mM $Na_2ATP$, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to −50 mV for 2000 ms, holding potential was −80 mV. Pulses are applied every 20 s and all experiments are performed at room temperature.

4.4.2 Data Analysis $IC_{50}$ and $IC_{20}$ values are calculated for each compound tested. The fold difference between the $IC_{20}$ and the unbound $C_{max}$ concentrations of the test compound obtained at relevant therapeutic doses as determined by results obtained from the rat CIA model is calculated.

For the concentration response curves, peak tail current amplitude is measured during the voltage step to −50 mV. Curve-fitting of concentration-response data is performed using the equation:

$$y = a + [(b-a)/(1+10^{((\log c - x)d)})]$$

where a is minimum response, b is maximum response and d is Hill slope, this equation can be used to calculate both $IC_{50}$ (where y=50 and c is the $IC_{50}$ value) and $IC_{20}$ (where y=20 and c is the $IC_{20}$ value). GraphPad® Prism® (Graphpad® Software Inc.) software is used for all curve fitting.

A difference of 100 fold or greater indicates a low potential for QT prolongation.

Example 4.5

Microsomal Stability

A 10 mM stock solution of compound in DMSO was diluted 1000 fold in a 182 mM phosphate buffer pH7.4 in a 96 deep well plate (Greiner, Cat no. 780285) and pre-incubated at 37° C.

40 µL of deionised water was added to a well of a polypropylene Matrix 2D barcode labelled storage tube (Thermo Scientific) and pre-incubated at 37° C.

A Glucose-6-phophate-dehydrogenase (G6PDH) working stock solution was prepared in 182 mM phosphate buffer pH7.4 and placed on ice before use. A co-factor containing $NMgCl_2$, glucose-6-phosphate and NADP+ was prepared in deionised water and placed on ice before use.

A final working solution containing liver microsomes (Xenotech) of a species of interest (human mouse, rat, dog), previously described G6PDH and co-factors was prepared and this mix was incubated for no longer than 20 minutes at room temperature.

30 µL of the pre-heated compound dilution was added to 40 µL of pre-heated water in the Matrix tubes and 30 µL of the microsomal mix was added. Final reaction concentrations were 3 µM compound, 1 mg microsomes, 0.4 U/mL GDPDH, 3.3 mM $MgCl_2$, 3.3 mM glucose-6-phosphate and 1.3 mM NADP+.

To measure percentage remaining of compound at time zero MeOH or ACN was added (1:1) to the well before adding the microsomal mix. The plates were sealed with Matrix Sepra Seals™ (Matrix, Cat. No. 464) and shaken for a few seconds ensure complete mixing of all components.

The samples which were not stopped are incubated at 37° C. 3001 rpm and after 1 hour of incubation the reaction was stopped with MeOH or ACN (1:1).

After stopping the reaction the samples were mixed and placed on ice for 30 min to precipitate the proteins. The plates were then centrifuged 30 min at 1200 rcf at 4° C. and the supernatant was transferred to a 96 v-bottom PP plate (Greiner, 651201) for analysis on LCMS.

These plates were sealed with sealing mats (MA96RD-04S) of www.kinesis.co.uk and samples were measured at room temperature on LCMS (ZQ 1525 from Waters) under optimized conditions using Quanoptimize to determine the appropriate mass of the parent molecule.

The samples were analyzed on LCMS with a flow rate of 1 mL/min. Solvent A was 15 mM ammonia and solvent B was methanol or acetonitrile, depending on the stop solution used. The samples were run under positive ion spray on an XBridge C18 3.5 µM (2.1×30 mm) column, from Waters. The solvent gradient had a total run time of 2 minutes and ranges from 5% B to 95% B. Peak area from the parent compound at time 0 was considered to be 100% remaining. The percentage remaining after 1 hour incubation was calculated from time 0 and was calculated as the percentage remaining. The solubility of the compound in the final test concentration in buffer is inspected by microscope and results are reported.

The data on microsomal stability are expressed as a percentage of the total amount of compound remaining after 60 minutes.

TABLE IX

Microsomal Stability of Compounds

| Compound # | Human (%) | Rat (%) |
|---|---|---|
| 7 | ** | ** |
| 10 | **** | ** |
| 11 | **** | **** |
| 12 | *** | **** |
| 13 | *** | **** |
| 15 | ** | * |
| 17 | **** | ** |
| 18 | **** | ** |
| 19 | **** | *** |
| 21 | *** | **** |
| 23 | * | ** |
| 25 | * | * |
| 29 | *** | ** |
| 30 | * | * |
| 33 | **** | ** |
| 36 | * | *** |
| 37 | *** | *** |
| 39 | ** | ** |
| 40 | * | * |
| 41 | ** | ** |
| 42 | *** | **** |
| 43 | **** | **** |
| 46 | * | * |
| 48 | *** | *** |
| 49 | * | * |
| 50 | ** | * |

TABLE IX-continued

Microsomal Stability of Compounds

| Compound # | Human (%) | Rat (%) |
|---|---|---|
| 51 | * | * |
| 52 | * | * |
| 54 | **** | *** |
| 56 | **** | * |
| 57 | ** | ** |
| 58 | * | * |
| 59 | **** | *** |
| 60 | ** | * |
| 62 | ** | * |
| 64 | **** | *** |
| 66 | **** | * |
| 71 | * | **** |
| 72 | * | * |
| 74 | * | **** |
| 75 | * | * |
| 76 | * | * |
| 77 | ** | ** |
| 78 | **** | **** |
| 85 | * | * |
| 87 | * | * |
| 88 | * | * |
| 89 | *** | * |
| 90 | ** | ** |
| 92 | ** | * |
| 96 | * | * |
| 97 | * | ** |
| 98 | ** | ** |
| 99 | ** | * |
| 100 | * | * |
| 104 | * | * |
| 106 | * | * |
| 107 | * | * |
| 108 | * | * |
| 109 | * | * |
| 111 | ** | ** |
| 113 | ** | *** |
| 114 | * | * |
| 115 | *** | ** |
| 116 | *** | * |
| 118 | * | * |
| 119 | * | ** |
| 120 | * | * |
| 121 | * | * |
| 122 | * | * |
| 123 | * | * |
| 124 | * | * |
| 125 | *** | **** |
| 134 | *** | ** |
| 137 | *** | **** |
| 138 | ** | *** |
| 144 | ** | * |
| 145 | *** | * |
| 148 | *** | ** |
| 150 | *** | * |
| 156 | ** | ** |
| 157 | * | * |
| 163 | *** | ** |
| 164 | ** | ** |
| 166 | *** | * |
| 168 | **** | *** |
| 169 | * | * |
| 175 | * | * |
| 176 | **** | **** |
| 177 | **** | **** |
| 178 | * | ** |
| 179 | * | * |
| 182 | * | * |
| 189 | ** | ** |
| 190 | * | * |
| 192 | **** | **** |
| 196 | **** | **** |
| 197 | ** | *** |
| 198 | *** | *** |
| 199 | **** | **** |
| 200 | **** | *** |
| 201 | * | * |
| 202 | * | * |
| 203 | * | *** |
| 204 | * | * |
| 206 | **** | *** |
| 207 | **** | **** |
| 208 | *** | **** |
| 209 | **** | **** |
| 210 | **** | **** |
| 211 | * | * |
| 212 | *** | ** |
| 215 | **** | **** |
| 224 | * | * |
| 225 | * | * |
| 226 | * | * |
| 227 | ** | **** |
| 228 | ** | ** |
| 229 | *** | *** |
| 233 | *** | ** |
| 234 | ** | ** |
| 236 | * | * |
| 240 | ** | *** |
| 241 | *** | **** |
| 244 | * | * |
| 245 | * | * |
| 246 | * | * |
| 266 | * | **** |
| 267 | **** | **** |
| 271 | **** | **** |
| 273 | **** | **** |
| 280 | *** | ** |
| 297 | N/A | **** |
| 301 | N/A | * |
| 302 | *** | *** |
| 304 | N/A | **** |
| 306 | *** | ** |
| 316 | *** | **** |
| 317 | **** | *** |
| 319 | * | * |
| 325 | *** | *** |
| 328 | **** | **** |
| 330 | **** | **** |
| 331 | * | * |

\* 0-25
\*\* 26-50
\*\*\* 51-75
\*\*\*\* 76-100

Example 4.6

Caco2 Permeability

Bi-directional Caco-2 assays were performed as described below. Caco-2 cells were obtained from European Collection of Cell Cultures (ECACC, cat 86010202) and used after a 21 day cell culture in 24-well Transwell plates (Fisher TKT-545-020B).

$2 \times 10^5$ cells/well were seeded in plating medium consisting of DMEM+GlutaMAXI+1% NEAA+10% FBS (FetalClone II)+1% Pen/Strep. The medium was changed every 2-3 days.

Test and reference compounds (propranolol and rhodamine123 or vinblastine, all purchased from Sigma) were prepared in Hanks' Balanced Salt Solution containing 25 mM HEPES (pH7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) was added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 hour incubation at 37° C. while shaking at an orbital shaker at 150 rpm, 70 µL aliquots were taken from both apical (A) and basal (B) chambers and added to 100 µL1 50:50 acetonitrile:water solution containing analytical internal standard (0.5 µM carbamazepine) in a 96 well plate.

Lucifer yellow was measured with a Spectramax Gemini XS (Ex 426 nm and Em 538 nm) in a clean 96 well plate containing 150 µL of liquid from basolateral and apical side.

Concentrations of compound in the samples were measured by high performance liquid-chromatography/mass spectroscopy (LC-MS/MS).

Apparent permeability ($P_{app}$) values were calculated from the relationship:

$$P_{app} = [\text{compound}]_{acceptor\,final} \times V_{acceptor} / ([\text{compound}]_{donor\,initial} \times V_{donor}) / T_{inc} \times V_{donor} / \text{surface area} \times 60 \times 10^{-6} \text{ cm/s}$$

V=chamber volume
$T_{inc}$=incubation time.
Surface area=0.33 cm²

The Efflux ratios, as an indication of active efflux from the apical cell surface, were calculated using the ratio of $P_{app}$ B>A/$P_{app}$ A>B.

The following assay acceptance criteria were used:
Propranolol: $P_{app}$ (A>B) value ≥20(×10⁶ cm/s)
Rhodamine 123 or Vinblastine: $P_{app}$ (A>B) value <5 (×10⁻⁶ cm/s) with Efflux ratio ≥5.
Lucifer yellow permeability: ≤100 nm/s

TABLE X $P_{app}$ and Efflux Values of Compounds

| Cpd # | $P_{app}$ (A2B) cm × 10-6 sec−1 | Efflux ratio |
|---|---|---|
| 12 | 23.43 | 0.82 |
| 13 | 3.03 | 11.86 |
| 15 | 25.8 | 0.91 |
| 17 | 11.43 | 2.97 |
| 29 | 7.78 | 5.2 |
| 36 | 36.55 | 0.89 |
| 40 | 44.86 | 0.67 |
| 42 | 0.45 | 68.75 |
| 48 | 28.75 | 1 |
| 51 | 10.95 | 3.64 |
| 52 | 31.83 | 1.02 |
| 59 | 3.7 | 16.5 |
| 60 | 16.95 | 2.55 |
| 72 | 14.93 | 1.31 |
| 74 | 23.34 | 1.14 |
| 75 | 18.2 | 2.5 |
| 76 | 8.14 | 5.09 |
| 78 | 2 | 1.5 |
| 87 | 20.94 | 1.81 |
| 96 | 34.65 | 1 |
| 97 | 23.79 | 2.61 |
| 99 | 38.91 | 0.81 |
| 100 | 11.78 | 3.23 |
| 104 | 28 | 0.9 |
| 106 | 4.23 | 7.38 |
| 107 | 24.15 | 1.05 |
| 108 | 27.71 | 1.4 |
| 109 | 19 | 2.5 |
| 111 | 8.23 | 2.9 |
| 145 | 14.65 | 2 |
| 156 | 4.1 | 11.5 |
| 163 | 13.4 | 0.85 |
| 164 | 6.9 | 2.5 |
| 168 | 11 | 3.5 |
| 175 | 6.95 | 2 |
| 176 | 10.6 | 0.8 |
| 179 | 0.5 | 1 |
| 192 | 12.5 | 2 |
| 199 | 4.53 | 8.83 |
| 200 | 4.65 | 11.85 |
| 207 | 0.05 | 103.93 |
| 209 | 0.5 | 35.95 |
| 210 | 0.45 | 76.2 |
| 215 | 6.05 | 9.3 |
| 228 | 0.4 | 129.55 |
| 229 | 25.93 | 1.6 |
| 234 | 36.55 | 0.9 |
| 240 | 29.65 | 1.3 |
| 257 | 24 | 1.1 |
| 271 | 4 | 13 |
| 280 | 11.45 | 1.14 |
| 297 | 1.05 | 70.22 |
| 301 | 13.95 | 1.31 |
| 302 | 8.45 | 5.98 |
| 304 | 0.3 | 69.68 |
| 306 | 6.55 | 6.55 |
| 316 | 0.3 | 104.13 |
| 317 | 4.3 | 10.07 |
| 319 | 11.16 | 5.4 |
| 325 | 3.2 | 14.56 |
| 328 | 0.2! | 80.14! |
| 330 | 6.5 | 5.5 |

Example 4.7

Pharmacokinetic Study in Rodents 3.1.3 Pharmacokinetic Study

Compounds are formulated in PEG200/physiological saline or PEG400/DMSO/physiological saline mixtures for the intravenous route and in 0.5% methylcellulose or 10-30% hydroxylpropyl-β-cyclodextrine pH3 or pH7.4 for the oral route. Test compounds are orally dosed as a single esophageal gavage at 5-10 mg/kg and intravenously dosed as a bolus via the caudal vein at 1 mg/kg. Each group consists of 3 rats. Blood samples are collected either via the jugular vein using cannulated rats or at the retro-orbital sinus with lithium heparin as anti-coagulant at the time points in the following range: 0.05 to 8 hours (intravenous route), and 0.25 to 6 or 24 hours (oral route). Whole blood samples are centrifuged at 5000 rpm for 10 min and the resulting plasma samples are stored at −20° C. pending analysis.

3.1.4 Quantification of Compound Levels in Plasma

Plasma concentrations of each test compound are determined by an LC-MS/MS method in which the mass spectrometer was operated in positive electrospray mode.

3.1.5 Determination of Pharmacokinetic Parameters

Pharmacokinetic parameters are calculated using Winnonlin® (Pharsight®, United States).

Example 4.8

7-Day Rat Toxicity Study

A 7-day oral toxicity study with test compounds is performed in Sprague-Dawley male rats to assess their toxic potential and toxicokinetics, at daily doses of 100, 300 and 500 mg/kg/day, by gavage, at the constant dosage-volume of 5 mL/kg/day.

The test compounds are formulated in 30% (v/v) HPβCD in purified water. Each group included 5 principal male rats as well as 3 satellite animals for toxicokinetics. A fourth group is given 30% (v/v) HPβCD in water only, at the same frequency, dosage volume and by the same route of administration, and acted as the vehicle control group.

The goal of the study is to determine the lowest dose that resulted in no adverse events being identified (no observable adverse effect level—NOAEL).

It will be appreciated by those skilled in the art that the foregoing descriptions are exemplary and explanatory in nature, an as indiced intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

REFERENCES

Choy E H, Panayi G S. (2001). N Engl J Med. 344: 907-16.
Chubinskaya S and Kuettner K E (2003). Regulation of osteogenic proteins by chondrocytes. The international journal of biochemistry & cell biology 35 (9)1323-1340.
Clegg D O et al. (2006) N Engl J Med. 2006 354:795-808. Glucosamine, chondroitin sulfate, and the two in combination for painful knee osteoarthritis.
Firestein G S. (2003). Nature. 423:356-61.
Kachigian L M. (2006) Collagen antibody-induced arthritis, Nature Protocols 2512-2516:
Lcc D M, Weinblatt M E (2001). Lancet. 358: 903-11.
Legendre F, Dudhia J, Pujol J-P, Bogdanowiez P. (2003) JAK/STAT but not ERK1/ERK2 pathway mediates interleuking (IL)-6/soluble IL-6R down-regulation of type II collagen, aggrecan core, and link protein transcription in articular chondrocytes. J Biol Chem. 278 (5) 2903-2912.
Li W Q, Dehnade F, Zafarullah M. (2001) Oncostatin M-induced matrix metalloproteinase and tissue inhibitor of metalloproteinase-3 genes expression in chondrocytes requires janus kinase/STAT signaling pathway. (2001) J Immunol 166:3491-3498.
O'Dell J R. (2004) Therapeutic strategies for rheumatoid arthritis. N Engl J Med. 350(25):2591-602.
Osaki M, Tan L, Choy B K, Yoshida Y, Cheah K S E, Auron P E, Goldring M B. (2003) The TATA-containing core promoter of the type II collagen gene (COL2A1) is the target of interferon-gamma-mediated inhibition in human chondrocytes: requirement for STAT1alpha, JAK1 and JAK2. Biochem J 369:103-115.
Oste L et al., ECTC Montreal 2007: A high throughput method of measuring bone architectural disturbance in a murine CIA model by micro-CT morphometry
Otero M, Lago R, Lago F, Gomez Reino J J, Gualillo O. (2005) Signalling pathway involved in nitric oxide synthase type II activation in chondrocytes: synergistic effect of leptin with interleukin-1. Arthritis Research & Therapy 7:R581-R591.
Rodig S J, Meraz M A, White J M, Lampe P A, Riley J K, Arthur C D, King K L, Sheehan K C F, Yin L, Pennica D, Johnson E M, Schreiber R D. (1998) Disruption of the Jak1 gene demonstrates obligatory and nonredundant roles of the jaks in cytokine-induced biologic responses Cell 93: 373-383.
Sims N A et al., (2004) Targeting osteoclasts with zoledronic acid prevents bone destruction in collagen-induced arthritis, Arthritis Rheum. 50 2338-2346:
Smolen J S, Steiner G. (2003). Nat Rev Drug Discov. 2: 473-88.
Wernig et al. (2008) Efficacy of TG101348, a selective JAK2 inhibitor, in treatment of a murine model of JAK2V617F-induced polycythemia vera, Cancer Cell 13(4), 311-320
Geron et al. (2008) Selective inhibition of JAK2-driven erythroid differentiation of polycythemia vera progenitors Cancer Cell 13 (4), 321-30
Wieland H A, Michaelis M, Kirschbaum B J, Rudolphi K A. (2005). Nat Rev Drug Discov. 4:331-44. Osteoarthritis—an untreatable disease?
Wirtz et al. (2007) Mouse Models of Inflammatory Bowel Disease, Advanced Drug Delivery Reviews, 2007, 1073-1083:
Tam, L., McGlynn, L. M., Traynor, P., Mukherjee, R., Bartlett, J. M. S., Edwards, J. (2007) British Journal of Cancer, 97, 378-383
Constantinescu et al., 2007, Trends in Biochemical Sciences 33(3): 122-131
Tetsuji Naka, Norihiro Nishimoto and Tadamitsu Kishimoto, Arthritis Res 2002, 4 (suppl 3):S233-S242
O'Shea, J. J., Pesu, M., Borie, D. C., Changelian, P. S., Nature Reviews, 2004, 555-564
Nials et al. (2008) Mouse Models of Allergic Asthma: Acute and Chronic Allergen Challenge, Disease Models & Mechanisms, 213-220.
Ip et al. (2006) Interleukin (IL)-4 and IL-13 up-regulate monocyte chemoattractant protein-1 expression in human bronchial epithelial cells: involvement of p38 mitogen-activated protein kinase, extracellular signal-regulated kinase ½ and Janus kinase-2 but not c-Jun NH2-terminal kinase ½ signalling pathways, Clin. Exp. Immun, 162-172.
Pernis et al. (2002) JAK-STAT signaling in asthma J. Clin. Invest. 1279.
Kudlacz et al. (2008) The JAK-3 inhibitor CP-690550 is a potent anti-inflammatory agent in a murine model of pulmonary eosinophilia, Eur J Pharmaco 154-161.
Mullighan C G, Zhang J, Harvey R C, Collins-Underwood J R, Schulman B A, Phillips L A, Tasian S K, Loh M L, Su X, Liu W, Devidas M, Atlas S R, Chen I-M, Clifford R J, Gerhard D S, Carroll W L, Reaman G H, Smith M, Downing J R, Hunger S P Willmane C L; (2009) JAK mutations in high-risk childhood acute lymphoblastic leukemia, PNAS May 22. [Epub ahead of print]
Argiles J M, Lopez-Soriano F J. (1998) Catabolic proinflammatory cytokines. Curr Opin Clin Nutr Metab Care. 1:245-51.
Bush K A, Farmer K M, Walker J S, Kirkham B W. (2002) Reduction of joint inflammation and bone erosion in rat adjuvant arthritis by treatment with interleukin-17 receptor IgG1 Fc fusion protein. Arthritis Rheum. 46: 802-5.
Jou I M, Shiau A L, Chen S Y, Wang C R, Shieh D B, Tsai C S, Wu C L. (2005) Thrombospondin 1 as an effective gene therapeutic strategy in collagen-induced arthritis. Arthritis Rheum. 52:339-44.
Nishida K, Komiyama T, Miyazawa S, Shen Z N, Furumatsu T, Doi H, Yoshida A, Yamana J, Yamamura M, Ninomiya Y, Inoue H, Asahara H. (2004) Histone deacetylase inhibitor suppression of autoantibody-mediated arthritis in mice via regulation of p16INK4a and p21(WAF1/Cip1) expression. Arthritis Rheum. 10: 3365-76.
Rall L C, Roubenoff R. (2004) Rheumatoid cachexia: metabolic abnormalities, mechanisms and interventions. Rheumatology; 10:1219-23.
Salvemini D, Mazzon E, Dugo L, Serraino I, De Sarro A, Caputi A P, Cuzzocrea S. (2001) Amelioration of joint disease in a rat model of collagen-induced arthritis by M40403, a superoxide dismutase mimetic. Arthritis Rheum. 44:2909-21.

Shelton D L, Zeller J, Ho W H, Pons J, Rosenthal A. (2005) Nerve growth factor mediates hyperalgesia and cachexia in auto-immune arthritis. Pain. 116:8-16.

Sims N A, Green J R, Glatt M, Schlict S, Martin T J, Gillespie M T, Romas E. (2004) Targeting osteoclasts with zoledronic acid prevents bone destruction in collagen-induced arthritis. Arthritis Rheum., 50: 2338-46.

Walsmith J, Abad L, Kehayias J, Roubenoff R. (2004) Tumor necrosis factor-alpha production is associated with less body cell mass in women with rheumatoid arthritis. J Rheumatol.; 31:23-9.

Khachigian, L. M. Collagen antibody-induced arthritis. (2006) Nature Protocols 1, 2512-6.

Lin H S, Hu C Y, Chan H Y, Liew Y Y, Huang H P, Lepescheux L, Bastianelli E, Baron R, Rawadi G, Clément-Lacroix P. (2007) Anti-rheumatic activities of histone deacetylase (HDAC) inhibitors in vivo in collagen-induced arthritis in rodents. Br J Pharmacol. April; 150 (7):829-31.

All publications, including but not limited to patents and patent applications, cited in this specification are herein incorporated by reference as if each individual publication were specifically and individually indicated to be incorporated by reference herein as though fully set forth.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A method for the treatment of ulcerative colitis, said method comprising administering a therapeutically effective amount of a compound according to Formula III:

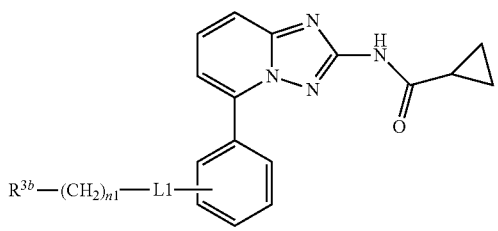

wherein the group

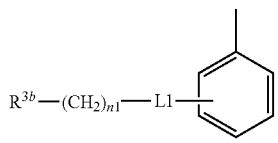

is selected from:

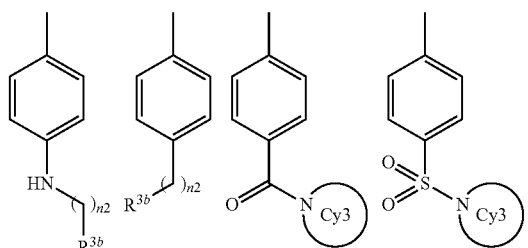

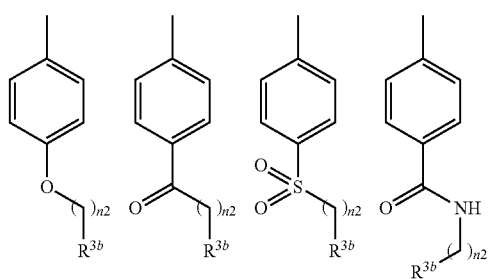

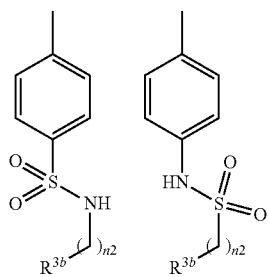

n2 is n1, and n1 is 0, 1, 2, 3 or 4;

$R^{3b}$ is

—OPh, and O-(4-F-Ph), or

CO—$R^{3c}$; and $R^{3c}$ is:

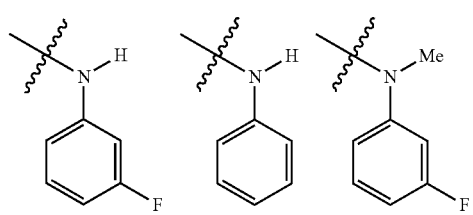

-continued

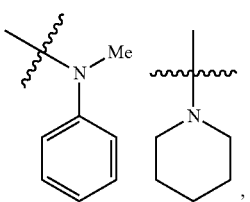

or
R³ᵇ is

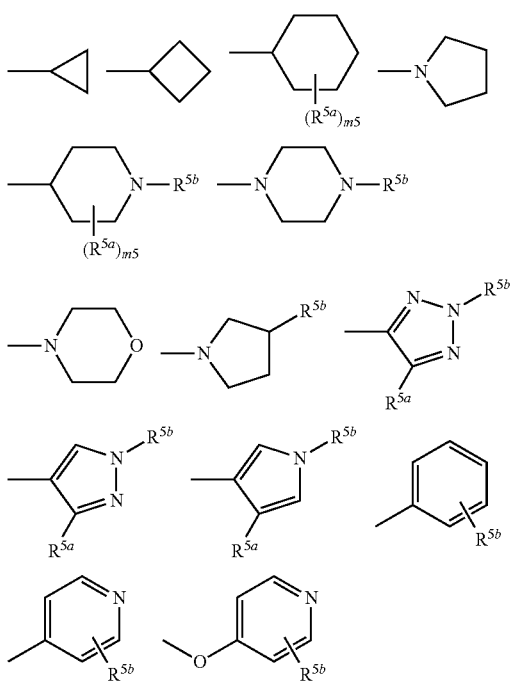

Cy3 is selected from:

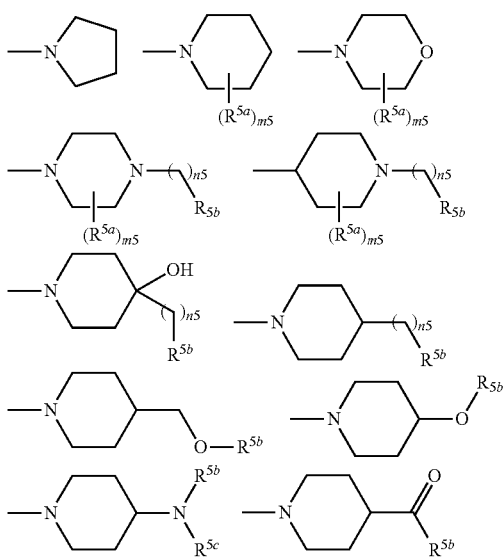

-continued

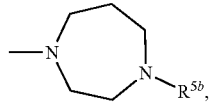

each $R^{5a}$ is independently $C_1$-$C_4$ alkyl, halo, $CF_3$ or Phenyl;
$R^{5b}$ is H, aryl, 5-10 membered heteroaryl, $C_3$-$C_6$ cycloalkyl, or 4-7 membered heterocycloalkyl;
$R^{5c}$ is H, or $C_1$-$C_4$ alkyl;
m5 is 0, 1, or 2;
n5 is 0, 1, or 2,
or a pharmaceutically acceptable salt thereof.

2. The method of claim 1 wherein said compound is prepared and administered as a pharmaceutical composition comprising a pharmaceutically acceptable carrier and a pharmaceutically effective amount of said compound or a pharmaceutically acceptable salt thereof.

3. A method for the treatment of ulcerative colitis, said method comprising administering a therapeutically effective amount of a compound according to formulae Va, Vb, Vc, or Vd:

Va

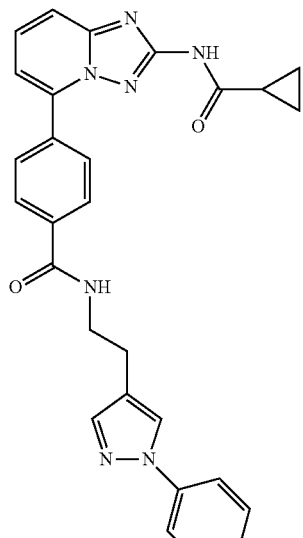

Vb

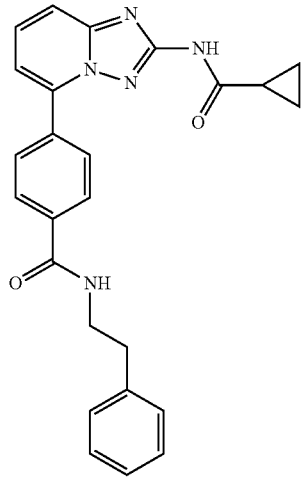

Vc

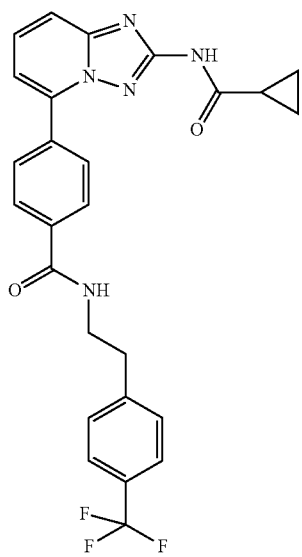

Vd

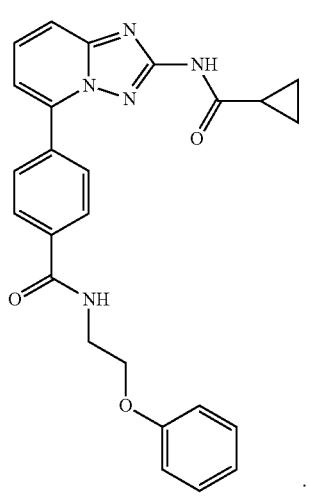

4. A method for the treatment of ulcerative colitis, said method comprising administering a therapeutically effective amount of a compound according to formulae VIc, or VId:

VIc

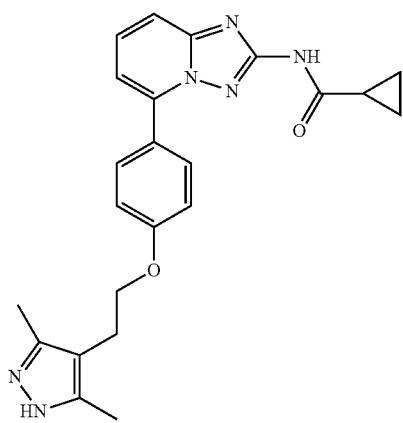

VId

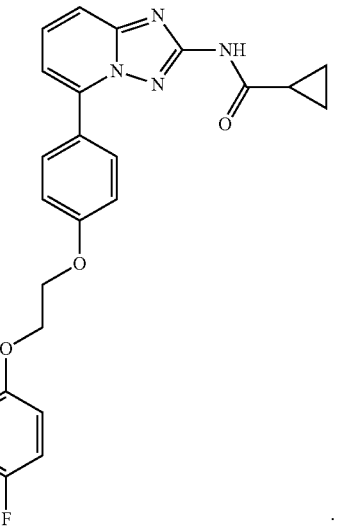

5. A method for the treatment of ulcerative colitis, said method comprising administering a therapeutically effective amount of a compound according to formulae VIIa, VIIb, VIIc, VIId, VIIe or VIIf:

VIIa

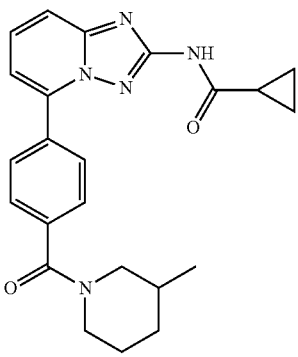

VIIb

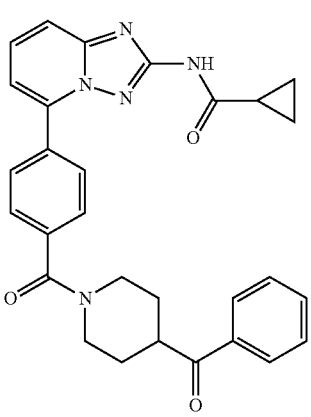

387
-continued

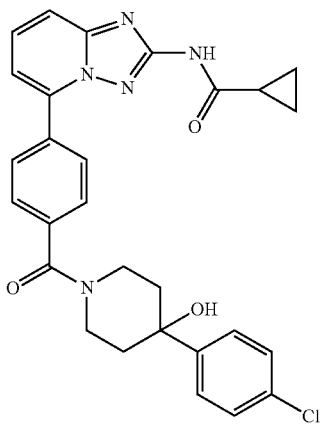
VIIc

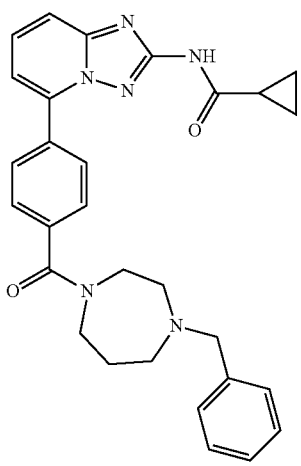
VIId

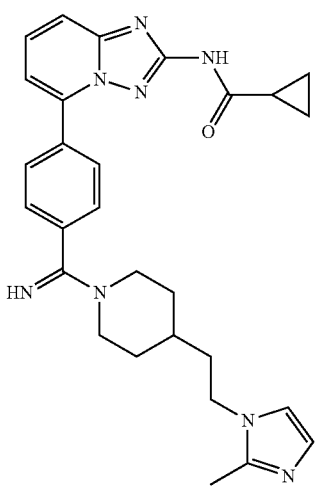
VIIe

388
-continued

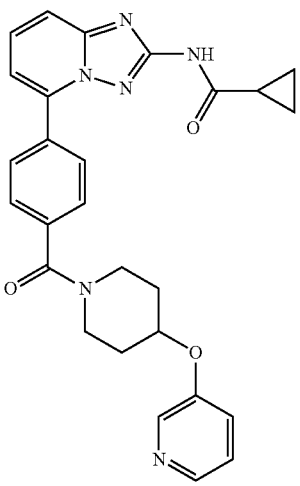
VIIf

6. A method for the treatment of ulcerative colitis, said method comprising administering a therapeutically effective amount of a compound selected from
N-(5-(4-(4-methylpiperazin-1-yl)phenyl)-[1,2,4]triazolo[1,5-a]pyridin-2-yl)cyclopropanecarboxamide,
N-(5-(3-(morpholinomethyl)phenyl)-[1,2,4]triazolo[1,5-a]pyridin-2-yl)cyclopropanecarboxamide,
N-(5-(biphenyl-4-yl)-[1,2,4]triazolo[1,5-a]pyridin-2-yl)cyclopropanecarboxamide,
N-(5-(4-benzoylphenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-cyclopropylbenzamide,
N-(5-(4-(benzyloxy)phenyl)-[1,2,4]triazolo[1,5-a]pyridin-2-yl)cyclopropanecarboxamide,
N-(5-(4-(N-cyclopropylsulfamoyl)phenyl)-[1,2,4]triazolo[1,5-a]pyridin-2-yl)cyclopropanecarboxamide,
N-(5-(3-(benzyloxy)phenyl)-[1,2,4]triazolo[1,5-a]pyridin-2-yl)cyclopropanecarboxamide,
N-(5-(4-(benzyloxy)-3-fluorophenyl)-[1,2,4]triazolo[1,5-a]pyridin-2-yl)cyclopropanecarboxamide,
N-(5-(2-(benzyloxy)phenyl)-[1,2,4]triazolo[1,5-a]pyridin-2-yl)cyclopropanecarboxamide,
N-(5-(4-(piperidine-1-carbonyl)phenyl)-[1,2,4]triazolo[1,5-a]pyridin-2-yl)cyclopropanecarboxamide,
N-(5-(4-(morpholinomethyl)phenyl)-[1,2,4]triazolo[1,5-a]pyridin-2-yl)cyclopropanecarboxamide,
N-(5-(4-(pyrrolidine-1-carbonyl)phenyl)-[1,2,4]triazolo[1,5-a]pyridin-2-yl)cyclopropanecarboxamide,
N-(5-(4-(thiophen-2-yl)phenyl)-[1,2,4]triazolo[1,5-a]pyridin-2-yl)cyclopropanecarboxamide,
N-(4-(2-(cyclopropanecarboxamido)-[1,2,4]triazolo[1,5-a]pyridin-5-yl)phenyl)benzamide,
N-(4-(2-(cyclopropanecarboxamido)-[1,2,4]triazolo[1,5-a]pyridin-5-yl)phenyl)-4-(trifluoromethyl)benzamide,
N-(5-(4-(2-phenylacetamido)phenyl)-[1,2,4]triazolo[1,5-a]pyridin-2-yl)cyclopropanecarboxamide,
N-(5-(4-(morpholine-4-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(pyridin-4-yl)benzamide,
N-cyclohexyl-4-(2-(cyclopropanecarboxamido)-[1,2,4]triazolo[1,5-a]pyridin-5-yl)benzamide,
N-(5-(4-(4-tert-butylpiperidine-1-carbonyl)phenyl)-[1,2,4]triazolo[1,5-a]pyridin-2-yl)cyclopropanecarboxamide, N-(5-(4-(1,4-diazepane-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(3-fluorobenzyl)benzamide,
4-(2-(cyclopropanecarboxamido)-[1,2,4]triazolo[1,5-a]pyridin-5-yl)-N-methyl-N-phenylbenzamide,
4-(2-(cyclopropanecarboxamido)-[1,2,4]triazolo[1,5-a]pyridin-5-yl)-N-(4-methoxybenzyl)-N-methylbenzamide,
4-(2-(cyclopropanecarboxamido)-[1,2,4]triazolo[1,5-a]pyridin-5-yl)-N-(1-methylpiperidin-4-yl)benzamide,
N-(5-(4-(4-fluorophenylsulfonamido)phenyl)-[1,2,4]triazolo[1,5-a]pyridin-2-yl)cyclopropanecarboxamide,
N-(4-(2-(cyclopropanecarboxamido)-[1,2,4]triazolo[1,5-a]pyridin-5-yl)phenyl)-2-fluorobenzamide,
N-(4-(2-(cyclopropanecarboxamido)-[1,2,4]triazolo[1,5-a]pyridin-5-yl)phenyl)pyrazine-2-carboxamide,
N-(5-(4-(pyridin-3-ylmethoxy)phenyl)-[1,2,4]triazolo[1,5-a]pyridin-2-yl)cyclopropanecarboxamide,
N-(5-(4-(pyridin-2-ylmethoxy)phenyl)-[1,2,4]triazolo[1,5-a]pyridin-2-yl)cyclopropanecarboxamide,
N-(5-(4-(3-(trifluoromethoxy)benzyloxy)phenyl)-[1,2,4]triazolo[1,5-a]pyridin-2-yl)cyclopropanecarboxamide,
N-(5-(4-(cyclobutylmethoxy)phenyl)-[1,2,4]triazolo[1,5-a]pyridin-2-yl)cyclopropanecarboxamide,
N-(5-(4-(cyclopentyloxy)phenyl)-[1,2,4]triazolo[1,5-a]pyridin-2-yl)cyclopropanecarboxamide,
N-(5-(4-(cyclohexylmethoxy)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(pyridin-3-ylmethyl)benzamide,
4-(2-(cyclopropanecarboxamido)-[1,2,4]triazolo[1,5-a]pyridin-5-yl)-N-phenylbenzamide,
N-(5-(2-(cyclopropanecarboxamido)-[1,2,4]triazolo[1,5-a]pyridin-5-yl)pyridin-2-yl)benzamide,
N-(4-(2-(cyclopropanecarboxamido)-[1,2,4]triazolo[1,5-a]pyridin-5-yl)phenyl)cyclohexanecarboxamide,
N-(5-(4-phenoxyphenyl)-[1,2,4]triazolo[1,5-a]pyridin-2-yl)cyclopropanecarboxamide,
N-(5-(4-((1-methyl-1H-pyrazol-3-yl)methylmethyl-1H-pyrazol-3-yl)methoxy)phenyl)-[1,2,4]triazolo[1,5-a]pyridin-2-yl)cyclopropanecarboxamide,
N-(5-(4-((3,5-dimethylisoxazol-4-yl)methoxy)phenyl)-[1,2,4]triazolo[1,5-a]pyridin-2-yl)cyclopropanecarboxamide,
N-(5-(4-((1,3-dimethyl-1H-pyrazol-5-yl)methyldimethyl-1H-pyrazol-5-yl)methoxy)phenyl)-[1,2,4]triazolo[1,5-a]pyridin-2-yl)cyclopropanecarboxamide,
N-(5-(4-(2-(3,5-dimethyl-1H-pyrazol-4-yl)ethyldimethyl-1H-pyrazol-4-yl)ethoxy)phenyl)-[1,2,4]triazolo[1,5-a]pyridin-2-yl)cyclopropanecarboxamide,
N-(5-(4-((5-methylisoxazol-3-yl)methoxy)phenyl)-[1,2,4]triazolo[1,5-a]pyridin-2-yl)cyclopropanecarboxamide,
N-(4-(2-(cyclopropanecarboxamido)-[1,2,4]triazolo[1,5-a]pyridin-5-yl)phenyl)-3-methoxybenzamide,
N-(5-(4-(2-fluorophenylsulfonamido)phenyl)-[1,2,4]triazolo[1,5-a]pyridin-2-yl)cyclopropanecarboxamide,
N-(4-(2-(cyclopropanecarboxamido)-[1,2,4]triazolo[1,5-a]pyridin-5-yl)phenyl)picolinamide,
N-benzyl-4-(2-(cyclopropanecarboxamido)-[1,2,4]triazolo[1,5-a]pyridin-5-yl)benzamide,
N-(5-(4-(1,2,3,4-tetrahydroisoquinoline-2-carbonyl)phenyl)-[1,2,4]triazolo[1,5-a]pyridin-2-yl)cyclopropanecarboxamide,
N-(5-(4-(cyclopropanesulfonamido)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(2-phenoxyethyl)benzamide,
N-(5-(4-((1,5-dimethyl-1H-pyrazol-3-yl)methyldimethyl-1H-pyrazol-3-yl)methoxy)phenyl)-[1,2,4]triazolo[1,5-a]pyridin-2-yl)cyclopropanecarboxamide,
N-(5-(4-((2,5-dimethyloxazol-4-yl)methoxy)phenyl)-[1,2,4]triazolo[1,5-a]pyridin-2-yl)cyclopropanecarboxamide,
N-(5-(4-(pyridine-3-sulfonamido)phenyl)-[1,2,4]triazolo[1,5-a]pyridin-2-yl)cyclopropanecarboxamide,
N-(5-(4-(1,3-dimethyl-1H-pyrazole-4-sulfonamido)phenyl)-[1,2,4]triazolo[1,5-a]pyridin-2-yl)cyclopropanecarboxamide,
N-(5-(4-(pyridin-3-yl)phenyl)-[1,2,4]triazolo[1,5-a]pyridin-2-yl)cyclopropanecarboxamide,
N-(5-(4-(1H-pyrazol-4-yl)phenyl)-[1,2,4]triazolo[1,5-a]pyridin-2-yl)cyclopropanecarboxamide,
N-(4-(2-(cyclopropanecarboxamido)-[1,2,4]triazolo[1,5-a]pyridin-5-yl)phenyl)-1-methyl-3-propyl-1H-pyrazole-5-carboxamide,
N-(4-(2-(cyclopropanecarboxamido)-[1,2,4]triazolo[1,5-a]pyridin-5-yl)phenyl)cyclobutanecarboxamide,
N-(5-(4-(4-methylpiperazine-1-carbonyl)phenyl)-[1,2,4]triazolo[1,5-a]pyridin-2-yl)cyclopropanecarboxamide,
N-(5-(4-(benzylamino)phenyl)-[1,2,4]triazolo[1,5-a]pyridin-2-yl)cyclopropanecarboxamide,
N-(5-(4-(4-(ethoxymethyl)piperidine-1-carbonyl)phenyl)-[1,2,4]triazolo[1,5-a]pyridin-2-yl)cyclopropanecarboxamide,
N-(5-(4-(4-benzoylpiperidine-1-carbonyl)phenyl)-[1,2,4]triazolo[1,5-a]pyridin-2-yl)cyclopropanecarboxamide,
N-(5-(4-(4-benzyl-1,4-diazepane-1-carbonyl)phenyl)-[1,2,4]triazolo[1,5-a]pyridin-2-yl)cyclopropanecarboxamide,
N-(5-(4-(2-phenylethylsulfonamido)phenyl)-[1,2,4]triazolo[1,5-a]pyridin-2-yl)cyclopropanecarboxamide,
N-(5-(4-(phenylmethylsulfonamido)phenyl)-[1,2,4]triazolo[1,5-a]pyridin-2-yl)cyclopropanecarboxamide,
N-(5-(4-((6-(trifluoromethyl)pyridin-3-yl)methoxy)phenyl)-[1,2,4]triazolo[1,5-a]pyridin-2-yl)cyclopropanecarboxamide,
N-(5-(4-(phenylsulfonamido)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(2-(pyrrolidin-1-yl)ethyl)benzamide,
4-(2-(cyclopropanecarboxamido)-[1,2,4]triazolo[1,5-a]pyridin-5-yl)-N-(3-morpholinopropyl)benzamide,
N-(5-(4-(4-propylphenylsulfonamido)phenyl)-[1,2,4]triazolo[1,5-a]pyridin-2-yl)cyclopropanecarboxamide,
N-(5-(4-(4-(4-chlorophenyl)piperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-phenethylbenzamide,
N-(5-(4-(2-(3-fluorophenyl)ethylsulfonamido)phenyl)-[1,2,4]triazolo[1,5-a]pyridin-2-yl)cyclopropanecarboxamide,
N-(5-(2-fluoro-4-(piperidine-1-carbonyl)phenyl)-[1,2,4]triazolo[1,5-a]pyridin-2-yl)cyclopropanecarboxamide,
N-butyl-4-(2-(cyclopropanecarboxamido)-[1,2,4]triazolo[1,5-a]pyridin-5-yl)-N-(3-morpholinopropyl)benzamide,
N-(5-(4-((2-(4-(trifluoromethyl)phenyl)thiazol-4-yl)methoxy)phenyl)-[1,2,4]triazolo[1,5-a]pyridin-2-yl)cyclopropanecarboxamide,
N-(5-(4-(4-acetamidobenzyloxy)phenyl)-[1,2,4]triazolo[1,5-a]pyridin-2-yl)cyclopropanecarboxamide, N-(5-(6-(2-(tetrahydro-2H-pyran-4-yl)ethylamino)pyridin-3-yl)-[1,2,4]triazolo[1,5-a]pyridin-2-yl)cyclopropanecarboxamide,
N-(5-(4-(4-(2-morpholinoethyl)piperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-methyl-N-phenethylbenzamide,
4-(2-(cyclopropanecarboxamido)-[1,2,4]triazolo[1,5-a]pyridin-5-yl)-N-(4-(trifluoromethyl)phenethyl)benzamide,
N-(5-(4-(2-(1H-pyrazol-1-yl)ethyl1H-pyrazol-1-yl)ethoxy)phenyl)-[1,2,4]triazolo[1,5-a]pyridin-2-yl)cyclopropanecarboxamide,
N-(5-(4-((1,2,4-oxadiazol-3-yl)methoxy)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-3-fluoro-N-(2-phenoxyethyl)benzamide,
N-(5-(4-(4-morpholinopiperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(2-methyl-1-morpholinopropan-2-yl)benzamide,
N-(5-(4-(4-(benzyl(methyl)amino)piperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(3,4-dimethoxyphenethyl)-N-methylbenzamide,
4-(2-(cyclopropanecarboxamido)-[1,2,4]triazolo[1,5-a]pyridin-5-yl)-N-(2-(1-phenyl-1H-pyrazol-4-yl)ethyl)benzamide,
N-(5-(4-(3-phenoxypropanamido)phenyl)-[1,2,4]triazolo[1,5-a]pyridin-2-yl)cyclopropanecarboxamide,
N-(5-(4-(3-phenylpropanamido)phenyl)-[1,2,4]triazolo[1,5-a]pyridin-2-yl)cyclopropanecarboxamide,
N-(5-(4-(4-(pyridin-3-yloxy)piperidine-1-carbonyl)phenyl)-[1,2,4]triazolo[1,5-a]pyridin-2-yl)cyclopropanecarboxamide
4-(2-(cyclopropanecarboxamido)-[1,2,4]triazolo[1,5-a]pyridin-5-yl)-3-fluoro-N-phenethylbenzamide,
N-(5-(4-(4-(3-chlorophenyl)piperazine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(3-phenylpropyl)benzamide,
N-(5-(4-(2-(4-fluorophenoxy)ethoxy)phenyl)-[1,2,4]triazolo[1,5-a]pyridin-2-yl)cyclopropanecarboxamide,
N-(5-(4-(2-(3-fluorophenylamino)-2-oxoethoxy)phenyl)-[1,2,4]triazolo[1,5-a]pyridin-2-yl)cyclopropanecarboxamide,
N-(5-(4-(2-oxo-2-(piperidin-1-yl)ethoxy)phenyl)-[1,2,4]triazolo[1,5-a]pyridin-2-yl)cyclopropanecarboxamide,
N-(5-(4-(2-(methyl(phenyl)amino)-2-oxoethoxy)phenyl)-[1,2,4]triazolo[1,5-a]pyridin-2-yl)cyclopropanecarboxamide,
(S)—N-(1-benzylpyrrolidin-3-yl)-4-(2-(cyclopropanecarboxamido)-[1,2,4]triazolo[1,5-a]pyridin-5-yl)benzamide,
(R)—N-(1-benzylpyrrolidin-3-yl)-4-(2-(cyclopropanecarboxamido)-[1,2,4]triazolo[1,5-a]pyridin-5-yl)benzamide,
N-(5-(4-(2-phenoxyethylsulfonamido)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(2-(pyridin-3-yl)ethyl)benzamide,
N-(5-(4-(1H-pyrazol-1-yl)benzyloxy)phenyl)-[1,2,4]triazolo[1,5-a]pyridin-2-yl)cyclopropanecarboxamide,
N-(5-(4-(4-((4-methylpiperazin-1-yl)methyl)benzyloxy)phenyl)-[1,2,4]triazolo[1,5-a]pyridin-2-yl)cyclopropanecarboxamide,
N-(5-(4-(2-(pyridin-3-yl)ethoxy)phenyl)-[1,2,4]triazolo[1,5-a]pyridin-2-yl)cyclopropanecarboxamide,
N-(5-(4-(4-(1H-benzo[d]imidazol-2-yl)piperidine-1-carbonyl)phenyl)-[1,2,4]triazolo[1,5-a]pyridin-2-yl)cyclopropanecarboxamide,
N-(5-(4-morpholinophenyl)-[1,2,4]triazolo[1,5-a]pyridin-2-yl)cyclopropanecarboxamide,
N-(5-(4-((4-methylpiperazin-1-yl)methyl)phenyl)-[1,2,4]triazolo[1,5-a]pyridin-2-yl)cyclopropanecarboxamide,
N-(5-(4-(4-(2-methoxyphenyl)piperidine-1-carbonyl)phenyl)-[1,2,4]triazolo[1,5-a]pyridin-2-yl)cyclopropanecarboxamide,
N-(5-(4-(4-(4-chlorophenyl)-4-hydroxypiperidine-1-carbonyl)phenyl)-[1,2,4]triazolo[1,5-a]pyridin-2-yl)cyclopropanecarboxamide,
N-(5-(4-(4-(o-tolyloxymethyl)piperidine-1-carbonyl)phenyl)-[1,2,4]triazolo[1,5-a]pyridin-2-yl)cyclopropanecarboxamide,
N-(5-(4-(3,5-dimethylpiperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-isopropyl-N-(4-(piperidin-1-yl)benzyl)benzamide,
4-(2-(cyclopropanecarboxamido)-[1,2,4]triazolo[1,5-a]pyridin-5-yl)-N-propyl-N-((tetrahydrofuran-2-yl)methyl)benzamide,
N-(5-(4-(4-fluoropiperidine-1-carbonyl)phenyl)-[1,2,4]triazolo[1,5-a]pyridin-2-yl)cyclopropanecarboxamide,
N-(5-(4-(4-(1H-indol-2-yl)piperidine-1-carbonyl)phenyl)-[1,2,4]triazolo[1,5-a]pyridin-2-yl)cyclopropanecarboxamide,
N-(5-(4-(piperidin-1-ylmethyl)phenyl)-[1,2,4]triazolo[1,5-a]pyridin-2-yl)cyclopropanecarboxamide,
1-(cyclopropanecarboxamido)-[1,2,4]triazolo[1,5-a]pyridin-5-yl)benzyl)piperidine-4-carboxamide,
N-(5-(4-((4-acetylpiperazin-1-yl)methyl)phenyl)-[1,2,4]triazolo[1,5-a]pyridin-2-yl)cyclopropanecarboxamide,
N-(5-(4-((4-(pyridin-2-yl)piperazin-1-yl)methyl)phenyl)-[1,2,4]triazolo[1,5-a]pyridin-2-yl)cyclopropanecarboxamide,
N-(5-(4-((4-(pyrimidin-2-yl)piperazin-1-yl)methyl)phenyl)-[1,2,4]triazolo[1,5-a]pyridin-2-yl)cyclopropanecarboxamide,
N-(5-(4-(2-methylpiperidine-1-carbonyl)phenyl)-[1,2,4]triazolo[1,5-a]pyridin-2-yl)cyclopropanecarboxamide,
N-(5-(4-(3-methylpiperidine-1-carbonyl)phenyl)-[1,2,4]triazolo[1,5-a]pyridin-2-yl)cyclopropanecarboxamide,
N-(5-(4-(4-methylpiperidine-1-carbonyl)phenyl)-[1,2,4]triazolo[1,5-a]pyridin-2-yl)cyclopropanecarboxamide,
N-(5-(4-(4-phenethylpiperidine-1-carbonyl)phenyl)-[1,2,4]triazolo[1,5-a]pyridin-2-yl)cyclopropanecarboxamide,
N-(5-(4-(4-(trifluoromethyl)piperidine-1-carbonyl)phenyl)-[1,2,4]triazolo[1,5-a]pyridin-2-yl)cyclopropanecarboxamide,
N-(5-(4-(4-(6-fluorobenzo[d]isoxazol-3-yl)piperidine-1-carbonyl)phenyl)-[1,2,4]triazolo[1,5-a]pyridin-2-yl)cyclopropanecarboxamide,
N-benzyl-4-(2-(cyclopropanecarboxamido)-[1,2,4]triazolo[1,5-a]pyridin-5-yl)-N-(2-(dimethylamino)ethyl)benzamide, 4-(2-(cyclopropanecarboxamido)-[1,2,4]triazolo[1,5-a]pyridin-5-yl)-N-(4-fluorobenzyl)-N-(1-methoxypropan-2-yl)benzamide,
N-(5-(4-(4-(1H-benzo[d][1,2,3]triazol-1-yl)piperidine-1-carbonyl)phenyl)-[1,2,4]triazolo[1,5-a]pyridin-2-yl)cyclopropanecarboxamide,
4-(2-(cyclopropanecarboxamido)-[1,2,4]triazolo[1,5-a]pyridin-5-yl)-N-(4-fluorobenzyl)-N-((tetrahydrofuran-2-yl)methyl)benzamide,
N-(5-(4-(imino(4-(2-(2-methyl-1H-imidazol-1-yl)ethyl)piperidin-1-yl)methyl)phenyl)-[1,2,4]triazolo[1,5-a]pyridin-2-yl)cyclopropanecarboxamide,
N-(5-(4-((methyl(2-(pyridin-2-yl)ethyl)amino)methyl)phenyl)-[1,2,4]triazolo[1,5-a]pyridin-2-yl)cyclopropanecarboxamide,
N-(5-(4-(4-benzyl-4-hydroxypiperidine-1-carbonyl)phenyl)-[1,2,4]triazolo[1,5-a]pyridin-2-yl)cyclopropanecarboxamide,
N-(5-(4-(benzyl(methyl)amino)phenyl)-[1,2,4]triazolo[1,5-a]pyridin-2-yl)cyclopropanecarboxamide,
N-(5-(4-((1H-tetrazol-5-yl)methyl1H-tetrazol-5-yl)methoxy)phenyl)-[1,2,4]triazolo[1,5-a]pyridin-2-yl)cyclopropanecarboxamide,
N-(5-(4-((methyl(4-(pyridin-2-yl)benzyl)amino)methyl)phenyl)-[1,2,4]triazolo[1,5-a]pyridin-2-yl)cyclopropanecarboxamide,
N-(5-(4-(((((1,5-dimethyl-1H-pyrazol-3-yl)methyl)(methyl)amino)methyl)phenyl)-[1,2,4]triazolo[1,5-a]pyridin-2-yl)cyclopropanecarboxamide,
N-(5-(4-((methyl(4-(pyrimidin-5-yl)benzyl)amino)methyl)phenyl)-[1,2,4]triazolo[1,5-a]pyridin-2-yl)cyclopropanecarboxamide
N-(5-(4-(methyl(pyridin-3-ylmethyl)amino)phenyl)-[1,2,4]triazolo[1,5-a]pyridin-2-yl)cyclopropanecarboxamide,
N-(5-(4-(benzyloxy)phenyl)-[1,2,4]triazolo[1,5-a]pyridin-2-yl)acetamide,
N-(5-(4-(3-(trifluoromethyl)piperidine-1-carbonyl)phenyl)-[1,2,4]triazolo[1,5-a]pyridin-2-yl)cyclopropanecarboxamide,
N-(5-(4-((6-morpholinopyridin-3-yl)methoxy)phenyl)-[1,2,4]triazolo[1,5-a]pyridin-2-yl)cyclopropanecarboxamide,
N-(5-(4-((6-(1H-pyrazol-4-yl)pyridin-3-yl)methyl1H-pyrazol-4-yl)pyridin-3-yl)methoxy)phenyl)-[1,2,4]triazolo[1,5-a]pyridin-2-yl)cyclopropanecarboxamide,
N-(5-(4-((6-(4-methylpiperazin-1-yl)pyridin-3-yl)methoxy)phenyl)-[1,2,4]triazolo[1,5-a]pyridin-2-yl)cyclopropanecarboxamide,
N-(5-(4-(4,4-difluoropiperidine-1-carbonyl)phenyl)-[1,2,4]triazolo[1,5-a]pyridin-2-yl)cyclopropanecarboxamide,
N-(5-(4-(3-phenylpiperidine-1-carbonyl)phenyl)-[1,2,4]triazolo[1,5-a]pyridin-2-yl)cyclopropanecarboxamide,
N-(5-(4-((6-(pyrrolidin-1-yl)pyridin-3-yl)methoxy)phenyl)-[1,2,4]triazolo[1,5-a]pyridin-2-yl)cyclopropanecarboxamide,
N-(5-(4-(3,3-dimethylpiperidine-1-carbonyl)phenyl)-[1,2,4]triazolo[1,5-a]pyridin-2-yl)cyclopropanecarboxamide,
N-(5-(4-((6-cyanopyridin-3-yl)methoxy)phenyl)-[1,2,4]triazolo[1,5-a]pyridin-2-yl)cyclopropanecarboxamide,
1-cyano-N-(4-(2-(cyclopropanecarboxamido)-[1,2,4]triazolo[1,5-a]pyridin-5-yl)phenyl)cyclopropanecarboxamide,
N-(5-(4-((6-(1-methyl-1H-pyrazol-4-yl)pyridin-3-yl)methylmethyl-1H-pyrazol-4-yl)pyridin-3-yl)methoxy)phenyl)-[1,2,4]triazolo[1,5-a]pyridin-2-yl)cyclopropanecarboxamide,
N-(cyanomethyl)-4-(2-(cyclopropanecarboxamido)-[1,2,4]triazolo[1,5-a]pyridin-5-yl)-N-phenethylbenzamide,
N-(5-(4-(pyridin-3-ylmethylamino)phenyl)-[1,2,4]triazolo[1,5-a]pyridin-2-yl)cyclopropanecarboxamide,
N-(5-(4-((6-(1H-tetrazol-5-yl)pyridin-3-yl)methyl1H-tetrazol-5-yl)pyridin-3-yl)methoxy)phenyl)-[1,2,4]triazolo[1,5-a]pyridin-2-yl)cyclopropanecarboxamide,
N-(5-(4-(1-(pyridin-2-yl)ethoxy)phenyl)-[1,2,4]triazolo[1,5-a]pyridin-2-yl)cyclopropanecarboxamide,
Methyl 6-((4-(2-(cyclopropanecarboxamido)-[1,2,4]triazolo[1,5-a]pyridin-5-yl)phenylcyclopropanecarboxamido)-[1,2,4]triazolo[1,5-a]pyridin-5-yl)phenoxy)methyl)nicotinate,
5-((4-(2-(cyclopropanecarboxamido)-[1,2,4]triazolo[1,5-a]pyridin-5-yl)phenylcyclopropanecarboxamido)-[1,2,4]triazolo[1,5-a]pyridin-5-yl)phenoxy)methyl)picolinamide,
N-(5-(1-(pyridin-2-ylmethyl)-1H-1,2,3-triazol-4-yl)-[1,2,4]triazolo[1,5-a]pyridin-2-yl)cyclopropanecarboxamide,
N-(5-(4-(pyridin-2-ylmethylsulfonyl)phenyl)-[1,2,4]triazolo[1,5-a]pyridin-2-yl)cyclopropanecarboxamide,
N-(5-(4-(pyridin-3-ylmethylsulfonyl)phenyl)-[1,2,4]triazolo[1,5-a]pyridin-2-yl)cyclopropanecarboxamide,
Cyclopropanecarboxylic acid {5-[4-(1-hydroxy-pyridin-3-ylmethoxy)-phenyl]-[1,2,4]triazolo[1,5-a]pyridin-2-yl}-amide,
Cyclopropanecarboxylic acid {5-[4-(6-methyl-pyridin-3-ylmethoxy)-phenyl]-[1,2,4]triazolo[1,5-a]pyridin-2-yl}-amide
Cyclopropanecarboxylic acid {5-[4-(6-chloro-pyridin-3-ylmethoxy)-phenyl]-[1,2,4]triazolo[1,5-a]pyridin-2-yl}-amide
Cyclopropanecarboxylic acid {5-[4-(1-methyl-1H-[1,2,4]triazol-3-ylmethoxy)-phenyl]-[1,2,4]triazolo[1,5-a]pyridin-2-yl}-amide,
Cyclopropanecarboxylic acid {5-[4-(1,1-dioxo-thiomorpholin-4-ylmethyl)-phenyl]-[1,2,4]triazolo[1,5-a]pyridin-2-yl}-amide,
Cyclopropanecarboxylic acid (5-{4-[2-(3,5-dimethyl-isoxazol-4-yl)-ethoxy]-phenyl}-[1,2,4]triazolo[1,5-a]pyridin-2-yl)-amide,
Cyclopropanecarboxylic acid {5-[4-(acetyl-pyridin-3-ylmethyl-amino)-phenyl]-[1,2,4]triazolo[1,5-a]pyridin-2-yl}-amide,
4-[2-(Cyclopropanecarbonyl-amino)-[1,2,4]triazolo[1,5-a]pyridin-5-yl]-N-(6-methoxy-pyridin-3-yl)-benzamide,
4-[2-(Cyclopropanecarbonyl-amino)-[1,2,4]triazolo[1,5-a]pyridin-5-yl]-N-(6-morpholin-4-yl-pyridin-3-yl)-benzamide,
4-[2-(Cyclopropanecarbonyl-amino)-[1,2,4]triazolo[1,5-a]pyridin-5-yl]-N-[6-(4-methyl-piperazin-1-yl)-pyridin-3-yl]-benzamide,
4-[2-(Cyclopropanecarbonyl-amino)-[1,2,4]triazolo[1,5-a]pyridin-5-yl]-N-pyridin-3-yl-benzamide,
Cyclopropanecarboxylic acid {5-[4-(acetyl-pyridin-2-ylmethyl-amino)-phenyl]-[1,2,4]triazolo[1,5-a]pyridin-2-yl}-amide,
Cyclopropanecarboxylic acid {5-[4-(4-hydroxy-piperidine-1-carbonyl)-phenyl]-[1,2,4]triazolo[1,5-a]pyridin-2-yl}-amide, Cyclopropanecarboxylic acid {5-[4-(4-cyano-piperidine-1-carbonyl)-phenyl]-[1,2,4]triazolo[1,5-a]pyridin-2-yl}-amide,
Cyclopropanecarboxylic acid {5-[4-(2-pyridin-2-yl-ethyl)-phenyl]-[1,2,4]triazolo[1,5-a]pyridin-2-yl}-amide,
Cyclopropanecarboxylic acid (5-{4-[(4-chloro-2-fluoro-phenylamino)-methyl]-phenyl}-[1,2,4]triazolo[1,5-a]pyridin-2-yl)-amide,
Cyclopropanecarboxylic acid {5-[4-(3,3-dimethyl-morpholin-4-ylmethyl)-phenyl]-[1,2,4]triazolo[1,5-a]pyridin-2-yl}-amide,
Cyclopropanecarboxylic acid {5-[4-((2R,6S)-2,6-dimethyl-morpholin-4-ylmethyl)-phenyl]-[1,2,4]triazolo[1,5-a]pyridin-2-yl}-amide,
Cyclopropanecarboxylic acid {5-[4-(2,6-dimethyl-morpholine-4-carbonyl)-phenyl]-[1,2,4]triazolo[1,5-a]pyridin-2-yl}-amide,
Cyclopropanecarboxylic acid {5-[4-(3,3-dimethyl-morpholine-4-carbonyl)-phenyl]-[1,2,4]triazolo[1,5-a]pyridin-2-yl}-amide,
Cyclopropanecarboxylic acid {5-[4-((1S,4S)-2-oxa-5-aza-bicyclo[2.2.1]heptane-5-carbonyl)-phenyl]-[1,2,4]triazolo[1,5-a]pyridin-2-yl}-amide,
4-[2-(Cyclopropanecarbonyl-amino)-[1,2,4]triazolo[1,5-a]pyridin-5-yl]-N-(5-cyclopropyl-2-methyl-2H-pyrazol-3-yl)-benzamide,
Cyclopropanecarboxylic acid (5-{4-[4-(morpholine-4-carbonyl)-piperidine-1-carbonyl]-phenyl}-[1,2,4]triazolo[1,5-a]pyridin-2-yl)-amide,
Cyclopropanecarboxylic acid {5-[4-(4-acetyl-piperazine-1-carbonyl)-phenyl]-[1,2,4]triazolo[1,5-a]pyridin-2-yl}-amide,
4-[2-(Cyclopropanecarbonyl-amino)-[1,2,4]triazolo[1,5-a]pyridin-5-yl]-N-pyridazin-3-yl-benzamide,
Cyclopropanecarboxylic acid {5-[4-(pyridazin-3-ylaminomethyl)-phenyl]-[1,2,4]triazolo[1,5-a]pyridin-2-yl}-amide,
Cyclopropanecarboxylic acid {5-[4-(pyridin-3-ylaminomethyl)-phenyl]-[1,2,4]triazolo[1,5-a]pyridin-2-yl}-amide,
Cyclopropanecarboxylic acid (5-{4-[(4-cyanomethyl-phenylamino)-methyl]-phenyl}-[1,2,4]triazolo[1,5-a]pyridin-2-yl)-amide,
Cyclopropanecarboxylic acid (5-{4-[(2-cyanomethyl-phenylamino)-methyl]-phenyl}-[1,2,4]triazolo[1,5-a]pyridin-2-yl)-amide,
Cyclopropanecarboxylic acid (5-{4-[(2-fluoro-phenylamino)-methyl]-phenyl}-[1,2,4]triazolo[1,5-a]pyridin-2-yl)-amide,
4-{4-[2-(Cyclopropanecarbonyl-amino)-[1,2,4]triazolo[1,5-a]pyridin-5-yl]-benzylamino}-benzamide,
3-{4-[2-(Cyclopropanecarbonyl-amino)-[1,2,4]triazolo[1,5-a]pyridin-5-yl]-benzylamino}-benzamide,
Cyclopropanecarboxylic acid {5-[4-(pyrimidin-2-ylaminomethyl)-phenyl]-[1,2,4]triazolo[1,5-a]pyridin-2-yl}-amide,
Cyclopropanecarboxylic acid (5-{4-[(1S,4S)-1-(2-oxa-5-aza-bicyclo[2.2.1]hept-5-yl)methyl]-phenyl}-[1,2,4]triazolo[1,5-a]pyridin-2-yl)-amide,
Cyclopropanecarboxylic acid {5-[4-(2-phenyl-morpholin-4-ylmethyl)-phenyl]-[1,2,4]triazolo[1,5-a]pyridin-2-yl}-amide,
Cyclopropanecarboxylic acid {5-[4-(4-cyano-piperidin-1-ylmethyl)-phenyl]-[1,2,4]triazolo[1,5-a]pyridin-2-yl}-amide,
Cyclopropanecarboxylic acid {5-[4-(4-fluoro-piperidin-1-ylmethyl)-phenyl]-[1,2,4]triazolo[1,5-a]pyridin-2-yl}-amide,
Cyclopropanecarboxylic acid {5-[4-(4,4-difluoro-piperidin-1-ylmethyl)-phenyl]-[1,2,4]triazolo[1,5-a]pyridin-2-yl}-amide,
Cyclopropanecarboxylic acid [5-(4-{[6-(4-methyl-piperazin-1-yl)-pyridin-3-ylamino]-methyl}-phenyl)-[1,2,4]triazolo[1,5-a]pyridin-2-yl]-amide,
Cyclopropanecarboxylic acid (5-{4-[(6-methoxy-pyridin-3-ylamino)-methyl]-phenyl}-[1,2,4]triazolo[1,5-a]pyridin-2-yl)-amide,
Cyclopropanecarboxylic acid (5-{4-[(6-morpholin-4-yl-pyridin-3-ylamino)-methyl]-phenyl}-[1,2,4]triazolo[1,5-a]pyridin-2-yl)-amide,
Cyclopropanecarboxylic acid [5-(4-phenoxymethyl-phenyl)-[1,2,4]triazolo[1,5-a]pyridin-2-yl]-amide,
Cyclopropanecarboxylic acid {5-[4-(6-cyano-pyridin-3-yl)-phenyl]-[1,2,4]triazolo[1,5-a]pyridin-2-yl}-amide,
Cyclopropanecarboxylic acid {5-[4-(4-trifluoromethyl-piperidin-1-ylmethyl)-phenyl]-[1,2,4]triazolo[1,5-a]pyridin-2-yl}-amide,
Cyclopropanecarboxylic acid (5-{4-[4-(2,2,2-trifluoro-ethyl)-piperazin-1-ylmethyl]-phenyl}-[1,2,4]triazolo[1,5-a]pyridin-2-yl)-amide,
Cyclopropanecarboxylic acid {5-[4-(4-hydroxy-piperidin-1-ylmethyl)-phenyl]-[1,2,4]triazolo[1,5-a]pyridin-2-yl}-amide,
Cyclopropanecarboxylic acid (5-{4-[4-(1-hydroxy-1-methyl-ethyl)-piperidin-1-ylmethyl]-phenyl}-[1,2,4]triazolo[1,5-a]pyridin-2-yl)-amide,
Cyclopropanecarboxylic acid {5-[4-(pyridin-2-ylaminomethyl)-phenyl]-[1,2,4]triazolo[1,5-a]pyridin-2-yl}-amide,
Cyclopropanecarboxylic acid (5-{4-[(2,4-difluoro-3-methoxy-phenylamino)-methyl]-phenyl}-[1,2,4]triazolo[1,5-a]pyridin-2-yl)-amide,
Cyclopropanecarboxylic acid (5-{4-[(2,6-difluoro-phenylamino)-methyl]-phenyl}-[1,2,4]triazolo[1,5-a]pyridin-2-yl)-amide,
Cyclopropanecarboxylic acid {5-[4-(4-diethylamino-piperidin-1-ylmethyl)-phenyl]-[1,2,4]triazolo[1,5-a]pyridin-2-yl}-amide,
Cyclopropanecarboxylic acid (5-{4-[(2-fluoro-5-trifluoromethyl-phenylamino)-methyl]-phenyl}-[1,2,4]triazolo[1,5-a]pyridin-2-yl)-amide,
3-{4-[2-(Cyclopropanecarbonyl-amino)-[1,2,4]triazolo[1,5-a]pyridin-5-yl]-benzylamino}-4-methyl-benzamide,
Cyclopropanecarboxylic acid {5-[4-(4-hydroxymethyl-piperidin-1-ylmethyl)-phenyl]-[1,2,4]triazolo[1,5-a]pyridin-2-yl}-amide,
3-{4-[2-(Cyclopropanecarbonyl-amino)-[1,2,4]triazolo[1,5-a]pyridin-5-yl]-benzyloxy}-benzamide,
Cyclopropanecarboxylic acid {5-[4-(3-diethylamino-pyrrolidin-1-ylmethyl)-phenyl]-[1,2,4]triazolo[1,5-a]pyridin-2-yl}-amide,
Cyclopropanecarboxylic acid {5-[4-((1R,4R)-5-ethyl-2,5-diaza-bicyclo[2.2.1]hept-2-ylmethyl)-phenyl]-[1,2,4]triazolo[1,5-a]pyridin-2-yl}-amide,
Cyclopropanecarboxylic acid {5-[4-(3-oxo-morpholin-4-ylmethyl)-phenyl]-[1,2,4]triazolo[1,5-a]pyridin-2-yl}-amide,
3-{4-[2-(Cyclopropanecarbonyl-amino)-[1,2,4]triazolo[1,5-a]pyridin-5-yl]-benzylamino}-4-methoxy-benzamide, Cyclopropanecarboxylic acid (5-{4-[(2-fluoro-6-methyl-pyridin-3-ylamino)-methyl]-phenyl}-[1,2,4]triazolo[1,5-a]pyridin-2-yl)-amide,
Cyclopropanecarboxylic acid (5-{4-[(3,5-difluoro-pyridin-2-ylamino)-methyl]-phenyl}-[1,2,4]triazolo[1,5-a]pyridin-2-yl)-amide,
Cyclopropanecarboxylic acid (5-{4-[(4-cyano-2-fluoro-phenylamino)-methyl]-phenyl}-[1,2,4]triazolo[1,5-a]pyridin-2-yl)-amide,
Cyclopropanecarboxylic acid (5-{4-[(2-fluoro-4-methyl-phenylamino)-methyl]-phenyl}-[1,2,4]triazolo[1,5-a]pyridin-2-yl)-amide
Cyclopropanecarboxylic acid [5-(4-pyrrolidin-1-ylmethyl-phenyl)-[1,2,4]triazolo[1,5-a]pyridin-2-yl]-amide,
Cyclopropanecarboxylic acid [5-(4-phenylaminomethyl-phenyl)-[1,2,4]triazolo[1,5-a]pyridin-2-yl]-amide,
Cyclopropanecarboxylic acid (5-{4-[3-(acetyl-methyl-amino)-pyrrolidin-1-ylmethyl]-phenyl}-[1,2,4]triazolo[1,5-a]pyridin-2-yl)-amide,
Cyclopropanecarboxylic acid {5-[4-(3-dimethylamino-pyrrolidin-1-ylmethyl)-phenyl]-[1,2,4]triazolo[1,5-a]pyridin-2-yl}-amide,
Cyclopropanecarboxylic acid {5-[4-(3,3-difluoro-pyrrolidin-1-ylmethyl)-phenyl]-[1,2,4]triazolo[1,5-a]pyridin-2-yl}-amide,
Cyclopropanecarboxylic acid (5-{4-[3-(4-cyano-phenoxymethyl)-azetidin-1-ylmethyl]-phenyl}-[1,2,4]triazolo[1,5-a]pyridin-2-yl)-amide,
Cyclopropanecarboxylic acid {5-[4-(2-oxo-2-piperidin-1-yl-ethyl)-phenyl]-[1,2,4]triazolo[1,5-a]pyridin-2-yl]-amide,
Cyclopropanecarboxylic acid (5-{4-[2-(1,1-dioxo-thiomorpholin-4-yl)-2-oxo-ethyl]-phenyl}-[1,2,4]triazolo[1,5-a]pyridin-2-yl)-amide,
Cyclobutanecarboxylic acid 4-[2-(cyclopropanecarbonyl-amino)-[1,2,4]triazolo[1,5-a]pyridin-5-yl]-benzylamide,
Cyclopropanecarboxylic acid {5-[4-(3-dimethylamino-piperidine-1-carbonyl)-phenyl]-[1,2,4]triazolo[1,5-a]pyridin-2-yl}-amide,
Cyclopropanecarboxylic acid {5-[4-(3-hydroxy-piperidine-1-carbonyl)-phenyl]-[1,2,4]triazolo[1,5-a]pyridin-2-yl}-amide,
Cyclopropanecarboxylic acid {5-[4-(3,3-difluoro-pyrrolidine-1-carbonyl)-phenyl]-[1,2,4]triazolo[1,5-a]pyridin-2-yl}-amide,
Cyclopropanecarboxylic acid 4-[2-(cyclopropanecarbonyl-amino)-[1,2,4]triazolo[1,5-a]pyridin-5-yl]-benzylamide,
4-[2-(Cyclopropanecarbonyl-amino)-[1,2,4]triazolo[1,5-a]pyridin-5-yl]-N-(1,1-dioxo-tetrahydrothiophen-3-yl)-N-methyl-benzamide,
1-{4-[2-(Cyclopropanecarbonyl-amino)-[1,2,4]triazolo[1,5-a]pyridin-5-yl]-benzoyl}-piperidine-4-carboxylic acid amide,
1-{4-[2-(Cyclopropanecarbonyl-amino)-[1,2,4]triazolo[1,5-a]pyridin-5-yl]-benzoyl}-piperidine-2-carboxylic acid amide,
Cyclopropanecarboxylic acid {5-[4-(3-hydroxymethyl-piperidine-1-carbonyl)-phenyl]-[1,2,4]triazolo[1,5-a]pyridin-2-yl}-amide,
Cyclopropanecarboxylic acid {5-[4-(3-oxo-piperazine-1-carbonyl)-phenyl]-[1,2,4]triazolo[1,5-a]pyridin-2-yl}-amide,
Cyclopropanecarboxylic acid (5-{4-[3-(4-cyano-phenoxy)-azetidin-1-ylmethyl]-phenyl}-[1,2,4]triazolo[1,5-a]pyridin-2-yl)-amide,
(1-{4-[2-(Cyclopropanecarbonyl-amino)-[1,2,4]triazolo[1,5-a]pyridin-5-yl]-benzyl}-azetidin-3-yl)-carbamic acid tert-butyl ester,
Cyclopropanecarboxylic acid {5-[4-(3-fluoro-piperidin-1-ylmethyl)-phenyl]-[1,2,4]triazolo[1,5-a]pyridin-2-yl}-amide,
Cyclopropanecarboxylic acid {5-[4-(4-methoxy-piperidin-1-ylmethyl)-phenyl]-[1,2,4]triazolo[1,5-a]pyridin-2-yl}-amide,
Cyclopropanecarboxylic acid {5-[4-(4-ethoxy-piperidin-1-ylmethyl)-phenyl]-[1,2,4]triazolo[1,5-a]pyridin-2-yl}-amide,
Cyclopropanecarboxylic acid (5-{4-[3-(acetyl-methyl-amino)-azetidin-1-ylmethyl]-phenyl}-[1,2,4]triazolo[1,5-a]pyridin-2-yl)-amide,
Cyclopropanecarboxylic acid (5-{4-[3-(4-cyano-benzyloxy)-azetidin-1-yl]-phenyl}-[1,2,4]triazolo[1,5-a]pyridin-2-yl)-amide,
Cyclopropanecarboxylic acid {5-[4-(3-diethylamino-pyrrolidine-1-carbonyl)-phenyl]-[1,2,4]triazolo[1,5-a]pyridin-2-yl}-amide,
Cyclopropanecarboxylic acid {5-[4-(4-hydroxy-4-phenyl-piperidine-1-carbonyl)-phenyl]-[1,2,4]triazolo[1,5-a]pyridin-2-yl}-amide,
Cyclopropanecarboxylic acid {5-[4-(3-acetylamino-azetidine-1-carbonyl)-phenyl]-[1,2,4]triazolo[1,5-a]pyridin-2-yl}-amide,
Cyclopropanecarboxylic acid {5-[4-(3-cyano-azetidin-1-yl)-phenyl]-[1,2,4]triazolo[1,5-a]pyridin-2-yl}-amide,
Cyclopropanecarboxylic acid {5-[4-(3-dimethylamino-pyrrolidine-1-carbonyl)-phenyl]-[1,2,4]triazolo[1,5-a]pyridin-2-yl}-amide,
Cyclopropanecarboxylic acid (5-{4-[3-(piperidine-1-carbonyl)-piperidine-1-carbonyl]-phenyl}-[1,2,4]triazolo[1,5-a]pyridin-2-yl)-amide,
Cyclopropanecarboxylic acid {5-[4-(3-dimethylamino-azetidin-1-ylmethyl)-phenyl][1,2,4]triazolo[1,5-a]pyridin-2-yl}-amide,
Cyclopropanecarboxylic acid (5-{4-[4-(pyridin-3-yloxymethyl)-piperidine-1-carbonyl]-phenyl}-[1,2,4]triazolo[1,5-a]pyridin-2-yl)-amide,
Cyclopropanecarboxylic acid {5-[4-(4-methoxy-piperidine-1-carbonyl)-phenyl]-[1,2,4]triazolo[1,5-a]pyridin-2-yl}-amide,
Cyclopropanecarboxylic acid {5-[4-(4-ethoxy-piperidine-1-carbonyl)-phenyl]-[1,2,4]triazolo[1,5-a]pyridin-2-yl}-amide,
1-{4-[2-(Cyclopropanecarbonyl-amino)-[1,2,4]triazolo[1,5-a]pyridin-5-yl]-benzoyl}-piperidine-3-carboxylic acid diethylamide,
Cyclopropanecarboxylic acid {5-[4-(3-acetylamino-piperidine-1-carbonyl)-phenyl]-[1,2,4]triazolo[1,5-a]pyridin-2-yl}-amide,
Cyclopropanecarboxylic acid (5-{4-[acetyl-(6-cyano-pyridin-3-ylmethyl)-amino]-phenyl}-[1,2,4]triazolo[1,5-a]pyridin-2-yl)-amide,
Cyclopropanecarboxylic acid {5-[4-(3-dimethylaminomethyl-azetidin-1-ylmethyl)-phenyl]-[1,2,4]triazolo[1,5-a]pyridin-2-yl}-amide,
1-{4-[2-(Cyclopropanecarbonyl-amino)-[1,2,4]triazolo[1,5-a]pyridin-5-yl]-benzyl}-azetidine-3-carboxylic acid dimethylamide, Cyclopropanecarboxylic acid {5-[4-(3-morpholin-4-yl-azetidin-1-ylmethyl)-phenyl]-[1,2,4]triazolo[1,5-a]pyridin-2-yl}-amide,
Cyclopropanecarboxylic acid {5-[4-(4-cyanomethyl-phenoxymethyl)-phenyl]-[1,2,4]triazolo[1,5-a]pyridin-2-yl}-amide,
Cyclopropanecarboxylic acid {5-[4-(isoxazol-3-ylaminomethyl)-phenyl]-[1,2,4]triazolo[1,5-a]pyridin-2-yl}-amide,
Cyclopropanecarboxylic acid {5-[4-(3-cyano-azetidin-1-ylmethyl)-phenyl]-[1,2,4]triazolo[1,5-a]pyridin-2-yl}-amide,
Cyclopropanecarboxylic acid (5-{4-[(1,1-dioxo-tetrahydro-thiophen-3-ylamino)-methyl]-phenyl}-[1,2,4]triazolo[1,5-a]pyridin-2-yl)-amide,
Cyclopropanecarboxylic acid {5-[4-((S)-3-hydroxy-pyrrolidin-1-ylmethyl)-phenyl]-[1,2,4]triazolo[1,5-a]pyridin-2-yl}-amide,
2-{4-[2-(Cyclopropanecarbonyl-amino)-[1,2,4]triazolo[1,5-a]pyridin-5-yl]-benzylamino}-benzamide,
Cyclopropanecarboxylic acid {5-[4-((R)-3-hydroxy-pyrrolidin-1-ylmethyl)-phenyl]-[1,2,4]triazolo[1,5-a]pyridin-2-yl}-amide,
4-Methyl-piperazine-1-carboxylic acid 4-[2-(cyclopropanecarbonyl-amino)-[1,2,4]triazolo[1,5-a]pyridin-5-yl]-benzylamide,
Morpholine-4-carboxylic acid 4-[2-(cyclopropanecarbonyl-amino)-[1,2,4]triazolo[1,5-a]pyridin-5-yl]-benzylamide,
(1-{4-[2-(Cyclopropanecarbonyl-amino)-[1,2,4]triazolo[1,5-a]pyridin-5-yl]-benzyl}-piperidin-4-yl)-carbamic acid tert-butyl ester,
Cyclopropanecarboxylic acid {5-[4-(3-oxo-piperazin-1-ylmethyl)-phenyl]-[1,2,4]triazolo[1,5-a]pyridin-2-yl}-amide,
Cyclopropanecarboxylic acid [5-(4-cyclopropylaminomethyl-phenyl)-[1,2,4]triazolo[1,5-a]pyridin-2-yl]-amide
Cyclopropanecarboxylic acid {5-[4-(3-hydroxy-piperidin-1-ylmethyl)-phenyl]-[1,2,4]triazolo[1,5-a]pyridin-2-yl}-amide,
Cyclopropanecarboxylic acid {5-[4-(3,3-dimethyl-azetidin-1-ylmethyl)-phenyl]-[1,2,4]triazolo[1,5-a]pyridin-2-yl}-amide,
Cyclopropanecarboxylic acid {5-[4-(3,3-difluoro-azetidin-1-ylmethyl)-phenyl]-[1,2,4]triazolo[1,5-a]pyridin-2-yl}-amide,
Cyclopropanecarboxylic acid {5-[4-(pyridin-3-ylcarbamoylmethyl)-phenyl]-[1,2,4]triazolo[1,5-a]pyridin-2-yl}-amide,
Cyclopropanecarboxylic acid (5-{4-[2-(3,3-difluoro-azetidin-1-yl)-2-oxo-ethyl]-phenyl}-[1,2,4]triazolo[1,5-a]pyridin-2-yl)-amide,
Cyclopropanecarboxylic acid {5-[4-(2-azetidin-1-yl-2-oxo-ethyl]-phenyl]-[1,2,4]triazolo[1,5-a]pyridin-2-yl}-amide,
Cyclopropanecarboxylic acid (5-{4-[2-oxo-2-(4-trifluoromethyl-piperidin-1-yl)-ethyl]-phenyl}-[1,2,4]triazolo[1,5-a]pyridin-2-yl)-amide,
Cyclopropanecarboxylic acid (5-{4-[2-(3,5-dimethyl-piperidin-1-yl)-2-oxo-ethyl]-phenyl}-[1,2,4]triazolo[1,5-a]pyridin-2-yl)-amide,
Cyclopropanecarboxylic acid (5-{4-[2-(3-methoxy-azetidin-1-yl)-2-oxo-ethyl]-phenyl}-[1,2,4]triazolo[1,5-a]pyridin-2-yl)-amide,
Cyclopropanecarboxylic acid (5-{4-[2-(3-acetylamino-azetidin-1-yl)-2-oxo-ethyl]-phenyl}-[1,2,4]triazolo[1,5-a]pyridin-2-yl)-amide,
Cyclopropanecarboxylic acid (5-{4-[2-(4-acetylamino-piperidin-1-yl)-2-oxo-ethyl]-phenyl}-[1,2,4]triazolo[1,5-a]pyridin-2-yl)-amide,
1-(2-{4-[2-(Cyclopropanecarbonyl-amino)-[1,2,4]triazolo[1,5-a]pyridin-5-yl]-phenyl}-acetyl)-azetidine-3-carboxylic acid dimethylamide,
Cyclopropanecarboxylic acid (5-{4-[3-(4-cyano-benzyloxy)-azetidine-1-carbonyl]-phenyl}-[1,2,4]triazolo[1,5-a]pyridin-2-yl)-amide,
Cyclopropanecarboxylic acid {5-[4-(3-morpholin-4-yl-azetidine-1-carbonyl)-phenyl]-[1,2,4]triazolo[1,5-a]pyridin-2-yl}-amide,
Cyclopropanecarboxylic acid {5-[4-(3-dimethylamino-azetidine-1-carbonyl)-phenyl]-[1,2,4]triazolo[1,5-a]pyridin-2-yl}-amide,
Cyclopropanecarboxylic acid {5-[4-(3-cyano-azetidine-1-carbonyl)-phenyl]-[1,2,4]triazolo[1,5-a]pyridin-2-yl}-amide,
Cyclopropanecarboxylic acid {5-[4-(3-dimethylaminomethyl-azetidine-1-carbonyl)-phenyl]-[1,2,4]triazolo[1,5-a]pyridin-2-yl}-amide, and
4-[2-(Cyclopropanecarbonyl-amino)-[1,2,4]triazolo[1,5-a]pyridin-5-yl]-N-(1H-1,2,4-triazol-3-yl)-benzamide.

* * * * *